US012492404B2

(12) United States Patent
Joyce et al.

(10) Patent No.: US 12,492,404 B2
(45) Date of Patent: Dec. 9, 2025

(54) SELF-LIMITING NOCTUIDS

(71) Applicant: Oxitec Limited, Abingdon (GB)

(72) Inventors: Stephen Joyce, Abingdon (GB); Nathan Rose, Abingdon (GB); Kelly Matzen, Abingdon (GB); Catherine Reavey, Abingdon (GB); Lucy Broom, Abingdon (GB); Adam Walker, Abingdon (GB); Simon Warner, Abingdon (GB); Neil Morrison, Abingdon (GB)

(73) Assignee: Oxitec Limited (GB)

( * ) Notice: Subject to any disclaimer, the term of this patent is extended or adjusted under 35 U.S.C. 154(b) by 1384 days.

(21) Appl. No.: 17/042,572

(22) PCT Filed: Mar. 28, 2019

(86) PCT No.: PCT/GB2019/050897
§ 371 (c)(1),
(2) Date: Sep. 28, 2020

(87) PCT Pub. No.: WO2019/186175
PCT Pub. Date: Oct. 3, 2019

(65) Prior Publication Data

US 2022/0098597 A1 Mar. 31, 2022

Related U.S. Application Data

(60) Provisional application No. 62/649,912, filed on Mar. 29, 2018.

(51) Int. Cl.
*C12N 15/63* (2006.01)
*A01K 67/68* (2025.01)
*C12N 15/85* (2006.01)

(52) U.S. Cl.
CPC .............. *C12N 15/63* (2013.01); *A01K 67/68* (2025.01); *C12N 15/8509* (2013.01); *A01K 2217/054* (2013.01); *A01K 2227/706* (2013.01); *A01K 2267/02* (2013.01); *C12N 2830/42* (2013.01); *C12N 2830/75* (2013.01)

(58) Field of Classification Search
None
See application file for complete search history.

(56) References Cited

U.S. PATENT DOCUMENTS 5,254,801 A 10/1993 Dotson et al.
5,278,057 A 1/1994 Jorgense
5,670,353 A 9/1997 Ahlquist et al.
5,674,747 A 10/1997 Hammock et al.
5,773,697 A 6/1998 Tomes et al.
5,851,796 A 12/1998 Schatz
5,977,441 A 11/1999 Oliver et al.
6,200,800 B1 3/2001 Choulika et al.
6,235,278 B1 5/2001 Miller et al.
6,338,040 B1 1/2002 Buman et al.
6,962,810 B2 11/2005 Fraser et al.
7,998,475 B2 8/2011 Alphey
8,124,404 B2 2/2012 Alphey
8,704,041 B2 4/2014 Gordon-Kamm et al.
9,121,036 B2 9/2015 Alphey
9,125,388 B2 9/2015 Alphey et al.
9,133,477 B2 9/2015 Alphey
9,487,801 B2 11/2016 Alphey
9,970,025 B2 5/2018 Alphey
10,059,961 B2 8/2018 Alphey
10,844,402 B2 11/2020 Alphey
10,941,416 B2 3/2021 Alphey
2003/0150007 A1 8/2003 Savakis et al.
2003/0213005 A1 11/2003 Alphey et al.
2004/0082032 A1 4/2004 Bovi et al.
2005/0221430 A1 10/2005 Prentice
2006/0212949 A1 9/2006 Alphey
2006/0242717 A1 10/2006 Alphey
2006/0275276 A1 12/2006 Alphey
2007/0056051 A1 3/2007 Alphey
2008/0115233 A1 5/2008 Alphey et al.
2009/0170793 A1 7/2009 Gaur
2009/0183269 A1 7/2009 Alphey
2013/0298266 A1 11/2013 Alphey et al.
2015/0143552 A1 5/2015 Alphey
2016/0044902 A1 2/2016 Alphey et al.
2016/0060651 A1 3/2016 Alphey
(Continued)

FOREIGN PATENT DOCUMENTS

CA 2012311 C 6/2003
EP 636310 A1 2/1995
(Continued)

OTHER PUBLICATIONS

Fryxell et al., "Autocidal Biological Control: A General Strategy for Insect Control Based on genetic transformation with a highly conserved gene", J Econ Entomol, vol. 88, No. 5, 1995, pp. 1221-1232.
Hadjieconomou et al., "Flybow: genetic multicolor cell labeling for neural circuit analysis in *Drosophila melanogaster*", Nature Methods, vol. 8, 2011, pp. 260-266.
International Search Report and Written Opinion received for PCT Patent Application No. PCT/GB2019/050897, mailed on Jun. 18, 2019, 10 pages.
Bennett et al., "Ectopic Expression of Inhibitors of Protein Phosphatase Type 1 (PP1) Can Be Used to Analyze Roles of PP1 in *Drosophila* Development", Department of Zoology, Oxford University, Oxford OX1 3PS, United Kingdom, Genetics 164, 2003, pp. 235-245.
(Continued)

*Primary Examiner* — Teresa E Knight
(74) *Attorney, Agent, or Firm* — MORRISON & FOERSTER LLP

(57) ABSTRACT

The invention provides a Noctuid dsx splice cassette for expression of a gene of interest on a sex-specific basis, gene expression systems for imparting a self-limiting trait to transformed Noctuidae, as well as transgenic Noctuidae and methods of suppressing populations of Noctuidae and reducing, inhibiting or eliminating crop damage caused by the Noctuid insects.

42 Claims, 19 Drawing Sheets

Specification includes a Sequence Listing.

(56) References Cited

U.S. PATENT DOCUMENTS

| | | | |
|---|---|---|---|
| 2016/0122780 | A1 | 5/2016 | Alphey |
| 2017/0009253 | A1 | 1/2017 | Alphey |
| 2017/0188559 | A1 | 7/2017 | Koukidou et al. |
| 2018/0251785 | A1 | 9/2018 | Alphey |
| 2018/0312870 | A1 | 11/2018 | Alphey |
| 2020/0367479 | A1 | 11/2020 | Kandul et al. |
| 2020/0407748 | A1 | 12/2020 | Alphey et al. |
| 2021/0137083 | A1 | 5/2021 | Koukidou et al. |
| 2021/0324409 | A1 | 10/2021 | Turkle et al. |

FOREIGN PATENT DOCUMENTS

| | | | |
|---|---|---|---|
| EP | 955364 | A2 | 11/1999 |
| EP | 3152311 | B1 | 8/2019 |
| GB | 2355459 | A | 4/2001 |
| GB | 2404382 | A | 2/2005 |
| GB | 2443186 | A | 4/2008 |
| GB | 2500113 | A | 9/2013 |
| JP | 2008-67678 | A | 3/2008 |
| WO | WO-1990008830 | A1 | 8/1990 |
| WO | WO-1994003619 | A2 | 2/1994 |
| WO | WO-1996004393 | A2 | 2/1996 |
| WO | WO-1996024605 | A1 | 8/1996 |
| WO | WO-1997030162 | A1 | 8/1997 |
| WO | WO-1998008960 | A1 | 3/1998 |
| WO | WO-1999010488 | A1 | 3/1999 |
| WO | WO-2000073510 | A1 | 12/2000 |
| WO | 01/39599 | A2 | 6/2001 |
| WO | WO-2001059088 | A2 | 8/2001 |
| WO | WO-2001091802 | A1 | 12/2001 |
| WO | WO-2002046444 | A2 | 6/2002 |
| WO | WO-2002101061 | A2 | 12/2002 |
| WO | WO-2004044150 | A2 | 5/2004 |
| WO | 2004/098278 | A1 | 11/2004 |
| WO | WO-2004108933 | A1 | 12/2004 |
| WO | WO-2005003364 | A2 | 1/2005 |
| WO | 2005/012534 | A1 | 2/2005 |
| WO | 2007/091099 | A1 | 8/2007 |
| WO | WO-2008134068 | A2 | 11/2008 |
| WO | WO-2009016627 | A1 | 2/2009 |
| WO | WO-2009115569 | A1 | 9/2009 |
| WO | WO-2009157771 | A2 | 12/2009 |
| WO | WO-2013131920 | A1 | 9/2013 |
| WO | 2014/135604 | A1 | 9/2014 |
| WO | WO-2015185933 | A1 | 12/2015 |
| WO | 2018/029534 | A1 | 2/2018 |
| WO | WO-2019186175 | A1 | 10/2019 |
| WO | WO-2020035673 | A1 | 2/2020 |

OTHER PUBLICATIONS

Bieschke et al., "Doxycycline-Induced Transgene Expression During Drosophila Development and Aaina", Mol. Gen Genet. vol. 258, No. 6, Jun. 1998, pp. 571-579.

Cande et al., "Apoptosis-Inducing Factor (AIF): Key to the Conserved Caspase-Independent Pathways of Cell Death?", Journal of Cell Science, vol. 115, No. 24, 2002, pp. 4727-4734.

Wilson et al., "Hepatocyte-directed Gene Transfer in Vivo Leads to Transient Improvement of Hypercholesterolemia In Low Density Lipoprotein Receptor-deficient Rabbits," vol. 267, 1992, pp. 963-967.

Fu et al., "Female-specific insect lethality engineered using alternative splicing", Nature Biotechnology, vol. 25, No. 3, 2007, pp. 353-357.

Handler et al., "The Lepidopteran Transposon Vector, Piggybac, Mediates Germ-Line Transformation in The Mediterranean Fruit Fly", Proceedings of the National Academy of Sciences, vol. 95, 1998, pp. 7520-7525.

Hansen et al., "Quantifying changes in the rates of forest clearing in Indonesia from 1990 to 2005 using remotely sensed data sets", Environmental Research Letters, vol. 4, 2009, 12 pages.

Heinrich et al., "A Repressible Female-Specific Lethal Genetic System for Making Transgenic Insect Strains Suitable for a Sterile-Release Program", Proceedings of the National Academy of Sciences of the United States of America, vol. 97, Jul. 18, 2000, pp. 8229-8232.

Hendrichs et al., "Strategic Options in using Sterile Insects For Area-Wide Integrated Pest Management", Sterile Insect Technique, Springer, Netherlands, 2005, pp. 563-600.

Horn et al., "A Transgene-Based, Embryo-specific Lethality System for Insect Pest Management", Nature Biotechnology, vol. 21 (1), 2003, pp. 64-70.

Jin et al., "Engineered Female-Specific Lethality for Control of Pest Lepidoptera", ACS Synthetic Biology, American Chemical Society, USA, vol. 2 (3), Jan. 8, 2013, pp. 160-166.

Li et al., "piggyBac internal sequences are necessary for efficient transformation of target genomes", Insect Molecular Biology, vol. 14 (1), Jan. 2005, pp. 17-30.

Loew et al., "Improved Tet-Responsive Promoters with Minimized Background Expression", BMC Biotechnology, vol. 10, No. 81, 2010, 13 pages.

Lukyanov et al., "Natural Animal Coloration Can Be Determined by a Nonfluorescent Green Fluorescent Protein Homolog", The Journal of Biological Chemistry, vol. 275 (34), 2000, pp. 25879-25882.

Matz et al., "Fluorescent Proteins from Nonbioluminescent Anthozoa Species", Nature Biotechnology, vol. 17, No. 10. 1999, pp. 969-973.

Nagaraju et al., "Lepidopteran Sex Determination: A Cascade of Surprises", Sexual Development, vol. 8, Available online at : <https://doi.org/10.1159/000357483>, 2014, pp. 104-112.

O'Brochta et al., "Gene Vector and Transposable Element Behavior in Mosquitos", The Journal of Experimental Biology, vol. 206, 2003, pp. 3823-3834.

Olson et al., "A GH3-like Domain in Reaper Is Required for Mitochondrial Localization and Induction of IAP Degradation", The Journal Of Biological Chemistry, vol. 278 (45), 2003, pp. 44758-44768.

Parker et al., "Functional Interaction between Nuclear Inhibitor of Protein Phosphatase Type 1 (NIPP1) and Protein Phosphatase Type 1 (PP1) in *Drosophila*: Consequences of Overexpression Of NIPP1 in Flies and Suppression by Co-expression of PP1", Biochemical Journal, vol. 368, 2002, pp. 789-797.

Shukla et al., "Two female-specific DSX proteins are encoded by the sex-specific transcripts of dsx, and are required for female sexual differentiation in two wild silkmoth species, Antheraea assama and Antheraea mylitta (Lepidoptera, Saturniidae)", Insect Biochemistry and Molecular Biology, vol. 40 (9), Sep. 2010, pp. 672-682.

Suzuki et al., "Role of the male BmDSX protein in the sexual differentiation of Bombyx mori", Evolution & Development, vol. 7 (1), 2005, pp. 58-68.

Toshiki et al., "Germline Transformation of The Silkworm Bombyx *Mori* L. using a Piggyback Transposon-derived Vector", Nature Biotechnology, vol. 18, No. 1, 2000, pp. 81-84.

Tan et al., "Transgene-based, female-specific lethality system for genetic sexing of the silkworm, Bombyx mori", PNAS, vol. 110 (17) Available online at: <https://doi.org/10.1073/pnas.1221700110>, Apr. 23, 2013, pp. 6766-6770.

Thibault et al., "Precise excision and transposition of piggyBac in pink bollworm embryos", Insect Molecular Biology, vol. 8 (1), Feb. 1999, pp. 119-123.

Vernooy et al., "Cell Death Regulation in Drosophila: Conservation of Mechanism and Unique Insights", The Journal of Cell Biology, vol. 150 (2), 2000, pp. F69-F75.

Wang et al., "Conserved RNA cis-elements regulate alternative splicing of Lepidopteran doublesex", Insect Biochemistry and Molecular Biology, vol. 44, Jan. 2014, 11 pages.

White et al., "Cell Killing by the *Drosophila* Gene reaper", Science, vol. 271, Feb. 9, 1996, pp. 805-807.

Wing et al., "The RHG motifs of Drosophila Reaper and Grim are important for their distinct cell death-inducing abilities", Mechanisms of Development, vol. 102, 2001, pp. 193-203.

Xu et al., "Sexually dimorphic traits in the silkworm, Bombyx mori, are regulated by doublesex", Insect Biochemistry and Molecular Biology vol. 80, Jan. 2017, pp. 42-51.

(56) References Cited

OTHER PUBLICATIONS

Wu et al., "Receptor-mediated Gene Delivery and Expression in Vivo," J. Biological Chemistry, vol. 263, 1988, pp. 14621-14624.
Adelman, "Formation and loss of large, unstable tandem arrays of the piggyBac transposable element in the yellow ever mosquito, Aedes aegypti", Transgenic Res, vol. 13, No. 5, 2004, pp. 411-425.
Alignment of SEQ ID No. 22 of D1 (WO 2005/012534) with tTAV, Jul. 4, 2014.
Allen et al., "Flight muscle-specific expression of acl88F: GFP in transgenic Culex quinauefasciatus Say (Diptera: Culicidae)", Parasitoloqy Int vol. 53, No. 4, 2004, pp. 307-317.
Allen et al., "PiggyBac transformation of the New World screw-worm, Cochliomyia hominivorax, produces multiple distinct mutant strains", Med. Vet. Entomol vol. 18, Mar. 2004, pp. 1-9.
Allen et al., "Stable, germ-line transformation of Culex quinquefasciatus (Diptera: Culicidae)", J Med Entomol vol. 38 No. 5, 2001, pp. 701-710.
Alphey et al., "Dominant Lethality and Insect Population Control", Mol. Biochem Parasitol. vol. 121 No. 2, May 2002, p. 173-178.
Alphey et al., "Malaria control with genetically manipulated insect vectors", Science vol. 298, Oct. 4, 2002, pp. 119-121.
Alphey et al., "Managing Insecticide Resistance by Mass Release of Engineered Insects", J Econ. Entomol, vol. 100, No. 5, 2007, pp. 1642-1649.
Alphey et al., "Modeling resistance to genetic control of insects", Journal of Theoretical Biology, vol. 270, 2011, pp. 12-55.
Alphey et al., (2002). "Re-engineering the sterile insect technique," Insect Biochem Mol Biol., 32:1243-1247. Abstract Only.
Alphey, "Engineering Insects for the Sterile Insect Technique," in: Area-wide Control of Insect Pests: from Research to Field Implementation, Vreysen et al., (eds.), Dordrecht, The Netherlands, Springer (2007) pp. 51-60.
Ant et al., "Control of the olive fruit fly using genetics-enhanced sterile insect technique", BMC Biology vol. 10, No. 51, 2012, 8 pages.
Arama et al., "Caspase activity and a specific cytochrome Care required for sperm differentiation in *Drosophila*", Dev Cell vol. 4, No. 5, May 1, 2003, pp. 687-697.
Arribas et al., "The ubiquitin genes in D. melanogaster: transcription and polymorphism", Biochimica et Biophysica Acta, vol. 868, 1986, pp. 119-127.
Arya et al., "Basic principles of real-time quantitative PCR", Expert Rev Mol Diagn, vol. 5, No. 2, 2005, pp. 209-219.
Atkinson et al., "Genetic transformation systems in insects", Annu Rev Entomol vol. 46, Jan. 2001, pp. 317-346.
Atkinson et al., "Hermes and other hAT Elements as Gene Vectors in Insects", Insect Transgenesis: Methods and Applications, Hadler et al. {eds.), Boca Raton CRC Press, 2000, pp. 219-235.
Barreau et al., "Post-Meiotic Transcription in *Drosophila* Testes", Development, vol. 135, No. 11, 2008, pp. 1897-1902.
Bauer Dumont et al., "Recurrent positive selection at bgcn, a key determinant of germ line differentiation, does not ppear to be driven by simple coevolution with its partner protein barn", Mol Biol Evol vol. 24 No. 1, 2007, pp. 182-191.
Beall et al., "Discovery of tMAC: a *Drosophila* testis-specific meiotic arrest complex paraloqous to Myb-Muv B", 3enes Dev vol. 21, No. 8, 2007, pp. 904-919.
Bello et al., "Spatial and temporal targeting of gene expression in *Drosophila* by means of a tetracycline-dependent transactivator system", Development vol. 125, No. 12, 1998, pp. 2193-2202.
Berghammer et al., "A universal marker for transgenic insects", Nature vol. 402, No. 6760, 1999, pp. 370-371.
Beullens et al., "Inactivation of nuclear inhibitory polypeptides of protein phosphatase-1 {NIPP-1) by protein kinase A", J Biol Chem vol. 268, No. 18, 1993, pp. 13172-13177.
Beullens et al., "Molecular determinants of nuclear protein phosphatase-1 regulation by NIPP-1", J Biol Chem, vol. J74, No. 20, 1999, pp. 14053-14061.
Beullens et al., "The isolation of novel inhibitory polypeptides of protein phosphatase 1 from bovine thymus nuclei", J Biol Chem vol. 267, No. 23, 1992, pp. 16538-16544.
Beumer et al., "Efficient gene targeting in *Drosophila* with zinc-finger nucleases", Genetics, vol. 172, No. 4, 2006, pp. 391-2403.
Bibikova et al., "Targeted chromosomal cleavage and mutagenesis in *Drosophila* using zincfinaer nucleases", Genetics, vol. 161, No. 3, 2002, pp. 1169-1175.
Black et al., Why RIDL is not SIT, Trends Parasitol, vol. 27, No., 8, 2001, pp. 362-370.
Blitvich et al., "Developmental-and tissue-specific expression of an inhibitor of apoptosis protein 1 homologue from Aedes triseriatus mosquitos", Insect Molecular Biology, vol. 11, No. 5, 2002, pp. 431-442.
Boudrez et al., "Identification of MYPT1 and NIPP1 as subunits of protein phosphatase 1 in rat liver cytosol", FEBS Letters, vol. 455, 1999, pp. 175-178.
Brand et al., "Ectopic expression in *Drosophila*", Methods Cell Biol, vol. 44, 1994, pp. 635-654.
Brand et al., "Targeted gene expression as a means of altering cell fates and generating dominant phenotypes", Development, vol. 118, No. 2, 1993, pp. 401-415.
Burcin et al., "A regulatory system for target gene expression", Frontiers in Biosc. vol. 3(c), 1998, pp. 1-7.
Burn et al., "Alternative 5C actin transcripts are localized in different patterns during *Drosophila* embryogenesis", Dev Biol, vol. 131, No. 2, 1989, pp. 345-355.
Burt et al., "Site-specific selfish genes as tools for the control and genetic engineering of natural populations", Proc Biol Sci. vol. 270, 2003, pp. 921-928.
Cabrera et al., "Expression Pattern of Gal4 Enhancer Trap Insertions into the bric a brae Locus Generated by P Element Replacement", Genesis, vol. 34, 2002, pp. 62-65.
Caceres et al., "Mass rearing of temperature sensitive genetic sexing strains in the Mediterranean fruit fly (Ceratitis Capitata)", Genetica, vol. 115, No. 1, 2002, pp. 107-116.
Cagan et al., "Spermatogenesis: Borrowing the Apoptotic Machinery", Curr Biol, vol. 13, 2003, pp. R600-R602.
Carriere and Tabashnik, "Reversing Insect Adaptation to Transgenic Insecticidal Plants", Proc. R. Soc. Lond. B. vol. 268, 2001, pp. 1475-1480.
Catteruccia et al., "An Anopheles transgenic sexing strain for vector control", Nat Biotechnol, vol. 23, No. 11, 2005, pp. 1414-1417.
Catteruccia et al., "Impact of genetic manipulation on the fitness of Anopheles stephensi mosquitoes", Science, vol. 299, No. 5610, 2000, pp. 1225-1227.
Catteruccia et al., "Stable germline transformation of the malaria mosquito Anopheles stephensi", Nature, vol. 105, No. 6789, 2000, pp. 959-962.
Catteruccia et al., "Transgenic technologies to induce sterility", Malaria Journal, vol. 8(SUPP2)S7, 2009.
Cenik et al., "Genome analysis reveals interplay between 5'UTR intrans and nuclear mRNA export for secretory and mitochondrial genes", PLoS Genet, vol. 794:e1001366, 2011.
Cha et al., "Expression of green fluorescent protein in insect larvae and its application for heteroloaous protein roduction", Biotechnol Bioena, vol. 56, No. 3, 1997, pp. 239-247.
Chalfie et al., "Green fluorescent protein as a marker for gene expression", Science, vol. 263, No. 5148, 1994, pp. 802-805.
Chen et al., "Apoptotic Activity of REAPER is Distinct from Signaling by the Tumor Necrosis Factor Receptor 1 Death Domain", The Journal of Biological Chemistry, vol. 271, No. 42, 1996, pp. 25735-25737.
Chen et al., "The Use of Modified Tetracycline Regulatory Expression System with Reduced Basal Level to Develop nd In Vivo Biopesticide Expression System", Food Science Agriculture Chem. vol. 2, No. 4, Oct. 2000, pp. 20-225.
Cheng et al., "Cellular transformation by Simian Virus 40 and Murine Polyoma Virus T antigens", Semin Cancer Biol, vol. 19, No. 4, 2009, pp. 218-228.
Chintapalli et al., "Using FlyAllas to identify better *Drosophila melanogaster* models of human disease", Nature Genetics, vol. 39, No. 6, 2007, pp. 715-720.

(56) References Cited

OTHER PUBLICATIONS

Cho, "Enhancers", WIREs Dev Biol vol. 1, 2012, pp. 469-478.
Choi et al., "The Baculovirus Transactivator IE1 Binds to Viral Enhancer Elements in the Absence of Insect Cell ractors", Journal of Virology, vol. 69, No. 7, 1995, pp. 4548-4551.
Curtis et al., "Assessment of the impact of potential tetracycline exposure on the phenotype of Aedes aegypti OX513A: Implications for field use", PLOS Neglected Tropical Diseases, vol. 9, No. 8, 2015.
Dafa'Alla et al., "Transposon-Free Insertions for Insect Genetic Engineering", Nature Biotechnology, vol. 24, No. 7, Jul. 2006, pp. 820-821.
Dane et al., "The Transformer Gene in Ceratitis Capitata Provides a Genetic Basis for Selecting and remembering the Sexual Fate", Dipartimento di Genetica, Biologia Generale e Molecolare, Development 129, 2002, pp. 3715-3725.
Dapathanos et al., "Sex Separation Strategies: Past Experience and New Approaches", Malaria Journal, vol. 8, J009.
Darker et al., "Functional Interaction between Nuclear Inhibitor of Protein Phosphatase Type 1 (NIPP1) and Protein Phosphatase Type 1 (PP1) in *Drosophila*: Consequences of Overexpression Of NIPP1 in Flies and Suppression by Co-expression of PP1", Biochemical Journal, vol. 368, 2002, pp. 789-797.
Davis et al., "Engineered Underdominance Allows Efficient and Economical Introgression of Traits into Pest Populations", J Theor. Biol., vol. 212, No. 1, 2001, pp. 83-98.
De Valdez et al., "Genetic Elimination of Dengue Vector Mosquitoes", Proceedings of the National Academy of Sciences of the United States of America, vol. 108, No. 12, 2011, 4772-4775.
Definition of "pest" from the Concise Oxford American Dictionary, Concise Oxford American Dictionary, 2006, p. 661.
Deng et al., "A targeted gene silencing technique shows that *Drosophila myosin* VI is required for egg chamber and maginal disc morphogenesis", J Cell Science, vol. 112, 1999, pp. 3677-3690.
Deredec et al., "The population genetics of using homing endonuclease genes in vector and pest management", Genetics, vol. 179, No. 4, 2008, pp. 2013-2026.
Derezgasga et al., "Regulation of Transcription of Meiotic Cell Cycle and Terminal Differentiation Genes by the Testis-specific Zn-finger Protein Matotopelli", Development, vol. 131, No. 8, 2004, pp. 1691-1702.
Devault et al., "Biotechnology and new integrated pest management approaches", Nature Biotechnology, vol. 14, 1996, pp. 46-49.
Dhillon, "The melon fruit fly, Bactrocera cucurbitae: A review of its biology and management", J Insect Sci., vol. 5, 2005, 40 Pages.
Diamantidis et al., (2008). "Life-history evolution of an invasive tephritid," J. Appl. Entomol., 132:695-705. Abstract Only.
Dyck et al., "Genetic sexing strains in the Mediterranean Fruit Fly, an example for other species amenable to large-scale rearing for the sterile insect technique", Sterile Insect Technique, Principles and Practice in Area-Wide Integrated Pest Management and The Netherlands, Springer, 2005, pp. 427-451.
Egloff et al., "Structural basis for the recognition of regulatory subunits by the catalytic subunit of protein Phosphatase 1", EMBO J, vol. 16, No. 8, 1997, pp. 1876-1887.
Elick et al., "Analysis of the Cis-Acting DNA Elements Required for piggyback Transposable Element Excision", Mol. Gen. Genet., vol. 255, 1997, pp. 605-610.
Ernst U, "Regulation of Sexual Differentiation in Drosophila: Alternative Splicing of the Transformer Primary Transcript Requires Masking of the Non-Specific Acceptor Site in Females", Inaugural Dissertation, Aus Frankfurt | Main, BRO., 1991, 32 pages.
FAO/IAEA/USDA, "Product Quality Control and Shipping Procedures for Sterile Mass-reared Tephritid Fruit Flies", AEA, Vienna, Version 5.0, May 2003, 2 pages.
Franz, "Genetic sexing strains in the Mediterranean Fruit Fly, an example for other species amenable to large-scale rearing for the sterile insect technique" in:Sterile Insect Technique, Principles and Practice in Area-Wide Integrated Pest Management, Dyck et al., (eds), The Netherlands, Springer (2005) pp. 427-451.
Franz, "Recombination between homologous autosomes in medfly (Ceratitis capitata) males: type-1 recombination and the implications for the stability of genetic sexing strains", Genetica, vol. 116, No. 1, 2012, pp. 73-84.
Fraser, "Insect transgenesis: current applications and future prospects", Annu Rev Entomol, vol. 57, 2012, pp. 267-289.
Fu et al., "Female-specific flightless phenotype for mosquito control", Proc Nall Acad Sci USA, vol. 107, No. 10, 2010, pp. 4550-4554.
Fuller, "Spermatogenesis", The Development of Drosophila Melanogaster, Bate et al., Cold Spring Harbor Laboratory Press, 1993, pp. 71-147.
Funaguma et al., "The Bmdsx transgene including trimmed introns is sex-specifically spliced in tissues of the silkworm, Bombyx mori", Journal of Insect Science (online), vol. 5, No. 17, 2005, pp. 1-6.
Fussenegger et al., "Autoregulated multicistronic expression vectors provide one-step cloning of regulated product gene expression in mammalian cells", Biotechnol. Prog., vol. 13, 1997, pp. 733-740.
Fussenegger et al., "Regulated Multicistronic Expression Technology for Mammalian Metabolic Engineering", Biotechnology, vol. 28, 1998, pp. 111-126.
Fussenegger et al., "Streptogramin-based gene regulation systems for mammalian cells", Nat Biotechnol, vol. 18, No. 11, 2000, pp. 1203-1208.
Fussenegger et al., "The impact of mammalian gene regulation concepts on functional genomic research, metabolic engineering, and advanced gene therapies", Biotechnol Prog, vol. 17, No. 1, 2001, pp. 1-51.
Fux et al., "Novel Macrolide-Adjustable Bidirectional Expression Modules for Coordinated Expression of Two Different Transgenes in Mice", J Gene Medicine, vol. 5, 2003, pp. 1067-1079.
Ghosh et al., "Transcription factor binding and induced transcription alter chromosomal c-myc replicator activity", Mol gen Biol, vol. 24, No. 23, 2004, pp. 10193-10207.
Gill et al., (1988). "Negative effect of the transcriptional activator GAL4," Nature, 334(6184):721-724.
Gloor et al., "Targeted Gene Replacement in Drosophila Via p. Element-Induced Gap Repair", Science, vol. 253, 1991, pp. 1110-1117.
Golovnin et al., "The su{Hw) insulator can disrupt enhancer-promoter interactions when localed more than 20 ilobases away from the *Drosophila achaete*-scute complex", Mol Cell Biol, vol. 19, No. 5, 1999, pp. 3443-3456.
Gonczy, "Bag-of-marbles and benign genial cell neoplasm act in the germline to restrict proliferation during *Drosophila spermatogenesis*", Development, vol. 124, No. 21, 1997, pp. 4361-4371.
Gong et al., "A dominant lethal genetic system for autocidal control of the Mediterranean fruit fly", Nat Biotechnol, vol. 23, No. 4, 2005, pp. 453-456.
Gong et al., "Ends—Out, or replacement, gene targeting in *Drosophila*", Proc Nall Acad Sci {USA), vol. 100, No. 5, J003, pp. 2556-2561.
Gonzy-Treboul et al., "Enhancer-Trap Targeting at the Broad-Complex Locus of *Drosophila melanogaster*", Genes Dev. vol. 9, 1995, pp. 1137-1148.
Gossen et al., "Studying gene function in eukaryotes by conditional gene inactivation", Annu Rev Genet, vol. 36, 2002, pp. 153-173.
Gossen et al., "Tetracycline in Biology, Chemistry and Medicine", 2001, pp. 139-157.
Gossen et al., "Tight control of gene expression in mammalian cells by tetracycline-responsive promoters", Proc Natl Acad Sci {USA), vol. 89, No. 12, 1992, pp. 5547-5551.
Graham et al., "Larval diets containing dyes for tagging pink bollworm moth internally", J Econ Entomol, vol. 64, 1971, pp. 376-379.
Great Britain Application No. 1303932.6, filed Mar. 5, 2013, 42 pages.
GSN: AAD40186, Retrieved from the internet: <http://ibis.internal.epo.org/exam/dbfetch.jsp?id=GSN:AAD40186>, Oct. 22, 2002.
GSN: BB010346, Retrieved from the internet: <http://ibis.internal.epo.org/exam/dbfetch.jsp?id=GSN:BB010346>, Nov. 6, 2014.

(56) References Cited

OTHER PUBLICATIONS

Guo et al., "Species-specific signals for the splicing of a short *Drosophila intron* in vitro", Mol Cell Biol, vol. 13, No. 02, 1993, pp. 1104-1118.
Hagler et al., "Methods for marking insects: current techniques and future prospects", Annu. Rev. Entomol. vol. 46, 2001, pp. 511-543.
Hagler et al., (1994). "Determining the frequency of heteropteran predation on sweetpotato whitefly and pink bollworm using multiple ELISAs," Entomol. Exp. Appl., 72:59-66.
Hagler, "An Alternative to Conventional Insect Marking Procedures; Detection of a Protein Mark on Pink Bollworm by ELISA", Entomologia Experimentalis et Applicata, vol. 103, No. 1, 2002, pp. 1-9.
Han et al., "Enhancer-Driven Membrane Markers for Analysis of Nonautonomous Mechanisms Reveal Neuron-Glia Interactions in *Drosophila*", Proceedings of the National Academy of Sciences, vol. 108, No. 23, Jun. 7, 2011, pp. 9673-9678.
Handler et al., "A Current Prospective on Insect Gene Transformation", Insect Biochemistry and Molecular Biology, vol. 31, No. 2, 2002, pp. 111-128.
Handler et al., "Germline Transformation of *Drosophila melanogaster* with the Piggybac Transooson Vector", Insect Molecular Biology, vol. 8, No. 4, 1999, pp. 449-457.
Handler et al., "Polyubiquitin-Regulated DsRed Marker for Transgenic Insects", Bio Techniques, vol. 31, 2001, pp. 820-828.
Handler et al., "Prospects for Using Genetic Transformation for Improved SIT and New Biocontrol Methods", Genetics, vol. 116, 2002, pp. 137-149.
Handler et al., "Use of piggyback Transposon for Germ-Line Transformation of Insects", Insect Biochemistry and Molecular Biology, vol. 32, 2002, pp. 1211-1220.
Hansen et al., (2009). "Genome-Wide Identification of Alternative Splice Forms Down-Regulated by Nonsense-Mediated mRNA Decay in *Drosophila*, " PLOS Genetics, 5(6):e1000525, 14 pages.
Harris et al., "Field performance of engineered male mosquitoes", Nature Biotechnology, vol. 29 (11), November J011, pp. 1034-1037.
Hartl et al., "Gene Linkage and Genetic Mapping", in Essential Genetics, Jones and Bartlett Publishers, Sudbury, Massachussetts, 1999, pp. 126-127.
He et al., "The Actin Gene Family in the Oriental Fruit Fly Bactrocera Dorsalis, Muscle Specific Actins", Insect Biochemistry and Molecular Biology, vol. 24, No. 9, 1994, pp. 891-906.
Heslip et al., "Targeted Transposition at the Vestigial Locus of *Drosophila melanogaster*", Genetics, vol. 138, 1994, p. 1127-1135.
Hiller, "Testis-Specific TAF Homologs Collaborate to Control a Tissue-Specific Transcription Program", Development, vol. 131, 2004, pp. 5297-5308.
Hockemeyer et al., "Genetic Engineering of Human Pluripotent Cells Using TALE Nucleases", Nature Biotechnology, Vo. 28, No. 8, 2011, pp. 731-734.
Hofmann et al., "Rapid Retroviral Delivery of Tetracycline-Inducible Genes in a Single Autoregulatory Cassette", Proceedings of the National Academy of Sciences of the United States of America, vol. 93, 1996, pp. 5185-5190.
Hollenhorst et al., "Expression profiles frame the promoter specificity dilemma of the ETS family of transcription actors", Nucleic Acids Res, vol. 32, No. 18, 2004, pp. 5693-5702.
Hondred et al., "Use of Ubiquitin Fusions to Augment Protein Expression in Transgenic Plants", Plant Physiology, vol. 119, 1999, pp. 713-723.
Horn et al., "Fluorescent Transformation Markers for Insect Transgenesis", Insect Biochemistry and Molecular Biology, vol. 32, 2002, pp. 1221-1235.
Horn et al., "Highly Sensitive, Fluorescent Transformation Marker for *Drosophila transgenesis*", Development Genes and Evolution, vol. 210, 2000, pp. 623-629.
Horn,"PiggyBac-Based Insertional Mutagenesis and Enhancer Detection as a Tool for Functional Insect Genomics", Genetics, Vo. 163, 2003, pp. 647-661.
Huang et al., "Evolutionary conservation of apoptosis mechanisms: Lepidopteran and baculoviral inhibitor of poptosis proteins are inhibitors of mammalian caspase-9", PNAS, vol. 97, No. 4, Feb. 15, 2000, pp. 1427-1432.
Imai et al., "Control of insecticide resistance in a filed population of houseflies, Musca domestica, by releasing susceptible flies", Researches on Population Ecology, vol. 29, 1987, pp. 129-146.
Inoue, "Binding of the *Drosophila* Sex-Lethal Gene Product to the Alternative Splice Site of Transformer Primary Transcript", Nature, vol. 344, 1990, pp. 461-463.
Irvin et al., "Assessing Fitness Costs for Transgenic Aedes Aegypti Expressing the GFP Marker and Transposase 3enes", Proceedings of the National Academy of Sciences of the United States of America, vol. 101, No. 3, January JO, 2004, pp. 891-896.
Jagiello et al., "NIPP-1, A Nuclear Inhibitory Subunit of Protein Phosphatase-1, Has RNA-Binding Properties", Journal of Biological Chemistry, vol. 272, No. 35, 1997, pp. 22067-22071.
Jattani et al., "Deficiency Screen Identifies a Novel Role for Beta 2 Tubulin in Salivary Gland and Myoblast Migration n the *Drosophila* Embryo", Developmental Dynamics, vol. 238, No. 4, Apr. 2009, pp. 853-863.
Jiang et al., "Tombola, a Tesmin/TS01-Family Protein, Regulates Transcriptional Activation in the *Drosophila* Male 3ermline and Physically Interacts with Always Early", Development, vol. 134, No. 8, 2007, pp. 1549-1559.
Jiang et al., "Transcriptional Activation in *Drosophila spermatogenesis* Involves the Mutually Dependent Function of Aly and a Novel Meiotic Arrest Gene Cookie Monster", Development, vol. 130, No. 3, 2003, pp. 563-573.
Jin et al., "Mapping of The RNA-Binding and Endoribonuclease Domains of NIPP1, A Nuclear Targeting Subunit of Protein Phosphatase 1", Biochemical Journal, vol. 342, 1999, pp. 13-19.
Johnson-Schlitz et al., "P-Element-Induced Interallelic Gene Conversion of Insertions and Deletions in *Drosophila melanogaster*", Molecular and Cellular Biology, vol. 13, No. 11, 1993, pp. 7006-7018.
Kawase et al., "Gbb/Bmp Signalling Is Essential for Maintaining Germline Stem Cells and for Repressing Barn Transcription in the *Drosophila testis*", Development, vol. 131, No. 6, 2004, pp. 1365-1375.
Kelly et al., "*Drosophila* MEF2 is a Direct Regulator of Actin57B Transcription in Cardiac, Skeletal, and Visceral Muscle Lineages", Mechanisms of Development, vol. 110, No. 1-2, 2002, pp. 39-50.
Kim et al., "Hybrid Restriction Enzymes: Zinc Finger Fusions to Fok I Cleavage Domain", Proceedings of the National Academy of Sciences of the United States of America, vol. 93, 1996, pp. 1156-1160.
Klassen et al., "Sterile Insect Technique, in: Sterile Insect Technique", Principles and Practice in Area-Wide Integrated Pest Management, The Netherlands, Springer, Curtis et al., 2005, pp. 33-36.
Knipling et al., "Possibilities of Insect Control or Eradication Through the Use of Sexually Sterile Males", Journal of Economic Entomology, vol. 48, 1955, pp. 459-462.
Koukidou et al., "Germ Line Transformation of the Olive Fly Bactrocera Oleae Using a Versatile Transgenesis Marker", Insect Molecular Biology, vol. 15, No. 1, Feb. 2006 pp. 95-103.
Krafsur et al., "Bionomics of the Face Fly, Musca Autumnalis", Annual Review of Entomology, vol. 42, 1997, pp. 503-523.
Lankenau et al., "Comparison of Targeted-Gene Replacement Frequencies in *Drosophila melanogaster* at the Forked and White Loci", Molecular and Cellular Biology, vol. 16, No. 7, 1996, pp. 3535-3544.
Leftwich et al., (2014). "Genetic elimination of field-cage populations of Mediterranean fruit flies," Proc Biol Sci, 281(1792):20141372.
Leftwich, Philip T., "Male reproductive success and population control in the Mediterranean Fruit Fly, Ceratitis apitata", School of Biological Sciences, Aug. 2012, 226 pages.
Louis et al., "A Theoretical Model for the Regulation of Sex-Lethal, a Gene that Controls Sex Determination and Dosage Compensation in Drosophila Melanogaster", Genetics, vol. 165, Nov. 2003, pp. 1355-1384.

(56) References Cited

OTHER PUBLICATIONS

Loukeris et al., "Gene Transfer Into the Medfly, Ceratitis Capilala, with a *Drosophila hydei* Transposable Element", Science, vol. 270, No. 5244, 1999, pp. 2002-2005.
Loukeris et al., "Introduction of the Transposable Element Minos into the Germ Line of *Drosophila melanogaster*", Proceedings of the National Academy of Sciences, vol. 92, 1995, pp. 9485-9489.
Lycett et al., "Conditional Expression in the Malaria Mosquito Anopheles stephensi with Tel-On and Tel-Off Systems", Genetics, vol. 167, No. 4, Aug. 2004, pp. 1781-1790.
Mahfouz et al., "De nova-engineered transcription activator-like effector (TALE) hybrid nuclease with novel DNA binding specificity creates double-strand breaks", Proc Nall Acad Sci, vol. 101, No. 6, 2011, pp. 2623-2628.
Marrelli et al., "Mosquito Transgenesis: what is the fitness cost?", Trends Parasitol, Vo. 22, No. 5, 2006, pp. 197-202.
Mattox et al., "Alternative splicing of the sex determination gene transformer-2 is sex-specific in tile germ line but not in the soma", Genes & Development, vol. 4, No. 5, 1990, pp. 789-805.
Mattox et al., "Autoregulation of the splicing of transcripts from the transformer-2 gene of *Drosophila*", Genes & Development, vol. 5, 1991, pp. 786-796.
May et al., "Tropical Arthropod Species, More or Less?", Science, vol. 329, 2010, pp. 41-42.
Maynard-Smith et al., "A Directed Approach for Engineering Conditional Protein Stability Using Biologically Silent Small Molecules", Journal of Biological Chemistry, vol. 282, No. 34, 2007, pp. 24866-24872.
McInnis et al., "Mating and Remating of Medflies (Diptera: Tephritidae) in Guatemala: Individual Fly Marking in Field ages", Florida Entomologist, vol. 85(1), Mar. 2002, pp. 126-137.
Michiels et al., "A 14 Bp Promoter Element Directs the Testis Specificity of the *Drosophila* B2 Tubulin Gene", The EMBO Journal vol. 8, No. 5, 1989, pp. 1559-1565.
Miller et al., "A TALE Nuclease Architecture for Efficient Genome Editing", Nature Biotechnology, vol. 29, No. 2, 2011, pp. 143-148.
Miller et al., "An Improved Zinc-finger Nuclease Architecture for Highly Specific Genome Editing", Nature Biotechnology, vol. 25, No. 7, 2007, pp. 778-785.
Mishra et al., "Understanding Forest Biology", Discovery publishing house, 2009, 3 pages.
Morrison et al., "Engineered repressible lethality for controlling the pink bollworm, a lepidopteran pest of cotton", DLOS One, vol. 7, No. 12:e50922, 2012.
Morrison et al., "Genetic Improvements to The Sterile Insect Technique for Agricultural Pests", Asia-Pacific Journal of Molecular Biology and Biotechnology, vol. 18, No. 2, 2010, pp. 275-295.
Mounier et al., "Insect Muscle Actins Differ Distinctly from Invertebrate and Vertebrate Cytoplasmic Actins", Journal of Molecular Evolution, vol. 34, No. 5, 1992, pp. 406-415.
Mumford, John D., "Science, Regulation, and Precedent for Genetically Modified Insects", PLoS, vol. 6, Issue 1, Jan. 2012, 4 pages.
Munoz et al., "The AeAct-4 Gene is Expressed in the Developing Flight Muscles of Female Aedes Aegypti", Insect Molecular Biology, vol. 13, No. 5, Oct. 2004, pp. 563-568.
Namciu et al., "Human Matrix Attachment Regions Insulate Transgene Expression from Chromosomal Position Effects in *Drosophila melanogaster*", Molecular and Cellular Biology, vol. 18, No. 4, 1998, pp. 2382-2391.
Nene et al., Genome sequence of Aedes aegypti, a major arbovirus vectM, Science, vol. 316, No. 5832, 2007, pp. 1718-1723.
Nielsen et al., "Axoneme-specific Beta-tubulin Specialization: A Conserved C-terminal Motif Specifies The Central Pair", Current Biology, vol. 11, No. 7, 2001, pp. 529-533.
Nitasaka et al., "Repressor of P Elements in *Drosophila melanogaster*: Cytotype Determination by a Defective p. Element Carrying Only Open Reading Frames O Through 2", Proceedings of the National Academy of Sciences of the United States of America, vol. 84, No. 21, 1987, pp. 7605-7608.
Nongthomba et al., "Expression and Function of the *Drosophila* Act88F Actin Isoform is not Restricted to the indirect Flight Muscles", Journal of Muscle Research and Cell Motility, vol. 22, No. 2, 2001, 1 Page.
Ohshima et al., "Reassessment of 79B actin gene expression in the abdomen of adult *Drosophila melanogaster*", nsect Molecular Biology, vol. 6, No. 3, 1997, 2 pages.
Olsen, "Fibroblast Growth Factor {FGF) Homologous Factors Share Structural but Not Functional Homology with rGFs", J Biol. Chem. vol. 278, 2003, pp. 34226-34236.
Osanai-Futahasi et al., "A Visible Dominant Marker for Insect Transgenesis", Nature Communications, vol. 3, No. 1295, 2012.
Osterwalder et al., "A Conditional Tissue-specific Transgene Expression System using Inducible GAL4", Proceedings of the National Academy of Sciences of the United States of America, vol. 98, No. 22, 2001, pp. 12596-12601.
Oxitec, Newsletter, http://www.oxitec.com/our-news/newsletters/november- J011-newsletter/, downloaded, Dec. 13, 2011, 6 pages.
Pane et al., (2002). "The transformer gene in Ceratitis capitata provides a genetic basis for selecting and remembering the sexual fate," Development, 129:3715-3725.
Papathanos et al., "Sex separation strategies: past experience and new approaches," Malar J. (2009) 8 Supp 2:S5.
Parker, "Mass-rearing for sterile insect release," The Netherlands, Springer (2005) pp. 209-232.
Peloquin et al., "Germ-line Transformation of Pink Bollworm (Lepidoptera: Gelechiidae) Mediated by The Piggybac Transposable Element", Insect Molecular Biology, vol. 9, No. 3, 2000, pp. 323-333.
Perera et al., "Germ-line Transformation of the South American Malaria Vector, Anopheles albimanus, with a Piggybac/Egfp Transposon Vector, is Routine and Highly Efficient", Insect Molecular Biology, vol. 11, No. 4, 2002, pp. 91-297.
Perezgasga et al., "Regulation of transcription of meiotic cell cycle and terminal differentiation genes by the testis-specific Zn-finger protein matotopetli," Development (2004) 131 (8):1691-1702.
Perrin et al., "The Actin Gene Family: Function follows Isoform", Cytoskeleton, vol. 67, No. 10, 2010, pp. 630-634.
Phuc et al., "Late-acting dominant lethal genetic systems and mosquito control," BMC Biol (2007) 5:11.
PiggyBac Website, http://piggybac.bio.nd.edu/, Mar. 21, 2006.
Pinkerton et al., "Green Fluorescent Protein as a Genetic Marker in Transgenic Aedes Aegypti", Insect Molecular Biology, vol. 9, No. 1, 2000, pp. 1-10.
Prasher et al., "Primary structure of the Aequorea victoria green-fluorescent protein," Gene (1992) 111 (2):229-233.
Qin et al., "Systematic Comparison of Constitutive Promoters and the Doxycycline-inducible Promoter", PLOS One, vol. 5, No. 5, 2010.
Raja et al., "Replacement by *Drosophila melanogaster* Protamines and Mst77F of Histones during Chromatin condensation in Late Spermatids and Role of Sesame in the Removal of These Proteins from the Male Pronucleus", Molecular and Cellular Biology, vol. 25, No. 14, 2005, pp. 6165-6177.
Remy et al., "Zinc-finger Nucleases: A Powerful Tool for Genetic Engineering of Animals", Transgenic Research, vol. 19, 2010, pp. 363-371.
Rendon et al., "Medfly {Diptera: Tephritidae) Genetic Sexing: Large-scale Field Comparison of Males-only and Bisexual Sterile Fly Releases in Guatemala", Journal of Economic Entomology, vol. 97, No. 5, 2004, pp. 1547-1553.
Robinson et al., "Ceratitis Capitata—a Suitable Case for Genetic Sexing", Genetica, vol. 58, No. 3, 1982, pp. 229-237.
Robinson et al., "Genetic Basis of the Sterile Insect Technique", in: Sterile Insect Technique, Principles and Practice in Area-Wide Integrated Pest Management, 2005, pp. 95-114.
Robinson et al., "Prospects for The Future Development and Application of the Sterile Insect Technique", The Netherlands, Springer, 2005, pp. 727-760.
Robinson et al., "Recent Findings on Medfly Sexual Behaviour: Implications for SIT", Florida Entomologist, 85(1), Mar. 2002, pp. 171-181.

(56) References Cited

OTHER PUBLICATIONS

Robinson et al., "Mutations and Their Use in Insect Control", Mutation Research, vol. 511, 2002, pp. 113-132.
Ronaldson et al., "Two independent cis-acting elements regulate the sex-and tissue specific expression of yp3 in *Drosophila melanogaster*", Genet Res., vol. 6, No. 1, 1995, pp. 9-17.
Rong et al., "A Targeted Gene Knockout in *Drosophila*", Genetics, vol. 157, No. 3, 2001, pp. 1307-1312.
Rong et al., "Gene Targeting by Homologous Recombination in *Drosophila*", Science, vol. 288, No. 5473, 2000, pp. 2013-2018.
Rong et al., "Targeted Mutagenesis by Homologous Recombination in D. Melanogaster", Genes & Development, vol. 16, 2002, pp. 1568-1581.
Roper et al., "Contribution of Sequence Variation in *Drosophila* Actins to their Incorporation Into Actin-based Structures in Vivo", Journal of Cell Science, vol. 118, 2005, pp. 3937-3948.
Rossler et al., "The Genetics of the Mediterranean Fruit Fly: A "White Pupae" Mutant", Annals of the Entomological Society of America, vol. 72, 1979, pp. 583-585.
Rubin et al., "Genetic Transformation of *Drosophila* with Transposable Element Vectors", Science, vol. 218, No. 1570, 1982, pp. 348-353.
Russ et al., "Self-Deleting Retrovirus Vectors for Gene Therapy", Journal of Virology, vol. 70, No. 8, 1996, pp. 4927-4932.
Saccone et al., "Sex Determination in Flies, Fruit Flies and Butterllies", Genetica, vol. 116, 2002, pp. 15-23.
Saccone et al., "Sex Determination in Medfly: A Molecular Approach", Area-Wide Control of Fruit Flies and other nsect Pests I IAEA, 2000, pp. 491-496.
Salvemini et al., "Genomic organization and splicing evolution of the double sex gene, a *Drosophila* regulator of sexual differentiation, in the dengue and yellow fever mosquito Aedes aegypti", BMC Evolutionary Biology, vol. 11, No. 1:41, 2011.
Santel et al., The *Drosophila* Don Juan (Di) Gene Encodes a Novel Sperm Specific Protein Component Characterized by an Unusual Domain of a Repetitive Amino Acid Motif, Mechanisms of Development, vol. 64, No. 1-2, 1997, pp. 19-30.
Scali et al., "Identification of Sex-specific Transcripts of the Anopheles Gambiae Doublesex Qene", Journal of Experimental Biology, vol. 208, No. 19, Oct. 2005, pp. 3701-3709.
Schetelig et al., "Strategy for Enhanced Transgenic Strain Development for Embryonic Conditional Lethality in Anastrepha Suspensa", Proceedings of the National Academy of Sciences of the United States of America, vol. 24, J012, pp. 9348-9353.
Schwechheimer et al., "Transactivation of a Target Gene Through Feedforward Loop Activation in Plants", Functional & Integrative Genomics, vol. 1, 2000, pp. 35-43.
Scolari et al., "A transgenic sperm marking system in the medfly, as a tool for pest control strategies and sperm use analysis", Entomological Research, vol. 37, 2007, pp. A56.
Sepp et al., "Conversion of Lacz Enhancer Trap Lines to Gal4 Lines using Targeted Transposition in *Drosophila melanogaster*", Genetics, vol. 151, 1999, pp. 1093-1101.
Shah et al., "Cardiac remodeling in *Drosophila* arises from changes in actin gene expression and from a contribution of lymph gland-like cells to the heart musculature", Mechanisms of Development, vol. 128, No. 3, 2011, pp. 222-233.
Shelton et al., "Field Tests on Managing Resistance to BI-engineered Plants", Nature Biotechnology, vol. 18, 2000, Jp. 339-342.
Shockett et al., "A Modified Tetracycline-Regulated System Provides Autoregulatory, Inducible Gene Expression in Cultured Cells and Transgenic Mice", Proceedings of the National Academy of Sciences of the United States of America, vol. 92, Jul. 1995, pp. 6522-6526.
Simmons et al., "Field Performance of a Genetically Engineered Strain of Pink Bollworm", PLoS ONE, vol. 6 (9), 24110, Sep. 2011, 11 pages.
Smith et al., "Testis-specific Expression of The Beta2 Tubulin Promoter of Aedes Aegypti and It's Armlication as a Aenetic Sex-separation Marker", Insect Molecular Biology, vol. 16, No. 1, 2007, pp. 16-71.
Sondergaard et al., "Nutritional Response in a *Drosophila* Yolk Protein Gene Promoter", Molecular Genetics and 3enomics, vol. 248, No. 1, 1995, pp. 25-32.
Spradling et al., "P Element-mediated Transformation", *Drosophila*: A Practical Approach, Chapter 8, 1986, pp. 175-197.
Spradling et al., "Transposition of Cloned P Elements Into *Drosophila* Germ Line Chromosomes", Science, vol. J18, No. 4570, 1982, pp. 341-347.
Stadtfeld et al., Without A Trace? Piggybac-ing Toward Pluripotency, Nature Methods, vol. 6, No. 5, 2009, pp. 329-330.
Stebbins et al., "Adaptable Doxycycline-Regulated Gene Expression Systems for *Drosophila*", Gene, vol. 270, 2001, pp. 103-111.
Stebbins et al., "Tetracycline-Inducible Systems for *Drosophila*", Proceedings of the National Academy of Sciences of the United States of America, vol. 98, 2001, pp. 10775-10780.
Steiner et al., "Homologous Recombination as the Main Mechanism for DNA Integration and Cause of Rearrangements in the Filamentous Ascomycete Ashbya Gossypii", Genetics, vol. 140, 1995, pp. 973-987.
Theodoraki et al., "cDna Cloning, Heat Shock Regulation and Developmental Expression of the Hsp83 Gene in the Mediterranean Fruit Fly Ceratitis Capitata", Insect Molecular Biology, vol. 15, No. 6, 2006, pp. 839-852.
Thomas et al., "Insect Population Control using a Dominant, Repressible, Lethal Genetic System", Science, vol. 287, No. 5462, 2000, pp. 2474-2476.
Timoshevskiy et al., "An integrated linkage, chromosome, and Genome map for the Yellow Fever Mosquito Aedes egypti", PLOS Neglected Tropical Diseases, vol. 7, No. 2:e2052, 2013.
Timoshevskiy et al., "Genomic composition and evolution of Aedes aegypti chromosomes revealed by the analysis of physically mapped supercontigs", BMC Biology vol. 12, No. 1:27, 2014.
Urnov et al., "Highly Efficient Endogenous Human Gene Correction using Designed Zinc—finger Nucleases", Nature, vol. 435, 2005, pp. 646-651.
Van Eynde et al., "Molecular cloning of NIPP-1, a nuclear inhibitor of protein phosphatase-1, reveals homology with polypeptides involved in RNA processing," J Biol Chem (1995) 270(47}:28068-28074.
Van Eynde et al., "Organization and alternate splice products of the gene encoding nuclear inhibitor of protein phosphatase-1 (IPP-1)," Eur J Biochem (1999) 261(1):291-300.
Viktorinova et al., "Comparative Analysis of Binary Expression Systems for Directed Gene Expression in Transgenic Insects", Insect Biochemistry and Molecular Biology, vol. 37, 2007, pp. 246-254.
Vivinus et al., "An element within the 5' untranslated region of human Hsp70 mRNA which acts as a general enhancer of mRNA translation," European Journal of Biochemistry, vol. 268, 2001, pp. 1908-1917.
Vreysen et al., "Engineering Insects for the Sterile Insect Technique", Dordrecht, The Netherlands, Springer, 2007, pp. 51-60.
Vulsteke et al., "Properties And Phosphorylation Sites Of Baculovirus-expressed Nuclear Inhibitor Of Protein Dhosphatase-1 (Nipp-1 }", Journal of Biological Chemistry, vol. 272, No. 52, 1997, pp. 32972-32978.
Webster et al., (1988). "The yeast UASG is a transcriptional enhancer in human hela cells in the presence of the GAL4 trans-activator," Cell, 52:169-178.
Weinmann et al., "A Chimeric Transactivator Allows Tetracycline-responsive Gene Expression In Whole Plants", The Diani Journal, vol. 5, No. 4, 1994, pp. 559-569.
Wera et al., "Inhibition Of Translation By Mrna Encoding Nipp-1, A Nuclear Inhibitor Of Protein Phosphatase-1", European Journal of Biochemistry, vol. 247, No. 1, 1997, pp. 411-415.
Wharton et al., "CNS Midline Enhancers Of The *Drosophila* Slit And Toll Genes", Mechanisms of Development, vol. 10, No. 3, 1993, pp. 141-154.

(56) References Cited

OTHER PUBLICATIONS

White-Cooper et al., "Transcription Of Meiotic Cell Cycle And Terminal Differentiation Genes Depends On A conserved Chromatin Associated Protein, Whose Nuclear Localisation Is Regulated", Development, vol. 127, 2000, p. 5463-5473.
Wilson et al., "Position Effects On Eukaryotic Gene Expression", Annual Review of Cell and Developmental Biology, vol. 6, 1990, pp. 679-714.
Wilson et al., "Sperm Plasma Membrane Breakdown During *Drosophila* Fertilization Requires Sneakv, An Acrosoma Membrane Protein", Development, vol. 133, No. 24, 2006, pp. 4871-4879.
Wimmer et al., "Eco-friendly Insect Management", Nature Biotechnology, vol. 23, No. 4, 2005, pp. 432-433.
Windbichler et al., "A Synthetic Homing Endonuclease-based Gene Drive System In The Human Malaria Mosquito", Nature, vol. 473, No. 7346, 2011, pp. 212-215.
Windbichler et al., "Homing Endonuclease Mediated Gene Targeting in Anopheles Gambiae Cells and Embryos", Nucleic Acids Research, vol. 35, 2007, pp. 5922-5933.
Windbichler et al., "Targeting The X Chromosome During Spermatogenesis Induces Y Chromosome Transmission Ratio Distortion And Early Dominant Embryo Lethality In Anopheles Qambiae", PLOS Genetics, vol. 4, No. 12, 2008.
Wing et al., "Distinct Cell Killing Properties of the *Drosophila* reaper, Head Involution Defective, and Grim Genes", Cell Death and Differentiation, 1998, pp. 930-939.
Wise De Valdez et al., "Genetic elimination of dengue vector mosquitoes," Proc Natl Acad Sci USA (2011} 108(12):4772-4775.
Wobus et al., "A New Transposable Element in Chironomus thummi", Molecular Genetics and Genomics, vol. 222, 1990, pp. 311-316.
Woltjen et al., "Piggybac Transposition Reprograms Fibroblasts to Induced Pluripotent Stem Cells", Nature, vol. 158, No. 7239, 2009, 766-770.
Wool et al., "Genetically-Induced Susceptibility to Malathion in Tribolium Castaneum Despite Selection for Resistance", Entomologia Experimentalis et Applicata, 1980, pp. 183-190.
Wu et al., "Expression of Highly Controllable Genes in Insect Cells using a Modified Tetracycline-regulated Gene Expression System", Journal of Biotechnology, vol. 80, Issue 1, Jun. 2000, pp. 75-83.
Zhao et al., "Male Germ Cell Specification and Differentiation", Developmental Cell, vol. 2, No. 5, May 2002, pp. 37-547.
Zimowska et al., "The Beta2-tubulin Gene from three Tephritid Fruit Fly Species and Use of Its Promoter for Sperm Marking", Insect Biochemistry and Molecular Biology, vol. 39, No. 8, 2009, pp. 508-515.
Advisory Action for U.S. Appl. No. 11/733,737, mailed Jun. 3, 2013, 7 pages.
Advisory Action for U.S. Appl. No. 11/733,737, mailed Aug. 5, 2009, 4 pages.
Amendment for U.S. Appl. No. 10/562,843, filed Feb. 24, 2009, 13 pages.
Amendment for U.S. Appl. No. 10/562,843, filed Nov. 30, 2010, 7 pages.
Amendment for U.S. Appl. No. 10/562,843, filed Oct. 5, 2009, 10 pages.
Amendment for U.S. Appl. No. 10/566,448, filed Oct. 27, 2010, 20 pages.
Amendment for U.S. Appl. No. 10/566,448, filed Jul. 7, 2009, 15 pages.
Amendment for U.S. Appl. No. 11/352,177, filed Dec. 10, 2009, 20 pages.
Amendment for U.S. Appl. No. 11/352,177, filed Oct. 14, 2010, 13 pages.
Appeal Brief for U.S. Appl. No. 11/733,737, filed Feb. 3, 2014, 40 pages.
Appeal Brief for U.S. Appl. No. 12/278,849, filed Oct. 16, 2014, 31 pages.
Communication pursuant to Article 94(3) EPC for EP 07712717.3, mailed Jul. 11, 2014, 8 pages.
Communication pursuant to Article 94(3) EPC for EP 07712717.3, mailed Nov. 6, 2015, 4 pages.
Communication pursuant to Article 96(2) EPC for EP 00979774.7, mailed Aug. 2, 2005, 4 pages.
Communication pursuant to Article 96(2) EPC for EP 00979774.7, mailed Nov. 28, 2003, 5 pages.
Communication pursuant to Article 96(2) EPC for EP 00979774.7, mailed Oct. 4, 2004, 4 pages.
Communication pursuant to Article 96(2) EPC for EP 00979774.7, mailed Mar. 8, 2006, 4 pages.
Communication under Rule 51 (4) EPC, directed to EP 00979774.7, mailed May 9, 2007, 4 pages.
Communication under Rule 71 (3) EPC for EP 07712717.3, issued Jun. 20, 2016, 7 pages.
Decision on Further Processing for EP 00979774.7, mailed Jan. 29, 2007, 1 page.
EP First Office Action, dated Feb. 16, 2012, in European Patent Application No. 04743590.4, a corresponding application, 8 pages.
Examination Report for EP 04743590.4, mailed Nov. 14, 2008, 4 pages.
Examination Report for NZ 519175, mailed Nov. 28, 2003, 1 page.
Examination Report for NZ 519175, mailed Jul. 9, 2002, 2 pages.
Examiner's Answer to Appeal Brief for U.S. Appl. No. 11/733,737, mailed Jul. 18, 2014, 12 pages.
Final Office Action for U.S. Appl. No. 10/148,041, mailed Mar. 7, 2006, 9 pages.
Final Office Action for U.S. Appl. No. 10/562,843, filed Aug. 25, 2011, 5 pages.
Final Office Action for U.S. Appl. No. 10/562,843, mailed Feb. 3, 2010, 5 pages.
Final Office Action for U.S. Appl. No. 10/566,448, mailed Nov. 10, 2009, 18 pages.
Final Office Action for U.S. Appl. No. 10/566,448, mailed Aug. 14, 2014, 24 pages.
Final Office Action for U.S. Appl. No. 10/566,448, mailed Feb. 2, 2011, 13 pages.
Final Office Action for U.S. Appl. No. 11/352,177, mailed Oct. 14, 2014, 6 pages.
Final Office Action for U.S. Appl. No. 11/352,177, mailed Mar. 16, 2011, 18 pages.
Final Office Action for U.S. Appl. No. 11/733,737, mailed Apr. 17, 2009, 16 pages.
Final Office Action for U.S. Appl. No. 11/733,737, mailed Aug. 4, 2010, 18 pages.
Final Office Action for U.S. Appl. No. 11/733,737, mailed Jan. 7, 2013, 26 pages.
Final Office Action for U.S. Appl. No. 12/278,849, dated Jun. 6, 2013, 24 pages.
Final Office Action for U.S. Appl. No. 12/278,849, mailed Mar. 17, 2014, 24 pages.
Final Office Action for U.S. Appl. No. 12/278,849, mailed Oct. 9, 2015, 7 pages.
Final Office Action for U.S. Appl. No. 13/942,601, mailed Jul. 31, 2014, 23 pages.
Formal Report (translation) for BR PI0707579-0, issued Jun. 21, 2016, 2 pages.
Formal Report (translation} for BR PI0413024-3, issued Jun. 7, 2016, 10 pages.
Further International Search Report GB 9928181.8; Apr. 30, 2001, 2 pages.
International Preliminary Examination Report for PCT/GB00/04541, mailed Apr. 4, 2002, 2 pages.
International Preliminary Report on Patentability for PCT/EP2014/054290, issued Sep. 8, 2015, 7 pages.
International Preliminary Report on Patentability for PCT/GB2004/002021, issued Nov. 18, 2005, 6 pages.
International Preliminary Report on Patentability for PCT/GB2004/002869, issued Jan. 3, 2006, 9 pages.
International Preliminary Report on Patentability for PCT/GB2004/003263, issued Jan. 30, 2006, 6 pages.
International Preliminary Report on Patentability for PCT/GB2007/000488, dale of search May 5, 2008, 11 pages.

(56) References Cited

OTHER PUBLICATIONS

International Search Report and Written Opinion for PCT/EP2013/054417, dated Jul. 12, 2013, 14 pages.
International Search Report and Written Opinion for PCT/EP2014/054290, mailed Jun. 18, 2014, 11 pages.
International Search Report and Written Opinion received for PCT Patent Application No. PCT/GB2015/051633, mailed on Oct. 16, 2015, 11 pages.
International Search Report and Written Opinion received for PCT Patent Application No. PCT/IB2017/001128, mailed on Dec. 13, 2017, 17 pages.
International Search Report for PCT/GB2000/04541, dated Nov. 19, 2001.
International Search Report for PCT/GB2004/002021, mailed Oct. 6, 2004, 3 pages.
International Search Report for PCT/GB2004/002869, mailed Jan. 11, 2005, 5 pages.
International Search Report for PCT/GB2004/003263, mailed Nov. 5, 2004, 3 pages.
International Search Report for PCT/GB2007/000488, mailed Jun. 6, 2007, 3 pages.
Notice of Allowance for U.S. Appl. No. 10/566,448, mailed Jul. 13, 2015, 10 pages.
Notice of Allowance for U.S. Appl. No. 10/566,448, mailed Mar. 19, 2015, 10 pages.
Notice of Allowance for U.S. Appl. No. 11/352,177, mailed Mar. 17, 2015, 10 pages.
Notice of Allowance for U.S. Appl. No. 11/352,177, mailed Jul. 7, 2015, 9 pages.
Notice of Allowance for U.S. Appl. No. 13/942,601, mailed Apr. 10, 2015, 11 pages.
Notice of Allowance for U.S. Appl. No. 13/942,601, mailed Jul. 7, 2015, 9 pages.
Notice of Appeal for U.S. Appl. No. 10/566,448, filed Feb. 18, 2015, 4 pages.
Notice of Appeal for U.S. Appl. No. 11/733,737, filed Jul. 3, 2013, 1 page.
Notice of Appeal for U.S. Appl. No. 12/278,849, filed Jun. 17, 2014, 1 page.
Notice of Appeal for U.S. Appl. No. 13/942,601, filed Feb. 2, 2015, 1 page.
Noting of loss of rights (R. 69(1) EPC) for EP 00979774.7, mailed Jul. 17, 2004, 1 page.
Office Action for AU 17165/01, mailed Jul. 13, 2004, 3 pages.
Office Action for CN 00818682.0, fax dated Feb. 4, 2005, 7 pages.
Office Action for IL 149885, dated Apr. 26, 2007, 4 pages.
Office Action for U.S. Appl. No. 10/148,041, mailed Jul. 1, 2005, 14 pages.
Office Action for U.S. Appl. No. 10/148,041, mailed Oct. 10, 2006, 8 pages.
Office Action for U.S. Appl. No. 10/556,804, mailed Feb. 1, 2011, 4 pages.
Office Action for U.S. Appl. No. 10/556,804, mailed May 12, 2010, 8 pages.
Office Action for U.S. Appl. No. 10/562,843, mailed Nov. 12, 2008, 6 pages.
Office Action for U.S. Appl. No. 10/562,843, mailed Feb. 16, 2011, 4 pages.
Office Action for U.S. Appl. No. 10/562,843, mailed Jul. 30, 2010, 7 pages.
Office Action for U.S. Appl. No. 10/562,843, mailed Jun. 9, 2009, 5 pages.
Office Action for U.S. Appl. No. 10/566,448, mailed Nov. 22, 2013, 24 pages.
Office Action for U.S. Appl. No. 10/566,448, mailed Apr. 27, 2010, 12 pages.
Office Action for U.S. Appl. No. 10/566,448, mailed Jan. 7, 2009, 14 pages.
Office Action for U.S. Appl. No. 11/352,177, dated Jan. 30, 2014, 17 pages.
Office Action for U.S. Appl. No. 11/352,177, mailed Jun. 10, 2009, 14 pages.
Office Action for U.S. Appl. No. 11/352,177, mailed Apr. 14, 2010, 15 pages.
Office Action for U.S. Appl. No. 11/733,737, mailed Oct. 1, 2009, 21 pages.
Office Action for U.S. Appl. No. 11/733,737, mailed Apr. 10, 2008, 8 pages.
Office Action for U.S. Appl. No. 11/733,737, mailed Mar. 27, 2012, 17 pages.
Office Action for U.S. Appl. No. 11/733,737, mailed Jun. 28, 2011, 14 pages.
Office Action for U.S. Appl. No. 11/733,737, mailed Feb. 8, 2011, 6 pages.
Office Action for U.S. Appl. No. 12/278,849, dated Aug. 9, 2013, 22 pages.
Office Action for U.S. Appl. No. 12/278,849, dated Oct. 10, 2012, 12 pages.
Office Action for U.S. Appl. No. 12/278,849, mailed Mar. 10, 2015, 18 pages.
Office Action for U.S. Appl. No. 12/278,849, mailed Dec. 5, 2014, 15 pages.
Office Action for U.S. Appl. No. 13/942,601, mailed Nov. 4, 2013, 17 pages.
Prosecution history for related application U.S. Appl. No. 10/148,041, 64 pages.
Prosecution history for related application U.S. Appl. No. 10/556,804, 27 pages.
Prosecution history for related application U.S. Appl. No. 10/562,843, 63 pages.
Prosecution history for related application U.S. Appl. No. 10/566,448, 142 pages.
Prosecution history for related application U.S. Appl. No. 11/352,177, 129 pages.
Prosecution history for related application U.S. Appl. No. 11/733,737, 175 pages.
Prosecution history for related application U.S. Appl. No. 12/278,849, 20 pages.
Rejection for CN 00818682.0, fax dated Jan. 26, 2006, 4 pages.
Reply Brief and Request for Oral Hearing for U.S. Appl. No. 11/733,737, filed Sep. 18, 2014, 16 pages.
Request for Continued Examination for U.S. Appl. No. 10/148,041, filed Sep. 11, 2006, 8 pages.
Request for Continued Examination for U.S. Appl. No. 10/566,448, filed Jun. 18, 2015, 3 pages.
Request for Continued Examination for U.S. Appl. No. 10/566,448, filed Aug. 2, 2011, 23 pages.
Request for Continued Examination for U.S. Appl. No. 10/566,448, filed Feb. 25, 2010, 18 pages.
Request for Continued Examination for U.S. Appl. No. 11/352,177, filed Sep. 16, 2011, 3 pages.
Request for Continued Examination for U.S. Appl. No. 11/352,177, filed Jun. 17, 2015, 3 pages.
Request for Continued Examination for U.S. Appl. No. 11/733,737, filed Aug. 14, 2009, 1 page.
Request for Continued Examination for U.S. Appl. No. 13/942,601, filed Jun. 19, 2015, 3 pages.
Request for Further Processing for EP 00979774.7, filed Jan. 4, 2007, 4 pages.
Response for U.S. Appl. No. 10/562,843, filed Feb. 24, 2009, 13 pages.
Response for U.S. Appl. No. 10/562,843, filed Nov. 30, 2010, 8 pages.
Response for U.S. Appl. No. 10/562,843, filed Oct. 5, 2009, 10 pages.
Response for U.S. Appl. No. 11/352,177, filed Dec. 10, 2009, 20 pages.
Response for U.S. Appl. No. 11/352,177, filed Oct. 14, 2010, 13 pages.
Response to Communication for EP 00979774.7, filed Apr. 14, 2005, 7 pages.
Response to Communication for EP 00979774.7, filed Sep. 20, 2004, 8 pages.

(56) References Cited

OTHER PUBLICATIONS

Response to Communication pursuant to Article 94(3) EPC, for EP 07712717.3 filed Mar. 16, 2016, 5 pages.
Response to Communication pursuant to Article 96(2) EPC for EP 00979774.7, filed Feb. 13, 2006, 8 pages.
Response to Final Office Action for U.S. Appl. No. 10/562,843, filed Nov. 21, 2011, 6 pages.
Response to Final Office Action for U.S. Appl. No. 10/566,448, filed Dec. 15, 2014, 9 pages.
Response to Final Office Action for U.S. Appl. No. 11/352,177, filed Sep. 16, 2011, 15 pages.
Response to Final Office Action for U.S. Appl. No. 11/352,177, filed Dec. 3, 2014, 8 pages.
Response to Final Office Action for U.S. Appl. No. 11/733,737, filed Jul. 17, 2009, 26 pages.
Response to Final Office Action for U.S. Appl. No. 11/733,737, filed Dec. 6, 2010, 26 pages.
Response to Final Office Action for U.S. Appl. No. 11/733,737, filed Apr. 8, 2013, 25 pages.
Response to Office Action for U.S. Appl. No. 10/148,041, filed Dec. 5, 2005, 11 pages.
Response to Office Action for U.S. Appl. No. 10/556,804, filed Nov. 12, 2010, 12 pages.
Response to Office Action for U.S. Appl. No. 10/556,804, filed Mar. 25, 2011, 9 pages.
Response to Office Action for U.S. Appl. No. 10/562,843, filed Jun. 16, 2011, 9 pages.
Response to Office Action for U.S. Appl. No. 10/566,448, filed Apr. 22, 2014, 17 pages.
Response to Office Action for U.S. Appl. No. 10/566,448, filed Oct. 27, 2010, 20 pages.
Response to Office Action for U.S. Appl. No. 10/566,448, filed Aug. 28, 2009, 15 pages.
Response to Office Action for U.S. Appl. No. 10/566,448, filed Jul. 7, 2009, 15 pages.
Response to Office Action for U.S. Appl. No. 11/352,177, dated May 28, 2014, 14 pages.
Response to Office Action for U.S. Appl. No. 11/733,737, filed Oct. 10, 2008, 8 pages.
Response to Office Action for U.S. Appl. No. 11/733,737, filed Feb. 18, 2011, 11 pages.
Response to Office Action for U.S. Appl. No. 11/733,737, filed Oct. 28, 2011, 27 pages.
Response to Office Action for U.S. Appl. No. 11/733,737, filed Jan. 29, 2010, 23 pages.
Response to Office Action for U.S. Appl. No. 11/733,737, filed Aug. 9, 2012, 24 pages.
Response to Office Action for U.S. Appl. No. 12/278,849, dated Apr. 10, 2013, 19 pages.
Response to Office Action for U.S. Appl. No. 12/278,849, dated Jan. 9, 2014, 21 pages.
Response to Office Action for U.S. Appl. No. 12/278,849, filed Aug. 7, 2015, 24 pages.
Response to Office Action for U.S. Appl. No. 13/942,601, dated Feb. 4, 2014, 45 pages.
Response to Restriction Requirement for U.S. Appl. No. 10/148,041, filed Apr. 13, 2005, 10 pages.
Response to Restriction Requirement for U.S. Appl. No. 10/556,804, filed Jun. 29, 2009, 2 pages.
Response to Restriction Requirement for U.S. Appl. No. 10/562,843, filed Jun. 27, 2008, 2 pages.
Response to Restriction Requirement for U.S. Appl. No. 10/566,448, filed Dec. 1, 2008, 9 pages.
Response to Restriction Requirement for U.S. Appl. No. 10/566,448, filed Feb. 8, 2008, 9 pages.
Response to Restriction Requirement for U.S. Appl. No. 11/352,177, filed Mar. 13, 2009, 12 pages.
Response to Restriction Requirement for U.S. Appl. No. 11/352,177, filed Nov. 3, 2008, 8 pages.
Response to Restriction Requirement for U.S. Appl. No. 11/352,177, filed Jun. 9, 2008, 9 pages.
Response to Restriction Requirement for U.S. Appl. No. 11/733,737, filed Jan. 26, 2009, 8 pages.
Response to Restriction Requirement for U.S. Appl. No. 12/278,849, filed Sep. 28, 2010, 13 pages.
Restriction Requirement for U.S. Appl. No. 10/148,041, mailed Mar. 10, 2005, 5 pages.
Restriction Requirement for U.S. Appl. No. 10/556,804, mailed May 28, 2009, 5 pages.
Restriction Requirement for U.S. Appl. No. 10/562,843, mailed Jun. 12, 2008, 6 pages.
Restriction Requirement for U.S. Appl. No. 10/566,448, mailed Aug. 29, 2008, 7 pages.
Restriction Requirement for U.S. Appl. No. 10/566,448, mailed Jan. 9, 2008, 5 pages.
Restriction Requirement for U.S. Appl. No. 11/352,177, mailed Jan. 13, 2009, 10 pages.
Restriction Requirement for U.S. Appl. No. 11/352,177, mailed Sep. 2, 2008, 5 pages.
Restriction Requirement for U.S. Appl. No. 11/352,177, mailed Mar. 31, 2008, 8 pages.
Restriction Requirement for U.S. Appl. No. 11/733,737, mailed Dec. 31, 2008, 9 pages.
Restriction Requirement for U.S. Appl. No. 12/278,849, mailed May 28, 2010, 7 pages.
Search Report for GB 0317656.7, date of search Nov. 25, 2003, 1 page.
Search Report for GB 0621234.4, dated of search Feb. 21, 2007, 1 page.
Second Office Action for AU 17165/01, mailed Mar. 21, 2006, 2 pages.
Second Office Action for CN 00818682.0, dated Jul. 28, 2006, 4 pages.
Summary of Office Action for MX PA/a/2002/005337, mailed Jan. 3, 2007, 2 pages.
Supplemental Amendment for U.S. Appl. No. 11/352,177, filed Oct. 21, 2010, 15 pages.
Supplemental Response for U.S. Appl. No. 11/352,177, filed Dec. 6, 2010, 4 pages.
Written Opinion received from International Preliminary Examining Authority for PCT Patent Application No. PCT/GB2004/002869, mailed on Jan. 12, 2005, 8 pages.
Written Opinion received from International Preliminary Examining Authority for PCT Patent Application No. PCT/GB2004/003263, mailed on Nov. 5, 2004, 5 pages.
Written Opinion received from International Preliminary Examining Authority for PCT Patent Application No. PCT/GB2007/000488, mailed on Jun. 6, 2007, 8 pages.
Written Opinion received from International Preliminary Examining Authority for PCT Patent Application No. PCT/GB2004/002021, mailed on Oct. 4, 2004, 5 pages.

Early larva

Final instar larvae

Pupa

Adult moths

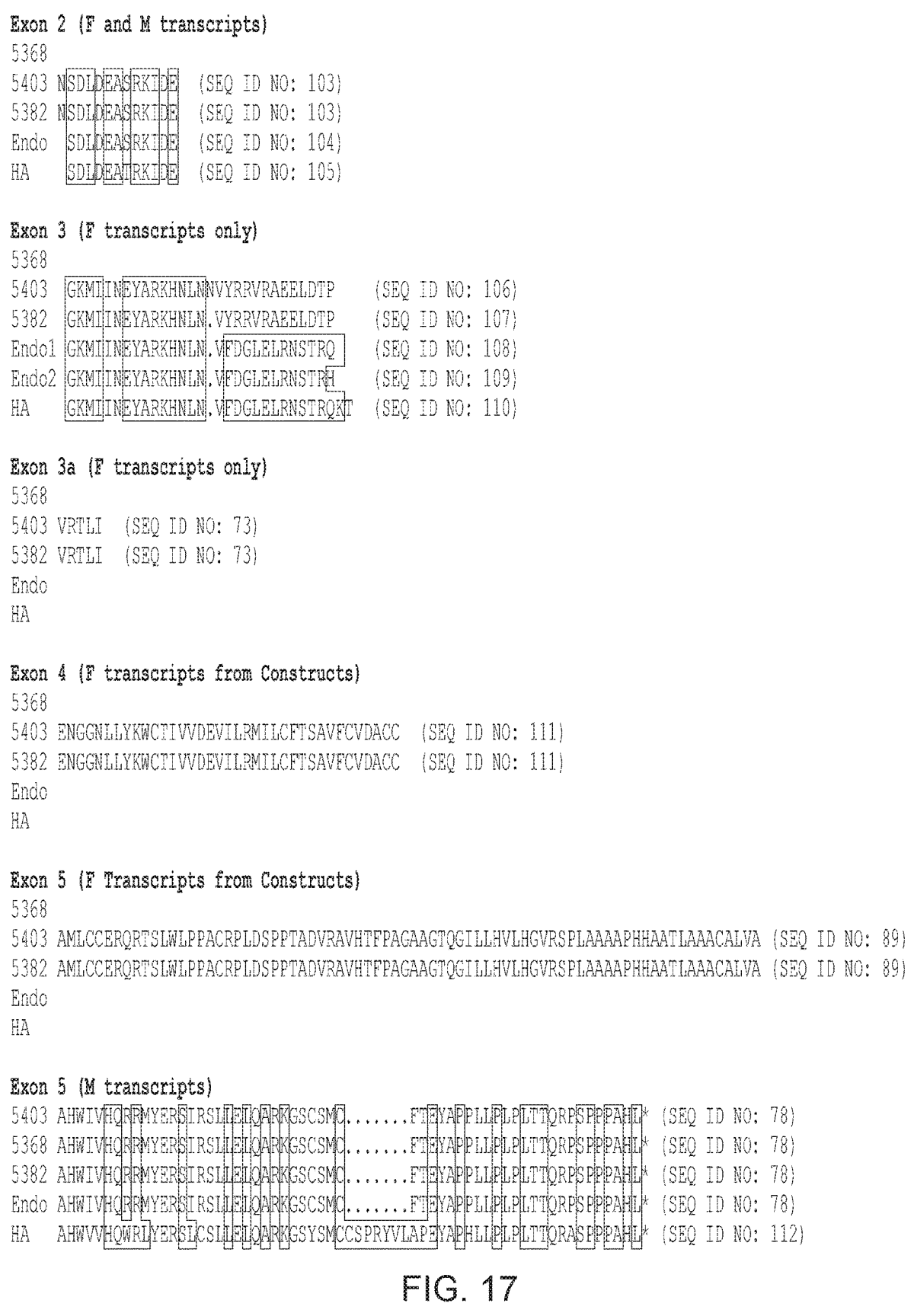

Exon 2 (F and M transcripts)

```
5368
5403 NSDLDEASRKIDE  (SEQ ID NO: 103)
5382 NSDLDEASRKIDE  (SEQ ID NO: 103)
Endo  SDLDEASRKIDE  (SEQ ID NO: 104)
HA    SDLDEATRKIDE  (SEQ ID NO: 105)
```

Exon 3 (F transcripts only)

```
5368
5403  GKMIINEYARKHNLNNVYRRVRAEELDTP    (SEQ ID NO: 106)
5382  GKMIINEYARKHNLN.VYRRVRAEELDTP    (SEQ ID NO: 107)
Endo1 GKMIINEYARKHNLN.VFDGLELRNSTRQ    (SEQ ID NO: 108)
Endo2 GKMIINEYARKHNLN.VFDGLELRNSTRH    (SEQ ID NO: 109)
HA    GKMIINEYARKHNLN.VFDGLELRNSTRQKT  (SEQ ID NO: 110)
```

Exon 3a (F transcripts only)

```
5368
5403 VRTLI  (SEQ ID NO: 73)
5382 VRTLI  (SEQ ID NO: 73)
Endo
HA
```

Exon 4 (F transcripts from Constructs)

```
5368
5403 ENGGNLLYKWCTIVVDEVILRMILCFTSAVFCVDACC  (SEQ ID NO: 111)
5382 ENGGNLLYKWCTIVVDEVILRMILCFTSAVFCVDACC  (SEQ ID NO: 111)
Endo
HA
```

Exon 5 (F Transcripts from Constructs)

```
5368
5403 AMLCCERQRTSLWLPPACRPLDSPPTADVRAVHTFPAGAAGTQGILLHVLHGVRSPLAAAAPHHAATLAAACALVA (SEQ ID NO: 89)
5382 AMLCCERQRTSLWLPPACRPLDSPPTADVRAVHTFPAGAAGTQGILLHVLHGVRSPLAAAAPHHAATLAAACALVA (SEQ ID NO: 89)
Endo
HA
```

Exon 5 (M transcripts)

```
5403 AHWIVHQRRMYERSIRSLLELQARKGSCSMC.......FTEYAPPLLPLPLTTQRPSPPPAHL* (SEQ ID NO: 78)
5368 AHWIVHQRRMYERSIRSLLELQARKGSCSMC.......FTEYAPPLLPLPLTTQRPSPPPAHL* (SEQ ID NO: 78)
5382 AHWIVHQRRMYERSIRSLLELQARKGSCSMC.......FTEYAPPLLPLPLTTQRPSPPPAHL* (SEQ ID NO: 78)
Endo AHWIVHQRRMYERSIRSLLELQARKGSCSMC.......FTEYAPPLLPLPLTTQRPSPPPAHL* (SEQ ID NO: 78)
HA   AHWVVHQWRLYERSLCSLLELQARKGSYSMCCSPRYVLAPEYAPHLLPLPLTTQRASPPPAHL* (SEQ ID NO: 112)
```

FIG. 17

SELF-LIMITING NOCTUIDS

CROSS-REFERENCE TO RELATED APPLICATIONS

This Application is a National Stage Application of PCT Application No. PCT/GB2019/050897, filed Mar. 28, 2019, which claims the benefit of U.S. Provisional Application No. 62/649,912, filed Mar. 29, 2018. The disclosures of which are hereby incorporated by reference in their entirety."

REFERENCE TO SEQUENCE LISTING

This application incorporates by reference a "Sequence Listing" (identified below) which is submitted concurrently herewith in text file. The text file copy of the Sequence Listing submitted herewith is labeled "Sequence Listing", and is a file of 131,925 bytes in size, and was created on Mar. 27, 2019; this Sequence Listing is incorporated by reference in its entirety herein.

BACKGROUND OF THE INVENTION

Noctuids, or Noctuidae, are known by several common names, including cutworms, army worms and owlet moths. Noctuidae encompasses over 1,000 genera and more than 11,000 species. Among the Noctuidae are some genera and species that are responsible for a considerable amount of crop damage every year, leading to billions of dollars in losses. Several genera, including *Spodoptera, Hehcoverpa, Chrysodeixis, Anticarsia, Peridroma* and *Heliothis*, are the main insects responsible for worldwide crop loss. Important species include, for example, *Spodoptera frugiperda* (fall armyworm), *Spodoptera exigua* (beet armyworm), *Spodoptera littoralis* (African cotton leafworm), *Hehcoverpa armigera* (cotton bollworm; corn earworm; Old World bollworm; African bollworm), *Peridroma saucia* (variegated cutworm), *Hehcoverpa zea* (corn earworm; other common names include cotton bollworm and tomato fruitworm), *Chrysodeixis includens* (soybean looper), *Anticarsia gemmatalis* (velvetbean caterpillar), and *Heliothis virescens* (tobacco budworm).

*Spodoptera frugiperda*, for example, affects a wide range of crops including corn, rice, cotton, sugar cane, and sorghum. Females lay about 2,000 eggs in clusters of about 1,000 each. Larvae that hatch from these eggs eat the crops. Several generations of armyworms may occur each year.

Attempts to control Noctuidae have largely been through the use of pesticides. However, the insects have developed resistance to pesticides such as pyrethroids, carbamates and organophosphates. Other attempts to control the insects have included the use of transgenic crop plants, such as those that express insecticidal proteins (e.g., Cry1Fa) from microorganisms such as *Bacillus thuringiensis* (Bt Crops). However, the insects have also developed resistance to Bt crops.

There is a great need in the art to develop a solution for suppressing populations of Noctuidae in a manner that differs from existing modes of action, to reduce reliance on current practices and thereby mitigate resistance, and to potentially reverse the trend of insecticide resistance in insects.

The Sterile Insect Technique (SIT) in which insects are sterilized by irradiation and released to mate with wild insects of the same species has been effective in suppressing populations of insects (Sterile Insect Technique, Dyck, V. A. J. Hendrichs, J. Robinson, Eds; Springer Netherlands, 2005). A biological alternative to this SIT approach uses a self-limiting gene in which insects are genetically engineered to contain a repressible gene, that, when expressed, leads to the death of the insect. In the self-limiting gene approach, male insects carrying the self-limiting gene are released among wild insects of the same species and the offspring inherit the self-limiting gene and do not survive to adulthood.

A recent development in the self-limiting approach takes advantage of sex-specific expression of genes and has allowed engineering of insect species in which only the female insects express the self-limiting gene (WO 2007/091099). When male self-limiting insects are released among wild populations, all offspring inherit the self-limiting gene, but due to sex-specific expression, only the female insects do not survive to adulthood. This development allows for mass rearing of self-limiting male insects for release. In many cases, mass rearing and physical separation of the sexes would be impractical or at the very least quite labor-intensive.

The insect gene doublesex (dsx) has been used in Dipteran species to create sex-specific splicing (WO 2018/029534) as well as Lepidopteran species (Jin, L. et al. (2013) *ACS Synth. Biol.* 2(3):160-166; Tan, A. et al. (2013) *Proc. Natl. Acad. Sci. USA* 110(17):6766-6770). While there is some conservation between dipteran dsx and lepidopteran dsx, it appears that sex-specific splicing mechanisms in lepidopterans is different from other insects. Diptera, Coleoptera and Hymenoptera all regulate dsx pre-mRNA splicing by the TRA/TRA2 complex, whereas Lepidoptera appear to lack a TRA homolog and use different genes for sex determination with respect to dsx (Nagaraju, J. et al. (2014) *Sex. Devel.* 8(1-3):104-12). Lepidoptera produce male and female DSX protein isoforms which share a common N-terminal region but differ in the C-terminal portions of the protein, which are required for the different sex-specific functions of both the male and female DSX protein isoforms (Suzuki, M.G. et al. (2005) *Evol. Dev.* 7(1):58-68; Shukla, J. N. and J. Nagaraju (2010) *Insect Niochem. Mol. Biol.* 40(9):672-682; Xu, J. et al. (2017) *Insect Biochem. Mol. Biol.* 80:42-51).

There is a need in the art to develop self-limiting Noctuids to suppress populations of these insects which severely damage crops and reduce the world's food supply.

BRIEF SUMMARY OF THE INVENTION

The invention provides a splicing cassette for directing sex-specific splicing of a heterologous polynucleotide encoding a functional protein in an arthropod (wherein the coding sequence of the functional protein is defined between a start codon and a stop codon). The cassette comprises at least one Exon 2, or portion thereof, of a Noctuidae doublesex (dsx) gene; at least one Exon 3, or portion thereof, of a Noctuidae dsx gene; at least one Exon 5, or portion thereof, of a Noctuidae dsx gene; at least one Intron 2, or portion thereof, of a Noctuidae dsx gene; and at least one Intron 4, or portion thereof, of a Noctuidae dsx gene; wherein (a) a first splicing of an RNA transcript of said heterologous polynucleotide to produce a first spliced mRNA product, which does not have a continuous open reading frame extending from the start codon to the stop codon; and (b) an alternative splicing of said RNA transcript to yield an alternatively spliced mRNA product which comprises a continuous open reading frame extending from the start codon to the stop codon.

In some embodiments, the splicing cassette comprises at least one Exon 2, or portion thereof, of a Noctuidae doublesex (dsx) gene; at least one Exon 3, or portion thereof, of a Noctuidae dsx gene; at least one Exon 4, or portion thereof, of a Noctuidae dsx gene; at least one Exon 5, or portion thereof, of a Noctuidae dsx gene; at least one Intron 2, or portion thereof, of a Noctuidae dsx gene; at least one Intron 3, or portion thereof, of a Noctuidae dsx gene; and at least one Intron 4, or portion thereof, of a Noctuidae dsx gene; wherein (a) a first splicing of an RNA transcript of said heterologous polynucleotide to produce a first spliced mRNA product, which does not have a continuous open reading frame extending from the start codon to the stop codon; and (b) an alternative splicing of said RNA transcript to yield an alternatively spliced mRNA product which comprises a continuous open reading frame extending from the start codon to the stop codon.

In some embodiments, the cassette optionally includes at least one Exon 3a, or portion thereof, of a Noctuidae dsx gene and/or at least one Exon 4b, or portion thereof, of a Noctuidae dsx gene.

In some embodiments, the polynucleotide encoding the functional protein is located 3' of Exon 2, and Exon 3. In other embodiments, the polynucleotide encoding the functional protein is located 3' of Exon 2, Exon 3, and Exon 5. In other embodiments, the polynucleotide encoding the functional protein is located 3' of Exon 2, Exon 3, Exon 3a, Exon 4, Exon 4b, and Exon 5.

In some embodiments, the primary transcript from the splicing cassette is spliced in males such that translation terminates 5' of the polynucleotide encoding said functional protein and the functional protein is not translated. In other embodiments, the primary transcript from the splicing cassette is spliced in males such that the polynucleotide encoding the functional protein is spliced out of the primary transcript.

In some embodiments, Exon 2 of the splicing cassette comprises a polynucleotide that encodes an amino acid sequence that is 80%, 85%, 90%, 95%, 98% or 100% identical to the sequence of SEQ ID NO:71. In some embodiments, Exon 2 has a polynucleotide sequence that encodes an amino acid sequence of SEQ ID NO:71. In other embodiments, Exon 2 has a polynucleotide sequence of SEQ ID NO:7, SEQ ID NO:32, or SEQ ID NO:54.

In some embodiments, Exon 3 of the splicing cassette comprises a polynucleotide that encodes an amino acid sequence that is 80%, 85%, 90%, 95%, 98% or 100% identical to a sequence encoding the amino acid sequence of SEQ ID NO:72. In some embodiments, Exon 3 has a polynucleotide sequence that encodes an amino acid sequence of SEQ ID NO:72. In some embodiments, Exon 3 has a core polynucleotide sequence of SEQ ID NO:93, SEQ ID NO:56, or may be split into two portions (SEQ ID NO:94 and SEQ ID NO:9 and a polynucleotide encoding a protein that is lethal, detrimental or sterilizing (e.g., tTAV or an analog thereof) is inserted between the two portions by linkers. Examples of useful linkers include those shown as SEQ ID NO: 95 and SEQ ID NO:96 (see FIG. 19).

In some embodiments, Exon 3a of the splicing cassette comprises a polynucleotide that has a sequence that is 80%, 85%, 90%, 95%, 98% or 100% identical to a sequence that encodes the amino acid sequence of SEQ ID NO:73. In some embodiments, Exon 3a has a polynucleotide sequence that encodes an amino acid sequence of SEQ ID NO:73. In some embodiments, Exon 3 has a polynucleotide sequence of SEQ ID NO:12.

In some embodiments, Exon 4 of the splicing cassette comprises a polynucleotide that has a sequence that is 80%, 85%, 90%, 95%, 98% or 100% identical to a sequence that encodes an amino acid sequence of SEQ ID NO: 74. In some embodiments, Exon 4 has a polynucleotide sequence that encodes an amino acid sequence of SEQ ID NO:74. In some embodiments, Exon 4 has a polynucleotide sequence of SEQ ID NO:15.

In some embodiments, Exon 4b of the splicing cassette comprises a polynucleotide that has a sequence that is 80%, 85%, 90%, 95%, 98% or 100% identical to the polynucleotide sequence of SEQ ID NO:14.

In some embodiments, Exon 5 of the splicing cassette comprises a polynucleotide that encodes and amino acid sequence of SEQ ID NO:75. In some embodiments, Exon 5 has a polynucleotide sequence that encodes an amino acid sequence of SEQ ID NO:75. In some embodiments, Exon 5 has a polynucleotide sequence of SEQ ID NO:17.

In some embodiments, Intron 2 of the splicing cassette comprises a polynucleotide that has a sequence that is 80%, 85%, 90%, 95%, 98% or 100% identical to the sequence of SEQ ID NO:55.

In some embodiments, Intron 3 of the splicing cassette comprises a polynucleotide that has a sequence that is 80%, 85%, 90%, 95%, 98% or 100% identical to the sequence of SEQ ID NO:58.

In some embodiments, Intron 4 of the splicing cassette comprises a polynucleotide that has a sequence that is 80%, 85%, 90%, 95%, 98% or 100% identical to the sequence of SEQ ID NO:39.

In some embodiments, the splicing cassette comprises a Noctuidae dsx Exon 2 having a polynucleotide of sequence of SEQ ID NO:7 or SEQ ID NO:32; a Noctuidae dsx Exon 3 having a polynucleotide of sequence of SEQ ID NO:94, SEQ ID NO:34 or SEQ ID NO:56; a Noctuidae dsx Exon 5 having a polynucleotide of sequence of SEQ ID NO:17; an Intron 2 having a polynucleotide sequence of SEQ ID NO:55; and an Intron 4 having a polynucleotide sequence of SEQ ID NO:39 (See FIG. 18).

In other embodiments, the splicing cassette comprises a Noctuidae dsx Exon 2 having a polynucleotide of sequence of SEQ ID NO:7 or SEQ ID NO:32; a Noctuidae dsx Exon 3 having a polynucleotide of sequence of SEQ ID NO:94, SEQ ID NO:34 or SEQ ID NO:56; a Noctuidae dsx Exon 4 having a polynucleotide of sequence of SEQ ID NO:15; a Noctuidae dsx Exon 5 having a polynucleotide of sequence of SEQ ID NO:17; a Noctuidae dsx Intron 2 having a polynucleotide of sequence of SEQ ID NO:55; a Noctuidae dsx Intron 3 having a polynucleotide of sequence of SEQ ID NO:58; and a Noctuidae dsx Intron 4 having a polynucleotide of sequence of SEQ ID NO:39.

In some embodiments, the splicing cassette comprises a Noctuidae dsx Exon 2 comprising a polynucleotide of sequence of SEQ ID NO:7 or SEQ ID NO:32; a Noctuidae dsx Exon 3 comprising a polynucleotide of sequence of SEQ ID NO:94, SEQ ID NO:34 or SEQ ID NO:56; a Noctuidae dsx Exon 3a comprising a polynucleotide of sequence of SEQ ID NO:12; a Noctuidae dsx Exon 4 comprising a polynucleotide of sequence of SEQ ID NO:15; a Noctuidae dsx Exon 4b comprising a polynucleotide of sequence of SEQ ID NO:14; and a Noctuidae dsx Exon 5 comprising a polynucleotide of sequence of SEQ ID NO:17; a Noctuidae dsx Intron 2 comprising a polynucleotide of sequence of SEQ ID NO:55; a Noctuidae dsx Intron 3 comprising a polynucleotide of sequence of SEQ ID NO:58; and a Noctuidae dsx Intron 4 comprising a polynucleotide of sequence of SEQ ID NO:39.

In some embodiments, the splicing cassette comprises a Noctuidae dsx Exon 2 having a polynucleotide of sequence of SEQ ID NO:7 or SEQ ID NO:32; a Noctuidae dsx Exon 3 having a polynucleotide of sequence of SEQ ID NO:94, SEQ ID NO:34 or SEQ ID NO:56; a Noctuidae dsx Exon 3a having a polynucleotide of sequence of SEQ ID NO:12; a Noctuidae dsx Exon 4 having a polynucleotide of sequence of SEQ ID NO:15; a Noctuidae dsx Exon 4b having a polynucleotide of sequence of SEQ ID NO:14; and a Noctuidae dsx Exon 5 having a polynucleotide of sequence of SEQ ID NO:17. In other embodiments, the splicing cassette comprises a Noctuidae dsx Exon 2 having a polynucleotide of sequence of SEQ ID NO:7 or SEQ ID NO:32; a Noctuidae dsx Exon 3 having a polynucleotide of sequence of SEQ ID NO:94, SEQ ID NO:34 or SEQ ID NO:56; a Noctuidae dsx Exon 3a having a polynucleotide of sequence of SEQ ID NO:12; a Noctuidae dsx Exon 4 having a polynucleotide of sequence of SEQ ID NO:15; a Noctuidae dsx Exon 4b having a polynucleotide of sequence of SEQ ID NO:14; a Noctuidae dsx Exon 5 having a polynucleotide of sequence of SEQ ID NO:17; a Noctuidae dsx Intron 2 having a polynucleotide of sequence of SEQ ID NO:55; a Noctuidae dsx Intron 3 having a polynucleotide of sequence of SEQ ID NO:58; and a Noctuidae dsx Intron 4 having a polynucleotide of sequence of SEQ ID NO:39.

In other embodiments, the splicing cassette comprises a Noctuidae dsx Exon 2 having a polynucleotide of sequence of SEQ ID NO:7 or SEQ ID NO:32; a Noctuidae dsx Exon 3 having a polynucleotide of sequence of SEQ ID NO:94, SEQ ID NO:34 or SEQ ID NO:56; a Noctuidae dsx Exon 3a having a polynucleotide of sequence of SEQ ID NO:12; a Noctuidae dsx Exon 4 having a polynucleotide of sequence of SEQ ID NO:15; a Noctuidae dsx; a Noctuidae dsx Exon 5 having a polynucleotide of sequence of SEQ ID NO:17; a Noctuidae dsx Intron 2 having a polynucleotide of sequence of SEQ ID NO:55; a Noctuidae dsx Intron 3 having a polynucleotide of sequence of SEQ ID NO:58; and a Noctuidae dsx Intron 4 having a polynucleotide of sequence of SEQ ID NO:39.

The cassette may be used in an arthropod such as an insect. In some embodiments, the insect is of the Family Noctuidae. Non-limiting examples of such Noctuidae include insects of the genus *Spodoptera, Helicoverpa, Chrysodeixis, Anticarsia, Peridroma* or *Heliothis*. Specific species include, but are not limited to, *Spodoptera frugiperda* (fall armyworm), *Spodoptera exigua* (beet armyworm), *Spodoptera littoralis* (African cotton leafworm), *Helicoverpa armigera* (cotton bollworm; corn earworm; Old World bollworm; African bollworm), *Peridroma saucia* (variegated cutworm), *Helicoverpa zea* (corn earworm), *Chrysodeixis includens* (soybean looper), *Anticarsia gemmatalis* (velvetbean caterpillar), and *Heliothis virescens* (tobacco budworm).

In some embodiments, the cassette has exons and introns derived from the Noctuidae dsx of a Noctuid from a genus that includes, but is not limited to *Spodoptera, Helicoverpa, Chrysodeixis, Anticarsia, Peridroma* or *Heliothis*. In some embodiments, the exons and introns are derived from the dsx gene of at least one of *Spodoptera frupperda, Spodoptera exigua, Spodoptera littoralis, Helicoverpa armigera, Peridroma saucia, Helicoverpa zea, Chrysodeixis includens, Anticarsia gemmatalis*, or *Heliothis virescens.*

In some embodiments, the splicing cassette further comprises a ubiquitin leader sequence 5' of the polynucleotide encoding said functional protein.

The invention also provides a female-specific gene expression system for controlled expression of an effector gene in an arthropod comprising:

a. a promoter;
b. a polynucleotide encoding a functional protein, the coding sequence of which is defined between a start codon and a stop codon;
c. a splice control polynucleotide which, in cooperation with a spliceosome in the arthropod, is capable of sex-specifically mediating splicing of a primary transcript in the arthropod wherein the primary transcript comprises an Exon 2, or portion thereof, of a Noctuidae doublesex (dsx) gene; an Exon 3, or portion thereof, of a Noctuidae dsx gene; an Exon 4, or portion thereof, of a Noctuidae dsx gene; an Exon 5, or portion thereof, of a Noctuidae dsx gene; an Intron 2, or portion thereof, of a Noctuidae dsx gene; an Intron 4, or portion thereof, of a Noctuidae dsx gene; optionally, an Exon 3a, or portion thereof, of a Noctuidae dsx gene; optionally, an Intron 3, or portion thereof, of a Noctuidae dsx gene; and optionally, an Exon 4b, or portion thereof, thereby forming an Exon 4b-Exon 4,of a Noctuidae dsx gene; wherein:
 (1) a first splicing of an RNA transcript of a polynucleotide to produce a first spliced mRNA product, which does not have a continuous open reading frame extending from the start codon to the stop codon; and
 (2) an alternative splicing of the RNA transcript to yield an alternatively spliced mRNA product which comprises a continuous open reading frame extending from the start codon to the stop codon.

In some embodiments, the functional protein has a lethal, deleterious or sterilizing effect on the arthropod. Examples of functional proteins having include, but are not limited to Hid or homolog thereof, a Reaper (Rpr) or homolog thereof, a Nipp1Dm or homolog thereof, a calmodulin or homolog thereof, a Michelob-X or homolog thereof, a tTAV or homolog thereof, a tTAV2 or homolog thereof, a tTAV3 or homolog thereof, a tTAF or homolog thereof, a medea, or homolog thereof, or a nuclease. In other embodiments the polynucleotide encodes a microRNA toxin rather than a protein having a lethal, deleterious or sterilizing effect. In certain embodiments, the polynucleotide encoding the functional protein encodes a tTAV or homolog thereof, a tTAV2 or homolog thereof, a tTAV3 or homolog thereof, or a tTAF or homolog thereof. Non-limiting examples include proteins with the amino acid sequences of SEQ ID NO:80, SEQ ID NO:97, or SEQ ID NO:98. In some embodiments, the nuclease is FokI or EcoRI.

The arthropod female-specific gene expression system may further comprise a 3'UTR or portion thereof operatively linked to the polynucleotide encoding the functional protein. In some embodiments, the 3'UTR is a P10 3'UTR or portion thereof.

In some embodiments the arthropod female-specific gene expression system may further comprising a ubiquitin leader sequence 5' of the polynucleotide encoding a functional protein.

In some embodiments, of the arthropod female-specific gene expression system, the polynucleotide encoding the functional protein is located 3' of Exon 2, and within Exon 3 such that the polynucleotide encoding the functional protein is flanked by a first portion of Exon 3 5' of the polynucleotide encoding the functional protein, and a second portion of Exon 3 3' of the polynucleotide encoding the functional protein. In a non-limiting example, the first portion has a polynucleotide sequence of SEQ ID NO:94 and the second portion comprises a polynucleotide sequence of SEQ ID NO:9. In other embodiments, the polynucleotide encoding a functional protein is located 3' of the Exon 2, Exon 3, Exon 3a, Exon 4, Exon 4b, and Exon 5.

In some embodiments, the primary transcript is spliced in males such that translation terminates 5' of the polynucleotide encoding a functional protein. In other embodiments, the primary transcript is spliced in males such that the polynucleotide encoding the functional protein is spliced out of the primary transcript.

In some embodiments, Exon 2 comprises a polynucleotide that encodes an amino acid sequence of SEQ ID NO:71. Non-limiting examples of polynucleotides of Exon 2 include SEQ ID NO:7 and SEQ ID NO:32.

In some embodiments, Exon 3 comprises a polynucleotide that encodes an amino acid sequence of SEQ ID NO:72. This may be, for example, a polynucleotide comprising the nucleic acid sequence of SEQ ID NO:94, SEQ ID NO:34, or SEQ ID NO:56.

In some embodiments, Exon 3a comprises a polynucleotide that encodes an amino acid sequence of SEQ ID NO:73. Such amino acid sequence may be encoded by the nucleic acid sequence of SEQ ID NO:12, for example.

In some embodiments, Exon 4 comprises a polynucleotide that encodes an amino acid sequence of SEQ ID NO:74. Such amino acid sequence may be encoded by, for example the nucleic acid sequence of SEQ ID NO:15. In some embodiments, Exon 4b comprises a polynucleotide sequence of SEQ ID NO:14. In some embodiments, Exon 4b and Exon 4 are joined to form Exon 4b-Exon 4, and may have a polynucleotide sequence of, for example, SEQ ID NO:90, SEQ ID NO:91 or SEQ ID NO:92.

In some embodiments, Exon 5 comprises a polynucleotide that encodes an amino acid sequence of SEQ ID NO:75. Such amino acid sequence may be encoded by the nucleic acid sequence of, for example, SEQ ID NO:17.

In some embodiments, Intron 2 comprises a polynucleotide sequence of SEQ ID NO:55.

In some embodiments, Intron 3 comprises a polynucleotide sequence of SEQ ID NO:58.

In some embodiments, Intron 4 comprises a polynucleotide sequence of SEQ ID NO:39.

In certain embodiments, Exon 2 comprises a polynucleotide sequence that encodes an amino acid sequence of SEQ ID NO:71; Exon 3 comprises a polynucleotide sequence that encodes an amino acid sequence of SEQ ID NO:72; Exon 3a comprises a polynucleotide sequence that encodes an amino acid sequence of SEQ ID NO:73; Exon 4 comprises a polynucleotide sequence that encodes an amino acid sequence of SEQ ID NO:74; Exon 5 comprises a polynucleotide sequence that encodes an amino acid sequence of SEQ ID NO:75.

In other embodiments, Exon 2 has a polynucleotide sequence of SEQ ID NO:7 or SEQ ID NO:32; Exon 3 has a first portion with a polynucleotide of sequence of SEQ ID NO:94 and a second portion with a polynucleotide of sequence of SEQ ID NO:9; Exon 3a has a polynucleotide sequence of SEQ ID NO:12; Exon 4 has a polynucleotide sequence of SEQ ID NO:15; Exon 4b has a polynucleotide sequence of SEQ ID NO:14; and Exon 5 has a polynucleotide sequence of SEQ ID NO:17.

In still other embodiments, Exon 2 has a polynucleotide sequence of SEQ ID NO:7 or SEQ ID NO:32; Exon 3 has a polynucleotide sequence of SEQ ID NO:34 or SEQ ID NO:56; Exon 3a has a polynucleotide sequence of SEQ ID NO:12; Exon 4 has a polynucleotide sequence of SEQ ID NO:15; Exon 4b has a polynucleotide sequence of SEQ ID NO:14; and Exon 5 has a polynucleotide sequence of SEQ ID NO:17.

In other embodiments, Exon 2 has a polynucleotide sequence of SEQ ID NO:7 or SEQ ID NO:32; Exon 3 has a polynucleotide sequence of SEQ ID NO:34 or SEQ ID NO:56; Exon 3a has a polynucleotide sequence of SEQ ID NO:12; Exon 4 has a polynucleotide sequence of SEQ ID NO:15; Exon 4b has a polynucleotide sequence of SEQ ID NO:14; Exon 5 has a polynucleotide of sequence of SEQ ID NO:17; Intron 2 has a polynucleotide of sequence of SEQ ID NO:55; Intron 3 has a polynucleotide sequence of SEQ ID NO:58; and Intron 4 has a polynucleotide sequence of SEQ ID NO:39.

In the arthropod female-specific gene expression system, the promoter may be an Hsp70 promoter, a β-tubulin promoter, an Hsp83 promoter, a protamine promoter, an acting promoter, Hsp70 minimal promoter, a P minimal promoter, a CMV minimal promoter, an Acf5C-based minimal promoter, a TRE3G promoter, a BmA3 promoter fragment, or an Adh core promoter. In some embodiments, the promoter is an Hsp70 minimal promoter derived from *Drosophila melanogaster* (dmHsp70 minipro). In other embodiments, the promoter is a human CMV minimal promoter (hCMV minipro). In some embodiments, the hCMV minipro further comprises a turnip yellow mosaic virus (TYMV) 5'UTR. In some embodiments, the promoter has a polynucleotide sequence of SEQ ID NO:18, SEQ ID NO:41, SEQ ID NO:63, or SEQ ID NO:65.

The arthropod female-specific gene expression system of the invention may further comprise a transcription control element that controls transcription by the presence of the absence of a chemical ligand. In some embodiments, the transcription control element is a tetracycline-responsive element and the chemical ligand is tetracycline or an analog or derivative thereof. In some embodiments, the tetracycline-responsive element is a tetOx1, tetOx2, tetOx3, tetOx4, tetOx5, tetOx6, tetOx7, tetOx8, tetOx9, tetOx10, tetOx11, tetOx12, tetOx13, tetOx14, tetOx15, tetOx16, tetOx17, tetOx18, tetOx19, tetOx20 or tetOx21.

In some embodiments, the arthropod is an insect. In some embodiments, the insect is of the Family Noctuidae. Examples of insect genera in the Family Noctuidae include, but are not limited to *Spodoptera, Hehcoverpa, Chrysodeixis, Anticarsia, Peridroma* or *Heliothis*. In certain embodiments, the insect is *Spodoptera frupperda* (fall armyworm), *Spodoptera exigua* (beet armyworm), *Spodoptera httorahs* (African cotton leafworm), *Hehcoverpa armigera* (cotton bollworm; corn earworm; Old World bollworm; African bollworm), *Peridroma saucia* (variegated cutworm), *Hehcoverpa zea* (corn earworm), *Chrysodeixis includens* (soybean looper), *Anticarsia gemmatalis* (velvetbean caterpillar), or *Heliothis virescens* (tobacco budworm).

In some embodiments, the Noctuidae dsx gene is derived from a species of the genus *Spodoptera, Hehcoverpa, Chrysodeixis, Anticarsia, Peridroma* or *Heliothis*. In certain examples, the Noctuidae dsx gene is derived from *Spodoptera frugiperda, Spodoptera exigua, Spodoptera httorahs, Hehcoverpa armigera, Peridroma saucia, Hehcoverpa zea, Chrysodeixis includens, Anticarsia gemmatalis*, or *Heliothis virescens.*

The arthropod female-specific gene expression system may further comprise a second expression unit comprising a second promoter, a second transcription control element that controls transcription in the presence or absence of a chemical ligand, and a second polynucleotide encoding a second functional protein, the coding sequence of which is defined between a second start codon and a second stop codon, wherein the second functional protein encodes a Hid or homolog thereof, a Reaper (Rpr) or homolog thereof, a Nipp1Dm or homolog thereof, a calmodulin or homolog thereof, a Michelob-X or homolog thereof, a medea, or homolog thereof, a microRNA toxin, or a nuclease; and the first functional protein encodes a tTAV or homolog thereof, a tTAV2 or homolog thereof, a tTAV3 or homolog thereof, a tTAF or homolog thereof. This provides a positive feedback in which the transcription factor may drive expression of itself and transcription of the second expression unit in the presence or absence of a chemical ligand.

In some embodiments, the second expression unit comprises a second splice control polynucleotide operatively linked to the second polynucleotide encoding the second functional protein (e.g., transcription factor) which, in cooperation with a spliceosome in the arthropod, is capable of sex-specifically mediating splicing of a primary transcript in the arthropod wherein one sex of the arthropod splices the second splice control polynucleotide to produce an open reading frame that is in frame with the second polynucleotide encoding the second functional protein and the other sex of the arthropod splices the second splice control polynucleotide to produce an alternative reading frame that:

(a) is out of frame with the second polynucleotide encoding the second functional protein;

(b) splices out the second polynucleotide encoding the second functional protein; or (c) results in one or more stop codons in the alternative reading frame that prevents translation of the second functional protein.

In some embodiments, the second splice control polynucleotide is the same as the first splice control polynucleotide.

In some embodiments of the arthropod female-specific gene expression system, the system further comprises a second promoter operably linked to a polynucleotide encoding a marker protein. In some embodiments, the marker protein is a fluorescent protein. In particular embodiments, the fluorescent protein is DsRed2.

The invention provides plasmids for making genetically engineered Noctuid insects. In specific embodiments, these comprise SEQ ID NO:86 (pOX5403), SEQ ID NO:87 (pOX5368), and SEQ ID NO:88 (pOX5382).

The invention also provides methods of suppressing populations of wild arthropods, such as Noctuid insects, by releasing genetically engineered male arthropods (e.g., Noctuid insects) comprising an expression system of the invention, among a population of wild arthropods of the same species, whereupon the genetically engineered arthropods mate with the wild arthropods and the offspring of such matings differentially splice the primary transcript of the splicing cassette to produce (in the case of female arthropods) a functional protein having a lethal, deleterious or sterilizing effect and lead to the death of the female offspring or an inability of the female offspring to effectively reproduce, thereby suppressing the population of wild arthropods.

The invention also provides methods of reducing, inhibiting or eliminating crop damage from arthropods (such as Noctuid insects) comprising releasing genetically engineered male arthropods (e.g., Noctuid insects) comprising an expression system of the invention, among a population of wild arthropods of the same species, whereupon the genetically engineered arthropods mate with the wild arthropods and the offspring of such matings differentially splice the primary transcript of the splicing cassette to produce (in the case of female arthropods) a functional protein having a lethal, deleterious or sterilizing effect and lead to the death of the female offspring or an inability of the female offspring to effectively reproduce, thereby suppressing the population of wild arthropods and reducing, inhibiting or eliminating crop damage caused by the wild insects.

BRIEF DESCRIPTION OF THE DRAWINGS

FIG. 17 shows the amino acid sequences for Exons, 2, 3, 3a, 4, and 5 encoded by female (F) and male (M) transcripts of dsx for constructs OX5403, 0X5368, 0X5382, endogenous wild-type *S. frugiperda* (Endo) and *Helicoverpa armigera* (HA); A: Exon 2 for both male and female transcripts; B: Exon 3 for female transcripts only); C: Exon 3a for female transcripts from OX5403 and OX5382; D: Exon 4 for female transcripts from OX5403 and OX5382; E: Exon 5 for female transcripts from OX5403 and OX5382; F: Exon 5 for male transcripts; shaded areas for HA indicate conserved amino acids among lepidopterans (Wang X. Y. et al. (2014); shaded areas for OX5403, OX5368, OX5382, wild-type *S. frugiperda* indicate amino acid identities with conserved amino acids in *H. armigera.*

DETAILED DESCRIPTION OF THE INVENTION

Figure 1:
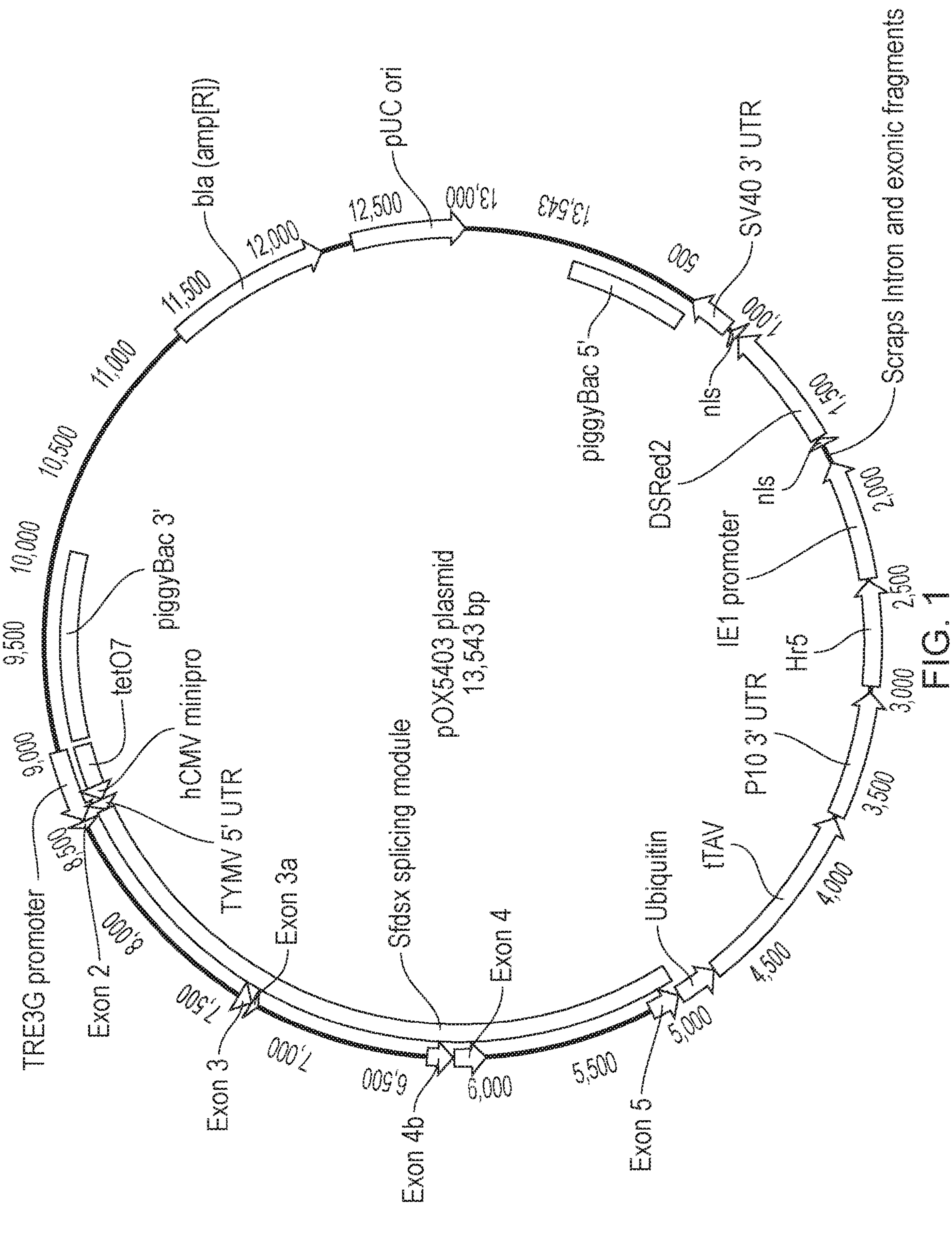
FIG. 1 shows a genetic map of pOX5403 plasmid. piggyBac 5' and 3' are sequences of the transposable element required for the insertion of OX5403 rDNA in the *Spodoptera frugiperda* genome. The DNA sequence between and including the two piggyBac elements is the rDNA that remains incorporated into the OX5403A genome.

This description contains citations to various journal articles, patent applications and patents. These are herein incorporated by reference as if each was set forth herein in its entirety.

As used herein, the term an "Exon" refers to a full-length Exon of dsx as well as portions thereof for ease of reference. Thus, "an Exon 2 of dsx" refers to a full-length wild-type dsx Exon 2 as well as a truncated form of Exon 2. An "Exon" also embraces full-length or truncated exons that contain point mutations that remove putative internal Start Codons (atg) or Stop Codons so an Open Reading Frame may be retained or lost. The 5' and 3' boundaries of an Exon/Intron must retain the splice donor and acceptor sites such that the Exon may be spliced to another Exon. In some instances, the Specification will refer to a "truncated Exon" to specify that some portion of the wild-type exon has been deleted. In other instances, the Specification will refer to a "modified Exon" to specify that some mutation(s) have been introduced to the exon that modified the polynucleotide sequence from the wild-type dsx exon sequence. Specific embodiments of Exons are also referred to with reference to their respective SEQ ID NOs. Also, it should be understood that the exon refers to a polynucleotide sequence which may be translated in different reading frames to yield different polypeptide sequences. A specific example will be the constructs allow the translation of Exon 5 in some female constructs to result in the amino acid sequence of SEQ ID NO:89, whereas, in males, the polynucleotide sequence is read in a different reading frame to yield an amino acid sequence of SEQ ID NO:78.

The term "Intron" means a polynucleotide sequence that is part of a primary transcript of an RNA molecule but which is spliced out of the final RNA to be translated.

The term "penetrance," as used herein, refers to the proportion of individuals carrying a particular variant of a gene that also express the phenotypic trait associated with that variant. Thus, "penetrance", in relation to the present invention, refers to the proportion of transformed organisms which express the lethal phenotype.

The term "construct," as used herein, refers to an artificially constructed segment of DNA for insertion into a host organism, for genetically modifying the host organism. At least a portion of the construct is inserted into the host organism's genome and alters the phenotype of the host organism. The construct may form part of a vector or be the vector.

The term "transgene," as used herein, refers to the polynucleotide sequence comprising a first and a second gene expression system to be inserted into a host organism's genome, to alter the host organism's phenotype. The portion of the plasmid vector containing the genes to be expressed is referred to herein as the transfer DNA or recombinant DNA (rDNA).

The term "gene expression system," as used herein, refers to a gene to be expressed together with any genes and DNA sequences which are required for expression of said gene to be expressed.

The term "splice control sequence," as used herein, refers to an RNA sequence associated with a gene, wherein the RNA sequence, together with a spliceosome, mediates alternative splicing of a RNA product of said gene. Preferably, the splice control sequence, together with the spliceosome, mediates splicing of a RNA transcript of the associated gene to produce an mRNA coding for a functional protein and mediates alternative splicing of said RNA transcript to produce at least one alternative mRNA coding for a non-functional protein. A "splice control module" may contain multiple splice control sequences that join multiple exons to form a polypeptide-encoding nucleic acid.

The term "transactivation activity," as used herein, refers to the activity of an activating transcription factor, which results in an increased expression of a gene. The activating transcription factor may bind a promoter or operator operably linked to said gene, thereby activating the promoter and, consequently, enhancing the expression of said gene. Alternatively, the activating transcription factor may bind an enhancer associated with said promoter, thereby promoting the activity of said promoter via said enhancer.

The term "lethal gene," as used herein, refers to a gene whose expression product has a lethal effect, in sufficient quantity, on the organism within which the lethal gene is expressed.

The term "lethal effect," as used herein, refers to a deleterious or sterilising effect, such as an effect capable of killing the organism per se or its offspring, or capable of reducing or destroying the function of certain tissues thereof, of which the reproductive tissues are particularly preferred, so that the organism or its offspring are sterile. Therefore, some lethal effects, such as poisons, will kill the organism or tissue in a short time-frame relative to their life-span, whilst others may simply reduce the organism's ability to function, for instance reproductively.

The term "tTAV gene variant," as used herein, refers to a polynucleotide encoding the functional tTA protein but which differ in the sequence of nucleotides. These nucleotides may encode different tTA protein sequences, such as, for example, tTAV2 and tTAV3, for example SEQ ID NO:97 and SEQ ID NO:98, respectively).

The term "promoter," as used herein, refers to a DNA sequence, generally directly upstream to the coding sequence, required for basal and/or regulated transcription of a gene. In particular, a promoter is sufficient to allow initiation of transcription, generally having a transcription initiation start site and a binding site for the RNA polymerase transcription complex.

The term "minimal promoter," as used herein, refers to a promoter as defined above, generally having a transcription initiation start site and a binding site for the polymerase complex, and further generally having sufficient additional sequence to permit these two to be effective. Other sequences, such as that which determines tissue specificity, for example, may be lacking.

The term "exogenous control factor," as used herein, refers to a substance which is not found naturally in the host organism and which is not found in a host organism's natural habitat, or an environmental condition not found in a host organism's natural habitat. Thus, the presence of the exogenous control factor is controlled by the manipulator of a transformed host organism in order to control expression of the gene expression system.

The term "tetO element," as used herein, refers to one or more tetO operator units positioned in series. The term, for example, "tetOx(number)," as used herein, refers to a tetO element consisting of the indicated number of tetO operator units. Thus, references to "tetOx7" indicate a tetO element consisting of seven tetO operator units. Similarly, references to "tetOx14" refer to a tetO element consisting of 14 tetO operator units, and so on.

Where reference to a particular nucleotide or protein sequence is made, it will be understood that this includes reference to any mutant or variant thereof, having substantially equivalent biological activity thereto. Preferably, the mutant or variant has at least 85%, preferably at least 90%, preferably at least 95%, preferably at least 99%, preferably at least 99.9%, and most preferably at least 99.99% sequence identity with the reference sequences.

However, it will be understood that despite the above sequence homology, certain elements, in particular the flanking nucleotides and splice branch site must be retained, for efficient functioning of the system. In other words, while portions may be deleted or otherwise altered, alternative splicing functionality or activity, to at least 30%, preferably 50%, preferably 70%, more preferably 90%, and most preferably 95% compared to the wild type should be retained. This could be increased compared to the wild type, as well, by suitably engineering the sites that bind alternative splicing factors or interact with the spliceosome, for instance.

As used herein, "splice control module" means a polynucleotide construct in that is incorporated into a vector that, when introduced into an insect, undergoes differential splicing (e.g., stage-specific, sex-specific, tissue-specific, germline-specific, etc.) and thus creates a different transcript in females than males if the splice control module confers differential splicing in a sex-specific manner.

As used herein, "5'UTR," refers to an untranslated region of an RNA transcript that is 5' of the translated portion of the transcript and often contains a promoter sequence.

As used herein, "3'UTR," refers to an untranslated region of an RNA transcript that is 3' of the translated portion of the transcript and often contains a polyadenylation sequence.

The invention provides plasmids, expression constructs and arthropods, particularly Noctuid insects, that have elements for sex-specific expression of a lethal gene that results in the death of one sex of the Noctuid insect. The elements are repressible, such as by a chemical entity (e.g., tetracycline or an analog thereof). In particular embodiments, the invention relates to Noctuid insects transformed with these constructs, particularly *Spodoptera, Helicoverpa, Chrysodeixis, Anticarsia, Peridroma* or *Heliothis*, including, but not limited to *Spodoptera frugiperda* (fall armyworm), *Spodoptera exigua* (beet armyworm), *Spodoptera littoralis* (African cotton leafworm), *Hehcoverpa armigera* (cotton bollworm; corn earworm; Old World bollworm; African bollworm), *Peridroma saucia* (variegated cutworm), *Helicoverpa zea* (corn earworm), *Chrysodeixis includens* (soybean looper), *Anticarsia gemmatalis* (velvetbean caterpillar), and *Heliothis virescens* (tobacco budworm).

Splice Control Modules

The present invention provides a splice control module polynucleotide sequence which provides for differential splicing (e.g., sex-specific, stage-specific, germline-specific, tissue-specific, etc.) in an organism. In particular, the invention provides a splice control module which provides for sufficient female-specificity of the expression of a gene of interest to be useful. In certain embodiments of the invention, the gene of interest is a gene that imparts a deleterious, lethal or sterilizing effect. For convenience, the description will refer to a lethal effect, however, it will be understood that the splice module may be used on other genes of interest as described in further detail below.

Expression of the dominant lethal genes of the transgene may be sex-specific, or be a combination of sex-specific and stage-specific, germline-specific or tissue-specific, due to the presence of at least one splice control module in each gene expression system operably linked to a gene of interest to be differentially expressed. In some embodiments, the sex-specific expression is female-specific. The splice control module in each gene expression sequence allows an additional level of control of protein expression, in addition to the promoter.

The gene of the splice control module comprises a coding sequence for a protein or polypeptide, i.e., at least two or more exons, capable of encoding a polypeptide, such as a protein or fragment thereof. Preferably, the different exons are differentially spliced together to provide alternative mRNAs. Preferably, said alternative spliced mRNAs have different coding potential, i.e., encode different proteins or polypeptide sequences. Thus, the expression of the coding sequence is regulated by alternative splicing.

Each splice control module in the system comprises at least one splice acceptor site and at least one splice donor site. The number of donor and acceptor sites may vary, depending on the number of segments of sequence that are to be spliced together.

In some embodiments, the splice control module regulates the alternative splicing by means of both intronic and exonic nucleotides. It will be understood that in alternative splicing, sequences may be intronic under some circumstances (i.e., in some alternative splicing variants where introns are spliced out), but exonic under other. In other embodiments, the splice control module is an intronic splice control module. In other words, it is preferred that said splice control sequence is substantially derived from polynucleotides that form part of an intron and are thus excised from the primary transcript by splicing, such that these nucleotides are not retained in the mature mRNA sequence.

As mentioned above, exonic sequences may be involved in the mediation of the control of alternative splicing, but it is preferred that at least some intronic control sequences are involved in the mediation of the alternative splicing.

The splice control module may be removed from the pre-mRNA, by splicing or retained so as to encode a fusion protein of at least a portion of the gene of interest to be differentially expressed. Preferably, the splice control module does not result in a frameshift in the splice variant produced. Preferably, this is a splice variant encoding a full-length functional protein.

Interaction of the splice control module with cellular splicing machinery, e.g., the spliceosome, leads to or mediates the removal of a series of, for example, at least 20, 30, 40 or 50 consecutive nucleotides or more from the primary transcript and ligation (splicing) together of nucleotide sequences that were not consecutive in the primary transcript (because they, or their complement if the antisense sequence is considered, were not consecutive in the original template sequence from which the primary transcript was transcribed). Said series of at least 50 consecutive nucleotides comprises an intron. This mediation acts preferably in a sex-specific, more preferably, female-specific, manner such that equivalent primary transcripts in different sexes, and optionally also in different stages, tissue types, etc., tend to remove introns of different size or sequence, or in some cases may remove an intron in one case but not another. This phenomenon, the removal of introns of different size or sequence in different circumstances, or the differential removal of introns of a given size or sequence, in different circumstances, is known as alternative splicing. Alternative splicing is a well-known phenomenon in nature, and many instances are known.

Where mediation of alternative splicing is sex-specific, it is preferred that the splice variant encoding a functional protein to be expressed in an organism is the F1 splice variant, or the F2 splice variant (or both F1 and F2), i.e., a splice variant where the F denotes it is found only or predominantly in females, although this is not essential.

When exonic nucleotides are to be removed, then these must be removed in multiples of three (entire codons), if it is desired to avoid a frameshift, but as a single nucleotide or multiples of two (that are not also multiples of three) if it is desired to induce a frameshift. It will be appreciated that if only one or certain multiples of two nucleotides are removed, then this could lead to a completely different protein sequence being encoded at or around the splice junction of the mRNA.

Correspondingly for configurations where all or part of a functional open reading frame is on a cassette exon, it is preferred that this cassette exon is included in transcripts found only or predominantly in females, and preferably such transcripts are, individually or in combination, the most abundant variants found in females, although this is not essential.

In one preferred embodiment, sequences are included in a hybrid or recombinant sequence or construct which are derived from naturally occurring intronic sequences which are themselves subject to alternative splicing, in their native or original context. Therefore, an intronic sequence may be considered as one that forms part of an intron in at least one alternative splicing variant of the natural analogue. Thus, sequences corresponding to single contiguous stretches of naturally occurring intronic sequence are envisioned, but also hybrids of such sequences, including hybrids from two different naturally occurring intronic sequences, and also sequences with deletions or insertions relative to single contiguous stretches of naturally occurring intronic sequence, and hybrids thereof. Said sequences derived from naturally occurring intronic sequences may themselves be associated, in the invention, with sequences not themselves part of any naturally occurring intron. If such sequences are transcribed, and preferably retained in the mature RNA in at least one splice variant, they may then be considered exonic.

It will also be appreciated that reference to a "frame shift" could also refer to the direct coding of a stop codon, which is also likely to lead to a non-functioning protein as would a disruption of the spliced mRNA sequence caused by insertion or deletion of nucleotides. Production from different splice variants of two or more different proteins or polypeptide sequences of differential function is also envisioned, in addition to the production of two or more different proteins or polypeptide sequences of which one or more has no predicted or discernable function. Also envisioned is the production from different splice variants of two or more different proteins or polypeptide sequences of similar function, but differing subcellular location, stability or capacity to bind to or associate with other proteins or nucleic acids.

A modified dsx intron is an example. In this instance, it may be preferable to delete, as we have done in the Examples, sizable amounts from alternatively spliced introns, e.g., 90% or more of an intron in some cases, whilst still retaining the alternative splicing function. Thus, whilst large deletions are envisioned, it is also envisaged that smaller, e.g., even single nucleotide insertions, substitutions or deletions are also preferred.

Splice Module Doublesex (dsx)

Introns typically consist of the following features (given here as the sense DNA sequence 5' to 3'); in RNA thymine (T) will be replaced by uracil (U)):

a. 5' end (known as the splice "donor"): GT (or possibly GC)
b. 3' end (known as the splice "acceptor"): AG
c. Upstream/5' of the acceptor (known as the "branch point"): A-polypyrimidine tract, i.e. AYYYYY . . . Yn The terminal nucleotides of exons immediately adjacent to the 5' intronic splice "donor" and the 3' intronic splice "acceptor" are typically G.

In some embodiments, the splice control module is immediately adjacent, in the 3' direction, the start codon, so that the G of the ATG is 5' to the start (5' end) of the splice control module. This may be advantageous as it allows the G of the ATG start codon to be the 5' G flanking sequence to the splice control module.

Alternatively, the splice control module is 3' to the start codon but within 10,000 exonic bp, 9,000 exonic bp, 8,000 exonic bp, 7,000 exonic bp, 6,000 exonic bp, 5,000 exonic bp, 4,000 exonic bp, exonic 3,000 bp, exonic 2000, bp, or 1000 exonic bp, 500 exonic bp, 300 exonic bp, 200 exonic bp, 150 exonic bp, 100 exonic bp, 75 exonic bp, 50 exonic bp, 30 exonic bp, 20 exonic bp, or 10 or even 5, 4, 3, 2, or 1 exonic bp.

Preferably, branch points are included in each splice control sequence, as described above. A branch point is the sequence to which the splice donor is initially joined which shows that splicing occurs in two stages, in which the 5' exon is separated and then is joined to the 3' exon.

The sequences provided can tolerate some sequence variation and still splice correctly. There are a few nucleotides known to be important. These are the ones required for all splicing. The initial GU and the final AG of the intron are particularly important and therefore preferred, as discussed elsewhere, though ~5% of introns start GC instead. This consensus sequence is preferred, although it applies to all splicing, not specifically to alternative splicing.

In insects, the dsx gene is composed of introns and exons that are differentially spliced between males and females. The splicing cassette of the invention is derived from insect dsx gene and may be derived from any insect source provided the primary transcript is differentially spliced between males and females. In some embodiments, the insect dsx sequences are derived from a Noctuid species of a genus that includes, but is not limited to *Spodoptera, Helicoverpa, Chrysodeixis, Anticarsia, Peridroma* or *Heliothis*. In specific examples, the dsx gene is derived from a species of Noctuid that includes, but is not limited to *Spodoptera frugiperda, Spodoptera exigua, Spodoptera littoralis, Helicoverpa armigera, Peridroma saucia, Helicoverpa zea, Chrysodeixis includens, Anticarsia gemmatalis*, or *Heliothis virescens*. In a certain specific example, dsx is derived from *Spodoptera frugiperda*.

Figure 19:
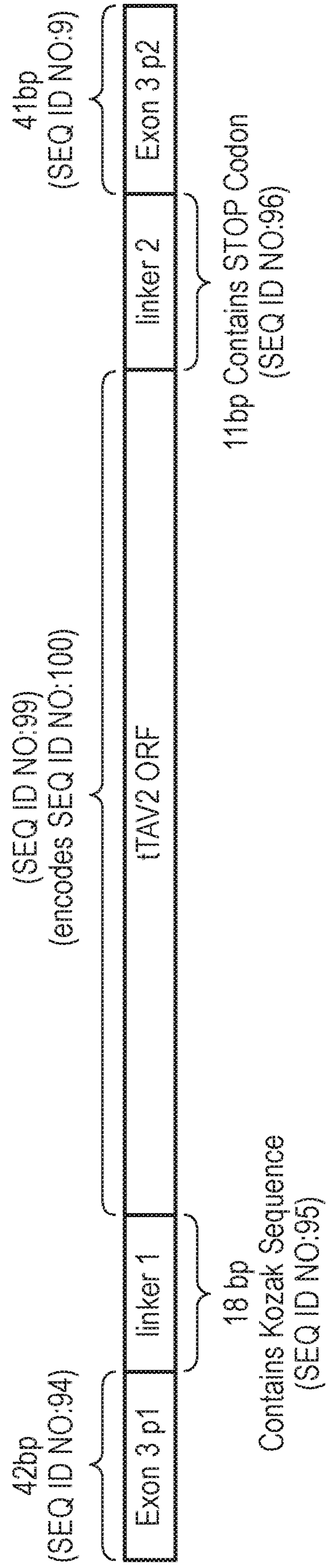
FIG. 19 shows an embodiment in which the lethal, deleterious or sterilizing gene (in this case tTAV) is positioned between a split Exon 3 which is joined by linkers to the 5' portion of Exon 3 and the 3' portion of Exon 3. In specific examples, the first portion of Exon 3 (Exon 3 p1; SEQ ID NO:94) is joined by a linker (linker 1; SEQ ID NO:95) to the tTAV open reading frame (ORF; SEQ ID NO:99) which is joined, in turn by a second linker (linker 2; SEQ ID NO:96) to the second portion of Exon 3 (Exon 3 p2; SEQ ID NO:9).

The dsx splicing cassette of the invention comprises both introns and exons, such that differential splicing may occur. In some embodiments, the splicing cassette comprises at least Exons 2, Intron 2, Exon 3, Intron 4 and Exon 5 of dsx. In such embodiments, the lethal gene (e.g., tTAV or a variant thereof) may be operably connected 3' of Exon 2, Intron 2 and in the middle of Exon 3, but 5' of Intron 4 and Exon 5 (See FIG. 6 and FIG. 19). Thus, females would splice a product of Exon 2-Exon 3-tTAV-Exon 4-Exon 5 and males would splice out the tTAV to provide Exon 2-Exon 5 (see, for example, FIG. 6). The constructs may also contain Exons 3a, 4, 4b and Intron 3.

In other arrangements, the lethal gene (e.g., tTAV) may be 3' of the dsx splice module elements Exon 2, Intron 2, Exon 3, Exon 3a, Intron 3, Exon 4b, Exon 4, Intron 4 and Exon 5. In such embodiments, females splice the primary transcript of the splice module to generate Exon2-Exon3-Exon4-Exon5 (see, for example, SEQ ID NO:76) or Exon2-Exon3-Exon3a-Exon4-Exon5 (see, for example, SEQ ID NO:77), while males splice the primary transcript of the splice cassette to generate Exon2-Exon5 wherein a stop codon is present prior to translating the lethal protein (See FIG. 3 and FIG. 9). Such stop codon may be due to the splicing of Exon 2 to Exon 5 wherein Exon 5 is out of frame with Exon 2, for example.

In some embodiments, Exon 2 has a polynucleotide sequence that encodes the amino acid sequence of SEQ ID NO:71. Exon 2 may have a polynucleotide sequence of, for example, SEQ ID NO:7 or SEQ ID NO:32. In some embodiments, Exon 3 has a polynucleotide sequence that encodes the amino acid sequence of SEQ ID NO:72. Exon 3 may have a polynucleotide sequence of, for example, SEQ ID NO:94, SEQ ID NO:34, or SEQ ID NO:56. In some embodiments, Exon 3a has a polynucleotide sequence that encodes the amino acid sequence of SEQ ID NO:73. Exon 3a may have a polynucleotide sequence of, for example, SEQ ID NO:12. In some embodiments, Exon 4 has a polynucleotide sequence that encodes the amino acid sequence of SEQ ID NO:74. Exon 4 may have a polynucleotide sequence of, for example, SEQ ID NO:15. In some embodiments, Exon 5 has a polynucleotide sequence that encodes the amino acid sequence of SEQ ID NO:75. Exon 5 may have a polynucleotide sequence of, for example, SEQ ID NO:17.

Exon 4b is joined to exon 4 without an intervening intron. Instead, there appears to be an internal recognition site for splicing such that Noctuids may splice out Exon 4b from primary transcripts leaving Exon 4. Thus, one may incorporate Exon 4b/Exon 4 in the constructs such as that shown in SEQ ID NO: 90 (FIG. 3), SEQ ID NO:91 (FIG. 6) or SEQ ID NO:92 (FIG. 9), or use constructs without Exon 4b.

In some embodiments, Intron 2 has a polynucleotide sequence of SEQ ID NO:55. In some embodiments, Intron 3 has a polynucleotide sequence of SEQ ID NO:58. In some embodiments, Intron 4 has a polynucleotide sequence of SEQ ID NO:39. Introns may be of varying length provided splice donor and splice acceptor sites are preserved. The specific Intron sequences provided herein and in the examples are merely illustrative and one of skill in the art would know how to modify the sequence and length of such introns to permit proper splicing together of exons from the primary transcript.

Examples of complete splice control modules are provided herein as SEQ ID NO:6, SEQ ID NO:31, and SEQ ID NO:53.

Heterologous Genes of Interest

The system is capable of expressing at least one protein of interest, i.e., a functional protein to be expressed in an organism. One such protein of interest may have a therapeutic effect or may, be a marker such as a fluorescent protein (for instance AmCyan, Clavularia, ZsGreen, ZsYellow, Discosoma striata, DsRed2, AsRed, Discosoma Green, Discosoma Magenta, HcRed-2A, mCherry, Green Fluorescent Protein (GFP), Red Fluorescent Protein (RFP), and HcRed-Cr1-tandem, and the like, or one or more of their mutants or variants), or other markers that are well known in the art such as drug resistance genes. Other proteins of interest may be, for example, proteins that have a deleterious, lethal or sterilizing effect. Alternatively, the heterologous gene of interest may encode an RNA molecule that has an inhibitory effect. Further proteins to be expressed in the organism are, or course envisaged, in combination with said functional protein, preferably a lethal gene as discussed below.

It is preferred that the expression of the heterologous polynucleotide sequence leads to a phenotypic consequence in the organism. In some embodiments, the functional protein is not beta-galactosidase, but can be associated with visible markers (including fluorescence), viability, fertility, fecundity, fitness, flight ability, vision, and behavioural differences. It will be appreciated, of course, that, in some embodiments, the expression systems are typically conditional, with the phenotype being expressed only under some, for instance restrictive or permissive, conditions.

A heterologous polynucleotide sequence may be expressed in the Noctuid. By "heterologous," it would be understood that this refers to a sequence that would not, in the wild type, be normally found in association with, or linked to, at least one element or component of the at least one splice control sequence. For example, where the splice control sequence is derived from a particular organism, and the heterologous polynucleotide is a coding sequence for a protein or polypeptide, i.e., is a polynucleotide sequence encoding a functional protein, then the coding sequence could be derived, in part or in whole, from a gene from the same organism, provided that that the origin of at least some part of the transcribed polynucleotide sequence was not the same as the origin of the at least one splice control sequence. Alternatively, the coding sequence could be from a different organism and, in this context, could be thought of as "exogenous". The heterologous polynucleotide could also be thought of as "recombinant," in that the coding sequence for a protein or polypeptide are derived from different locations, either within the same genome (i.e., the genome of a single species or sub-species) or from different genomes (i.e., genomes from different species or subspecies), or synthetic sources.

Heterologous can refer to a sequence other than the splice control sequence and can, therefore, relate to the fact the promoter, and other sequences such as 5' UTR and/or 3'UTR can be heterologous to the polynucleotide sequence to be expressed in the organism, provided that said polynucleotide sequence is not found in association or operably linked to the promoter, 5' UTR and/or 3'UTR, in the wild type, i.e., the natural context of said polynucleotide sequence, if any.

It will be understood that heterologous also applies to "designer" or hybrid sequences that are not derived from a particular organism but are based on a number of components from different organisms, as this would also satisfy the requirement that the sequence and at least one component of the splice control sequence are not linked or found in association in the wild type, even if one part or element of the hybrid sequence is so found, as long as at least one part or element is not. It will also be understood that synthetic versions of naturally occurring sequences are envisioned. Such synthetic sequences are also considered as heterologous, unless they are of identical sequence to a sequence which would, in the wild type or natural context, be normally found in association with, or linked to, at least one element or component of the at least one splice control sequence.

This applies equally to where the heterologous polynucleotide is a polynucleotide for interference RNA.

In one embodiment, where the polynucleotide sequence to be expressed comprises a coding sequence for a protein or polypeptide, it will be understood that reference to expression in an organism refers to the provision of one or more transcribed RNA sequences, preferably mature mRNAs, but this may, preferably, also refer to translated polypeptides in said organism.

Lethal Genes

In some embodiments, the functional protein to be expressed in an organism has a lethal or deleterious effect. Where reference is made herein to a lethal effect, it will be appreciated that this extends to a deleterious or sterilizing effect, such as an effect capable of killing the organism per se or its offspring, or capable of reducing or destroying the function of certain tissues thereof, of which the reproductive tissues are particularly preferred, so that the organism or its offspring are sterile. In other embodiments, a system may be employed that is not lethal, but detrimental, so as to impose a substantial fitness cost to the organism. Non-limiting examples include blindness, and flightlessness (for organisms that could normally fly). Therefore, some lethal effects, such as poisons, will kill the organism or tissue in a short time-frame relative to their life-span, whilst others may simply reduce the organism's ability to function, for instance reproductively.

In some embodiments, the lethal effect results in sterilization allowing the organism to compete in the natural environment ("in the wild") with wild organisms, but the sterile organism cannot then produce viable offspring. In this way, the present invention achieves a similar or better result to techniques such as the Sterile Insect Technique (SIT) in insects, without the problems associated with SIT, such as the cost, danger to the user, reduced competitiveness of the irradiated organism, and the lack of available and practical sexing systems.

In some embodiments, the system comprises at least one positive feedback mechanism, namely at least one functional protein to be differentially expressed, via alternative splicing, and at least one promoter therefor, wherein a product of a gene to be expressed serves as a positive transcriptional control factor for the at least one promoter, and whereby the product, or the expression of the product, is controllable. In some embodiments, an enhancer is associated with the promoter, the gene product serving to enhance activity of the promoter via the enhancer.

The present invention allows for selective control of the expression of the dominant lethal gene, thereby providing selective control of the expression of a lethal phenotype. It will therefore be appreciated that each of the lethal genes encodes a functional protein, such as Hid, Reaper (Rpr), Nipp1Dm, calmodulin, Michelob-X, tTAV, tTAV2, tTAV3, tTAF, and other tetracycline systems, Barnase/Barstar combinations, medea microRNA toxins, and nucleases, such as but not limited to FokI or EcoRI.

Each of the lethal genes has a lethal effect which is conditional. An example of suitable conditions includes temperature, so that the lethal is expressed at one temperature but not, or to a lesser degree, at another temperature. Another example of a suitable condition is the presence or absence of a substance, whereby the lethal is expressed in either the presence or absence of the substance, but not both. It is preferred that the effect of the lethal gene is conditional and is not expressed under permissive conditions requiring the presence of a substance which is absent from the natural environment of the organism, such that the lethal effect of the lethal system occurs in the natural environment of the organism.

Each lethal genetic system may act on specific cells or tissues or impose its effect on the whole organism. Systems that are not strictly lethal but impose a substantial fitness cost are also envisioned, for example leading to blindness, flightlessness (for organisms that could normally fly), or sterility. Systems that interfere with sex determination are also envisioned, for example transforming or tending to transform all or part of an organism from one sexual type to another.

In some embodiments, the product of at least one of the lethal genes is preferably an apoptosis-inducing factor, such as the AIF protein described for instance in Candé et al. (2002) *J. Cell Science* 115:4727-4734) or homologues thereof. AIF homologues are found in mammals and even in invertebrates, including insects, nematodes, fungi, and plants, meaning that the AIF gene has been conserved throughout the eukaryotic kingdom. In other embodiments, the product of at least one of the lethal genes is Hid, the protein product of the head involution defective gene of *Drosophila melanogaster*, or Reaper (Rpr), the product of the reaper gene of *Drosophila*, or mutants thereof. Use of Hid was described by Heinrich and Scott (2000) *Proc. Natl Acad. Sci USA* 97:8229-8232). Use of a mutant derivative, HidAla5 was described by Horn and Wimmer (2003) *Nature Biotechnology* 21:64-70). Use of a mutant derivative of Rpr, RprKR, is described in White et al. (1996); *Science* 271 (5250):805-807; Wing et al. (2001) *Mech. Dev.* 102(1-2): 193-203; and Olson et al. (2003) *J. Biol. Chem.* 278(45): 44758-44768. Both Rpr and Hid are pro-apoptotic proteins, thought to bind to IAP1. IAP1 is a well-conserved anti-apoptotic protein. Hid and Rpr are therefore expected to work across a wide phylogenetic range (Huang et al. (2002); Vernooy et al. (2000) *J. Cell Biol.* 150(2):F69-76) even though their own sequence is not well conserved.

Nipp1Dm, the *Drosophila* homologue of mammalian Nipp1 (Parker et al. (2002) *Biochemical Journal* 368:789-797; Bennett et al., (2003) *Genetics* 164:235-245) are utilized in some embodiments. Nipp1Dm is another example of a protein with lethal effect if expressed at a suitable level, as would be understood by the skilled person. Indeed, many other examples of proteins with a lethal effect will be known to the person skilled in the art.

In other embodiments, the lethal gene is tTA or a tTAV or tTAF gene variant, where tTA denotes 'tetracycline repressible Trans-Activator' and V denotes 'Variant.' tTAV is an analogue of tTA, wherein the sequence of tTA has been modified to enhance the compatibility with the desired insect species. Variants of tTAV are possible, encoding the tTA protein, such that the tTAV gene products have the same functionality as the tTA gene product. Thus, the variants of the tTAV gene comprise modified nucleotide sequences as compared to the tTA nucleotide sequence and to each other, but encode proteins with the same function. Thus, tTAV gene variants can be used in the place of tTA. Examples of tTAV and variants that may be used include, but are not limited to tTAV (SEQ ID NO:10), tTAV2 (SEQ ID NO:67) and tTAV3 (SEQ ID NO:68 (encoding the proteins of SEQ ID NO:80, SEQ ID NO:97, and SEQ ID NO:98, respectively). In some embodiments, the tTA Variant proteins contain amino acid substitutions, additions or deletions. Any combination of lethal genes may be used, and, in some embodiments, the lethal genes are the same while, in other embodiments, the lethal genes are different. The improved penetrance of the lethal effect and the earlier onset of lethality are achieved by an accumulation of lethal product.

In some embodiments, the lethal gene leads to the death of at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the insects.

In some embodiments, if more than one feedback loop is desired with more than one lethal gene, each of the first and second lethal genes may be independently tTA or a tTAV gene variant. In some embodiments, each of the first and second lethal gene is independently one encoding tTAV (SEQ ID NO:80), tTAV2 (SEQ ID NO:97) and tTAV3 (SEQ ID NO:98). In other embodiments, the first and second lethal genes are the same. In further embodiments, one of the first and second lethal genes encodes tTAV (SEQ ID NO:80) and the other gene encodes tTAV3 (SEQ ID NO:68). However, any combination of tTAV variants may be used; thus, in some embodiments, one of the first and second genes encodes tTAV (SEQ ID NO:80) and the other encodes tTAV2 (SEQ ID NO:97), while, in a further embodiment, one of the first and second genes encodes tTAV2 (SEQ ID NO:97) and the other gene encodes tTAV3 (SEQ ID NO:98). In other embodiments, the first lethal gene encodes tTAV (SEQ ID NO:80) and the second lethal gene encodes tTAV3 (SEQ ID NO:98). Examples of polynucleotides encoding tTAV, tTAV2 and tTAV3 are provided as SEQ ID NO:10, SEQ ID NO:81 and SEQ ID NO:82, respectively.

The polynucleotide sequence to be expressed to have the lethal, deleterious or sterilizing effect may comprise polynucleotides for interference RNA (RNAi). In some embodiments, where the polynucleotide sequence to be expressed comprises polynucleotides for interference RNA, it will also be understood that reference to expression in an organism refers to the interaction of the polynucleotides for interference RNA, or transcripts thereof, in the RNAi pathway, for instance by binding of Dicer (RNA Pol III-like enzyme) or formation of small interfering RNA (siRNA). Such sequences are capable of providing, for instance, one or more stretches of double-stranded RNA (dsRNA), preferably in the form of a primary transcript, which in turn is capable of processing by the Dicer. Such stretches include, for instance, stretches of single-stranded RNA that can form loops, such as those found in short-hairpin RNA (shRNA), or with longer regions that are substantially self-complementary.

In insects and nematodes especially, it is preferred to provide portion of dsRNA, for instance by hairpin formation, which can then be processed by the Dicer system. Mammalian cells generally produce an interferon response against long dsRNA sequences, so for mammalian cells it is more common to provide shorter sequences, such as siRNAs. Antisense sequences or sequences having homology to microRNAs that are naturally occurring RNA molecules targeting protein 3' UTRs are also envisaged as sequences for RNAi according to an embodiment of the present invention.

Thus, where the system is DNA, the polynucleotides for interference RNA are deoxyribonucleotides that, when transcribed into pre-RNA ribonucleotides, provide a stretch of dsRNA, as discussed above.

Polynucleotides for interference RNA are particularly preferred when said polynucleotides are positioned to minimise interference with alternative splicing. This may be achieved by distal positioning of these polynucleotides from the alternative splice control sequences, preferably 3' to the control sequences. In another preferred embodiment, substantially self-complementary regions may be separated from each other by one or more splice control sequences, such as an intron, that mediate alternative splicing. Preferably, the self-complementary regions are arranged as a series of two or more inverted repeats, each inverted repeat separated by splice control sequence, preferably an intron, as defined elsewhere.

In this configuration, different alternatively spliced transcripts may have their substantially self-complementary regions separated by different lengths of non-self-complementary sequence in the mature (post-alternative-splicing) transcript. It will be appreciated that regions that are substantially self-complementary are those that are capable of forming hairpins, for instance, as portions of the sequence are capable of base-pairing with other portions of the sequence. These two portions do not have to be exactly complementary to each other, as there can be some mismatching or toleration of stretches in each portion that do not base-pair with each other. Such stretches may not have an equivalent in the other portion, such that symmetry is lost and “bulges” form, as is known with base-pair complementation in general.

In another preferred embodiment, one or more segment of sequence substantially complementary to another section of the primary transcript is positioned, relative to the at least one splice control sequence, so that it is not included in all of the transcripts produced by alternative splicing of the primary transcript. By this method, some transcripts are produced that tend to produce dsRNA while others do not; by mediation of the alternative splicing, e.g., sex-specific mediation, stage-specific mediation, germline-specific mediation, tissue-specific mediation, and combinations thereof, dsRNA may be produced in a sex-specific, stage-specific, germline-specific or tissue-specific manner, or combinations thereof.

Fusion Leaders

In some embodiments it will be desirable to have the functional protein of interest free of the Splice Control Module protein sequence. In some embodiments, the Splice Control Module is operatively linked to a polypeptide-encoding polynucleotide that stimulates proteolytic cleave of a translated polypeptide (“Fusion Leader Sequences” for the polynucleotide and “Fusion Leader Polypeptide” for the encoded polypeptide). An example of such a Fusion Leader Sequence is a ubiquitin-encoding polynucleotide. Such a Fusion Leader Sequence may be operatively linked in frame to the 3' end of the Splice Control Module and operatively linked in frame to the protein encoding gene of interest (i.e., from 5' to 3': Splice Control Module-Fusion Leader Sequence-Gene of interest). In such a case, the Splice Control Module/Fusion Leader Polypeptide is cleaved from the protein of interest by specific proteases in the cell. Aside from ubiquitin, any other similar fusion may be made in place of ubiquitin that would have the effect of stimulating a cleavage of the N-terminal Splice Control Module. An example of a polynucleotide encoding ubiquitin is provided as SEQ ID NO:30. The ubiquitin fusion leader may be any polynucleotide encoding a functional ubiquitin leader polypeptide from any organism, provided that the ubiquitin leader is faithfully cleaved in the arthropod system. An example would be a *Drosophila melanogaster* ubiquitin (such as SEQ ID NO:79) that is cleaved from the functional protein that causes the lethal, deleterious or sterilizing effect.

Promoters and 5'UTRs

Each splicing module that is operatively linked to a gene with a lethal, deleterious or sterilizing effect is operably linked to a promoter, wherein said promoter is capable of being activated by an activating transcription factor or trans-activating transcription factor encoded by a gene also included in at least one of the gene expression systems. It is preferred that any combination of promoter and Splice Control Module is envisioned. The promoter is preferably specific to a particular protein having a short temporal or confined spatial effect, for example a cell-autonomous effect.

The promoter may be a large or complex promoter, but these often suffer the disadvantage of being poorly or patchily utilised when introduced into non-host insects. Accordingly, in some embodiments, it is preferred to employ minimal promoters. It will be appreciated that minimal promoters may be obtained directly from known sources of promoters, or derived from larger naturally-occurring, or otherwise known, promoters. Suitable minimal promoters and how to obtain them will be readily apparent to those skilled in the art. For example, suitable minimal promoters include a minimal promoter derived from Hsp70, a P minimal promoter, a CMV minimal promoter, an Act5C-based minimal promoter, a BmA3 promoter fragment, a srya embryo-specific promoter (Horn and Wimmer (2003) *Nat. Biotechnol.* 21(1):64-70) from *Drosophila melanogaster*, or its homologues, or promoters from other embryo-specific or embryo-active genes, such as that of the *Drosophila* gene slow as molasses (slam), or its homologues from other species, and an Adh core promoter (Bieschke, E. et al. (1998) *Mol. Gen. Genet.,* 258:571-579). It is readily apparent to those skilled in the art as to how to ensure that the promoter selected is active. It is preferred that at least one of the operably-linked promoters present in the invention is active during early development of the host organism, and particularly preferably during embryonic stages, in order to ensure that the lethal gene is expressed during early development of the organism.

In some embodiments, the promoter can be activated by environmental conditions, for instance the presence or absence of a particular factor such as tetracycline (or analogue thereof) in the tet system described herein, such that the expression of the gene of interest can be easily manipulated by the skilled person. In some embodiments, a suitable promoter is the hsp70 heat shock promoter, allowing the user to control expression by variation of the environmental temperature to which the hosts are exposed in a lab or in the field, for instance. Another example of temperature control is described in Fryxell and Miller (1995) *J. Econ. Entomol.* 88:1221-1232.

Alternatively, the promoter may be specific for a broader class of proteins or a specific protein that has a long-term and/or wide system effect, such as a hormone, positive or negative growth factor, morphogen or other secreted or cell-surface signaling molecule. This would allow, for instance, a broader expression pattern so that a combination of a morphogen promoter with a stage-specific alternative splicing mechanism could result in the morphogen being expressed only once a certain life-cycle stage was reached, but the effect of the morphogen would still be felt (i.e., the morphogen can still act and have an effect) beyond that life-cycle stage. Preferred examples would be the morphogen/signaling molecules Hedgehog, Wingless/WNTs, TGFβ/BMPs, EGF and their homologues, which are well-known evolutionarily-conserved signaling molecules.

It is also envisioned that a promoter that is activated by a range of protein factors, for instance transactivators, or which has a broad systemic effect, such as a hormone or morphogen, could be used in combination with an alternative splicing mechanism to achieve a tissue and sex-specific control or sex and stage-specific control, or other combinations of stage-, tissue, germline- and sex-specific control.

It is also envisioned that more than one promoter, and optionally an enhancer therefor, can be used in the present system, either as alternative means for initiating transcription of the same protein or by virtue of the fact that the genetic system comprises more than one gene expression system (i.e., more than one gene and its accompanying promoter).

In some embodiments, at least one of the promoters is a heat shock promoter, such as Hsp70. Examples of sequences comprising Hsp70 promoters (HSP70 minipro) are SEQ ID NO:18 and SEQ ID NO:41. In other embodiments, at least one of the promoters is the srya embryo-specific promoter (Horn and Wimmer (2003) *Nat. Biotechnol.* 21(1):64-70) from *Drosophila melanogaster*, or its homologues, or promoters from other embryo-specific or embryo-active genes, such as that of the *Drosophila* gene slow as molasses (slam), or its homologues from other species. In some embodiments, a human CMV minipro-based promoter is used, with or without other elements such as a tetOx7 and turnip yellow mosaic virus (TYMV) 5'UTR (collectively a "TRE3G promoter"). An example of the hCMV minipro-based promoter is provided as SEQ ID NO:65. An example of the turnip yellow mosaic virus (TYMV) 5'UTR sequence is provided as SEQ ID NO:64 and an example of the tetOx7 enhancer sequence is provided as SEQ ID NO:66. Collectively, these form an example of the TRE3G promoter (SEQ ID NO:63).

Other useful promoters include, but are not limited to, the Baculovirus Autographica californica nucleopolyhedrosisvirus (AcNPV) promoter IE1 (e.g., SEQ ID NO:26); the Hsp83 promoter; the srya embryo specific promoter (Horn and Wimmer (2003) *Nat. Biotechnol.* 21(1):64-70) from *Drosophila melanogaster*, or its homologues; the promoter from *Drosophila* gene slow as molasses (slam), or its homologues from other species; a β-tubulin promoter; a topi promoter; an aly promoter; a protamine promoter; and an actin promoter such as Act5c, an insect muscle actin promoter (WO 2014/135604); or an Opie2 promoter from *Orgyia pseudotsugata* multiple nucleopolyhedrovirus.

Transcription Control Elements

Preferably, the polynucleotide expression system is a recombinant dominant lethal genetic system, the lethal effect of which is conditional. Suitable conditions include temperature, so that the system is expressed at one temperature but not, or to a lesser degree, at another temperature, for example. The lethal genetic system may act on specific cells or tissues or impose its effect on the whole organism. It will be understood that all such systems and consequences are encompassed by the term lethal as used herein. Similarly, "killing," and similar terms refer to the effective expression of the lethal system and thereby the imposition of a deleterious or sex-distorting phenotype, for example death.

More preferably, the polynucleotide expression system is a recombinant dominant lethal genetic system, the lethal effect of which is conditional and is not expressed under permissive conditions requiring the presence of a substance which is absent from the natural environment of the organism, such that the lethal effect of the lethal system occurs in the natural environment of the organism.

In some embodiments, the coding sequences encode a lethal linked to a system such as the tet system described in WO 01/39599 and/or WO2005/012534.

Indeed, it is preferred that the expression of said lethal gene is under the control of a repressible transactivator protein. It is also preferred that the gene whose expression is regulated by alternative splicing encode a transactivator protein such as tTA, or variant thereof such as tTAV2 or tTAV3. Non-limiting examples of polynucleotides encoding tTAV proteins and variants include SEQ ID NO:10 (tTAV); SEQ ID NO:81 (tTAV2) and SEQ ID NO:82 (tTAV3). Proteins encoded by these are provided as SEQ ID NO:80 (tTAV), SEQ ID NO:97 (tTAV2) and SEQ ID NO:98 (tTAV3). This is not incompatible with the regulated protein being a lethal. Indeed, it is particularly preferred that it is both. In this regard, we particularly prefer that the system includes a positive feedback system as taught in WO2005/012534.

Preferably, the lethal effect of the dominant lethal system is conditionally repressible. In some embodiments, the lethal effect is exerted only in females. In other embodiments, the lethal effect is exerted only in males; that is, the lethal effect is expressed in males or females (as needed). For example, if the dominant lethal system is present in an insect, it is preferred that it leads to the death of at least 40% of the insects. In some embodiments, it leads to the death of at least 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the insects inheriting the system in the absence of the repressor.

Thus, in some embodiments wherein one or more of the dominant, lethal genes is tTA or a tTAV gene variant, an enhancer is a tetO element, comprising one or more tetO operator units. Upstream of a promoter, in either orientation, tetO is capable of enhancing levels of transcription from a promoter in close proximity thereto, when bound by the product of the tTA gene or a tTAV gene variant. In some embodiments, each enhancer is independently one of tetOx1, tetOx2, tetOx3, tetOx4, tetOx5, tetOx6, tetOx7, tetOx8, tetOx9, tetOx10, tetOx11, tetOx12, tetOx13, tetOx14, tetOx15, tetOx16, tetOx17, tetOx18, tetOx19, tetOx20 and tetOx21. In some embodiments, each enhancer is independently one of tetOx1, tetOx7, tetOx14 and tetOx21. In embodiments comprising more than one enhancer, the first enhancer is the same as or different from the second enhancer. Examples of the tetOx7 element is shown in SEQ ID NO:20, SEQ ID NO: 42 and SEQ ID NO:66. An example of the tetOX14 is shown in SEQ ID NO:83. An example of tetOx21 element is shown in SEQ ID NO:84.

Other Elements

In some embodiments, the system comprises other upstream, 5' factors and/or downstream 3' factors for controlling expression. Examples include enhancers such as the fat-body enhancers from the *Drosophila* yolk protein genes, and the homology region (hr) enhancers from baculoviruses, for example AcNPV Hr5 (SEQ ID NO:27 or SEQ ID NO:49). It will also be appreciated that the RNA products will include suitable 5' and 3' UTRs, for instance. Examples of 5' and 3'UTRs include, but are not limited to TYMV 5'UTR (SEQ ID NO:64); *Drosophila melanogaster* fs(1) K10 3'UTR (SEQ ID NO:19); SV40 3'UTR (SEQ ID NO:43), a P10 3'UTR (SEQ ID NO:28 or SEQ ID NO:50); or any other suitable 5' or 3'UTR that functions in the expression system.

It will be understood that reference is made to start and stop codons between which the polynucleotide sequence to be expressed in an organism is defined, but that this does not exclude positioning of the at least one splice control sequence, elements thereof, or other sequences, such as introns, in this region. In fact, it will be apparent from the present description that the splice control sequence, can, in some embodiments, be positioned in this region.

Furthermore, the splice control sequence, for instance, can overlap with the start codon at least, in the sense that the G of the ATG can be, in some embodiments, be the initial 5' G of the splice control sequence. Thus, the term "between" can be thought of as referring to from the beginning (3' to the initial nucleotide, i.e., A) of the start codon, preferably 3' to the second nucleotide of the start codon (i.e., T), up to the 5' side of the first nucleotide of the stop codon. Alternatively, as will be apparent by a simple reading of a polynucleotide sequence, the stop codon may also be included.

Other Expression Units in Combination

The Invention also provides for a plurality of expression units. In some embodiments, the first expression unit includes a dsx Splicing Module for the expression of a transcription factor such as tTAV, tTAV2, tTAV3, tTAF, or an analog of any of these. The expression unit includes a recognition sequence for the transcription factor such that expression of the transcription factor results in a positive feedback in the absence of tetracycline or tetracycline analog to drive further expression of the transcription factor which has a lethal or deleterious effect on the arthropod.

In other embodiments, the first expression unit includes a dsx Splicing Module for the expression of a transcription factor that may or may not have a deleterious or lethal effect, but acts on a second expression unit to drive transcription of a functional protein or nucleic acid that does have a deleterious, lethal, or sterilizing effect (such as Hid or homolog thereof, a Reaper (Rpr) or homolog thereof, a Nipp1Dm or homolog thereof, a calmodulin or homolog thereof, a Michelob-X or homolog thereof, a tTAV or homolog thereof, a tTAV2 or homolog thereof, a tTAV3 or homolog thereof, a tTAF or homolog thereof, a medea, or homolog thereof, a microRNA toxin, or a nuclease (e.g., EcoRI, FokI, etc.) and optionally also drives further expression of more transcription factor from the first expression unit (i.e., positive feedback). In this manner, the arthropod splices a primary transcript of the dsx/transcription factor expression unit in a sex-specific manner and the transcription factor drives expression of the second expression unit in one sex but not the other sex and optionally drives expression of additional transcription factor by positive feedback. In some embodiments, the first expression unit produces a tTAV or homolog thereof, a tTAV2 or homolog thereof, a tTAV3 or homolog thereof, a tTAF or homolog thereof and is under the control of a tetracycline-responsive transcription control element such as a tetO. The second transcription unit produces a protein with a deleterious, lethal, or sterilizing effect. In some embodiments, one or both of the expression units comprises a splice module. Preferably, transcription from the first expression unit is repressible with the presence or absence of a chemical ligand. The second expression unit may also be regulated in a sex-specific manner by the addition of a second Splice Control Module which may be the same or different from the first Splice Control Module provided it is functional in the arthropod. Other Splice Control modules have been described such as in WO 2018/029534 and WO 2007/091099.

Marker Proteins

The expression systems of the invention may further contain polynucleotides that encode marker proteins that can be expressed to identify the arthropods (e.g., insects) that contain the expression system. Such polynucleotides may be operatively linked to 5' and/or 3' elements to aid in expression. For example, a promoter and optionally an enhancer may be operatively linked to the polynucleotide encoding the marker protein. The promoter may be the same or different than the promoter used to express the gene having a lethal, deleterious or sterilizing effect. Examples of promoters that may be used include constitutive promoters such that the marker protein is expressed constitutively. Examples of useful promoters include, but are not limited to Baculovirus Autographica californica nucleopolyhedrosisvirus (AcNPV) promoter IE1 (e.g., SEQ ID NO:26); the Hsp83 promoter; the srya embryo-specific promoter (Horn and Wimmer (2003) *Nat. Biotechnol.* 21(1):64-70) from *Drosophila melanogaster*, or its homologues; the promoter from *Drosophila* gene slow as molasses (slam), or its homologues from other species; a β-tubulin promoter; a topi promoter; an aly promoter; a protamine promoter; and an actin promoter. In certain embodiments, the promoter is an IE1 promoter (e.g., SEQ ID NO:26). The expression system marker polynucleotide/promoter may further comprise an enhancer. Suitable enhancers may include, but are not limited to a Baculovirus Autographica californica nucleopolyhedrosisvirus (AcNPV) Hr5 enhancer (e.g., SEQ ID NO:27 or SEQ ID NO:49), a tetOx1, tetOx2, tetOx3, tetOx4, tetOx5, tetOx6, tetOx7, tetOx8, tetOx9, tetOx10, tetOx11, tetOx12, tetOx13, tetOx14, tetOx15, tetOx16, tetOx17, tetOx18, tetOx19, tetOx20 and tetOx21. In some embodiments, each enhancer is independently one of tetOx1, tetOx7, tetOx14 and tetOx21. In embodiments comprising more than one enhancer, the first enhancer is the same as or different from the second enhancer. Examples of the tetOx7 element is shown in SEQ ID NO:20, SEQ ID NO:42 and SEQ ID NO:66. An example of the tetOX14 is shown in SEQ ID NO:83. An example of tetOx21 element is shown in SEQ ID NO:84.

Marker proteins may be such proteins that impart drug resistance or may be a fluorescent protein. Examples of fluorescent proteins that may be used as marker proteins include, but are not limited AmCyan, Clavularia, ZsGreen, ZsYellow, Discosoma striata, DsRed2, AsRed, Discosoma Green, Discosoma Magenta, HcRed-2A, mCherry, Green Fluorescent Protein (GFP), Red Fluorescent Protein (RFP), and HcRed-Cr1-tandem, and the like, or one or more of their mutants or variants. As exemplified below, DsRed2 (Clontech) may be used. An example of a polynucleotide sequence encoding DsRed2 is provided as SEQ ID NO:1, SEQ ID NO:23 and SEQ ID NO:45). The polypeptide sequence encoded by SEQ ID NO:1 (DsRed2) is provided as SEQ ID NO:85.

Introduction of Constructs into Organisms

Methods of introduction or transformation of the gene system constructs and induction of expression are well known in the art with respect to the relevant organism. It will be appreciated that the system or construct is preferably administered as a plasmid, but generally tested after integrating into the genome. Plasmid vectors may be introduced into the desired host cells by methods known in the art, such as, for example by transfection, electroporation, microinjection, transduction, cell fusion, DEAE dextran, calcium phosphate precipitation, lipofection (lysosome fusion), use of a gene gun, or a DNA vector transporter (see, e.g., Wu et al., (1992) *J. Biol. Chem.* 267:963; Wu et al. (1988) *J. Biol. Chem.* 263:14621; and Canadian Patent Application No. 2,012,311 to Hartmut et al.). Administration by microinjection into embryos the preferred method of creating genetically engineered arthropods (e.g., insects). The plasmid may be linearised before or during administration. The plasmid vector may be integrated into the host chromosome by any means known. Well-known methods of locus-specific insertion may be used, including, homologous recombination and recombinase-mediated genome insertion. In another embodiment, locus-specific insertion may be carried out by recombinase-site specific gene insertion. In one example piggyBac sequences may be incorporated into the vector to drive insertion of the vector into the host cell chromosome. Other technologies such as CRISPRs, TALENs, AttP/AttB recombination may also be employed. Not all of the plasmid may be integrated into the genome. Where only part of the plasmid is integrated into the genome, it is preferred that this part include the at least one splice control module capable of mediating alternative splicing.

Genetically Engineered Insects

The vectors of the invention may be used to create transgenic insects of the genera *Spodoptera, Helicoverpa, Chrysodeixis, Anticarsia, Peridroma* and *Heliothis*. Examples of species of genetically-engineered insects that may be produced include, but are not limited to *Spodoptera frupperda* (fall armyworm), *Spodoptera exigua* (beet armyworm), *Spodoptera littoralis* (African cotton leafworm), *Helicoverpa armigera* (cotton bollworm; corn earworm; Old World bollworm; African bollworm), *Peridroma saucia* (variegated cutworm), *Helicoverpa zea* (corn earworm; other common names include cotton bollworm and tomato fruitworm), *Chrysodeixis includens* (soybean looper), *Anticarsia gemmatalis* (velvetbean caterpillar), and *Heliothis virescens* (tobacco budworm).

Specific Embodiments (pOX5403, pOX5368 and pOX5382)

In certain specific embodiments, the invention provides splicing cassettes comprising exons and introns derived from *Spodoptera frupperda* doublesex (dsx) gene. The splicing cassettes comprise Exons 2, 3, 3a, 4, 4b, and 5 and introns 2, 3, and 4 of dsx in various arrangements. In certain embodiments, the males splice Exon 2 to Exon 5. Thus, it is necessary to include Exons 2 and 5 for the male-specific splicing. The female splicing may occur by joining Exons 2 and 3 to the heterologous sequence encoding the lethal, deleterious or sterilizing functional protein. For these embodiments, Exons 2 and 3 and Intron 2 are required (see FIG. 6). Thus, differential splicing could be accomplished using Exons 2, 3, and 5 with Introns 2 and 4. Splicing for females may also be accomplished by joining Exons 2, 3, 4, and 5 or Exons 2, 3, 3a, 4 and 5 (see FIG. 3 and FIG. 9). Thus, in these constructs differential splicing may be accomplished using Exons 2, 3, 4 and 5 or Exons 2, 3, 3a, 4 and 5 (and optionally Exon 4b) along with Introns 2, 3 and 4.

Figure 3:
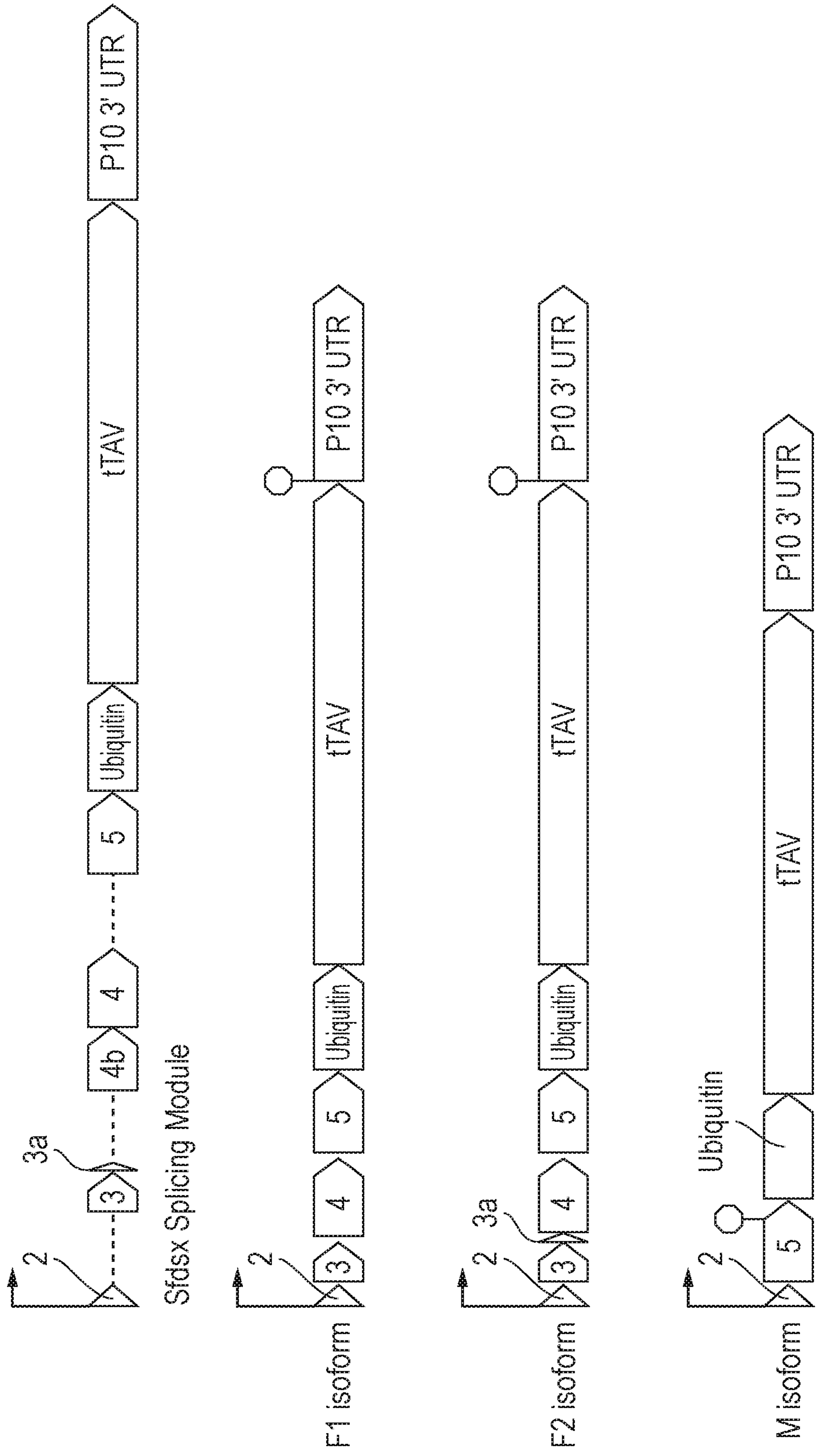
FIG. 3 shows splice variants of the self-limiting tTAV genes. The Sfdsx splice module consists of Sfdsx exons 2, 3, 3a, 4b, 4 and 5, together with Sfdsx introns 2, 3 and 4. In females, the female-specific transcripts F1 and F2 are produced. The F1 and F2 transcripts produced in female *Spodoptera frugiperda* expressing the transgenes in the absence of tetracycline antidote, results in tTAV protein expression in a female-specific manner. The F1 and F2 transcripts contain the Sfdsx start codon fused to ubiquitin_tTAV and the P10 3'UTR. tTAV is in frame with the start codon, and thus the F1 and F2 transcripts are able to be translated into tTAV protein. In males, only the transcripts M is produced. Transcript M contains Sfdsx exon 2 and exon 5, ubiquitin_tTAV and P10 3'UTR. The ORF in this transcript starts, as in the other two transcripts, upstream to Sfdsx exon 2 and ends in exon 5 (in a frame different to the ORF coding for tTAV protein). In the M transcript, the exclusion of the dsx exons 3, 3a, 4b and 4 prevents the production of tTAV protein, as the tTAV coding sequence is out of frame with the tTAV start codon, and also in frame with a stop codon which lies at the end of exon 5. The arrows indicate the position of the start codons and the red octagons indicate the position of in-frame stop codons. Male transcripts are likely degraded by nonsense-mediated decay (Hansen, K. D. et al. (2009) *PLoS Genet.* 5, e1000525).
Figure 9:
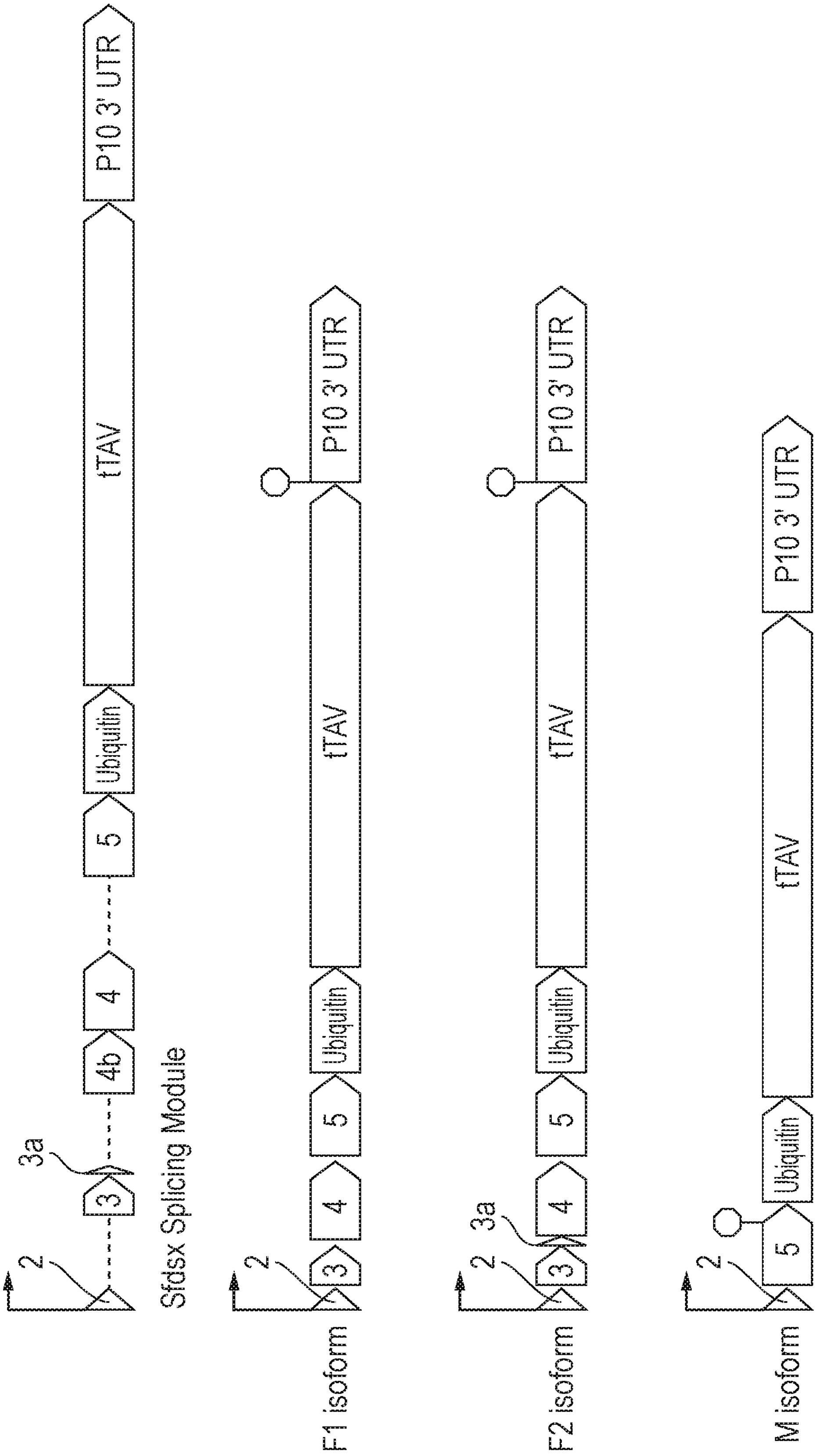
FIG. 9 shows splice variants of the self-limiting tTAV genes. The Sfdsx splice module consists of Sfdsx exons 2, 3, 3a, 4b, 4 and 5, together with Sfdsx introns 2, 3 and 4. In females, the female-specific transcripts F1 and F2 are produced. The F1 and F2 transcripts produced in female *Spodoptera frugiperda* expressing the transgenes in the absence of tetracycline antidote, results in tTAV protein expression in a female-specific manner. The F1 and F2 transcripts contain the Sfdsx start codon fused to ubiquitin_tTAV and the P10 3'UTR. tTAV is in frame with the start codon, and thus the F1 and F2 transcripts are able to be translated into tTAV protein. In males, only the transcripts M is produced. Transcript M contains Sfdsx exon 2 and exon 5, ubiquitin_tTAV and P10 3'UTR. The ORF in this transcript starts, as in the other two transcripts, upstream to Sfdsx exon 2 and ends in exon 5 (in a frame different to the ORF coding for tTAV protein). In the M transcript, the exclusion of the dsx exons 3, 3a, 4b and 4 prevents the production of tTAV protein, as the tTAV coding sequence is out of frame with the tTAV start codon, and also in frame with a stop codon which lies at the end of exon 5. The arrows indicate the position of the start codons and the red octagons indicate the position of in-frame stop codons. The sequences of these transcripts and their predicted encoded proteins are given in Appendix 5. Male transcripts are likely degraded by nonsense-mediated decay (Hansen et al., 2009).

The constructs of these embodiments may join the splicing cassette to a heterologous gene of interest such as one imparting a lethal effect, such as the tTAV gene and optionally to a 5' leader sequence such as ubiquitin (see FIG. 3 and FIG. 9). Alternatively, the heterologous sequence may be positioned in between the elements of the splicing cassette such that females splice the primary transcript of the splicing cassette to include the heterologous sequence in-frame, while males splice the primary transcript of the splicing cassette and heterologous sequence to splice out the heterologous sequence (see FIG. 6).

For these constructs, the Exons encode the following amino acid sequences: Exon 2 (SEQ ID NO:71), Exon 3 (SEQ ID NO:72), Exon 3a (SEQ ID NO:73), Exon 4 (SEQ ID NO:74), and Exon 5 (SEQ ID NO:75). The polynucleotide sequences in specific embodiments for the Exons and Introns are as follows: Exon 2 (SEQ ID NO:7 or SEQ ID NO:32); Exon 3 (SEQ ID NO:94, SEQ ID NO:34 or SEQ ID NO:56); Exon 3a (SEQ ID NO:12); Exon 4 (SEQ ID NO:15), Exon 4b (SEQ ID NO:14) (Exon 4b/Exon 4 sequences are shown in SEQ ID NO:90, SEQ ID NO:91 and SEQ ID NO:92), Exon 5 (SEQ ID NO:17), Intron 2 (SEQ ID NO:55), Intron 3 (SEQ ID NO:58), and Intron 4 (SEQ ID NO:39). The ubiquitin leader sequence in these constructs has the polynucleotide sequence of SEQ ID NO:30 or SEQ ID NO:52.

Figure 2:
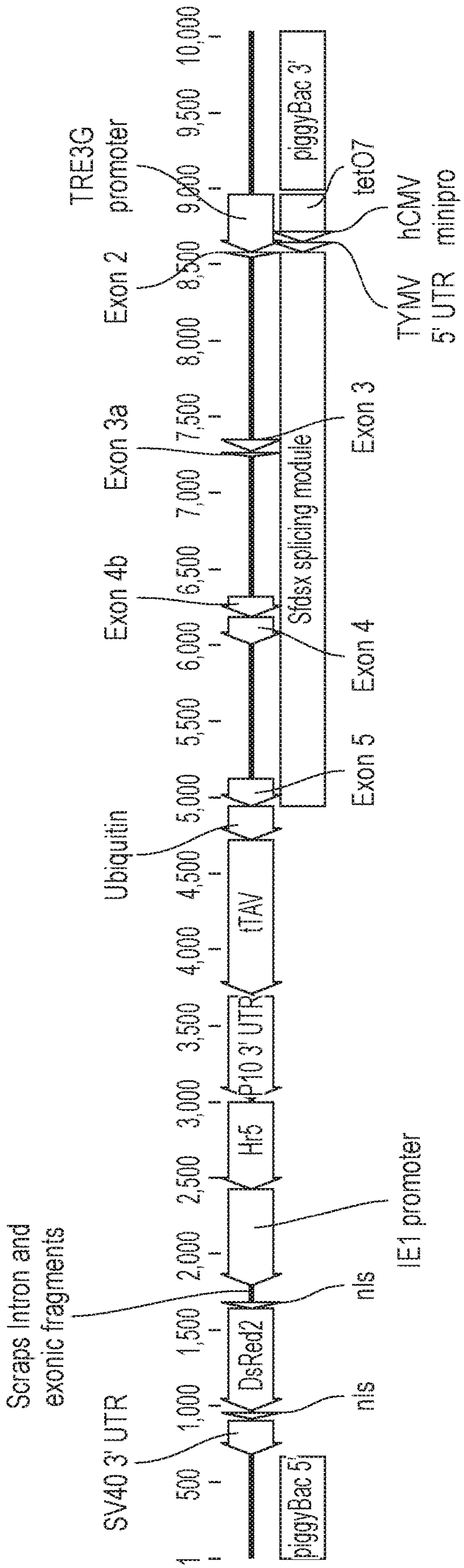
FIG. 2 shows a linear plasmid map showing the two genes (DsRed2, Sfdsx_tTAV) inserted in OX5403A. Due to the splice module tTAV protein is only expressed in females in the absence of tetracycline family antibiotics.
Figure 5:
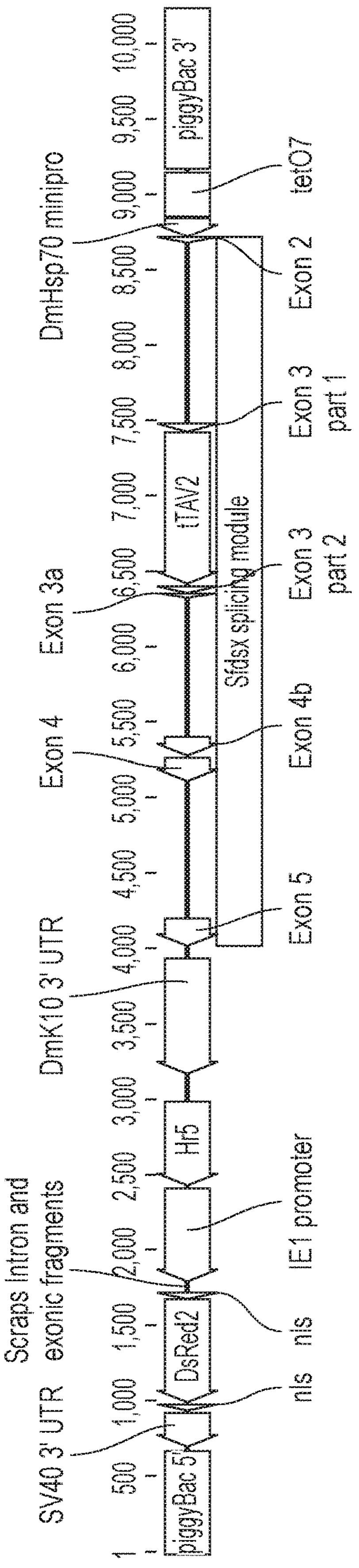
FIG. 5 shows a linear plasmid map showing the two genes (DsRed2, Sfdsx_tTAV2) inserted in OX5368. Due to the splice module tTAV2 protein is only expressed in females in the absence of tetracycline family antibiotics.
Figure 8:
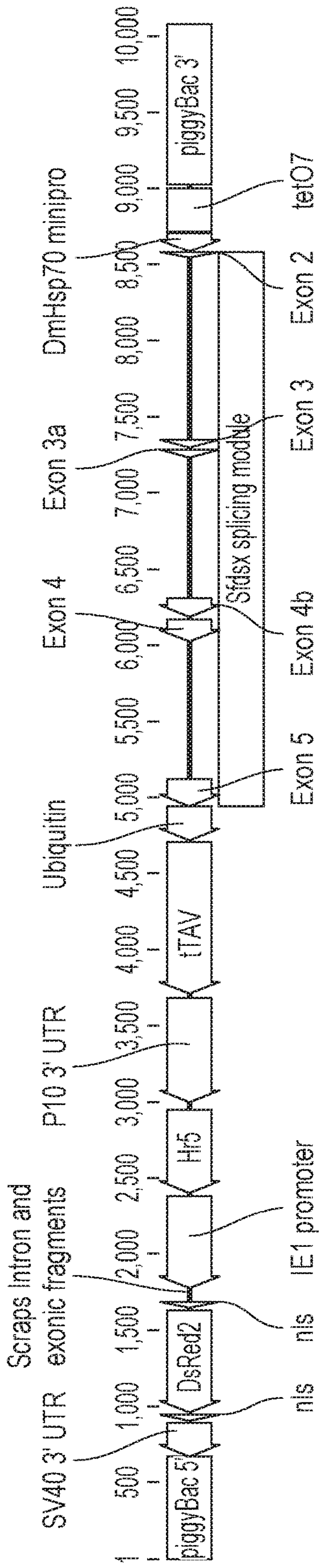
FIG. 8 shows a linear plasmid map showing the two genes (DsRed2, Sfdsx_tTAV) inserted in OX5382G. Due to the splice module tTAV protein is only expressed in females in the absence of tetracycline family antibiotics.

These specific embodiments have a *D. melanogaster* Hsp70 minipro promoter or human CMV minipro (with TYMV 5'UTR), operatively linked to a tetO enhancer sequence (in FIG. 2, FIG. 5 and FIG. 8, (showing pOX5403, pOX5368 and pOX5382, respectively) it is a tetOx7 enhancer. These SEQ ID NOs for the polynucleotide sequences for these elements are shown in Tables 1, 2 and 3.

Methods of Suppressing Populations of Arthropods/Insects and Reducing Crop Damage The invention also provides methods of suppressing populations of wild arthropods, such as Noctuid insects, by releasing genetically engineered male arthropods (e.g., Noctuid insects) comprising an expression system of the invention, among a population of wild arthropods of the same species, whereupon the genetically engineered arthropods mate with the wild arthropods and the offspring of such matings differentially splice the primary transcript of the splicing cassette to produce (in the case of female arthropods) a functional protein having a lethal, deleterious or sterilizing effect and lead to the death of the female offspring or an inability of the female offspring to effectively reproduce, thereby suppressing the population of wild arthropods.

Insects may be reared for breeding by including a compound to repress expression of the functional protein and rescuing the insects from the lethal, deleterious or sterilizing effect such that more adult insects may be produced. When rearing just male insects for release, the compound that represses functional protein is eliminated, and as the female insects will produce the functional protein, the female insects will die or be unable to reproduce. Male insects, which do not make the functional protein even in the absence of the repressing compound will survive without any untoward effects.

The invention also provides methods of reducing, inhibiting or eliminating crop damage from arthropods (such as Noctuid insects) comprising releasing genetically engineered male arthropods (e.g., Noctuid insects) comprising an expression system of the invention, among a population of wild arthropods of the same species, whereupon the genetically engineered arthropods mate with the wild arthropods and the offspring of such matings differentially splice the primary transcript of the splicing cassette to produce (in the case of female arthropods) a functional protein having a lethal, deleterious or sterilizing effect and lead to the death of the offspring or an inability of the female offspring to effectively reproduce, thereby suppressing the population of wild arthropods and reducing, inhibiting or eliminating crop damage caused by the wild insects.

The invention also provides methods of resistance management in Noctuid insects comprising releasing genetically engineered male Noctuid insects comprising an expression system of the invention, among a population of wild Noctuid insects of the same species, wherein the population contains a plurality of insects that are resistant to insecticides and biopesticides (e.g., Bt-type), whereupon the genetically engineered insects mate with the wild insects and the offspring of such matings differentially splice the primary transcript of the splicing cassette to produce (in the case of female Noctuid insects) a functional protein having a lethal, deleterious or sterilizing effect and lead to the death of the female offspring or an inability of the female offspring to effectively reproduce. Surviving male off-spring from such matings with wild females effectively also pass on susceptibility alleles present in the transgenic colony (i.e., the traits are introgressed into the wild population), and dilute the frequency of resistance in the wild pest population. Further description of such a strategy may be found, for example in WO2004098278. In this way, the method thereby suppresses the population of wild Noctuid insects and slows or reverses resistance to insecticides in the population of wild Noctuid insects.

The invention also comprises a method of detecting a genetically engineered insect comprising a female-specific gene expression system of the invention by including a reporter expression unit in the expression system for expression of a reporter gene (such as, but not limited to a fluorescent protein) where expression of the reporter gene in the system is detectable.

In some embodiments, the reporter gene is a fluorescent protein. In some embodiments, the fluorescent protein is DsRed2 (for example, encoded by SEQ ID NO:1, and having an amino acid sequence of SEQ ID NO:80). In some embodiments, the reporter gene is detected by examining the insect under a certain wavelength of light.

EXAMPLES

The Examples following Examples relate to constructs made based on the Noctuid, *Spodoptera frugiperda* dsx gene. Several alterations were engineered into some exons and introns in order to allow for open reading frames, reduce the possibility of internal start sites of translation, manage size of fragments for expression and to produce reliable sex-specific splicing between males and females.

The dsx used in the splicing cassettes and expression systems of the invention eliminate Exon 1 entirely. Exon 2 has been truncated approximately 75% and 5 nucleotides (atgaa) have been added to the 5' end to provide an initiating methionine and to keep the exon in-frame in OX5403 and OX5382. The entire Exon 3 and Exon 3a are retained in OX5382 and OX5403 and an additional g was added to the 3' end to maintain reading frame. In OX5368, the tTAV protein coding sequence including start and stop codon is placed within Exon 3 joined by polynucleotide linkers (See FIG. 19). While the entire Exon 4b and Exon 4 are retained, due to a splicing event within the coding regions of Exons 4b/4, only Exon 4 is spliced into the functional protein. The entire Exon 5 was used with an additional 6 nucleotides (gtagcg) provided at the 3' end of the exon.

In addition, the following point mutations were introduced for pOX5382 and pOX5403 (the numbering is with reference to the endogenous dsx cDNA with numbers starting at the beginning of Exon 1):

| Engineered Change | Location | Effect |
|---|---|---|
| 682_683insA | Female-specific exon 3 | Opens reading frame in female transcript to achieve female-specific tTAV protein production |
| 881A > T<br>884A > T<br>1007G > C | Female-specific exon 4 | Opens reading frame in female transcript to achieve female-specific tTAV protein production |
| 1052T > C<br>1076T > C | Exon 5 (shared) | Eliminates putative Start Codon (Met) to avoid alternative translation initiation sites |

Similarly, in addition to the truncations described above, the following point mutations were engineered for pOX5368 (the numbering is with reference to the endogenous dsx cDNA with numbers starting at the beginning of Exon 1):

| Engineered Change | Location | Effect |
|---|---|---|
| 642G > C | female-specific exon 3 | Introduced to get rid of a putative Start codon (Met) to avoid alternative translation initiation sites. |
| 676_677ins tTAV2 coding sequence and linker | Female-specific exon 3 | Introduction of in-frame tTAV2 CDS for female-specific protein production |

Example 1

Generation of OX5403 *Spodoptera frugiperda*

The plasmid pOX5403 (FIG. 1) is based on cloning vector pKC26-FB2 (Genbank #HQ998855). The plasmid backbone contains the pUC origin of replication and the betalactamase gene that confers ampicillin resistance for use in molecular cloning procedures. This plasmid section is not included in the rDNA or incorporated into the insect genome.

pOX5403 also contains the complete rDNA that is incorporated into the insect, including the synthetic DNA sequence that encodes DsRed2 red fluorescence marker protein (Clontech), synthetic DNA sequences for the tetracycline-repressible transcriptional activator tTAV (based on a fusion of sequences from *E. coli* and HSV-1 VP16 transcriptional activator), and the modified Sfdsx splicing module derived from *Spodoptera frugiperda*. The components shown in FIG. 2 are detailed in Table 1. The plasmid was prepared by using routine DNA cloning procedures.

The first gene is a DsRed2 gene under the control of the Hr5/IE1 promoter. This gene is responsible for the production of DsRed2 fluorescent protein which serves as a visual marker for the integration of rDNA in the genome of *Spodoptera frugiperda* and the identification of transgenic insects.

The second gene is the Sfdsx_tTAV gene under the control of a composite promoter (TRE3G) including a truncated version of the hCMV minimal promoter fused to a TYMV 5' UTR, downstream of a tetracycline-responsive operator (tetOx7) (Loew et al. (2010) *BMC Biotechnol.* 10:81). Expression of tTAV protein is rendered female-specific by the Sfdsx splicing module.

The Sfdsx_tTAV gene is expressed in a female-specific manner by the inclusion of portions of the *Spodoptera frugiperda* doublesex gene (Sfdsx). The gene is transcribed into three different sex-specific alternatively spliced transcripts, two female-specific (F1 and F2) and one male-specific (M) transcripts (FIG. 3). The variation in the three transcripts is due to sex-specific inclusion of different mRNA sequences which result from sex-specific splicing of the RNA encoded by the Sfdsx sex-specific alternative splicing module. In the F1 and F2 transcripts, the sequence encoding tTAV is in frame with the upstream start codon (FIG. 2). In the female transcripts, splicing occurs either to join Exons 2, 3, 4, and 5 to the ubiquitin leader sequence and tTAV sequence in-frame such that the tTAV sequence is translated and cleaved from the translated protein, or to join Exons 2, 3/3a, 4, and 5 to the ubiquitin leader sequence and tTAV sequence in-frame such that the tTAV sequence is translated and cleaved from the translated protein. In the M transcript, the exclusion of the dsx exons 3, 3a, 4b and 4 prevents the production of tTAV protein, as the tTAV coding sequence is out of frame with the tTAV start codon, and also in frame with a stop codon which lies downstream of exon 5, before the tTAV coding sequence. M transcripts thus contain in-frame stop codon(s) in their coding sequences which likely lead to M transcript mRNA degradation by nonsense-mediated decay (Hansen et al. (2009) *PLoS Genet.* 5: e1000525).

Plasmid pOX5403 contains the complete rDNA that is incorporated into the insect, including the synthetic DNA sequence that encodes DsRed2 red fluorescence marker protein, synthetic DNA sequences for the tetracycline repressible transcriptional activator tTAV (based on a fusion of sequences from *E. coli* and HSV-1 VP16 transcriptional activator), and the modified Sfdsx splicing module derived from *S. frugiperda*.

TABLE 1

Genetic components of OX5403

| Component | SEQ ID NO | Size (bp) | Source | Function |
|---|---|---|---|---|
| SV40 3' UTR | 43 | 228 | Synthetic non-coding fragment based on Simian virus (SV40) isolated from pDsRed2-N1 (Clontech plasmid) | A 3' untranslated sequence. It contains the transcription termination and polyadenylation signals |
| nls | 44, 46 | 21, 21 | Synthetic sequence | nls: Nuclear Localisation Signal. Synthetic DNA sequences that encode protein domains at the N- and Cterminal ends of DsRed2 for import into the cell nucleus by importins |
| DsRed2 | 45 | 675 | Synthetic DNA (Clontech) encoding a variant of red fluorescent protein originally identified in *Discosoma* | Marker gene - a red fluorescent protein. |
| scraps intron and exonic fragments | 47 | 87 | *Drosophila melanogaster* | An intron cloned upstream of the DsRed2 coding sequence to facilitate transcription of mRNA. |
| IE1 promoter | 48 | 633 | Baculovirus *Autographa californica* nuclear polyhedrovirus (AcNPV) | Promoter to drive the expression of DsRed2 protein. |
| Hr5 enhancer | 49 | 563 | Baculovirus *Autographa californica* nuclear polyhedrovirus (AcNPV) | Transcriptional enhancer to stimulate expression from the IE1 promoter. |
| P10 3' UTR | 50 | 667 | Baculovirus *Autographa californica* nuclear polyhedrovirus (AcNPV) | A 3' untranslated sequence. It contains the transcription termination and polyadenylation signals |

TABLE 1-continued

| Genetic components of OX5403 | | | | |
|---|---|---|---|---|
| Component | SEQ ID NO | Size (bp) | Source | Function |
| tTAV | 51 | 1011 | Synthetic DNA encoding the fusion tetracycline transactivator protein. Optimised for expression in insects. | Tetracycline repressible transcription factor. |
| Ubiquitin | 52 | 225 | Ubiquitin from *Drosophila melanogaster* | Stimulates cleavage of tTAV protein from the Sfdsx_ubiquitin that is N-terminally fused |
| | 53 | 3640 | Splicing Module | |
| Sfdsx splicing module | 62 | 172 | Sfdsx Exon 5 | Female-specific splicing module from *Spodoptera frugiperda* dsx gene generates tTAV protein only in female OX5403. |
| | 61 | 901 | Sfdsx Intron 4 | |
| | 60 | 166 | Sfdsx Exon 4 | |
| | 59 | 134 | Sfdsx Exon 4b | |
| | 58 | 933 | Sfdsx Intron 3 | |
| | 57 | 15 | Sfdsx Exon 3a | |
| | 56 | 84 | Sfdsx Exon 3 | |
| | 55 | 1195 | Sfdsx Intron 2 | |
| | 54 | 40 | Sfdsx Exon 2 | |
| | ATG | 3 | Sfdsx ATG start codon | |
| TRE3G | 63 | 376 | TYMV 5' UTR + hCMV minipromoter + tetO7 | TRE3G |
| | 64 | 58 | TYMV 5' UTR | Synthetic noncoding fragment based on turnip yellow mosaic virus (TYMV). |
| | 65 | 65 | hCMV minipromoter | Synthetic noncoding fragment based on the minimal promoter of the human cytomegalovirus (hCMV). Promotes expression when the tTAV is bound to the neighbouring TetO operator. |
| | 66 | 246 | tetOx7 | Synthetic DNA, contains 7 repeats of Tn10 tetoperon. Binds tTAV in the absence of tetracycline, facilitating expression by the neighbouring minipromoter. |

Transformation was effected with a non-autonomous piggyBac transposable element, first described in (Thibault et al., (1999) *Insect Mol. Biol.* 8:119-123), co-injected with a non-integrating source of piggyBac transposase (mRNA transcribed in vitro from plasmid pOX3022). The piggyBac transposon was originally isolated from a cell culture of *Trichoplusia ni*, and has been used in several insect transformations (Diptera, Lepidoptera, Coleoptera) (Handler, (2002) *Proc. Natl. Acad. Sci. USA* 95:7520-7525; O'Brochta et al., (2003) *J. Exp. Biol.* 206:3823-3834; Tamura et al., (2000) *Nat. Biotechnol.* 18:81-84). This transposon, as initially described, consists of two components, a coding sequence encoding the piggyBac transposase enzyme, and terminal inverted repeats which are recognised by the transposase and processed for integration into the target DNA. However, the piggyBac minimal elements used for integration of OX5382 rDNA into the fall armyworm genome are based on the minimal sequences (including, but not limited to, the terminal inverted repeat sequences) required by the piggyBac transposase for efficient integration into target DNA, and do not contain the coding sequence required for production of piggyBac transposase enzyme (Li et al., (2005) *Insect Mol. Biol.* 14:17-30).

Example 2

Generation of OX5368 *Spodoptera frugiperda*

Figure 4:
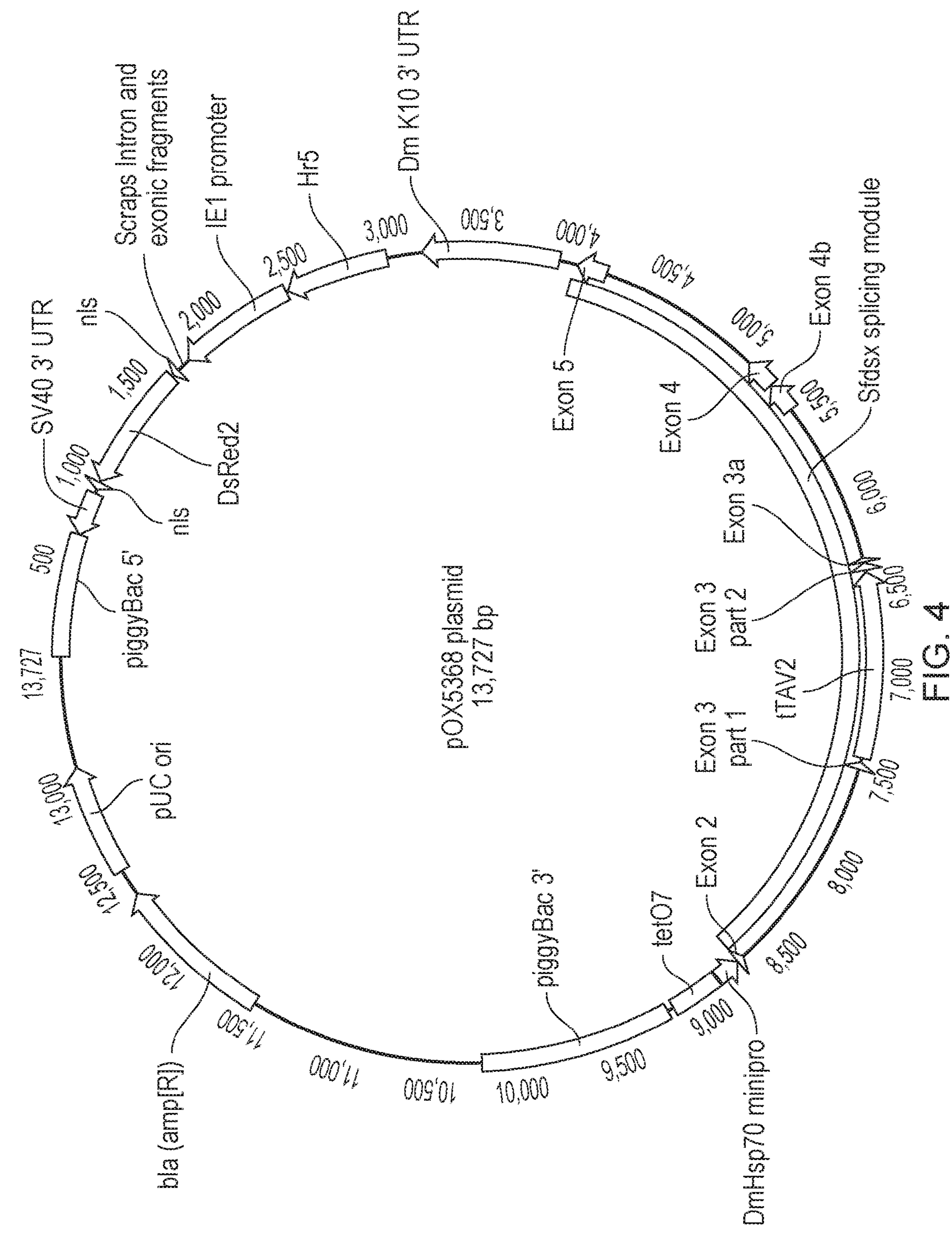
FIG. 4 shows a genetic map of pOX5368 plasmid. piggyBac 5' and 3' are sequences of the transposable element required for the insertion of OX5368 rDNA in the *Spodoptera frugiperda* genome. The DNA sequence between and including the two piggyBac elements is the rDNA that remains incorporated into the OX5368 genome.

The plasmid pOX5368 (FIG. 4) is based on cloning vector pKC26-FB2 (Genbank #HQ998855). The plasmid backbone contains the pUC origin of replication and the beta lactamase gene that confers ampicillin resistance for use in molecular cloning procedures. This plasmid section is not included in the rDNA or incorporated into the insect genome.

Plasmid pOX5368 also contains the complete rDNA that is incorporated into the insect, including the synthetic DNA sequence that encodes DsRed2 red fluorescence marker protein, synthetic DNA sequences for the tetracycline repressible transcriptional activator tTAV2 (based on a fusion of sequences from *E. coli* and HSV-1 VP16 transcriptional activator), and the modified Sfdsx splicing module derived from *Spodoptera frugiperda*. The components shown in FIG. 5 are detailed in Table 2. The plasmid was prepared using routine DNA cloning procedures.

Figure 6:
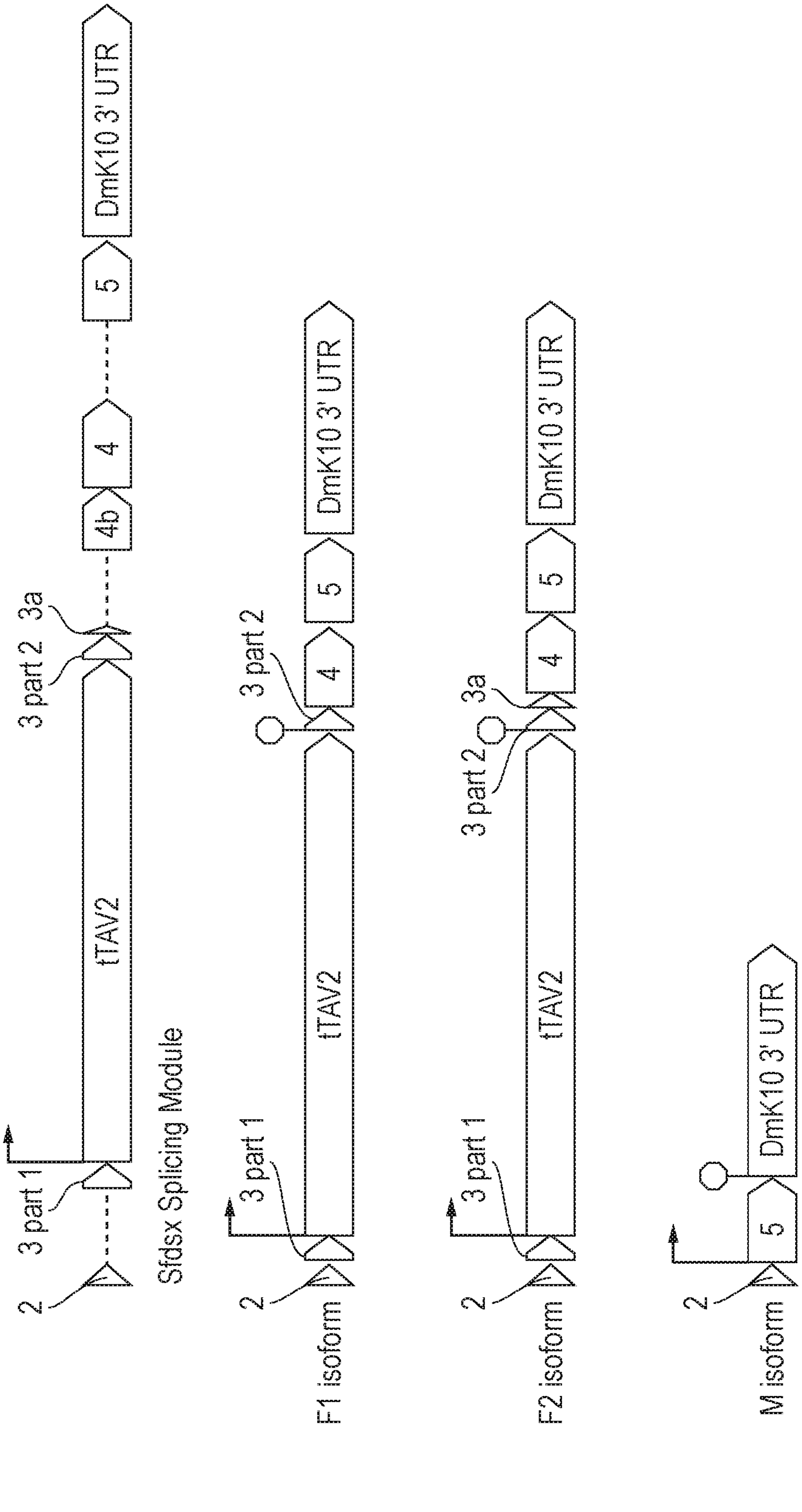
FIG. 6 shows splice variants of the self-limiting tTAV genes. The Sfdsx splice module consists of Sfdsx exons 2, 3, 3a, 4b, 4 and 5, together with Sfdsx introns 2, 3 and 4. In females, the female-specific transcripts F1 and F2 are produced. The F1 and F2 transcripts produced in female *Spodoptera frugiperda*, expressing the transgenes in the absence of tetracycline antidote, results in tTAV protein expression in a female-specific manner. The F1 and F2 transcripts contain the tTAV coding sequence and the DmK10 3'UTR and thus the F1 and F2 transcripts are able to be translated into tTAV protein. In males, only the transcripts M is produced. Transcript M contains Sfdsx exon 2 and exon 5 and DmK10 3'UTR. This transcript does not code for tTAV protein and only a short fragment of Sfdsx is produced. The arrows indicate the position of the start codons and the red octagons indicate the position of in-frame stop codons. The sequences of these transcripts and their predicted encoded proteins are given in Appendix 5. Male transcripts are likely degraded by nonsense-mediated decay (Hansen et al., 2009).

The Sfdsx_tTAV2 gene is expressed in a female-specific manner by the inclusion of portions of the *Spodoptera frupperda* doublesex gene (Sfdsx). The gene is transcribed into three different sex-specific alternatively spliced transcripts, two female-specific (F1 and F2) and one male-specific (M) transcripts (FIG. 6). The variation in the three transcripts is due to sex-specific inclusion of different mRNA sequences which result from sex-specific splicing of the RNA encoded by the Sfdsx sex-specific alternative splicing module. In the F1 and F2 transcripts, the mRNA sequence encoding tTAV2 is in-frame with the spliced Exon 2, Exon 3 5' portion and is translated into tTAV2 protein (FIG. 6). In the M transcript, the exclusion of the dsx Exons 3, 3a, 4b and 4 in the spliced transcript prevents the production of tTAV2 protein, as the tTAV2 coding sequence is spliced out of the mRNA entirely.

TABLE 2

Genetic components of OX5368

| Component | SEQ ID NO | Size (bp) | Source | Function |
|---|---|---|---|---|
| SV40 3' UTR | 43 | 228 | Synthetic non-coding fragment based on Simian virus (SV40) isolated from pDsRed2-N1 (Clontech plasmid) | A 3' untranslated sequence. It contains the transcription termination and polyadenylation signals |
| nls | 2, 46 | 21, 21 | Synthetic sequence | nls: Nuclear Localisation Signal. Synthetic DNA sequences that encode protein domains at the N- and Cterminal ends of DsRed2 for import into the cell nucleus by importins |
| DsRed2 | 1 | 675 | Synthetic DNA (Clontech) encoding a variant of red fluorescent protein originally identified in *Discosoma* | Marker gene - a red fluorescent protein. |
| scraps intron and exonic fragments | 3 | 87 | *Drosophila melanogaster* | An intron cloned upstream of the DsRed2 coding sequence to facilitate transcription of mRNA. |
| IE1 promoter | 4 | 633 | Baculovirus *Autographa californica* nuclear polyhedrovirus (AcNPV) | Promoter to drive the expression of DsRed2 protein. |
| Hr5 enhancer | 5 | 563 | Baculovirus *Autographa californica* nuclear polyhedrovirus (AcNPV) | Transcriptional enhancer to stimulate expression from the IE1 promoter. |
| DmK10 3' UTR | 19 | 772 | *Drosophila melanogaster* | A 3' untranslated sequence. It contains the transcription termination and polyadenylation signals |
| Sfdsx splicing module | 6 | 4702 | Splice Module | |
| | 17 | 194 | Sfdsx Exon 5 | Female-specific splicing module from *Spodoptera frugiperda* dsx |
| | 16 | 901 | Sfdsx Intron 4 | |
| | 15 | 166 | Sfdsx Exon 4 | |
| | 14 | 134 | Sfdsx Exon 4b | |
| | 13 | 933 | Sfdsx Intron 3 | |
| | 12 | 15 | Sfdsx Exon 3a | |

TABLE 2-continued

| Genetic components of OX5368 | | | | |
|---|---|---|---|---|
| Component | SEQ ID NO | Size (bp) | Source | Function |
| | 94, 9 | 41 and 42 | Sfdsx Exon 3 (with tTAV2 inserted) | |
| | 8 | 1195 | Sfdsx Intron 2 | |
| | 7 | 38 | Sfdsx Exon 2 | |
| Linker 1 | 95 | 18 | Linker to join tTAV2 to first portion of Exon 3 | |
| tTAV2 | 10 | 1014 | Synthetic DNA encoding the fusion tetracycline transactivator protein. Optimised for expression in insects. | Tetracycline repressible transcription factor. |
| Linker 2 | 96 | 11 | Linker to join tTAV2 to second portion of Exon 3 | |
| DmHsp70 minipro | 18 | 130 | Drosophila melanogaster | The minimal promoter (43 bp) and the 5' UTR (87 bp) from the hsp70 gene promotes expression when the tTAV2 is bound to the neighbouring TetO operator. |
| tetOx7 | 20 | 296 | Synthetic DNA contains 7 repeats of Tn10 tet-operon | Binds tTAV2 in the absence of tetracycline, facilitating expression by the neighbouring mini-promoter. |

Transformation was effected with a non-autonomous piggyBac transposable element, first described in (Thibault et al., 1999), co-injected with a non-integrating source of piggyBac transposase (mRNA transcribed in vitro from plasmid pOX3022). The piggyBac transposon was originally isolated from a cell culture of Trichoplusia ni, and has been used in several insect transformations (Diptera, Lepidoptera, Coleoptera) (Handler, 2002; O'Brochta et al., 2003; Tamura et al., 2000). This transposon, as initially described, consists of two components, a coding sequence encoding the piggyBac transposase enzyme, and terminal inverted repeats which are recognised by the transposase and processed for integration into the target DNA. However, the piggyBac minimal elements used for integration of OX5368 rDNA into the fall armyworm genome are based on the minimal sequences (including, but not limited to, the terminal inverted repeat sequences) required by the piggyBac transposase for efficient integration into target DNA, and do not contain the coding sequence required for production of piggyBac transposase enzyme (Li et al., 2005).

Example 3

Generation of OX5382 *Spodoptera frugiperda*

Figure 7:
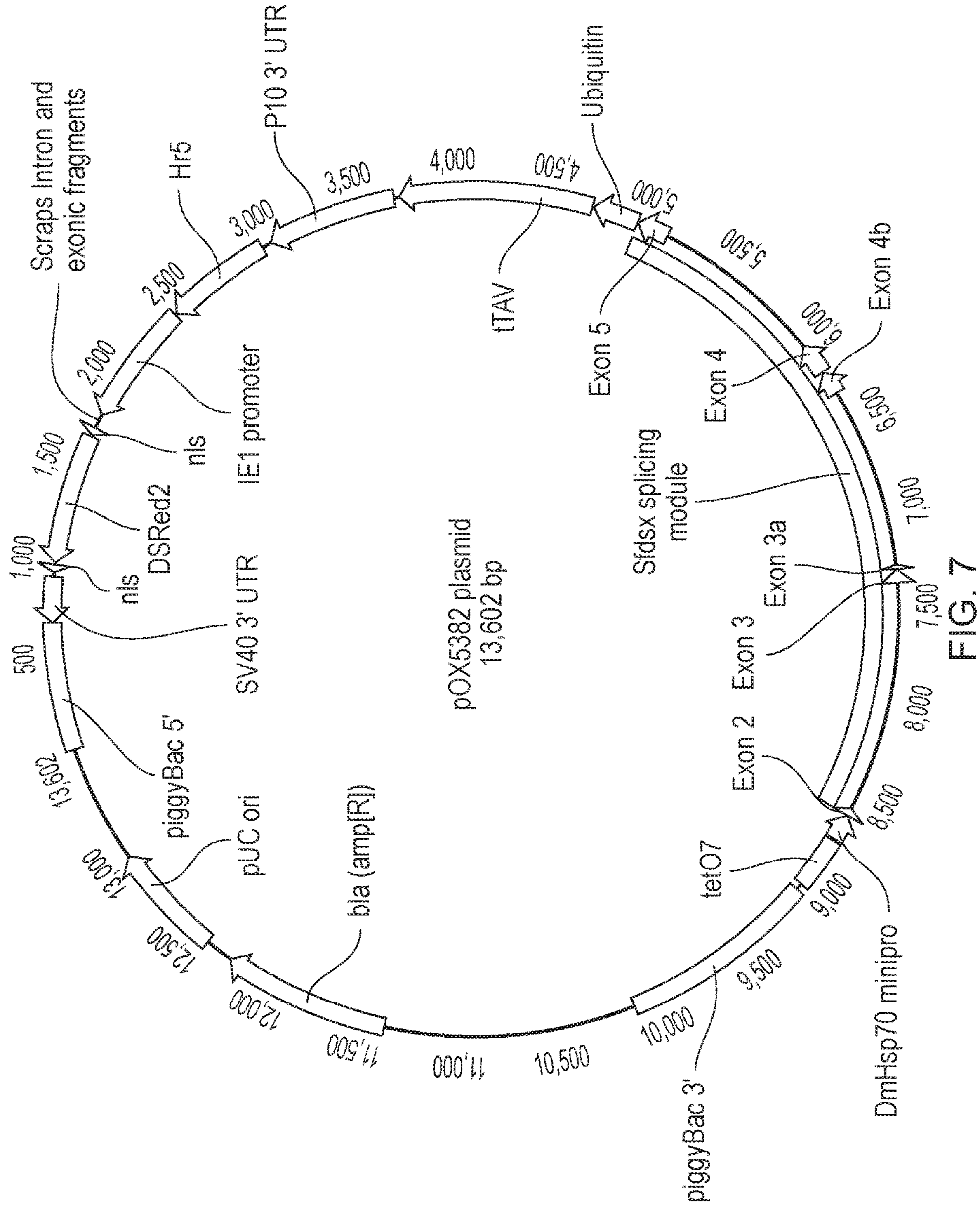
FIG. 7 shows a genetic map of pOX5382 plasmid. piggyBac 5' and 3' are sequences of the transposable element required for the insertion of OX5382 rDNA in the *Spodoptera frugiperda* genome. The DNA sequence between and including the two piggyBac elements is the rDNA that remains incorporated into the OX5382G genome.

The plasmid pOX5382 (FIG. 7) is based on cloning vector pKC26-FB2 (Genbank #HQ998855). The plasmid backbone contains the pUC origin of replication and the betalactamase gene that confers ampicillin resistance for use in molecular cloning procedures. This plasmid section is not included in the rDNA or incorporated into the insect genome.

pOX5382 also contains the complete rDNA that is incorporated into the insect, including the synthetic DNA sequence that encodes DsRed2 red fluorescence marker protein, synthetic DNA sequences for the tetracycline repressible transcriptional activator tTAV (based on a fusion of sequences from *E. coli* and HSV-1 VP16 transcriptional activator), and the modified Sfdsx splicing module derived from *Spodoptera frupperda*. The components shown in FIG. 8 are detailed in Table 3. The plasmid was prepared by Oxitec Ltd using routine DNA cloning procedures.

The Sfdsx_tTAV gene is expressed in a female-specific manner by the inclusion of portions of the *Spodoptera frupperda* doublesex gene (Sfdsx). The gene is transcribed into three different sex-specific alternatively spliced transcripts, two female-specific (F1 and F2) and one male-specific (M) transcripts (FIG. 9). The variation in the three transcripts is due to sex-specific inclusion of different mRNA sequences which result from sex-specific splicing of the RNA encoded by the Sfdsx sex-specific alternative splicing module. In the F1 and F2 transcripts, the sequence encoding tTAV is in frame with the upstream start codon (FIG. 9). In the M transcript, the exclusion of the dsx exons 3, 3a, 4b and 4 prevents the production of tTAV protein, as the tTAV coding sequence is out of frame with the tTAV start codon, and also in frame with a stop codon which lies downstream of exon 5, before the tTAV coding sequence. M transcripts thus contain in-frame stop codon(s) in their coding sequences which likely lead to M transcript mRNA degradation by nonsense-mediated decay (Hansen et al., 2009).

TABLE 3

Genetic Components of OX5382

| Component | Location | Size (bp) | Source | Function |
|---|---|---|---|---|
| SV40 3' UTR | 21 | 228 | Synthetic non-coding fragment based on Simian virus (SV40) isolated from pDsRed2-N1 (Clontech plasmid) | A 3' untranslated sequence. It contains the transcription termination and polyadenylation signals |
| nls | 22, 24 | 21, 21 | Synthetic sequence | nls: Nuclear Localisation Signal. Synthetic DNA sequences that encode protein domains at the Nand C-terminal ends of DsRed2 for import into the cell nucleus by importins |
| DsRed2 | 23 | 675 | Synthetic DNA (Clontech) encoding a variant of red fluorescent protein originally identified in *Discosoma* | Marker gene - a red fluorescent protein. |
| scraps intron and exonic fragments | 25 | 87 | *Drosophila melanogaster* | An intron cloned upstream of the DsRed2 coding sequence to facilitate transcription of mRNA. |
| IE1 promoter | 26 | 633 | Baculovirus *Autographa californica* nuclear polyhedrovirus (AcNPV) | Promoter to drive the expression of DsRed2 protein. |
| Hr5 enhancer | 27 | 563 | Baculovirus *Autographa californica* nuclear polyhedrovirus (AcNPV) | Transcriptional enhancer to stimulate expression from the IE1 promoter. |
| P10 3' UTR | 28 | 667 | Baculovirus *Autographa californica* nuclear polyhedrovirus (AcNPV) | A 3' untranslated sequence. It contains the transcription termination and polyadenylation signals |
| tTAV | 29 | 1011 | Synthetic DNA encoding the fusion tetracycline transactivator protein. Optimised for expression in insects. | Tetracycline repressible transcription factor. |
| Ubiquitin | 30 | 225 | Ubiquitin from *Drosophila melanogaster* | Stimulates cleavage of tTAV protein from the Sfdsx_ubiquitin that is N-terminally fused |
| Sfdsx splicing module | 31 | 3643 | Splicing module | |
| | 40 | 172 | Sfdsx Exon 5 | Female-specific splicing module from *Spodoptera frugiperda* dsx gene generates tTAV protein only in female OX5382. |
| | 39 | 901 | Sfdsx Intron 4 | |
| | 38 | 166 | Sfdsx Exon 4 | |
| | 37 | 134 | Sfdsx Exon 4b | |
| | 36 | 933 | Sfdsx Intron 3 | |
| | 35 | 15 | Sfdsx Exon 3a | |
| | 34 | 84 | Sfdsx Exon 3 | |
| | 33 | 1195 | Sfdsx Intron 2 | |
| | 32 | 40 | Sfdsx Exon 2 | |
| | ATG | 3 | Sfdsx ATG start codon | |

TABLE 3-continued

| Genetic Components of OX5382 | | | | |
|---|---|---|---|---|
| Component | Location | Size (bp) | Source | Function |
| DmHsp70 minipro | 41 | 130 | *Drosophila melanogaster* | The minimal promoter (43 bp) and the 5' UTR (87 bp) from the hsp70 gene promotes expression when the tTAV is bound to the neighbouring TetO operator. |
| tetOx7 | 42 | 296 | Synthetic DNA contains 7 repeats of Tn10 tetoperon | Binds tTAV in the absence of tetracycline, facilitating expression by the neighbouring minipromoter. |

Transformation was effected with a non-autonomous piggyBac transposable element, first described in (Thibault et al., 1999), co-injected with a non-integrating source of piggyBac transposase (mRNA transcribed in vitro from plasmid pOX3022). The piggyBac transposon was originally isolated from a cell culture of *Trichoplusia ni*, and has been used in several insect transformations (Diptera, Lepidoptera, Coleoptera) (Handler, 2002; O'Brochta et al., 2003; Tamura et al., 2000). This transposon, as initially described, consists of two components, a coding sequence encoding the piggyBac transposase enzyme, and terminal inverted repeats which are recognised by the transposase and processed for integration into the target DNA. However, the piggyBac minimal elements used for integration of OX5368 rDNA into the fall armyworm genome are based on the minimal sequences (including, but not limited to, the terminal inverted repeat sequences) required by the piggyBac transposase for efficient integration into target DNA, and do not contain the coding sequence required for production of piggyBac transposase enzyme (Li et al., 2005).

Figure 16:
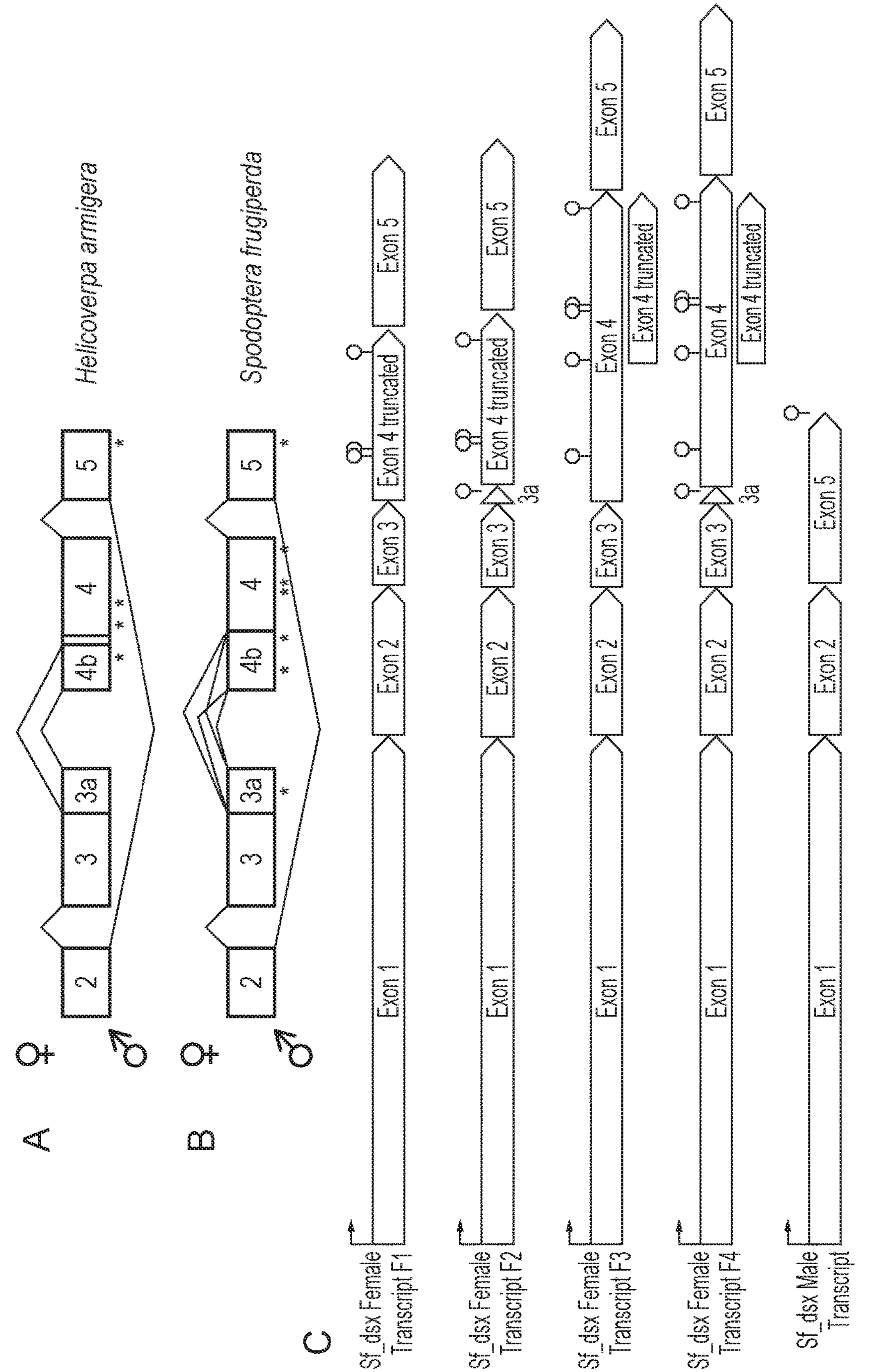
FIG. 16 shows the splice patterns of selected Noctuids for Exons 2, 3, 3a, 4b, 4 and 5 of dsx: A: Splice patterns of female (top) and male (bottom) of *Helicoverpa armigera* (Black boxes, exons; grey boxes alternative splice site within exon; white box: 3'UTR-type sequence; *: Stop Codon) as shown in Wang X. Y. et al. (2014) *Insect Biochem. Mol. Biol.* 44:1-11; B: Splice patterns of female (top) and male (bottom) of *Spodoptera frugiperda* (Black boxes, exons; grey boxes alternative splice site within exon); C: detail of endogenous spliced female (F1, F2, F3, and F4) and male transcripts (Stop Sign designates Stop Codons).
Figure 18:
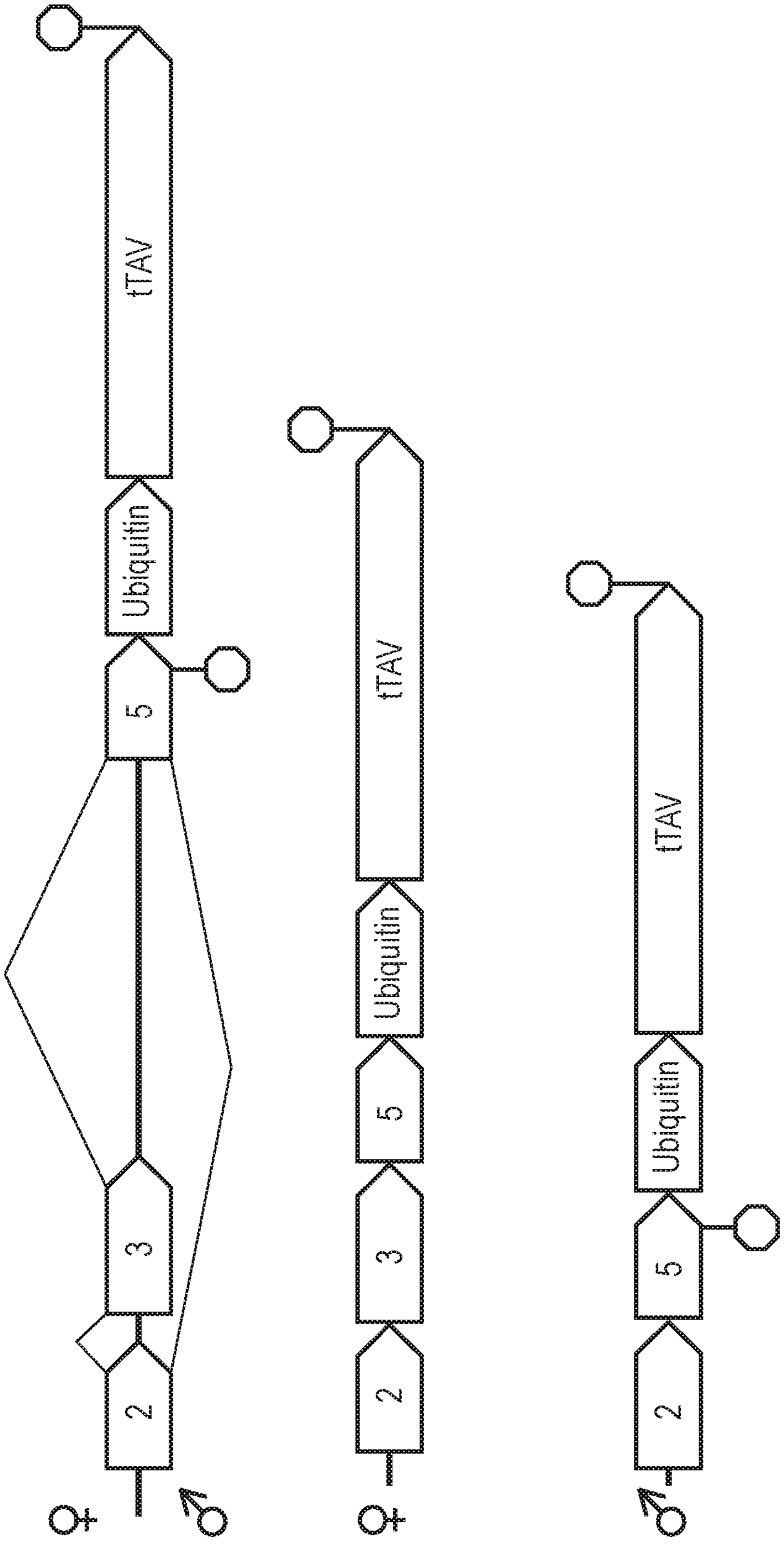
FIG. 18 shows an embodiment of the female-specific expression system that contains only Exons 2, 3 and 5 as part of the splicing cassette; in females, the splicing results in the joining of Exons 2, 3 and 5 (in-frame along with, in this case, a ubiquitin leader sequence and the tTAV gene) resulting in the death of females. In males, the splicing results in the joining of Exons 2 and 5 which results in a Stop Codon before translation of the ubiquitin leader or tTAV sequence, so males survive.

Female and male transcripts of wild-type *S. frugiperda* are shown diagrammatically in FIG. 16C in which endogenous Stop codons prevent translation of the spliced primary transcripts except in the case of male *S. frugiperda*. The splicing of exons in wild-type *S. frugiperda* and a related Noctuid (*Helicoverpa armigera*) are shown in FIGS. 16B and 16A, respectively. These related Noctuids splice the exons in a highly conserved manner.

FIG. 17 shows the amino acid sequences for Exons, 2, 3, 3a, 4, and 5 encoded by female (F) and male (M) transcripts of dsx for constructs OX5403, OX5368, OX5382, endogenous wild-type *S. frugiperda* (Endo) and *Helicoverpa armigera* (HA). As *H. armigera* and wild-type *S. frugiperda* have Stop codons in Exon 3, the females do not translate Exons 3a, 4b, 4, or 5. The constructs of the invention introduced changes to open the reading frames of Exons 3, 3a, 4 and 5 to allow the females to translate the entire set of exons, although the translation of Exon 5 is in a different reading frame from male transcripts and results in a different amino acid sequence. (compare FIG. 17E with FIG. 17F).

Example 4

Penetrance of Traits in Genetically-Engineered *Spodoptera frugiperda*

Figure 10:
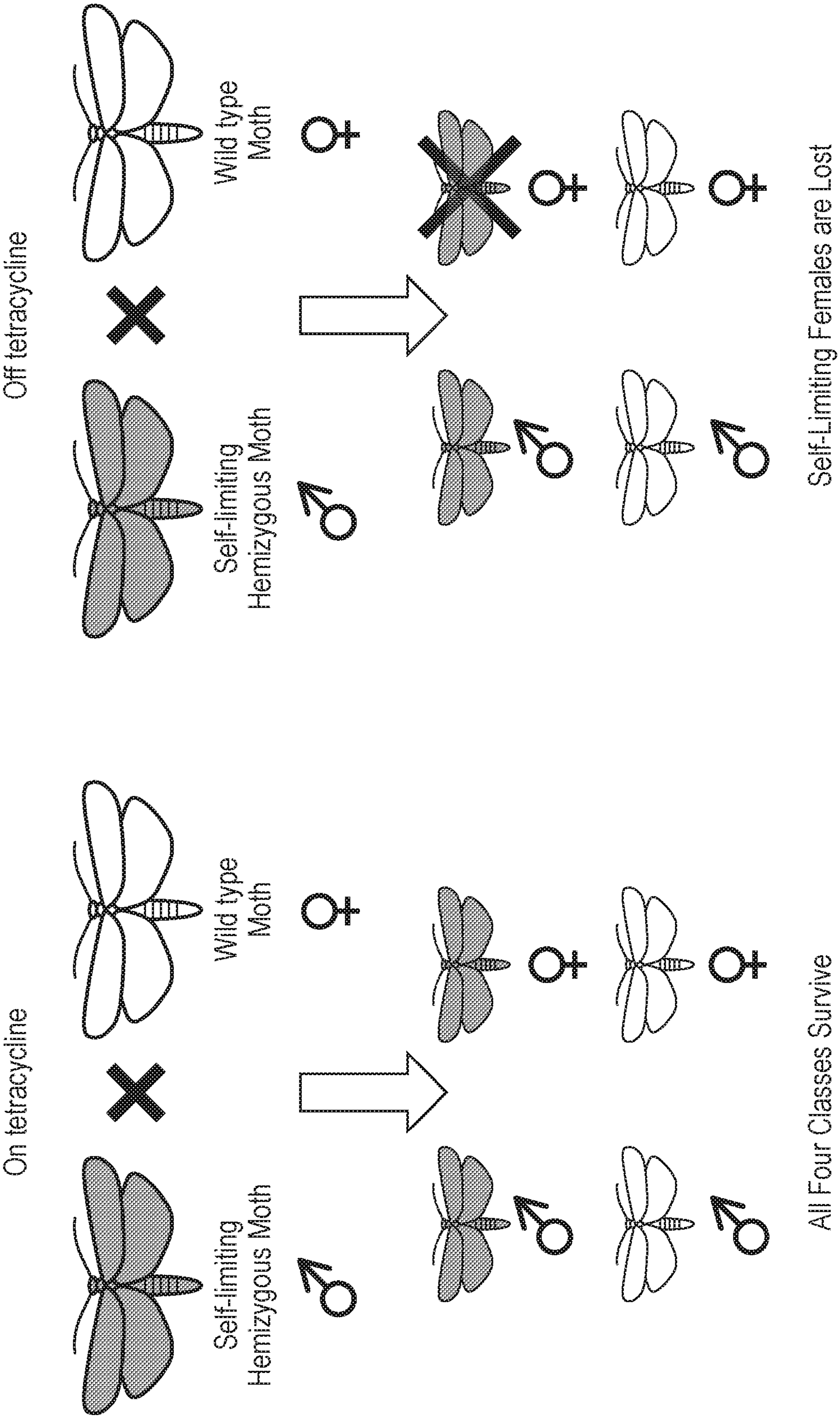
FIG. 10 shows the results of breeding of hemizygous Noctuid insects on tetracycline (left) or off tetracycline (right), in the feed of larval stages; shaded moths contain the female-specific gene expression system, white moths are wild-type; when raised on tetracycline, the female-specific expression system is turned off and both male and female offspring survive to adulthood; when reared off tetracycline, a copy of the female-specific gene expression system may be inherited by offspring, and of the moths inheriting the female-specific gene expression system, only the males will survive to adulthood.

To assess penetrance and repressibility of the early bisex self-limiting trait in OX5403, OX5368, and OX5382, test crosses were made between hemizygous male OX5403, OX5368, and OX5382, and wild-type female moths. First instar larvae were collected from these crosses and reared in individual cells and fed a diet that either contained 100 μg/ml doxycycline ("ondoxycycline") or did not contain doxycycline (0 μg/ml) ("off-doxycycline"). It was expected that there would be four classes of moths from these crosses: (1) male self-limiting moths; (2) female self-limiting moths; (3) wild-type male moths; and (4) wild-type female moths. If there was good penetrance of the self-limiting trait, all classes would survive on doxycycline, but in the absence of doxycycline, female self-limiting moths would die (FIG. 10). Several substrains of each of OX5403, OX5368, and OX5382 were tested. Strains that satisfied penetrance criteria were selected for further development. The results for each of strains, OX5368C, OX5403A and OX5382G and OX5382J are shown in FIG. 11, FIG. 12, FIG. 13, and FIG. 14, respectively.

Figure 11:
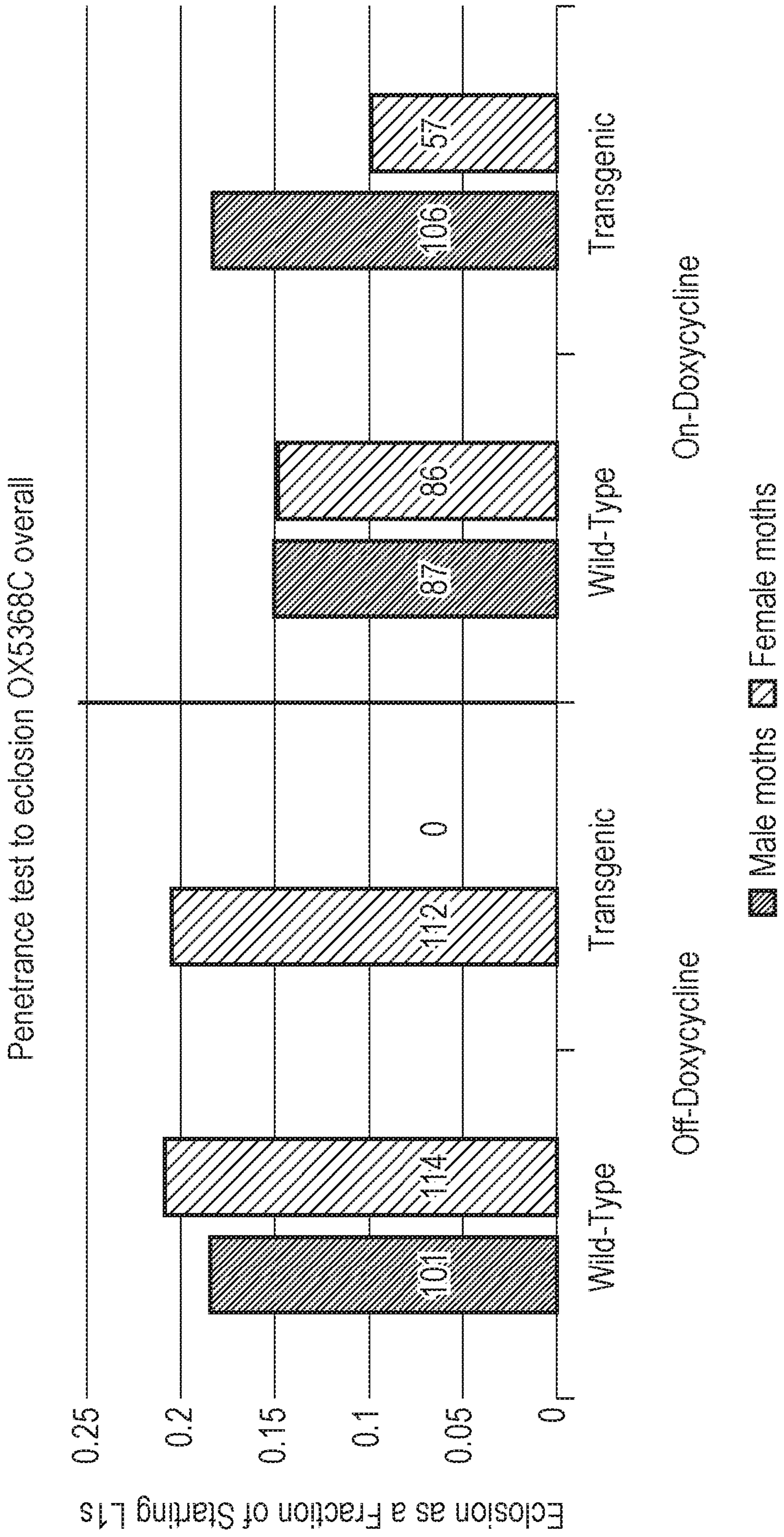
FIG. 11 shows survival of OX5368C male and female survival on doxycycline and off doxycycline. Without doxycycline, no females survive.
Figure 12:
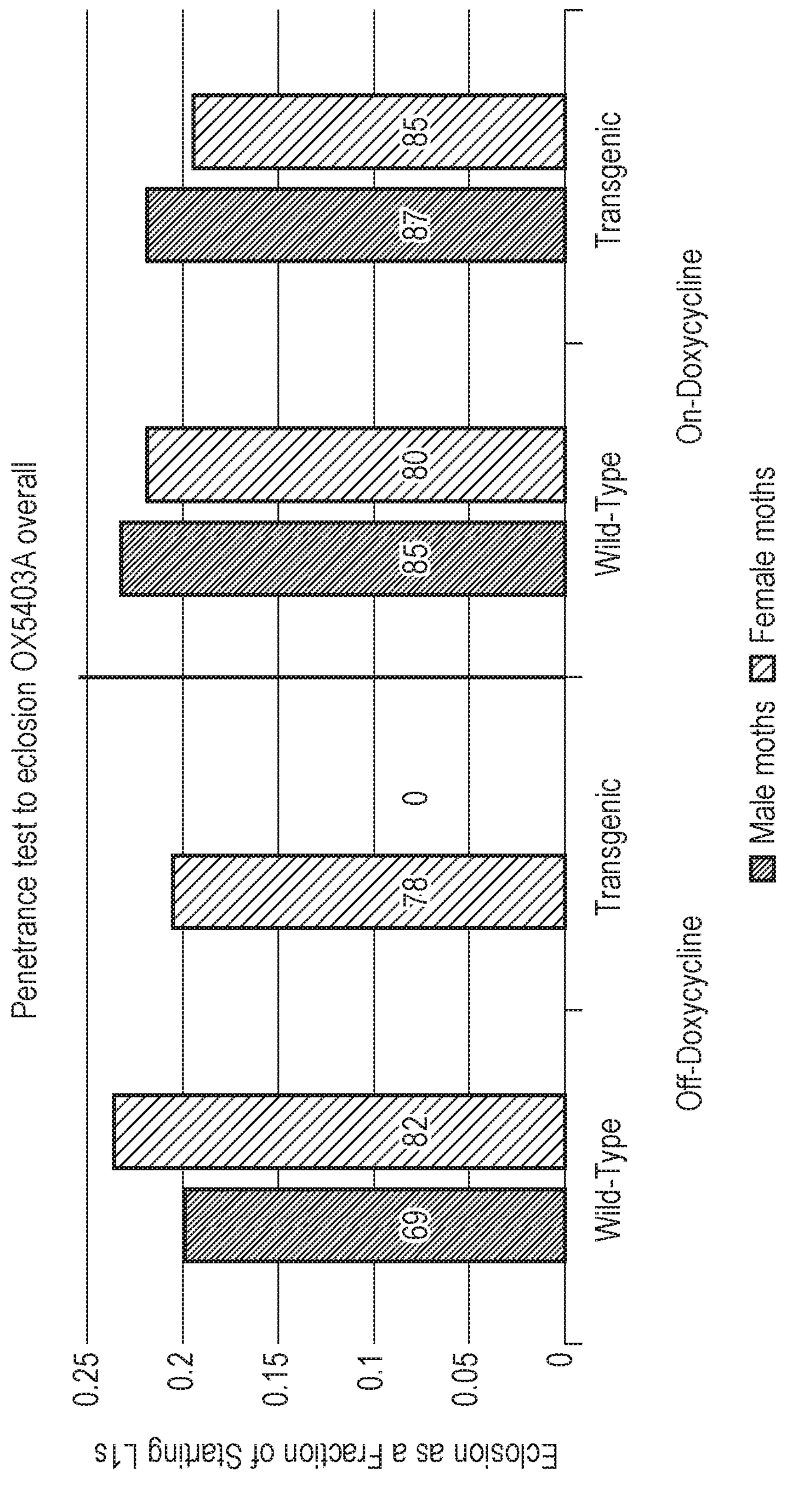
FIG. 12 shows survival of OX5403A male and female survival on doxycycline and off doxycycline. Without doxycycline, no females survive.

FIG. 11 shows that while OX5368C females carrying the self-limiting trait were fully viable on-doxycycline, no OX5368C females survived to adulthood off-doxycycline. Likewise, FIG. 12 shows that while OX5403A females carrying the self-limiting trait were fully viable ondoxycycline, no OX5403A females survived to adulthood off-doxycycline.

Figure 13:
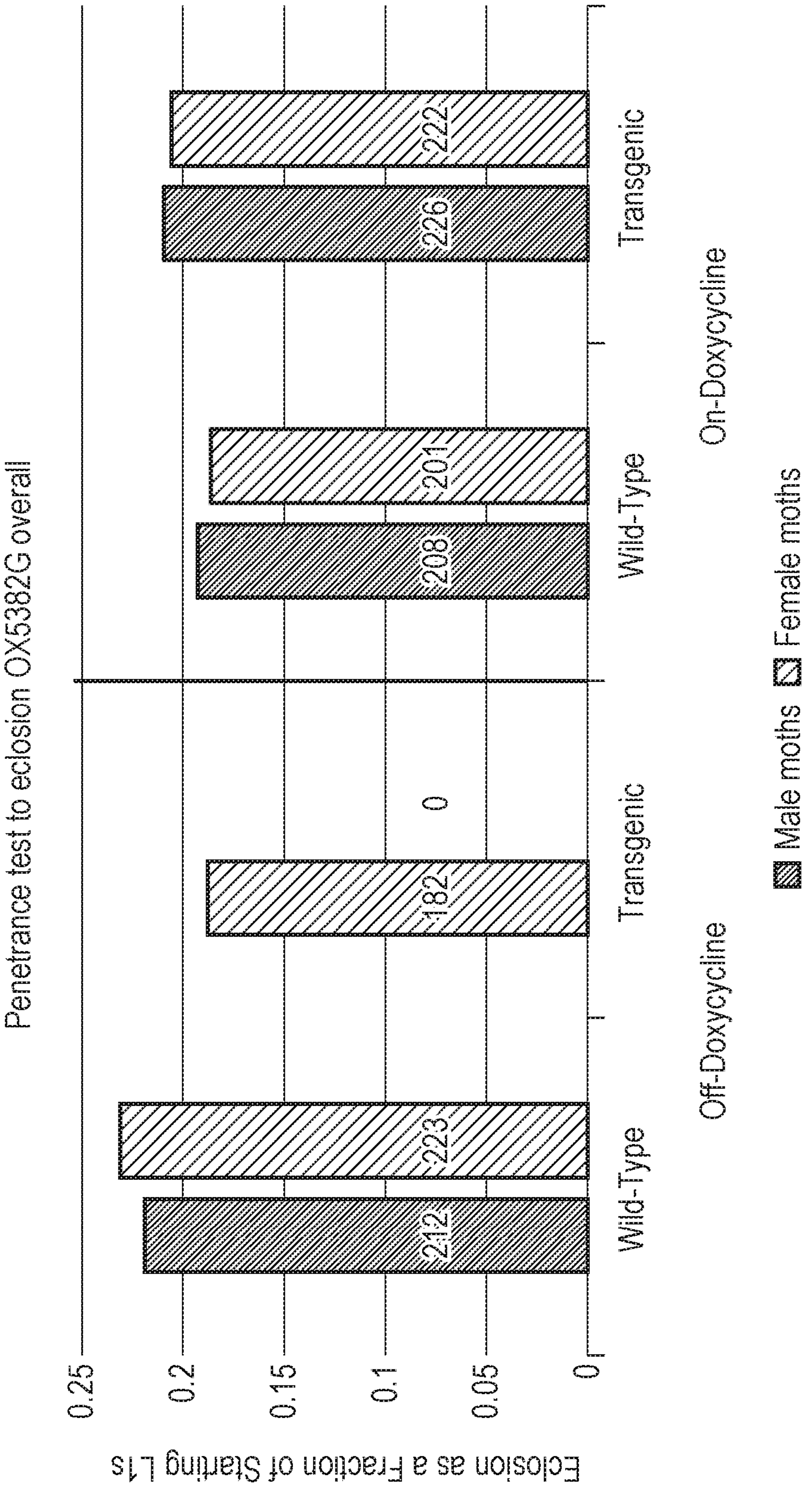
FIG. 13 shows survival of OX5382G male and female survival on doxycycline and off doxycycline. Without doxycycline, no females survive.
Figure 14:
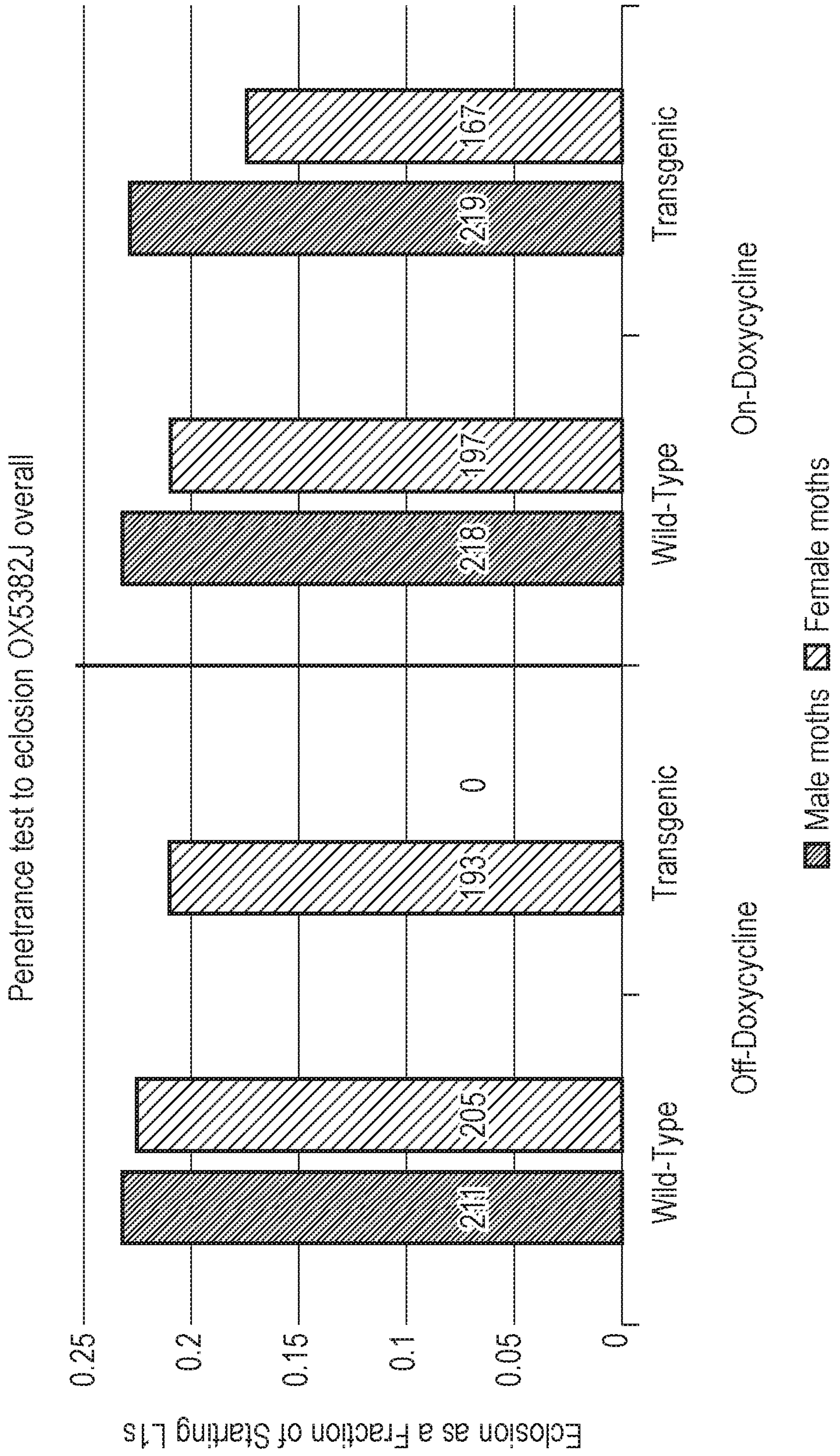
FIG. 14 shows survival of OX5382J male and female survival on doxycycline and off doxycycline. Without doxycycline, no females survive.

Two strains of OX5382 were selected for as fulfilling the penetrance objective: OX5382G and OX5382J. Similar to OX5403A and OX5368C, both OX5382G and OX5382J females carrying the self-limiting trait were viable on-doxycycline (although somewhat less so than their wild-type counterparts), but no OX5382G or OX5382J females survived to adulthood off-doxycycline (FIG. 13 and FIG. 14, respectively).

Example 5

Assessment of Fluorescence in Moth Life Stages

Transgenic strains carrying the self-limiting gene construct also carry and express the fluorescent protein DsRed2 (Clontech; Matz, M.V. et al. (1999) *Nature Biotechnol.* 17:969-973; Lukyanov et al., (2000) *J. Biol. Chem.* 275(34): 25879).

Assessment of expression of the DsRed2 transgene in moths was carried out by examining early larvae, final instar larvae, pupae and adults of both transgenic and wild type *S.*

Figure 15:
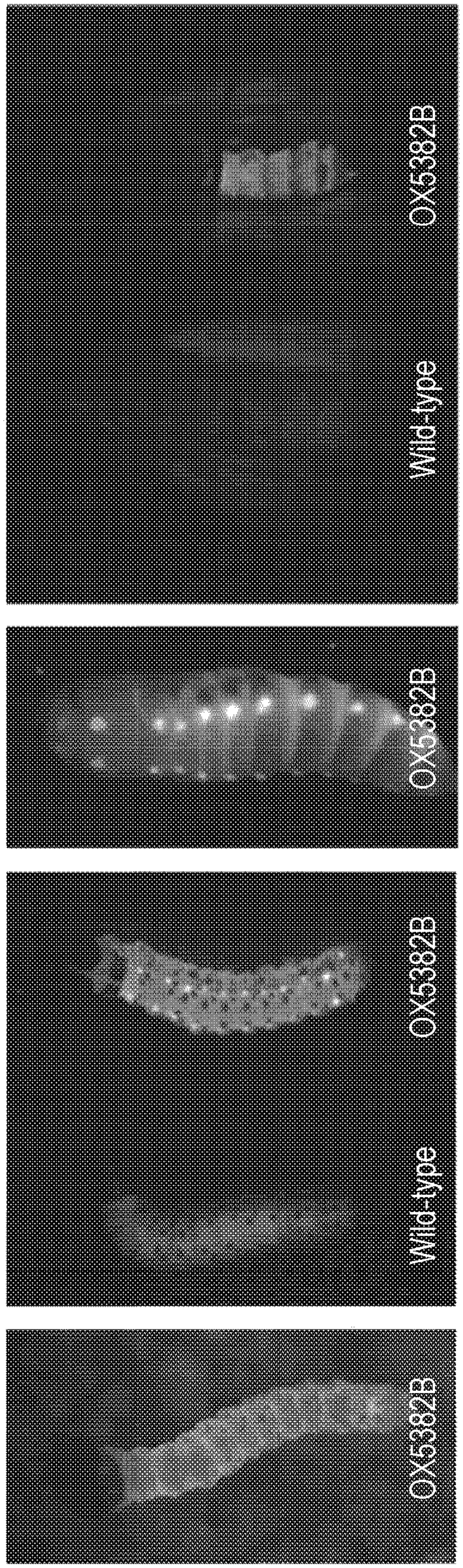
FIG. 15 shows DsRed2 fluorescence in various life stages of OX5382B transgenic *S. frugiperda* as compared to wild type *S. frugiperda.*

*frugiperda* for DsRed2 fluorescence using a Leica M80 microscope equipped with filters for detection: maximum excitation 563 nm, emission 582 nm. The results are shown in FIG. 15. DsRed2 fluorescence was detected in all life stages of *S. frugiperda*.

Sequence Listing Free Text

SEQ ID NO: 1: Variant of red fluorescent protein from Discosoma (clontech)
SEQ ID NO: 2: Synthetic DNA
SEQ ID NO: 6: Synthetic DNA based on *Spodoptera frugiperda* sequences
SEQ ID NO: 10: Optimised fusion tetracycline transactivator protein
SEQ ID NO: 20: Synthetic DNA contains 7 repeats of Tn10 tet-operon
SEQ ID NO: 22: Synthetic DNA
SEQ ID NO: 23: Variant of red fluorescent protein from Discosoma (Clontech)
SEQ ID NO: 24: Synthetic DNA
SEQ ID NO: 29: Optimised fusion tetracycline transactivator protein
SEQ ID NO: 31: Synthetic DNA based on *Spodoptera frugiperda* sequences
SEQ ID NO: 42: Synthetic DNA contains 7 repeats of Tn10 tet-operon
SEQ ID NO: 44: Synthetic DNA
SEQ ID NO: 45: Variant of red fluorescent protein from Discosoma (Clontech)
SEQ ID NO: 46: Synthetic DNA
SEQ ID NO: 51: Optimised fusion tetracycline transactivator protein
SEQ ID NO: 53: Synthetic DNA based on *Spodoptera frugiperda* sequences
SEQ ID NO: 63: Based on sequences from TYMV, hCMV & 7 repeats of Tn10 tet operon
SEQ ID NO: 64: Synthetic non-coding fragment based on TYMV sequence
SEQ ID NO: 66: Synthetic DNA contains 7 repeats of Tn10 tet-operon
SEQ ID NO: 67: tTAV2
SEQ ID NO: 68: tTAV3
SEQ ID NO: 80: tTAV
SEQ ID NO: 81: tTAV2
SEQ ID NO 82: tTAV3
SEQ ID NO: 83: Synthetic DNA contains 14 repeats of Tn10 tet-operon
SEQ ID NO: 84: Synthetic DNA contains 21 repeats of Tn10 tet-operon
SEQ ID NO: 85: Variant of red fluorescent protein from Discosoma (Clontech)
SEQ ID NO: 86: Plasmid construct for expression in arthropods
SEQ ID NO: 87: Plasmid construct for expression in arthropods
SEQ ID NO: 88: Plasmid construct for expression in arthropods
SEQ ID NO: 95: Synthetic DNA linker
SEQ ID NO: 96: Synthetic DNA linker
SEQ ID NO: 97: tTAV2
SEQ ID NO: 98: tTAV3
SEQ ID NO: 99: tTAV2 ORF
SEQ ID NO: 100: tTAV2
SEQ ID NO: 101: tTAV
SEQ ID NO: 102: tTAV
SEQ ID NO: 103: Translation of transcript from 5403 and 5382
SEQ ID NO: 104: Translation of Exon 2 from Endo
SEQ ID NO: 105: Translation of Exon 2 from HA
SEQ ID NO: 106: Translation of exon 3 F transcript from 5403
SEQ ID NO: 107: Translation of Exon 3 F transcript from 5382
SEQ ID NO: 108: Translation of Exon 3 F transcript from Endo 1
SEQ ID NO: 109: Translation of Exon 3 F transcript from Endo 2
SEQ ID NO: 110: Translation of Exon 3 F transcript from HA
SEQ ID NO: 111: Translation of Exon 4 F transcript from 5403 and 5382
SEQ ID NO: 112: Translation of Exon 5 M transcript from HA

The invention claimed is:

1. A splicing cassette for directing sex-specific splicing of a polynucleotide encoding a functional protein wherein the coding sequence of said functional protein is defined between a start codon and a stop codon, comprising in the following order:

at least one Exon 2, or portion thereof, of a Noctuidae doublesex (dsx) gene;

at least one Intron 2, or portion thereof, of a Noctuidae dsx gene, wherein said Intron 2 or portion thereof comprises a splice donor site and a splice acceptor site;

at least one Exon 3, or portion thereof, of a Noctuidae dsx gene;

at least one Exon 4, or portion thereof, of a Noctuidae dsx gene;

at least one Intron 4, or portion thereof, of a Noctuidae dsx gene, wherein said Intron 4 or portion thereof comprises a splice donor site and a splice acceptor site; and at least one Exon 5, or portion thereof, of a Noctuidae dsx gene; and optionally further comprising at least one Exon 3a, or portion thereof, of a Noctuidae dsx gene between the at least one Exon 3 or portion thereof and the at least one Exon 4 or portion thereof;

optionally further comprising at least one Intron 3, or portion thereof, of a Noctuidae dsx gene between the at least one Exon 3 or portion thereof and the at least one Exon 4 or portion thereof, wherein said Intron 3 or portion thereof comprises a splice donor site and a splice acceptor site; and optionally further comprising at least one Exon 4b, or portion thereof, of a Noctuidae dsx gene between the at least one Exon 3 or portion thereof and the at least one Exon 4 or portion thereof; wherein:

a. a first splicing of an RNA transcript in males of said polynucleotide produces a first spliced mRNA product, which does not have a continuous open reading frame extending from said start codon to said stop codon; and b. an alternative splicing of said RNA transcript in females produces an alternatively spliced mRNA product which comprises a continuous open reading frame extending from said start codon to said stop codon.

2. The splicing cassette of claim 1, wherein the polynucleotide encoding said functional protein is located:

a. 3' of said Exon 2, and at least a portion of Exon 3; or b. 3' of said Exon 2, Exon 3, and Exon 5, and optionally, 3' of Exon 3a, Exon 4, and Exon 4b.

3. The splicing cassette of claim 1, wherein said primary transcript is spliced in males such that translation terminates 5' of the polynucleotide encoding said functional protein, or such that the polynucleotide encoding said functional protein is spliced out of said primary transcript.

4. The splicing cassette of claim 1, wherein Exon 3 is divided into two portions wherein said Noctuidae dsx Exon 3 comprises a first portion having a polynucleotide sequence of SEQ ID NO:94 and a second portion comprising a polynucleotide sequence of SEQ ID NO:9, wherein the polynucleotide encoding said functional protein is positioned in between said first portion and said second portion, optionally with polynucleotide linkers of SEQ ID NO: 95 and SEQ ID NO:96.

5. The splicing cassette of claim 1, wherein said Noctuidae dsx gene comprises an Exon or Intron having a polynucleotide sequence selected from the group consisting of:

a. Exon 3 comprising a polynucleotide sequence of SEQ ID NO:94, SEQ ID NO:34, or SEQ ID NO:56;

b. Exon 2 comprising a polynucleotide sequence of SEQ ID NO:7 or SEQ ID NO: 32;

c. Exon 3a comprising a polynucleotide sequence of SEQ ID NO:12;

d. Exon 4 comprising a polynucleotide sequence of SEQ ID NO:15;

e. Exon 4b comprising a polynucleotide sequence of SEQ ID NO:14;

f. Exon 5 comprising a polynucleotide sequence of SEQ ID NO:17;

g. Intron 2 comprising a polynucleotide sequence of SEQ ID NO:55;

h. Intron 3 comprising a polynucleotide sequence of SEQ ID NO:58; and i. Intron 4 comprising a polynucleotide sequence of SEQ ID NO:39.

6. The splicing cassette of claim 1, wherein said Noctuidae dsx Exon 2 having a polynucleotide of sequence of SEQ ID NO:7 or SEQ ID NO:32; a Noctuidae dsx Exon 3 having a polynucleotide of sequence of SEQ ID NO:94, SEQ ID NO:34 or SEQ ID NO: 56; a Noctuidae dsx Exon 3a having a polynucleotide of sequence of SEQ ID NO: 12; a Noctuidae dsx Exon 4 having a polynucleotide of sequence of SEQ ID NO:15; a Noctuidae dsx Exon 4b having a polynucleotide of sequence of SEQ ID NO:14; and a Noctuidae dsx Exon 5 having a polynucleotide of sequence of SEQ ID NO:17; and, optionally, a Noctuidae dsx Intron 2 having a polynucleotide of sequence of SEQ ID NO:55; a Noctuidae dsx Intron 3 having a polynucleotide of sequence of SEQ ID NO:58; and a Noctuidae dsx Intron 4 having a polynucleotide of sequence of SEQ ID NO:39.

7. The splicing cassette of claim 1, wherein said Noctuidae dsx gene is derived from a species of the genus *Spodoptera, Helicoverpa, Chrysodeixis, Anticarsia, Peridroma* or *Heliothis.*

8. The splicing cassette of claim 1, wherein said splicing cassette further comprises a ubiquitin leader sequence 5' of the polynucleotide encoding said functional protein.

9. An arthropod female-specific gene expression system for controlled expression of an effector gene in an arthropod comprising:

a. a promoter;

b. a polynucleotide encoding a functional protein, the coding sequence of which is defined between a start codon and a stop codon; and c. the splicing cassette of claim 1.

10. A method of suppressing populations of wild arthropods and reducing, inhibiting or eliminating crop damage from arthropods, comprising releasing genetically engineered male arthropods comprising the expression system of claim 9 among a population of wild arthropods of the same species, allowing said genetically engineered male arthropods to mate with said wild arthropods, wherein a female offspring splices a primary transcript of said expression system to produce a functional protein having a lethal, deleterious or sterilizing effect, thereby suppressing the population of wild arthropods and reducing, inhibiting or eliminating crop damage caused by wild arthropods.

11. A method of slowing or reversing resistance to insecticides and/or biopesticides in Noctuid insects, comprising releasing insecticide- and/or biopesticide-susceptible, genetically engineered male Noctuid insects comprising the expression system of claim 9 among a population of wild Noctuid insects of the same species, wherein the population of wild Noctuid insects contains a plurality of insects that are resistant to insecticides, whereupon the genetically engineered male Noctuid insects mate with said wild Noctuid insects and a female offspring produces a functional protein having a lethal, deleterious or sterilizing effect, thereby introgressing susceptibility traits into said population of wild Noctuid insects, suppressing the population of wild Noctuid insects and diluting the population of wild Noctuid insects that are resistant to insecticides, thereby slowing or reversing resistance to insecticides and/or biopesticides in said population of wild Noctuid insects.

12. The arthropod female-specific gene expression system of claim 9, wherein said functional protein has a lethal, deleterious or sterilizing effect on said arthropod.

13. The arthropod female-specific gene expression system of claim 12, wherein said polynucleotide encoding said functional protein encodes a Hid or homolog thereof, a Reaper (Rpr) or homolog thereof, a Nipp1Dm or homolog thereof, a calmodulin or homolog thereof, a Michelob-X or homolog thereof, a tTAV or homolog thereof, a tTAV2 or homolog thereof, a tTAV3 or homolog thereof, a tTAF or homolog thereof, a medea or homolog thereof, a microRNA toxin, or a nuclease.

14. The arthropod female-specific gene expression system of claim 13, wherein said functional protein comprises a tTAV or homolog thereof, a tTAV2 or homolog thereof, a tTAV3 or homolog thereof, or a tTAF or homolog thereof comprising an amino acid sequence of SEQ ID NO:80, SEQ ID NO:97, or SEQ ID NO:98.

15. The arthropod female-specific gene expression system of claim 13, wherein said nuclease is FokI or EcoRI.

16. The arthropod female-specific gene expression system of claim 9, further comprising a 3'UTR or portion thereof operatively linked to said polynucleotide encoding said functional protein.

17. The arthropod female-specific gene expression system of claim 9, further comprising a ubiquitin leader sequence 5' of said polynucleotide encoding a functional protein.

18. The arthropod female-specific gene expression system of claim 9, wherein said polynucleotide encoding said functional protein is located:

a. 3' of Exon 2, and within Exon 3 such that said polynucleotide encoding said functional protein is flanked by a first portion of Exon 3 5' of said polynucleotide encoding said functional protein, and a second portion of Exon 3 3' of said polynucleotide encoding said functional protein; or b. 3' of said Exon 2, Exon 3, Exon 3a, Exon 4, Exon 4b, and Exon 5.

19. The arthropod female-specific gene expression system of claim 18, wherein said first portion comprises a polynucleotide sequence of SEQ ID NO:94 and said second portion comprises a polynucleotide sequence of SEQ ID NO:9.

20. The arthropod female-specific gene expression system of claim 9, wherein said primary transcript is spliced in males such that translation terminates 5' of said polynucleotide encoding a functional protein, or wherein said primary transcript is spliced in males such that the polynucleotide encoding said functional protein is spliced out of said primary transcript.

21. The arthropod female-specific gene expression system of claim 9, wherein said Exon or said Intron comprises a polynucleotide sequence selected from the group consisting of:

a. Exon 3 comprises a polynucleotide that encodes an amino acid sequence of SEQ ID NO: 72; SEQ ID NO:94, SEQ ID NO:34, or SEQ ID NO:56;

b. Exon 2 comprises a polynucleotide that encodes an amino acid sequence of SEQ ID NO: 71, SEQ ID NO:7 or SEQ ID NO:32; and c. Exon 4 comprises a polynucleotide that encodes an amino acid sequence of SEQ ID NO: 74 or SEQ ID NO:15.

22. The arthropod female-specific gene expression system of claim 9, wherein said Exon or said Intron comprises a polynucleotide sequence selected from the group consisting of:

a. Exon 3a comprises a polynucleotide that encodes an amino acid sequence of SEQ ID NO: 73 or SEQ ID NO:12;

b. Exon 4b-Exon 4 comprises a polynucleotide sequence of SEQ ID NO:90, SEQ ID NO: 91, SEQ ID NO:92 or SEQ ID NO:14;

c. Exon 5 comprises a polynucleotide that encodes an amino acid sequence of SEQ ID NO: 75 or SEQ ID NO:17;

d. Intron 2 comprises a polynucleotide sequence of SEQ ID NO:55;

e. Intron 3 comprises a polynucleotide sequence of SEQ ID NO:58; and f. Intron 4 comprises a polynucleotide sequence of SEQ ID NO:39.

23. The arthropod female-specific gene expression system of claim 9, wherein said Exon 2 comprises a polynucleotide sequence that encodes an amino acid sequence of SEQ ID NO:71; said Exon 3 comprises a polynucleotide sequence that encodes an amino acid sequence of SEQ ID NO:72; said Exon 3a comprises a polynucleotide sequence that encodes an amino acid sequence of SEQ ID NO:73; said Exon 4 comprises a polynucleotide sequence that encodes an amino acid sequence of SEQ ID NO:74; and said Exon 5 comprises a polynucleotide sequence that encodes an amino acid sequence of SEQ ID NO:75.

24. The arthropod female-specific gene expression system of claim 9, wherein said Exon 2 has a polynucleotide sequence of SEQ ID NO:7 or SEQ ID NO:32; said Exon 3 has a first portion with a polynucleotide of sequence of SEQ ID NO:94 and a second portion with a polynucleotide of sequence of SEQ ID NO:9; said Exon 3a has a polynucleotide sequence of SEQ ID NO:12; said Exon 4 has a polynucleotide sequence of SEQ ID NO:15; said Exon 4b has a polynucleotide sequence of SEQ ID NO:14; and said Exon 5 has a polynucleotide sequence of SEQ ID NO:17.

25. The arthropod female-specific gene expression system of claim 9, wherein said Exon 2 has a polynucleotide sequence of SEQ ID NO:7 or SEQ ID NO:32; said Exon 3 has a polynucleotide sequence of SEQ ID NO:34 or SEQ ID NO:56; said Exon 3a has a polynucleotide sequence of SEQ ID NO: 12; said Exon 4 has a polynucleotide sequence of SEQ ID NO: 15; said Exon 4b has a polynucleotide sequence of SEQ ID NO:14; and said Exon 5 has a polynucleotide sequence of SEQ ID NO:17; and, optionally, said Intron 2 has a polynucleotide of sequence of SEQ ID NO:55; said Intron 3 has a polynucleotide sequence of SEQ ID NO:58; and said Intron 4 has a polynucleotide sequence of SEQ ID NO:39.

26. The arthropod female-specific gene expression system of claim 9, wherein said promoter is an Hsp70 promoter, a β-tubulin promoter, an Hsp83 promoter, a protamine promoter, an acting promoter, Hsp70 minimal promoter, a P minimal promoter, a CMV minimal promoter, an Acf5C-based minimal promoter, a TRE3G promoter, a BmA3 promoter fragment, or an Adh core promoter.

27. The arthropod female-specific gene expression system of claim 26, wherein said hCMV minipro further comprises a turnip yellow mosaic virus (TYMV) 5'UTR.

28. The arthropod female-specific gene expression system of claim 26, wherein said promoter has a polynucleotide sequence of SEQ ID NO:18, SEQ ID NO:41, SEQ ID NO:63, or SEQ ID NO:65.

29. The arthropod female-specific gene expression system of claim 28, further comprising a second promoter, a second transcription control element that controls transcription in the presence or absence of a chemical ligand, and a second polynucleotide encoding a second functional protein, the coding sequence of which is defined between a second start codon and a second stop codon, wherein said second functional protein encodes a Hid or homolog thereof, a Reaper (Rpr) or homolog thereof, a Nipp1Dm or homolog thereof, a calmodulin or homolog thereof, a Michelob-X or homolog thereof, a medea, or homolog thereof, a microRNA toxin, or a nuclease; and said first functional protein encodes a tTAV or homolog thereof, a tTAV2 or homolog thereof, a tTAV3 or homolog thereof, a tTAF or homolog thereof.

30. The arthropod female-specific gene expression system of claim 29, further comprising a second splicing cassette operatively linked to said second polynucleotide encoding said second functional protein which, in cooperation with a spliceosome in said arthropod, is capable of sex-specifically mediating splicing of a primary transcript in said arthropod wherein one sex of said arthropod splices said second splicing cassette to produce an open reading frame that is in frame with said second polynucleotide encoding said second functional protein and the other sex of said arthropod splices said second splicing cassette to produce an alternative reading frame that:

(a) is out of frame with said second polynucleotide encoding said second functional protein;

(b) splices out said second polynucleotide encoding said second functional protein; or (c) results in one or more stop codons in said alternative reading frame that prevents translation of said second functional protein.

31. The arthropod female-specific gene expression system of claim 30, wherein said second splicing cassette is the same as said first splicing cassette.

32. The arthropod female-specific gene expression system of claim 29, further comprising a third promoter operably linked to a polynucleotide encoding a marker protein.

33. A method of detecting a genetically engineered insect comprising the female-specific gene expression system of claim 32, wherein said genetically engineered insect expresses the marker gene that is detectable.

34. The arthropod female-specific gene expression system of claim 32, wherein said marker protein is a fluorescent protein.

35. The arthropod female-specific gene expression system of claim 9, further comprising a transcription control element that controls transcription by the presence of the absence of a chemical ligand.

36. The arthropod female-specific gene expression system of claim 35, wherein said transcription control element is a tetracycline-responsive element.

37. The arthropod female-specific gene expression system of claim 36, wherein said tetracycline-responsive element is a tetOx1, tetOx2, tetOx3, tetOx4, tetOx5, tetOx6, tetOx7, tetOx8, tetOx9, tetOx10, tetOx11, tetOx12, tetOx13, tetOx14, tetOx15, tetOx16, tetOx17, tetOx18, tetOx19, tetOx20 or tetOx21.

38. The arthropod female-specific gene expression system of claim 9, wherein said arthropod is an insect.

39. The arthropod female-specific gene expression system of claim 38, wherein said insect is a species of the genus *Spodoptera, Helicoverpa, Chrysodeixis, Anticarsia, Peridroma* or *Heliothis*.

40. The arthropod female-specific gene expression system of claim 9, wherein said Noctuidae dsx gene is derived from a species of the genus *Spodoptera, Helicoverpa, Chrysodeixis, Anticarsia, Peridroma* or *Heliothis*.

41. An arthropod comprising the female-specific gene expression system of claim 9.

42. A plasmid comprising the female specific gene expression system of claim 9.

* * * * *

SEQUENCE LISTING

```
<160> NUMBER OF SEQ ID NOS: 102

<210> SEQ ID NO 1
<211> LENGTH: 675
<212> TYPE: DNA
<213> ORGANISM: Artificial Sequence
<220> FEATURE:
<223> OTHER INFORMATION: Synthetic DNA encoding a variant of red
      fluorescent protein originally identified in Discosoma (clontech)

<400> SEQUENCE: 1

atggcctcct ccgagaacgt catcaccgag ttcatgcgct tcaaggtgcg catggagggc     60

accgtgaacg gccacgagtt cgagatcgag ggcgagggcg agggccgccc ctacgagggc    120

cacaacaccg tgaagctgaa ggtgaccaag ggcggccccc tgcccttcgc ctgggacatc    180

ctgtcccccc agttccagta cggctccaag gtgtacgtga agcaccccgc cgacatcccc    240

gactacaaga agctgtcctt ccccgagggc ttcaagtggg agcgcgtgat gaacttcgag    300

gacggcggcg tggcgaccgt gacccaggac tcctccctgc aggacggctg cttcatctac    360

aaggtgaagt tcatcggcgt gaacttcccc tccgacggcc ccgtgatgca gaagaagacc    420
```

atgggctggg aggcctccac cgagcgcctg taccccccgcg acggcgtgct gaagggcgag 480
acccacaagg ccctgaagct gaaggacggc ggccactacc tggtggagtt caagtccatc 540
tacatggcca agaagcccgt gcagctgccc ggctactact acgtggacgc caagctggac 600
atcacctccc acaacgagga ctacaccatc gtggagcagt acgagcgcac cgagggccgc 660
caccacctgt tcctg 675

<210> SEQ ID NO 2
<211> LENGTH: 21
<212> TYPE: DNA
<213> ORGANISM: Artificial Sequence
<220> FEATURE:
<223> OTHER INFORMATION: Synthetic DNA

<400> SEQUENCE: 2
cccaagaaga agcgcaaacc g 21

<210> SEQ ID NO 3
<211> LENGTH: 87
<212> TYPE: DNA
<213> ORGANISM: Drosophila melanogaster

<400> SEQUENCE: 3
ttggggtaag ttttcccgtt cttttctggg ttcttccctt ttgctcatcc ttgctgcact 60
accttcaggt gcaagttgag attcagg 87

<210> SEQ ID NO 4
<211> LENGTH: 633
<212> TYPE: DNA
<213> ORGANISM: Autographa californica nucleopolyhedrovirus

<400> SEQUENCE: 4
gttgcacaac actattatcg atttgcagtt cgggacataa atgtttaaat atatcgatgt 60
ctttgtgatg cgcgcgacat ttttgtaggt tattgataaa atgaacggat acgttgcccg 120
acattatcat taaatccttg gcgtagaatt tgtcgggtcc attgtccgtg tgcgctagta 180
gcatgcccgt aacggacctc gtacttttgg cttcaaaggt tttgcgcaca gacaaaatgt 240
gccacacttg cagctctgca tgtgtgcgcg ttaccacaaa tcccaacggc gcagtgtact 300
tgttgtatgc aaataaatct cgataaaggc gcggcgcgcg aatgcagctg atcacgtacg 360
ctcctcgtgt tccgttcaag gacggtgtta ccgacctcag attaatgttt atcggccgac 420
tgttttcgta tccgctcacc aaacgcgttt ttgcattaac attgtatgtc ggcggatgtt 480
ctatatctaa tttgaataaa taaacgataa ccgcgttggt tttagagggc ataataaaag 540
aaatattgtt atcgtgttcg ccattagggc agtataaatt gacgttcatg ttggatattg 600
tttcagttgc aagttgacac tggcggcgac aag 633

<210> SEQ ID NO 5
<211> LENGTH: 617
<212> TYPE: DNA
<213> ORGANISM: Autographa californica nucleopolyhedrovirus

<400> SEQUENCE: 5
attgcttgtc atttattaat ttggatgatg tcatttgttt ttaaaattga actggcttta 60
cgagtagaat tctacgcgta aaacacaatc aagtatgagt cataagctga tgtcatgttt 120
tgcacacggc tcataaccga actggcttta cgagtagaat tctacttgta acgcacgatc 180
agtggatgat gtcatttgtt tttcaaatcg agatgatgtc atgttttgca cacggctcat 240
aaactcgctt tacgagtaga attctacgtg taacgcacga tcgattgatg agtcatttgt 300
tttgcaatat gatatcatac aatatgactc atttgttttt caaaaccgaa cttgatttac 360
gggtagaatt ctacttgtaa agcacaatca aaaagatgat gtcatttgtt tttcaaaact 420
gaactcgctt tacgagtaga attctacgtg taaaacacaa tcaagaaatg atgtcatttg 480
ttataaaaat aaaagctgat gtcatgtttt gcacatggct cataactaaa ctcgctttac 540
gggtagaatt ctacgcgtaa aacatgattg ataattaaat aattcatttg caagctatac 600
gttaaatcaa acggacg 617

<210> SEQ ID NO 6
<211> LENGTH: 4702
<212> TYPE: DNA
<213> ORGANISM: Artificial Sequence
<220> FEATURE:
<223> OTHER INFORMATION: Synthetic DNA based on Spodoptera frugiperda sequences

<400> SEQUENCE: 6
cagtgacgtg gacgaggcat cacggaaaat agacgaaggt aggcctttta ttgtttaaat 60
gccaattgca attgtccttc tgttatttat ttgcattgcg attgttcgct gtaaagttaa 120
agagatgaat tgagcgctaa aaagattttt catacaggaa tgtgtgaaaa gagttgttta 180
attcgtaatt tgcaactatg tattatgttt tatgttcact gtttttgtgt tgttaacagc 240
aaattaatgc cgataaagag aatgacagaa aaaacttaca atctcaatta atccgataat 300
tacaaaaagt gaatagttaa ccatcatgaa atcgttttag aaagcttttt agcgttcgta 360
caaattagtt gttcgtgcta cattgtaggt gagacgccta aatgtctttc gtacttcgag 420
tgcggatgta acagtgttat atgagcggcc attgttattt ccatacgtgc ctggaacgct 480
gctcagccca gcgtcgtagg gctccctgca gtctcgcacg aacgaacctt tatttagcca 540
ctgccgggaa ttgcattgga aatagatgcc tgcttataaa gtaggtaatc ataaacatat 600
cacgattgaa tttaataata atttaatctt agttccaatt ctttggatag gttagggttt 660
tttgacagac tccatctgag tgatgtcaaa aatcgatctt aaaacaaaga ttttaggctt 720
gtttcgaccg aatggccaaa ttacttcata ttgacttgac tcctttttt tcgcaatgcg 780 aatatgtgta cctattggaa aacttttgtt gtttttttaga atacatatag attttcgtta 840
aatttcaatc taagtcaatt gaatatattt aattaattat ttatctttat ttatttcctt 900
ctctttacga aatcttggaa tgtgaaaatt attatcattg tatcaacaaa aggtttctat 960
aaacgttttt ataaataaaa taaaaaaaaa actgcatttt aataatcata cattgatatg 1020
aataaagcta aacagaaaac aaacgatgtt ctaatttcaa gatacatttg acagatgtca 1080
caaccgaacc gttacggcca ttttgaattt gtctatggtt tatttttttt aaggagaaaa 1140
tgattcgatg tctctcccgc cgtgtctatg gtttaatgca gtttttttc acccgccaag 1200 cgattgtcca atttgcgcat tgtttgttct caggaaagat cattatcaac gaatacgcgc 1260
ggaagaacaa tctgataacg gaccgaaacc accatgggca gccgcctgga taagtccaaa 1320
gtcatcaact ccgcgttgga gctgttgaac gaagttggca ttgagggact gacgacccgc 1380
aagttggcgc agaagctggg cgtggagcag cccacctct actggcacgt gaagaataag 1440
cgggcgctgc tggatgccct ggccatcgag atgctcgacc gccaccacac gcatttttgc 1500
ccgttggaag gcgagtcctg gcaggacttc ctccgcaata acgccaagtc gttccgctgc 1560
gctctgctgt cccaccgaga cggtgccaaa gtccatctcg gcacgcgccc gaccgaaaag 1620
caatacgaga cactggagaa ccagctcgcg ttcctgtgcc agcaaggctt cagcctggaa 1680
aatgctctct acgctctgag cgccgtcggt cactttaccc tgggctgcgt gctggaggac 1740
caagagcatc aagtcgcaaa agaggagcgc gagaccccaa caaccgattc gatgccccca 1800
ctgctgcgtc aggcaatcga gctgttcgat catcaaggag ccgagccggc attcctgttc 1860
ggcttggagc tgattatctg cggattggaa aagcaactga aatgcgagtc gggctcgggc 1920
cccgcctaca gccgcgcccg caccaagaac aactacggca gcaccatcga gggcctgctg 1980
gatctgccgg atgatgatgc ccggaggag gcgggcctgg ccgccccgcg cctgagcttc 2040
ctgccggccg gacacacccg ccgcctgtcg accgccccgc cgaccgacgt gagcctgggc 2100
gatgagctgc acctggatgg cgaggatgtg gcgatggccc acgccgatgc cctggacgac 2160
ttcgacctgg acatgctggg cgatggcgat agcccgggac cgggattcac cccgcacgat 2220
agcgcccccct acggcgccct ggatatggcc gatttcgagt tcgagcagat gttcaccgac 2280
gccctgggca tcgatgaata cggcggctaa caccggtgac gtgttcgacg ggttagagct 2340
gaggaactcg acacgccagt acggacatta atagtaataa atagttttta ccaccaacaa 2400
cactgaaact gtgctaacac tttgacagtg acaggtgtag tgtaggggct gtgacaaact 2460
tcattctggt tcctatttta aatttaaatc atttattttc ggccagcggc aacagttttt 2520
cgtgttcctt tttttaattt aaatagtata atagtttctt ttatgccaga catttagttc 2580
tataaataag tatttgaaag aacgctattt aaaatgtttt ggactgtaac atctatttta 2640
attttgacaa gaatgaagtt tgttacatac gacatatttc acagcacatc gtcgtgtata 2700
taaataacac aacactttac agttacacaa agtatctacc tacacaagac atcactcatt 2760
acacataacg attagatact tatacacgtt cacattaaca tacagcagaa ccagtggaaa 2820
tggatggttt aggtcaagat tgcctaattt agtcaacgat cttctcacaa tttaattcat 2880
ttgttgtatt gggtatttgt aattttatat ggagatggta attttagaga gagggtagta 2940
taagagtaag tagtttaggt aagtagttga gaaatgtcgt tgtaaatgta gggttatttt 3000
atgagtgaaa ttgagtcgtg atttttgtct ccttaagtta aattttgata gaggtatttt 3060
attcatttgc atttgaaata tagaacagca accatgacgt aacaacgacg gtggcatccg 3120
tcaccgtctc gaacataatc aacaattctt agccatacat tgtgctacat tgcaacttga 3180
gtttcgtttc cacgttacac gttccacaca caaagtgaca caacaaaata gttgcacacg 3240
ataaagtggt taagtcagaa tcagctgtat taacaaagtc taaccagtcg tgatttcaac 3300
tttacagtga ccggacgaag gtggtgaaat tcgaaatgca acctcagtga cattccatat 3360
tcaaaaaatt cgaatttaac ggccatcgtg gtgctgtgct agtgtcgata ttttatttag 3420
aattattttc ttttttgtag gaaaatggcg gaaattaata atataagtgg tgtactatcg 3480
tcgtcgatga agttattttg cgaatgatac tttgttttac aagtgccgtg ttttgtgtgg 3540
acgcttgctg tgcgatgctg tgttgcgaac gacaacggac ttgactgtgg ctacctccgg 3600
cgtgtcggtg agtttatttg atattgttat tagcaattca atggacattg caacatgata 3660
gaatctcaat tattttaaaa gtgtctattg agttgtttta ttatttaaga attgcacaaa 3720
cgcttttcaa ttgtatacaa atgttagttg ccgatagatt tgtattacgt tgcatttctg 3780
agacgtttgt ttgccgtctt gccttctttg tgttcaaatg gaaagcgtta gtgtgcgtgt 3840
caatctgttt gttccaagta cttgtttact gctcatattc ataagtagaa ttttatgtta 3900
caacgtacac ataaaataaa atgctattta tgaaataaga caatttgcga tgcgacggaa 3960
tttatttatg tttttattgc ttttacaaaa cggaggaatg catgctattt cttgtcttta 4020
tctaagtttt tacattattt tatgatcatt aaaactcaca gttgtaaggc tctcttctaa 4080
ggtgtacaga actatgcctc tcttattact tcaaaatatt tacatattcg aaaaaaaaaa 4140
gtttttagta aaaaaaaatg tttccatact agggcggctg aacagtttgg agcctaaata 4200
cttattggac cttcggtaac tacactcaca cgggcataac acaacgcaag cgttgtttca 4260
cgccagcttt cttgaggccg tccaccgtgg aaacactccg gtcgagccag atcatttgaa 4320
atgatgctga agccttgttc ccacctttaa taccttaggc tcaaaagtat tcagagaccc 4380
tagtatagta catatacaaa acaaaaccgt tccacaaaca ccttaagcta ggtctaaaac 4440
acccagctgg tctacagaaa ccctcaaaat ccacaccaga aacctaatca ccccctttaa 4500
aattccagcc cactggatag tccaccaatg gcggatgtac gagcggtcca tatgttccct 4560
gctggagctg caggcacgca agggatcctg ctccatgtgc ttcacggagt acgctccccc 4620
cttgctgccg ctgcccctca ccacgcagcg accctcgccg ccgcctgcgc acttgtagcg 4680
atgcgaccat gcgccgcgac ca 4702

<210> SEQ ID NO 7
<211> LENGTH: 38
<212> TYPE: DNA
<213> ORGANISM: Spodoptera frugiperda

<400> SEQUENCE: 7
cagtgacgtg gacgaggcat cacggaaaat agacgaag 38

<210> SEQ ID NO 8
<211> LENGTH: 1195
<212> TYPE: DNA
<213> ORGANISM: Spodoptera frugiperda

<400> SEQUENCE: 8
gtaggccttt tattgtttaa atgccaattg caattgtcct tctgttattt atttgcattg 60
cgattgttcg ctgtaaagtt aaagagatga attgagcgct aaaaagattt ttcatacagg 120
aatgtgtgaa aagagttgtt taattcgtaa tttgcaacta tgtattatgt tttatgttca 180
ctgtttttgt gttgttaaca gcaaattaat gccgataaag agaatgacag aaaaaactta 240
caatctcaat taatccgata attacaaaaa gtgaatagtt aaccatcatg aaatcgtttt 300
agaaagcttt ttagcgttcg tacaaattag ttgttcgtgc tacattgtag gtgagacgcc 360
taaatgtctt tcgtacttcg agtgcggatg taacagtgtt atatgagcgg ccattgttat 420
ttccatacgt gcctggaacg ctgctcagcc cagcgtcgta gggctccctg cagtctcgca 480
cgaacgaacc tttatttagc cactgccggg aattgcattg gaaatagatg cctgcttata 540
aagtaggtaa tcataaacat atcacgattg aatttaataa taatttaatc ttagttccaa 600
ttctttggat aggttagggt tttttgacag actccatctg agtgatgtca aaaatcgatc 660
ttaaaacaaa gattttaggc ttgtttcgac cgaatggcca aattacttca tattgacttg 720
actccttttt tttcgcaatg cgaatatgtg tacctattgg aaaacttttg ttgtttttta 780
gaatacatat agattttcgt taaatttcaa tctaagtcaa ttgaatatat ttaattaatt 840
atttatcttt atttatttcc ttctctttac gaaatcttgg aatgtgaaaa ttattatcat 900
tgtatcaaca aaaggtttct ataaacgttt ttataaataa aataaaaaaa aaactgcatt 960
ttaataatca tacattgata tgaataaagc taaacagaaa acaaacgatg ttctaatttc 1020
aagatacatt tgacagatgt cacaaccgaa ccgttacggc cattttgaat ttgtctatgg 1080
tttatttttt ttaaggagaa aatgattcga tgtctctccc gccgtgtcta tggtttaatg 1140
cagttttttt tcacccgcca agcgattgtc caatttgcgc attgtttgtt ctcag 1195

<210> SEQ ID NO 9
<211> LENGTH: 41
<212> TYPE: DNA
<213> ORGANISM: Spodoptera frugiperda

<400> SEQUENCE: 9
acgtgttcga cgggttagag ctgaggaact cgacacgcca g 41

<210> SEQ ID NO 10
<211> LENGTH: 1014
<212> TYPE: DNA
<213> ORGANISM: Artificial Sequence
<220> FEATURE:
<223> OTHER INFORMATION: Synthetic DNA encoding the fusion tetracycline transactivator protein optimised for expression in insects

<400> SEQUENCE: 10
atgggcagcc gcctggataa gtccaaagtc atcaactccg cgttggagct gttgaacgaa 60
gttggcattg agggactgac gacccgcaag ttggcgcaga agctgggcgt ggagcagccc 120
accctctact ggcacgtgaa gaataagcgg gcgctgctgg atgccctggc catcgagatg 180
ctcgaccgcc accacacgca tttttgcccg ttggaaggcg agtcctggca ggacttcctc 240
cgcaataacg ccaagtcgtt ccgctgcgct ctgctgtccc accgagacgg tgccaaagtc 300
catctcggca cgcgcccgac cgaaaagcaa tacgagacac tggagaacca gctcgcgttc 360
ctgtgccagc aaggcttcag cctggaaaat gctctctacg ctctgagcgc cgtcggtcac 420
tttaccctgg gctgcgtgct ggaggaccaa gagcatcaag tcgcaaaaga ggagcgcgag 480
accccaacaa ccgattcgat gcccccactg ctgcgtcagg caatcgagct gttcgatcat 540
caaggagccg agccggcatt cctgttcggc ttggagctga ttatctgcgg attggaaaag 600
caactgaaat gcgagtcggg ctcgggcccc gcgtacagcc gcgcgcgtac gaaaaacaat 660
tacgggtcta ccatcgaggg cctgctcgat ctcccggacg acgacgcccc cgaagaggcg 720
gggctggcgg ctccgcgcct gtcctttctc cccgcgggac acacgcgcag actgtcgacg 780
gcccccccga ccgatgtcag cctgggggac gagctccact tagacggcga ggacgtggcg 840
atggcgcatg ccgacgcgct agacgatttc gatctggaca tgttggggga cggggattcc 900
ccgggtccgg gatttacccc ccacgactcc gccccctacg gcgctctgga tatggccgac 960
ttcgagtttg agcagatgtt taccgatgcc cttggaattg acgagtacgg tggg 1014

<210> SEQ ID NO 11
<211> LENGTH: 84
<212> TYPE: DNA
<213> ORGANISM: Spodoptera frugiperda

<400> SEQUENCE: 11
gaaagatgat tatcaacgaa tacgcgcgga agaacaatct gaacgtgtat cgacgggtta 60
gagctgagga actcgacacg ccag 84

<210> SEQ ID NO 12
<211> LENGTH: 15
<212> TYPE: DNA
<213> ORGANISM: Spodoptera frugiperda

<400> SEQUENCE: 12

```
tacggacatt aatag                                                    15


<210> SEQ ID NO 13
<211> LENGTH: 933
<212> TYPE: DNA
<213> ORGANISM: Spodoptera frugiperda

<400> SEQUENCE: 13

taataaatag tttttaccac caacaacact gaaactgtgc taacactttg acagtgacag     60

gtgtagtgta ggggctgtga caaacttcat tctggttcct attttaaatt taaatcattt    120

attttcggcc agcggcaaca gtttttcgtg ttcctttttt taatttaaat agtataatag    180

tttcttttat gccagacatt tagttctata aataagtatt tgaaagaacg ctatttaaaa    240

tgttttggac tgtaacatct attttaattt tgacaagaat gaagtttgtt acatacgaca    300

tatttcacag cacatcgtcg tgtatataaa taacacaaca ctttacagtt acacaaagta    360

tctacctaca caagacatca ctcattacac ataacgatta gatacttata cacgttcaca    420

ttaacataca gcagaaccag tggaaatgga tggtttaggt caagattgcc taatttagtc    480

aacgatcttc tcacaattta attcatttgt tgtattgggt atttgtaatt ttatatggag    540

atggtaattt tagagagagg gtagtataag agtaagtagt ttaggtaagt agttgagaaa    600

tgtcgttgta aatgtagggt tattttatga gtgaaattga gtcgtgattt ttgtctcctt    660

aagttaaatt ttgatagagg tattttattc atttgcattt gaaatataga acagcaacca    720

tgacgtaaca acgacggtgg catccgtcac cgtctcgaac ataatcaaca attcttagcc    780

atacattgtg ctacattgca acttgagttt cgtttccacg ttacacgttc cacacacaaa    840

gtgacacaac aaaatagttg cacacgataa agtggttaag tcagaatcag ctgtattaac    900

aaagtctaac cagtcgtgat ttcaacttta cag                                933


<210> SEQ ID NO 14
<211> LENGTH: 134
<212> TYPE: DNA
<213> ORGANISM: Spodoptera frugiperda

<400> SEQUENCE: 14

tgaccggacg aaggtggtga aattcgaaat gcaacctcag tgacattcca tattcaaaaa     60

attcgaattt aacggccatc gtggtgctgt gctagtgtcg atattttatt tagaattatt    120

ttcttttttg tagg                                                     134


<210> SEQ ID NO 15
<211> LENGTH: 166
<212> TYPE: DNA
<213> ORGANISM: Spodoptera frugiperda

<400> SEQUENCE: 15

aaaatggcgg aaatttatta tataagtggt gtactatcgt cgtcgatgaa gttattttgc     60

gaatgatact ttgttttaca agtgccgtgt tttgtgtgga cgcttgctgt gcgatgctgt    120

gttgcgaacg acaacggact tcactgtggc tacctccggc gtgtcg                 166


<210> SEQ ID NO 16
<211> LENGTH: 901
<212> TYPE: DNA
<213> ORGANISM: Spodoptera frugiperda

<400> SEQUENCE: 16
```

gtgagtttat ttgatattgt tattagcaat tcaatggaca ttgcaacatg atagaatctc 60
aattatttta aaagtgtcta ttgagttgtt ttattattta agaattgcac aaacgctttt 120
caattgtata caaatgttag ttgccgatag atttgtatta cgttgcattt ctgagacgtt 180
tgtttgccgt cttgccttct ttgtgttcaa atggaaagcg ttagtgtgcg tgtcaatctg 240
tttgttccaa gtacttgttt actgctcata ttcataagta gaattttatg ttacaacgta 300
cacataaaat aaaatgctat ttatgaaata agacaatttg cgatgcgacg gaatttattt 360
atgtttttat tgcttttaca aaacggagga atgcatgcta tttcttgtct ttatctaagt 420
ttttacatta ttttatgatc attaaaactc acagttgtaa ggctctcttc taaggtgtac 480
agaactatgc ctctcttatt acttcaaaat atttacatat tcgaaaaaaa aaagttttta 540
gtaaaaaaaa atgtttccat actagggcgg ctgaacagtt tggagcctaa atacttattg 600
gaccttcggt aactacactc acacgggcat aacacaacgc aagcgttgtt tcacgccagc 660
tttcttgagg ccgtccaccg tggaaacact ccggtcgagc cagatcattt gaaatgatgc 720
tgaagccttg ttcccacctt taatacctta ggctcaaaag tattcagaga ccctagtata 780
gtacatatac aaaacaaaac cgttccacaa acaccttaag ctaggtctaa aacacccagc 840
tggtctacag aaaccctcaa aatccacacc agaaacctaa tcaccccctt taaaattcca 900
g 901

<210> SEQ ID NO 17
<211> LENGTH: 172
<212> TYPE: DNA
<213> ORGANISM: Spodoptera frugiperda

<400> SEQUENCE: 17
cccactggat agtccaccaa cggcggatgt acgagcggtc catacgttcc ctgctggagc 60
tgcaggcacg caagggatcc tgctccatgt gcttcacgga gtacgctccc cccttgctgc 120
cgctgcccct caccacgcag cgaccctcgc cgccgcctgc gcacttgtag cg 172

<210> SEQ ID NO 18
<211> LENGTH: 130
<212> TYPE: DNA
<213> ORGANISM: Drosophila melanogaster

<400> SEQUENCE: 18
agcgccggag tataaataga ggcgcttcgt ctacggagcg acaattcaat tcaaacaagc 60
aaagtgaaca cgtcgctaag cgaaagctaa gcaaataaac aagcgcagct gaacaagcta 120
aacaatctgc 130

<210> SEQ ID NO 19
<211> LENGTH: 772
<212> TYPE: DNA
<213> ORGANISM: Drosophila melanogaster

<400> SEQUENCE: 19
taacattata cctaaaccca tggtcaagag taaacatttc tgcctttgaa gttgagaaca 60
caattaagca tcccctggtt aaacctgaca ttcatacttg ttaatagcgc cataaacata 120
gcaccaattt cgaagaaatc agttaaaagc aattagcaat tagcaattag caataactct 180
gctgacttca aaacgagaag agttgcaagt atttgtaagg cacagtttat agaccaccga 240
cggctcatta gggctcgtca tgtaactaag cgcggtgaaa cccaattgaa catatagtgg 300
aattattatt atcaatgggg aagatttaac cctcaggtag caaagtaatt taattgcaaa 360
tagagagtcc taagactaaa taatatattt aaaaatctgg ccctttgacc ttgcttgtca 420
ggtgcatttg ggttcaatcg taagttgctt ctatataaac actttcccca tccccgcaat 480
aatgaagaat accgcagaat aaagagagat ttgcaacaaa aaataaaggc attgcgaaaa 540
ctttttatgg gggatcatta cactcgggcc tacggttaca attcccagcc acttaagcga 600
caagtttggc caacaatcca tctaatagct aatagcgcaa tcactggtaa tcgcaagagt 660
atataggcaa tagaacccat ggatttgacc aaaggtaacc gagacaatgg agaagcaaga 720
ggatttcaaa ctgaacaccc acagtactgt gtactaccac tggcgcgttt gg 772

<210> SEQ ID NO 20
<211> LENGTH: 296
<212> TYPE: DNA
<213> ORGANISM: Artificial Sequence
<220> FEATURE:
<223> OTHER INFORMATION: Synthetic DNA contains 7 repeats of Tn10 tet-operon

<400> SEQUENCE: 20
gactttcact tttctctatc actgataggg agtggtaaac tcgactttca cttttctcta 60
tcactgatag ggagtggtaa actcgacttt cacttttctc tatcactgat agggagtggt 120
aaactcgact ttcacttttc tctatcactg atagggagtg gtaaactcga ctttcacttt 180
tctctatcac tgatagggag tggtaaactc gactttcact tttctctatc actgataggg 240
agtggtaaac tcgactttca cttttctcta tcactgatag ggagtggtaa actcga 296

<210> SEQ ID NO 21
<211> LENGTH: 228
<212> TYPE: DNA
<213> ORGANISM: Simian virus 40

<400> SEQUENCE: 21
gatcataatc agccatacca catttgtaga ggttttactt gctttaaaaa acctcccaca 60
cctccccctg aacctgaaac ataaaatgaa tgcaattgtt gttgttaact tgtttattgc 120
agcttataat ggttacaaat aaagcaatag catcacaaat ttcacaaata aagcattttt 180
ttcactgcat tctagttgtg gtttgtccaa actcatcaat gtatctta 228

<210> SEQ ID NO 22
<211> LENGTH: 21
<212> TYPE: DNA
<213> ORGANISM: Artificial Sequence
<220> FEATURE:
<223> OTHER INFORMATION: Synthetic DNA

<400> SEQUENCE: 22
cccaagaaaa agcggaaggt g 21

<210> SEQ ID NO 23
<211> LENGTH: 675
<212> TYPE: DNA
<213> ORGANISM: Artificial Sequence
<220> FEATURE:
<223> OTHER INFORMATION: Synthetic DNA encoding a variant of red fluorescent protein originally identified in Discosoma (Clontech)

<400> SEQUENCE: 23
atggcctcct ccgagaacgt catcaccgag ttcatgcgct tcaaggtgcg catggagggc 60
accgtgaacg gccacgagtt cgagatcgag ggcgagggcg agggccgccc ctacgagggc 120

```
cacaacaccg tgaagctgaa ggtgaccaag ggcggccccc tgcccttcgc ctgggacatc    180

ctgtcccccc agttccagta cggctccaag gtgtacgtga agcaccccgc cgacatcccc    240

gactacaaga agctgtcctt ccccgagggc ttcaagtggg agcgcgtgat gaacttcgag    300

gacggcggcg tggcgaccgt gacccaggac tcctccctgc aggacggctg cttcatctac    360

aaggtgaagt tcatcggcgt gaacttcccc tccgacggcc ccgtgatgca gaagaagacc    420

atgggctggg aggcctccac cgagcgcctg tacccccgcg acggcgtgct gaagggcgag    480

acccacaagg ccctgaagct gaaggacggc ggccactacc tggtggagtt caagtccatc    540

tacatggcca agaagcccgt gcagctgccc ggctactact acgtggacgc caagctggac    600

atcacctccc acaacgagga ctacaccatc gtggagcagt acgagcgcac cgagggccgc    660

caccacctgt tcctg                                                     675


<210> SEQ ID NO 24
<211> LENGTH: 21
<212> TYPE: DNA
<213> ORGANISM: Artificial Sequence
<220> FEATURE:
<223> OTHER INFORMATION: Synthetic DNA

<400> SEQUENCE: 24

cccaagaaga agcgcaaacc g                                               21


<210> SEQ ID NO 25
<211> LENGTH: 87
<212> TYPE: DNA
<213> ORGANISM: Drosophila melanogaster

<400> SEQUENCE: 25

ttggggtaag ttttcccgtt cttttctggg ttcttccctt ttgctcatcc ttgctgcact     60

accttcaggt gcaagttgag attcagg                                         87


<210> SEQ ID NO 26
<211> LENGTH: 633
<212> TYPE: DNA
<213> ORGANISM: Autographa californica nucleopolyhedrovirus

<400> SEQUENCE: 26

gttgcacaac actattatcg atttgcagtt cgggacataa atgtttaaat atatcgatgt     60

ctttgtgatg cgcgcgacat tttgtaggt tattgataaa atgaacggat acgttgcccg    120

acattatcat taaatccttg gcgtagaatt tgtcgggtcc attgtccgtg tgcgctagta    180

gcatgcccgt aacggacctc gtacttttgg cttcaaaggt tttgcgcaca gacaaaatgt    240

gccacacttg cagctctgca tgtgtgcgcg ttaccacaaa tcccaacggc gcagtgtact    300

tgttgtatgc aaataaatct cgataaaggc gcggcgcgcg aatgcagctg atcacgtacg    360

ctcctcgtgt tccgttcaag gacggtgtta ccgacctcag attaatgttt atcggccgac    420

tgttttcgta tccgctcacc aaacgcgttt ttgcattaac attgtatgtc ggcggatgtt    480

ctatatctaa tttgaataaa taaacgataa ccgcgttggt tttagagggc ataataaaag    540

aaatattgtt atcgtgttcg ccattagggc agtataaatt gacgttcatg ttggatattg    600

tttcagttgc aagttgacac tggcggcgac aag                                 633


<210> SEQ ID NO 27
<211> LENGTH: 563
<212> TYPE: DNA
<213> ORGANISM: Autographa californica nucleopolyhedrovirus
```

<400> SEQUENCE: 27
gctttacgag tagaattcta cgcgtaaaac acaatcaagt atgagtcata agctgatgtc 60
atgttttgca cacggctcat aaccgaactg gctttacgag tagaattcta cttgtaacgc 120
acgatcagtg gatgatgtca tttgtttttc aaatcgagat gatgtcatgt tttgcacacg 180
gctcataaac tcgctttacg agtagaattc tacgtgtaac gcacgatcga ttgatgagtc 240
atttgttttg caatatgata tcatacaata tgactcattt gtttttcaaa accgaacttg 300
atttacgggt agaattctac ttgtaaagca caatcaaaaa gatgatgtca tttgtttttc 360
aaaactgaac tcgctttacg agtagaattc tacgtgtaaa acacaatcaa gaaatgatgt 420
catttgttat aaaaataaaa gctgatgtca tgttttgcac atggctcata actaaactcg 480
ctttacgggt agaattctac gcgtaaaaca tgattgataa ttaaataatt catttgcaag 540
ctatacgtta aatcaaacgg acg 563

<210> SEQ ID NO 28
<211> LENGTH: 667
<212> TYPE: DNA
<213> ORGANISM: Autographa californica nucleopolyhedrovirus

<400> SEQUENCE: 28
atgaatcgtt tttaaaataa caaatcaatt gttttataat attcgtacga ttctttgatt 60
atgtaataaa atgtgatcat taggaagatt acgaaaaata taaaaaatat gagttctgtg 120
tgtataacaa atgctgtaaa cgccacaatt gtgtttgttg caaataaacc catgattatt 180
tgattaaaat tgttgttttc tttgttcata gacaatagtg tgttttgcct aaacgtgtac 240
tgcataaact ccatgcgagt gtatagcgag ctagtggcta acgcttgccc caccaaagta 300
gattcgtcaa aatcctcaat ttcatcaccc tcctccaagt ttaacatttg gccgtcggaa 360
ttaacttcta aagatgccac ataatctaat aaatgaaata gagattcaaa cgtggcgtca 420
tcgtccgttt cgaccatttc cgaaaagaac tcgggcataa actctatgat ttctctggac 480
gtggtgttgt cgaaactctc aaagtacgca gtcaggaacg tgcgcgacat gtcgtcggga 540
aactcgcgcg gaaacatgtt gttgtaaccg aacgggtccc atagcgccaa aaccaaatct 600
gccagcgtca atagaatgag cacgatgccg acaatggagc tggcttggat agcgattcga 660
gttaacg 667

<210> SEQ ID NO 29
<211> LENGTH: 1011
<212> TYPE: DNA
<213> ORGANISM: Artificial Sequence
<220> FEATURE:
<223> OTHER INFORMATION: Synthetic DNA encoding the fusion tetracycline transactivator protein optimised for expression in insects

<400> SEQUENCE: 29
gtcagccgcc tggataagtc caaagtcatc aactccgcgt tggagctgtt gaacgaagtt 60
ggcattgagg gactgacgac ccgcaagttg gcgcagaagc tgggcgtgga gcagcccacc 120
ctctactggc acgtgaagaa taagcgggcg ctgctggatg ccctggccat cgagatgctc 180
gaccgccacc acacgcattt ttgcccgttg gaaggcgagt cctggcagga cttcctccgc 240
aataacgcca agtcgttccg ctgcgctctg ctgtcccacc gagacggtgc caaagtccat 300
ctcggcacgc gcccgaccga aaagcaatac gagacactgg agaaccagct cgcgttcctg 360
tgccagcaag gcttcagcct ggaaaatgct ctctacgctc tgagcgccgt cggtcacttt 420

```
accctgggct gcgtgctgga ggaccaagag catcaagtcg caaaagagga gcgcgagacc    480

ccaacaaccg attcgatgcc cccactgctg cgtcaggcaa tcgagctgtt cgatcatcaa    540

ggagccgagc cggcattcct gttcggcttg gagctgatta tctgcggatt ggaaaagcaa    600

ctgaaatgcg agtcgggctc gggccccgcg tacagccgcg cgcgtacgaa aaacaattac    660

gggtctacca tcgagggcct gctcgatctc ccggacgacg acgcccccga agaggcgggg    720

ctggcggctc cgcgcctgtc ctttctcccc gcgggacaca cgcgcagact gtcgacggcc    780

cccccgaccg atgtcagcct gggggacgag ctccacttag acggcgagga cgtggcgatg    840

gcgcatgccg acgcgctaga cgatttcgat ctggacatgt tgggggacgg ggattccccg    900

ggtccgggat ttacccccca cgactccgcc ccctacggcg ctctggatat ggccgacttc    960

gagtttgagc agatgtttac cgatgccctt ggaattgacg agtacggtgg g            1011


<210> SEQ ID NO 30
<211> LENGTH: 225
<212> TYPE: DNA
<213> ORGANISM: Drosophila melanogaster

<400> SEQUENCE: 30

cagatcttcg tcaagaccct gaccggcaag accatcaccc tggaggtgga gccgagcgat     60

accatcgaga acgtgaaggc caagatccag gacaaggagg gcatcccgcc ggatcagcag    120

cgcctgatct tcgccggacg ccagctggag gatggccgca ccctgagcga ctacaacatc    180

cagaaggaga gcaccctgca cctggtgctg cgcctgcgcg gtggt                   225


<210> SEQ ID NO 31
<211> LENGTH: 3643
<212> TYPE: DNA
<213> ORGANISM: Artificial Sequence
<220> FEATURE:
<223> OTHER INFORMATION: Synthetic DNA based on Spodoptera frugiperda
      sequences

<400> SEQUENCE: 31

atgaacagtg acgtggacga ggcatcacgg aaaatagacg aaggtaggcc ttttattgtt     60

taaatgccaa ttgcaattgt ccttctgtta tttatttgca ttgcgattgt tcgctgtaaa    120

gttaaagaga tgaattgagc gctaaaaaga tttttcatac aggaatgtgt gaaaagagtt    180

gtttaattcg taatttgcaa ctatgtatta tgttttatgt tcactgtttt tgtgttgtta    240

acagcaaatt aatgccgata aagagaatga cagaaaaaac ttacaatctc aattaatccg    300

ataattacaa aaagtgaata gttaaccatc atgaaatcgt tttagaaagc tttttagcgt    360

tcgtacaaat tagttgttcg tgctacattg taggtgagac gcctaaatgt ctttcgtact    420

tcgagtgcgg atgtaacagt gttatatgag cggccattgt tatttccata cgtgcctgga    480

acgctgctca gcccagcgtc gtagggctcc ctgcagtctc gcacgaacga acctttattt    540

agccactgcc gggaattgca ttggaaatag atgcctgctt ataaagtagg taatcataaa    600

catatcacga ttgaatttaa taataattta atcttagttc caattctttg gataggttag    660

ggttttttga cagactccat ctgagtgatg tcaaaaatcg atcttaaaac aaagatttta    720

ggcttgtttc gaccgaatgg ccaaattact tcatattgac ttgactcctt ttttttcgca    780

atgcgaatat gtgtacctat tggaaaactt ttgttgtttt ttagaataca tatagatttt    840

cgttaaattt caatctaagt caattgaata tatttaatta attatttatc tttatttatt    900

tccttctctt tacgaaatct tggaatgtga aaattattat cattgtatca acaaaaggtt    960
```

```
tctataaacg tttttataaa taaaataaaa aaaaaactgc attttaataa tcatacattg   1020
atatgaataa agctaaacag aaaacaaacg atgttctaat ttcaagatac atttgacaga   1080
tgtcacaacc gaaccgttac ggccattttg aatttgtcta tggtttattt tttttaagga   1140
gaaaatgatt cgatgtctct cccgccgtgt ctatggttta atgcagtttt ttttcacccg   1200
ccaagcgatt gtccaatttg cgcattgttt gttctcagga aagatgatta tcaacgaata   1260
cgcgcggaag aacaatctga acgtgtatcg acgggttaga gctgaggaac tcgacacgcc   1320
agtacggaca ttaatagtaa taaatagttt ttaccaccaa caacactgaa actgtgctaa   1380
cactttgaca gtgacaggtg tagtgtaggg gctgtgacaa acttcattct ggttcctatt   1440
ttaaatttaa atcatttatt ttcggccagc ggcaacagtt tttcgtgttc cttttttttaa   1500
tttaaatagt ataatagttt cttttatgcc agacatttag ttctataaat aagtatttga   1560
aagaacgcta tttaaaatgt tttggactgt aacatctatt ttaattttga caagaatgaa   1620
gtttgttaca tacgacatat ttcacagcac atcgtcgtgt atataaataa cacaacactt   1680
tacagttaca caaagtatct acctacacaa gacatcactc attacacata acgattagat   1740
acttatacac gttcacatta acatacagca gaaccagtgg aaatggatgg tttaggtcaa   1800
gattgcctaa tttagtcaac gatcttctca caatttaatt catttgttgt attgggtatt   1860
tgtaatttta tatggagatg gtaattttag agagagggta gtataagagt aagtagttta   1920
ggtaagtagt tgagaaatgt cgttgtaaat gtagggttat tttatgagtg aaattgagtc   1980
gtgatttttg tctccttaag ttaaattttg atagaggtat tttattcatt tgcatttgaa   2040
atatagaaca gcaaccatga cgtaacaacg acggtggcat ccgtcaccgt ctcgaacata   2100
atcaacaatt cttagccata cattgtgcta cattgcaact tgagtttcgt ttccacgtta   2160
cacgttccac acacaaagtg acacaacaaa atagttgcac acgataaagt ggttaagtca   2220
gaatcagctg tattaacaaa gtctaaccag tcgtgatttc aactttacag tgaccggacg   2280
aaggtggtga aattcgaaat gcaacctcag tgacattcca tattcaaaaa attcgaattt   2340
aacggccatc gtggtgctgt gctagtgtcg atattttatt tagaattatt ttcttttttg   2400
taggaaaatg gcggaaattt attatataag tggtgtacta tcgtcgtcga tgaagttatt   2460
ttgcgaatga tactttgttt tacaagtgcc gtgttttgtg tggacgcttg ctgtgcgatg   2520
ctgtgttgcg aacgacaacg gacttcactg tggctacctc cggcgtgtcg gtgagtttat   2580
ttgatattgt tattagcaat tcaatggaca ttgcaacatg atagaatctc aattatttta   2640
aaagtgtcta ttgagttgtt ttattattta agaattgcac aaacgctttt caattgtata   2700
caaatgttag ttgccgatag atttgtatta cgttgcattt ctgagacgtt tgtttgccgt   2760
cttgccttct ttgtgttcaa atggaaagcg ttagtgtgcg tgtcaatctg tttgttccaa   2820
gtacttgttt actgctcata ttcataagta gaattttatg ttacaacgta cacataaaat   2880
aaaatgctat ttatgaaata agacaatttg cgatgcgacg gaatttattt atgtttttat   2940
tgcttttaca aaacggagga atgcatgcta tttcttgtct ttatctaagt ttttacatta   3000
ttttatgatc attaaaactc acagttgtaa ggctctcttc taaggtgtac agaactatgc   3060
ctctcttatt acttcaaaat atttacatat tcgaaaaaaa aaagttttta gtaaaaaaaa   3120
atgtttccat actagggcgg ctgaacagtt tggagcctaa atacttattg gaccttcggt   3180
aactacactc acacgggcat aacacaacgc aagcgttgtt tcacgccagc tttcttgagg   3240
ccgtccaccg tggaaacact ccggtcgagc cagatcattt gaaatgatgc tgaagccttg   3300
```

```
ttcccacctt taataccta ggctcaaaag tattcagaga ccctagtata gtacatatac   3360

aaaacaaaac cgttccacaa acaccttaag ctaggtctaa aacacccagc tggtctacag   3420

aaaccctcaa aatccacacc agaaacctaa tcaccccctt taaaattcca gcccactgga   3480

tagtccacca acggcggatg tacgagcggt ccatacgttc cctgctggag ctgcaggcac   3540

gcaagggatc ctgctccatg tgcttcacgg agtacgctcc ccccttgctg ccgctgcccc   3600

tcaccacgca gcgaccctcg ccgccgcctg cgcacttgta gcg                    3643


<210> SEQ ID NO 32
<211> LENGTH: 40
<212> TYPE: DNA
<213> ORGANISM: Spodoptera frugiperda

<400> SEQUENCE: 32

aacagtgacg tggacgaggc atcacggaaa atagacgaag                          40


<210> SEQ ID NO 33
<211> LENGTH: 1195
<212> TYPE: DNA
<213> ORGANISM: Spodoptera frugiperda

<400> SEQUENCE: 33

gtaggccttt tattgtttaa atgccaattg caattgtcct tctgttattt atttgcattg     60

cgattgttcg ctgtaaagtt aaagagatga attgagcgct aaaaagattt ttcatacagg    120

aatgtgtgaa aagagttgtt taattcgtaa tttgcaacta tgtattatgt tttatgttca    180

ctgtttttgt gttgttaaca gcaaattaat gccgataaag agaatgacag aaaaaactta    240

caatctcaat taatccgata attacaaaaa gtgaatagtt aaccatcatg aaatcgtttt    300

agaaagcttt ttagcgttcg tacaaattag ttgttcgtgc tacattgtag gtgagacgcc    360

taaatgtctt tcgtacttcg agtgcggatg taacagtgtt atatgagcgg ccattgttat    420

ttccatacgt gcctggaacg ctgctcagcc cagcgtcgta gggctccctg cagtctcgca    480

cgaacgaacc tttatttagc cactgccggg aattgcattg gaaatagatg cctgcttata    540

aagtaggtaa tcataaacat atcacgattg aatttaataa taatttaatc ttagttccaa    600

ttctttggat aggttagggt tttttgacag actccatctg agtgatgtca aaaatcgatc    660

ttaaaacaaa gattttaggc ttgtttcgac cgaatggcca aattacttca tattgacttg    720

actccttttt tttcgcaatg cgaatatgtg tacctattgg aaaacttttg ttgtttttta    780

gaatacatat agattttcgt taaatttcaa tctaagtcaa ttgaatatat ttaattaatt    840

atttatcttt atttatttcc ttctctttac gaaatcttgg aatgtgaaaa ttattatcat    900

tgtatcaaca aaaggtttct ataaacgttt ttataaataa aataaaaaaa aaactgcatt    960

ttaataatca tacattgata tgaataaagc taaacagaaa acaaacgatg ttctaatttc   1020

aagatacatt tgacagatgt cacaaccgaa ccgttacggc cattttgaat ttgtctatgg   1080

tttatttttt ttaaggagaa aatgattcga tgtctctccc gccgtgtcta tggtttaatg   1140

cagttttttt tcacccgcca agcgattgtc caatttgcgc attgtttgtt ctcag        1195


<210> SEQ ID NO 34
<211> LENGTH: 84
<212> TYPE: DNA
<213> ORGANISM: Spodoptera frugiperda

<400> SEQUENCE: 34

gaaagatgat tatcaacgaa tacgcgcgga agaacaatct gaacgtgtat cgacgggtta     60
```

gagctgagga actcgacacg ccag 84

<210> SEQ ID NO 35
<211> LENGTH: 15
<212> TYPE: DNA
<213> ORGANISM: Spodoptera frugiperda

<400> SEQUENCE: 35
tacggacatt aatag 15

<210> SEQ ID NO 36
<211> LENGTH: 933
<212> TYPE: DNA
<213> ORGANISM: Spodoptera frugiperda

<400> SEQUENCE: 36
taataaatag tttttaccac caacaacact gaaactgtgc taacactttg acagtgacag 60
gtgtagtgta ggggctgtga caaacttcat tctggttcct attttaaatt taaatcattt 120
attttcggcc agcggcaaca gtttttcgtg ttcctttttt taatttaaat agtataatag 180
tttcttttat gccagacatt tagttctata aataagtatt tgaaagaacg ctatttaaaa 240
tgttttggac tgtaacatct attttaattt tgacaagaat gaagtttgtt acatacgaca 300
tatttcacag cacatcgtcg tgtatataaa taacacaaca ctttacagtt acacaaagta 360
tctacctaca caagacatca ctcattacac ataacgatta gatacttata cacgttcaca 420
ttaacataca gcagaaccag tggaaatgga tggtttaggt caagattgcc taatttagtc 480
aacgatcttc tcacaattta attcatttgt tgtattgggt atttgtaatt ttatatggag 540
atggtaattt tagagagagg gtagtataag agtaagtagt ttaggtaagt agttgagaaa 600
tgtcgttgta aatgtagggt tattttatga gtgaaattga gtcgtgattt ttgtctcctt 660
aagttaaatt ttgatagagg tattttattc atttgcattt gaaatataga acagcaacca 720
tgacgtaaca acgacggtgg catccgtcac cgtctcgaac ataatcaaca attcttagcc 780
atacattgtg ctacattgca acttgagttt cgtttccacg ttacacgttc cacacacaaa 840
gtgacacaac aaaatagttg cacacgataa agtggttaag tcagaatcag ctgtattaac 900
aaagtctaac cagtcgtgat ttcaacttta cag 933

<210> SEQ ID NO 37
<211> LENGTH: 134
<212> TYPE: DNA
<213> ORGANISM: Spodoptera frugiperda

<400> SEQUENCE: 37
tgaccggacg aaggtggtga aattcgaaat gcaacctcag tgacattcca tattcaaaaa 60
attcgaattt aacggccatc gtggtgctgt gctagtgtcg atattttatt tagaattatt 120
ttcttttttg tagg 134

<210> SEQ ID NO 38
<211> LENGTH: 166
<212> TYPE: DNA
<213> ORGANISM: Spodoptera frugiperda

<400> SEQUENCE: 38
aaaatggcgg aaatttatta tataagtggt gtactatcgt cgtcgatgaa gttattttgc 60
gaatgatact ttgttttaca agtgccgtgt tttgtgtgga cgcttgctgt gcgatgctgt 120
gttgcgaacg acaacggact tcactgtggc tacctccggc gtgtcg 166

<210> SEQ ID NO 39
<211> LENGTH: 901
<212> TYPE: DNA
<213> ORGANISM: Spodoptera frugiperda

<400> SEQUENCE: 39
gtgagtttat ttgatattgt tattagcaat tcaatggaca ttgcaacatg atagaatctc 60
aattatttta aaagtgtcta ttgagttgtt ttattattta agaattgcac aaacgctttt 120
caattgtata caaatgttag ttgccgatag atttgtatta cgttgcattt ctgagacgtt 180
tgtttgccgt cttgccttct ttgtgttcaa atggaaagcg ttagtgtgcg tgtcaatctg 240
tttgttccaa gtacttgttt actgctcata ttcataagta gaattttatg ttacaacgta 300
cacataaaat aaaatgctat ttatgaaata agacaatttg cgatgcgacg gaatttattt 360
atgtttttat tgcttttaca aaacggagga atgcatgcta tttcttgtct ttatctaagt 420
ttttacatta ttttatgatc attaaaactc acagttgtaa ggctctcttc taaggtgtac 480
agaactatgc ctctcttatt acttcaaaat atttacatat tcgaaaaaaa aaagttttta 540
gtaaaaaaaa atgtttccat actagggcgg ctgaacagtt tggagcctaa atacttattg 600
gaccttcggt aactacactc acacgggcat aacacaacgc aagcgttgtt tcacgccagc 660
tttcttgagg ccgtccaccg tggaaacact ccggtcgagc cagatcattt gaaatgatgc 720
tgaagccttg ttcccacctt taatacctta ggctcaaaag tattcagaga ccctagtata 780
gtacatatac aaaacaaaac cgttccacaa acaccttaag ctaggtctaa aacacccagc 840
tggtctacag aaaccctcaa aatccacacc agaaacctaa tcaccccctt taaaattcca 900
g 901

<210> SEQ ID NO 40
<211> LENGTH: 172
<212> TYPE: DNA
<213> ORGANISM: Spodoptera frugiperda

<400> SEQUENCE: 40
cccactggat agtccaccaa cggcggatgt acgagcggtc catacgttcc ctgctggagc 60
tgcaggcacg caagggatcc tgctccatgt gcttcacgga gtacgctccc cccttgctgc 120
cgctgcccct caccacgcag cgaccctcgc cgccgcctgc gcacttgtag cg 172

<210> SEQ ID NO 41
<211> LENGTH: 130
<212> TYPE: DNA
<213> ORGANISM: Drosophila melanogaster

<400> SEQUENCE: 41
agcgccggag tataaataga ggcgcttcgt ctacggagcg acaattcaat tcaaacaagc 60
aaagtgaaca cgtcgctaag cgaaagctaa gcaaataaac aagcgcagct gaacaagcta 120
aacaatctgc 130

<210> SEQ ID NO 42
<211> LENGTH: 296
<212> TYPE: DNA
<213> ORGANISM: Artificial Sequence
<220> FEATURE:
<223> OTHER INFORMATION: Synthetic DNA contains 7 repeats of Tn10
tet-operon

<400> SEQUENCE: 42
gactttcact tttctctatc actgataggg agtggtaaac tcgactttca cttttctcta 60
tcactgatag ggagtggtaa actcgacttt cacttttctc tatcactgat agggagtggt 120
aaactcgact ttcacttttc tctatcactg atagggagtg gtaaactcga ctttcacttt 180
tctctatcac tgatagggag tggtaaactc gactttcact tttctctatc actgataggg 240
agtggtaaac tcgactttca cttttctcta tcactgatag ggagtggtaa actcga 296

<210> SEQ ID NO 43
<211> LENGTH: 228
<212> TYPE: DNA
<213> ORGANISM: Simian virus 40

<400> SEQUENCE: 43
gatcataatc agccatacca catttgtaga ggttttactt gctttaaaaa acctcccaca 60
cctccccctg aacctgaaac ataaaatgaa tgcaattgtt gttgttaact tgtttattgc 120
agcttataat ggttacaaat aaagcaatag catcacaaat ttcacaaata aagcattttt 180
ttcactgcat tctagttgtg gtttgtccaa actcatcaat gtatctta 228

<210> SEQ ID NO 44
<211> LENGTH: 21
<212> TYPE: DNA
<213> ORGANISM: Artificial Sequence
<220> FEATURE:
<223> OTHER INFORMATION: Synthetic DNA

<400> SEQUENCE: 44
cccaagaaaa agcggaaggt g 21

<210> SEQ ID NO 45
<211> LENGTH: 675
<212> TYPE: DNA
<213> ORGANISM: Artificial Sequence
<220> FEATURE:
<223> OTHER INFORMATION: Synthetic DNA encoding a variant of red
fluorescent protein originally identified in Discosoma (Clontech)

<400> SEQUENCE: 45
atggcctcct ccgagaacgt catcaccgag ttcatgcgct tcaaggtgcg catggagggc 60
accgtgaacg gccacgagtt cgagatcgag ggcgagggcg agggccgccc ctacgagggc 120
cacaacaccg tgaagctgaa ggtgaccaag ggcggccccc tgcccttcgc ctgggacatc 180
ctgtcccccc agttccagta cggctccaag gtgtacgtga agcaccccgc cgacatcccc 240
gactacaaga agctgtcctt ccccgagggc ttcaagtggg agcgcgtgat gaacttcgag 300
gacggcggcg tggcgaccgt gacccaggac tcctccctgc aggacggctg cttcatctac 360
aaggtgaagt tcatcggcgt gaacttcccc tccgacggcc ccgtgatgca gaagaagacc 420
atgggctggg aggcctccac cgagcgcctg taccccccgcg acggcgtgct gaagggcgag 480
acccacaagg ccctgaagct gaaggacggc ggccactacc tggtggagtt caagtccatc 540
tacatggcca agaagcccgt gcagctgccc ggctactact acgtggacgc caagctggac 600
atcacctccc acaacgagga ctacaccatc gtggagcagt acgagcgcac cgagggccgc 660
caccacctgt tcctg 675

<210> SEQ ID NO 46
<211> LENGTH: 21
<212> TYPE: DNA

<213> ORGANISM: Artificial Sequence
<220> FEATURE:
<223> OTHER INFORMATION: Synthetic DNA

<400> SEQUENCE: 46
cccaagaaga agcgcaaacc g 21

<210> SEQ ID NO 47
<211> LENGTH: 87
<212> TYPE: DNA
<213> ORGANISM: Drosophila melanogaster

<400> SEQUENCE: 47
ttggggtaag ttttcccgtt cttttctggg ttcttccctt ttgctcatcc ttgctgcact 60
accttcaggt gcaagttgag attcagg 87

<210> SEQ ID NO 48
<211> LENGTH: 633
<212> TYPE: DNA
<213> ORGANISM: Autographa californica nucleopolyhedrovirus

<400> SEQUENCE: 48
gttgcacaac actattatcg atttgcagtt cgggacataa atgtttaaat atatcgatgt 60
ctttgtgatg cgcgcgacat tttgtaggt tattgataaa atgaacggat acgttgcccg 120
acattatcat taaatccttg gcgtagaatt tgtcgggtcc attgtccgtg tgcgctagta 180
gcatgcccgt aacggacctc gtacttttgg cttcaaaggt tttgcgcaca gacaaaatgt 240
gccacacttg cagctctgca tgtgtgcgcg ttaccacaaa tcccaacggc gcagtgtact 300
tgttgtatgc aaataaatct cgataaaggc gcggcgcgcg aatgcagctg atcacgtacg 360
ctcctcgtgt tccgttcaag gacggtgtta ccgacctcag attaatgttt atcggccgac 420
tgttttcgta tccgctcacc aaacgcgttt ttgcattaac attgtatgtc ggcggatgtt 480
ctatatctaa tttgaataaa taaacgataa ccgcgttggt tttagagggc ataataaaag 540
aaatattgtt atcgtgttcg ccattagggc agtataaatt gacgttcatg ttggatattg 600
tttcagttgc aagttgacac tggcggcgac aag 633

<210> SEQ ID NO 49
<211> LENGTH: 563
<212> TYPE: DNA
<213> ORGANISM: Autographa californica nucleopolyhedrovirus

<400> SEQUENCE: 49
gctttacgag tagaattcta cgcgtaaaac acaatcaagt atgagtcata agctgatgtc 60
atgttttgca cacggctcat aaccgaactg gctttacgag tagaattcta cttgtaacgc 120
acgatcagtg gatgatgtca tttgtttttc aaatcgagat gatgtcatgt tttgcacacg 180
gctcataaac tcgctttacg agtagaattc tacgtgtaac gcacgatcga ttgatgagtc 240
atttgttttg caatatgata tcatacaata tgactcattt gtttttcaaa accgaacttg 300
atttacgggt agaattctac ttgtaaagca caatcaaaaa gatgatgtca tttgtttttc 360
aaaactgaac tcgctttacg agtagaattc tacgtgtaaa acacaatcaa gaaatgatgt 420
catttgttat aaaaataaaa gctgatgtca tgttttgcac atggctcata actaaactcg 480
ctttacgggt agaattctac gcgtaaaaca tgattgataa ttaaataatt catttgcaag 540
ctatacgtta aatcaaacgg acg 563

<210> SEQ ID NO 50
<211> LENGTH: 667
<212> TYPE: DNA
<213> ORGANISM: Autographa californica nucleopolyhedrovirus

<400> SEQUENCE: 50
atgaatcgtt tttaaaataa caaatcaatt gttttataat attcgtacga ttctttgatt 60
atgtaataaa atgtgatcat taggaagatt acgaaaaata taaaaaatat gagttctgtg 120
tgtataacaa atgctgtaaa cgccacaatt gtgtttgttg caaataaacc catgattatt 180
tgattaaaat tgttgttttc tttgttcata gacaatagtg tgttttgcct aaacgtgtac 240
tgcataaact ccatgcgagt gtatagcgag ctagtggcta acgcttgccc caccaaagta 300
gattcgtcaa aatcctcaat ttcatcaccc tcctccaagt ttaacatttg gccgtcggaa 360
ttaacttcta aagatgccac ataatctaat aaatgaaata gagattcaaa cgtggcgtca 420
tcgtccgttt cgaccatttc cgaaaagaac tcgggcataa actctatgat ttctctggac 480
gtggtgttgt cgaaactctc aaagtacgca gtcaggaacg tgcgcgacat gtcgtcggga 540
aactcgcgcg gaaacatgtt gttgtaaccg aacgggtccc atagcgccaa aaccaaatct 600
gccagcgtca atagaatgag cacgatgccg acaatggagc tggcttggat agcgattcga 660
gttaacg 667

<210> SEQ ID NO 51
<211> LENGTH: 1011
<212> TYPE: DNA
<213> ORGANISM: Artificial Sequence
<220> FEATURE:
<223> OTHER INFORMATION: Synthetic DNA encoding the fusion tetracycline transactivator protein optimised for expression in insects

<400> SEQUENCE: 51
gtcagccgcc tggataagtc caaagtcatc aactccgcgt tggagctgtt gaacgaagtt 60
ggcattgagg gactgacgac ccgcaagttg gcgcagaagc tgggcgtgga gcagcccacc 120
ctctactggc acgtgaagaa taagcgggcg ctgctggatg ccctggccat cgagatgctc 180
gaccgccacc acacgcattt ttgcccgttg gaaggcgagt cctggcagga cttcctccgc 240
aataacgcca agtcgttccg ctgcgctctg ctgtcccacc gagacggtgc caaagtccat 300
ctcggcacgc gcccgaccga aaagcaatac gagacactgg agaaccagct cgcgttcctg 360
tgccagcaag gcttcagcct ggaaaatgct ctctacgctc tgagcgccgt cggtcacttt 420
accctgggct gcgtgctgga ggaccaagag catcaagtcg caaaagagga gcgcgagacc 480
ccaacaaccg attcgatgcc cccactgctg cgtcaggcaa tcgagctgtt cgatcatcaa 540
ggagccgagc cggcattcct gttcggcttg gagctgatta tctgcggatt ggaaaagcaa 600
ctgaaatgcg agtcgggctc gggccccgcg tacagccgcg cgcgtacgaa aaacaattac 660
gggtctacca tcgagggcct gctcgatctc ccggacgacg acgcccccga agaggcgggg 720
ctggcggctc cgcgcctgtc ctttctcccc gcgggacaca cgcgcagact gtcgacggcc 780
cccccgaccg atgtcagcct gggggacgag ctccacttag acggcgagga cgtggcgatg 840
gcgcatgccg acgcgctaga cgatttcgat ctggacatgt tgggggacgg ggattccccg 900
ggtccgggat ttaccccccca cgactccgcc ccctacggcg ctctggatat ggccgacttc 960
gagtttgagc agatgtttac cgatgccctt ggaattgacg agtacggtgg g 1011

<210> SEQ ID NO 52
<211> LENGTH: 225

<212> TYPE: DNA
<213> ORGANISM: Drosophila melanogaster

<400> SEQUENCE: 52
cagatcttcg tcaagaccct gaccggcaag accatcaccc tggaggtgga gccgagcgat 60
accatcgaga acgtgaaggc caagatccag gacaaggagg gcatcccgcc ggatcagcag 120
cgcctgatct tcgccggacg ccagctggag gatggccgca ccctgagcga ctacaacatc 180
cagaaggaga gcaccctgca cctggtgctg cgcctgcgcg gtggt 225

<210> SEQ ID NO 53
<211> LENGTH: 3640
<212> TYPE: DNA
<213> ORGANISM: Artificial Sequence
<220> FEATURE:
<223> OTHER INFORMATION: Synthetic DNA based on Spodoptera frugiperda sequences

<400> SEQUENCE: 53
aacagtgacg tggacgaggc atcacggaaa atagacgaag gtaggccttt tattgtttaa 60
atgccaattg caattgtcct tctgttattt atttgcattg cgattgttcg ctgtaaagtt 120
aaagagatga attgagcgct aaaaagattt ttcatacagg aatgtgtgaa aagagttgtt 180
taattcgtaa tttgcaacta tgtattatgt tttatgttca ctgtttttgt gttgttaaca 240
gcaaattaat gccgataaag agaatgacag aaaaaactta caatctcaat taatccgata 300
attacaaaaa gtgaatagtt aaccatcatg aaatcgtttt agaaagcttt ttagcgttcg 360
tacaaattag ttgttcgtgc tacattgtag gtgagacgcc taaatgtctt tcgtacttcg 420
agtgcggatg taacagtgtt atatgagcgg ccattgttat ttccatacgt gcctggaacg 480
ctgctcagcc cagcgtcgta gggctccctg cagtctcgca cgaacgaacc tttatttagc 540
cactgccggg aattgcattg gaaatagatg cctgcttata aagtaggtaa tcataaacat 600
atcacgattg aatttaataa taatttaatc ttagttccaa ttctttggat aggttagggt 660
tttttgacag actccatctg agtgatgtca aaaatcgatc ttaaaacaaa gattttaggc 720
ttgtttcgac cgaatggcca aattacttca tattgacttg actccttttt tttcgcaatg 780
cgaatatgtg tacctattgg aaaacttttg ttgtttttta gaatacatat agattttcgt 840
taaatttcaa tctaagtcaa ttgaatatat ttaattaatt atttatcttt atttatttcc 900
ttctctttac gaaatcttgg aatgtgaaaa ttattatcat tgtatcaaca aaaggtttct 960
ataaacgttt ttataaataa aataaaaaaa aaactgcatt ttaataatca tacattgata 1020
tgaataaagc taaacagaaa acaaacgatg ttctaatttc aagatacatt tgacagatgt 1080
cacaaccgaa ccgttacggc cattttgaat ttgtctatgg tttattttt ttaaggagaa 1140 aatgattcga tgtctctccc gccgtgtcta tggtttaatg cagtttttt tcacccgcca 1200 agcgattgtc caatttgcgc attgtttgtt ctcaggaaag atgattatca acgaatacgc 1260
gcggaagaac aatctgaacg tgtatcgacg ggttagagct gaggaactcg acacgccagt 1320
acggacatta atagtaataa atagttttta ccaccaacaa cactgaaact gtgctaacac 1380
tttgacagtg acaggtgtag tgtaggggct gtgacaaact tcattctggt tcctatttta 1440
aatttaaatc atttattttc ggccagcggc aacagttttt cgtgttcctt tttttaattt 1500
aaatagtata atagtttctt ttatgccaga catttagttc tataaataag tatttgaaag 1560
aacgctattt aaaatgtttt ggactgtaac atctatttta attttgacaa gaatgaagtt 1620
tgttacatac gacatatttc acagcacatc gtcgtgtata taaataacac aacactttac 1680

```
agttacacaa agtatctacc tacacaagac atcactcatt acacataacg attagatact   1740
tatacacgtt cacattaaca tacagcagaa ccagtggaaa tggatggttt aggtcaagat   1800
tgcctaattt agtcaacgat cttctcacaa tttaattcat ttgttgtatt gggtatttgt   1860
aattttatat ggagatggta attttagaga gagggtagta taagagtaag tagtttaggt   1920
aagtagttga gaaatgtcgt tgtaaatgta gggttatttt atgagtgaaa ttgagtcgtg   1980
atttttgtct ccttaagtta aattttgata gaggtatttt attcatttgc atttgaaata   2040
tagaacagca accatgacgt aacaacgacg gtggcatccg tcaccgtctc gaacataatc   2100
aacaattctt agccatacat tgtgctacat tgcaacttga gtttcgtttc cacgttacac   2160
gttccacaca caaagtgaca caacaaaata gttgcacacg ataaagtggt taagtcagaa   2220
tcagctgtat taacaaagtc taaccagtcg tgatttcaac tttacagtga ccggacgaag   2280
gtggtgaaat tcgaaatgca acctcagtga cattccatat tcaaaaaatt cgaatttaac   2340
ggccatcgtg gtgctgtgct agtgtcgata ttttatttag aattattttc tttttgtag    2400
gaaaatggcg gaaatttatt atataagtgg tgtactatcg tcgtcgatga agttattttg   2460
cgaatgatac tttgttttac aagtgccgtg ttttgtgtgg acgcttgctg tgcgatgctg   2520
tgttgcgaac gacaacggac ttcactgtgg ctacctccgg cgtgtcggtg agtttatttg   2580
atattgttat tagcaattca atggacattg caacatgata gaatctcaat tattttaaaa   2640
gtgtctattg agttgtttta ttatttaaga attgcacaaa cgcttttcaa ttgtatacaa   2700
atgttagttg ccgatagatt tgtattacgt tgcatttctg agacgtttgt ttgccgtctt   2760
gccttctttg tgttcaaatg gaaagcgtta gtgtgcgtgt caatctgttt gttccaagta   2820
cttgtttact gctcatattc ataagtagaa ttttatgtta caacgtacac ataaaataaa   2880
atgctattta tgaaataaga caatttgcga tgcgacggaa tttatttatg tttttattgc   2940
ttttacaaaa cggaggaatg catgctattt cttgtcttta tctaagtttt tacattattt   3000
tatgatcatt aaaactcaca gttgtaaggc tctcttctaa ggtgtacaga actatgcctc   3060
tcttattact tcaaaatatt tacatattcg aaaaaaaaaa gtttttagta aaaaaaaatg   3120
tttccatact agggcggctg aacagtttgg agcctaaata cttattggac cttcggtaac   3180
tacactcaca cgggcataac acaacgcaag cgttgtttca cgccagcttt cttgaggccg   3240
tccaccgtgg aaacactccg gtcgagccag atcatttgaa atgatgctga agccttgttc   3300
ccacctttaa taccttaggc tcaaaagtat tcagagaccc tagtatagta catatacaaa   3360
acaaaaccgt tccacaaaca ccttaagcta ggtctaaaac acccagctgg tctacagaaa   3420
ccctcaaaat ccacaccaga aacctaatca cccccctttaa aattccagcc cactggatag   3480
tccaccaacg gcggatgtac gagcggtcca tacgttccct gctggagctg caggcacgca   3540
agggatcctg ctccatgtgc ttcacggagt acgctccccc cttgctgccg ctgcccctca   3600
ccacgcagcg accctcgccg ccgcctgcgc acttgtagcg                         3640
```

<210> SEQ ID NO 54
<211> LENGTH: 40
<212> TYPE: DNA
<213> ORGANISM: Spodoptera frugiperda

<400> SEQUENCE: 54

```
aacagtgacg tggacgaggc atcacggaaa atagacgaag                           40
```

<210> SEQ ID NO 55

<211> LENGTH: 1195
<212> TYPE: DNA
<213> ORGANISM: Spodoptera frugiperda

<400> SEQUENCE: 55

```
gtaggccttt tattgtttaa atgccaattg caattgtcct tctgttattt atttgcattg     60
cgattgttcg ctgtaaagtt aaagagatga attgagcgct aaaaagattt ttcatacagg    120
aatgtgtgaa aagagttgtt taattcgtaa tttgcaacta tgtattatgt tttatgttca    180
ctgtttttgt gttgttaaca gcaaattaat gccgataaag agaatgacag aaaaaactta    240
caatctcaat taatccgata attacaaaaa gtgaatagtt aaccatcatg aaatcgtttt    300
agaaagcttt ttagcgttcg tacaaattag ttgttcgtgc tacattgtag gtgagacgcc    360
taaatgtctt tcgtacttcg agtgcggatg taacagtgtt atatgagcgg ccattgttat    420
ttccatacgt gcctggaacg ctgctcagcc cagcgtcgta gggctccctg cagtctcgca    480
cgaacgaacc tttatttagc cactgccggg aattgcattg gaaatagatg cctgcttata    540
aagtaggtaa tcataaacat atcacgattg aatttaataa taatttaatc ttagttccaa    600
ttctttggat aggttagggt tttttgacag actccatctg agtgatgtca aaaatcgatc    660
ttaaaacaaa gattttaggc ttgtttcgac cgaatggcca aattacttca tattgacttg    720
actccttttt tttcgcaatg cgaatatgtg tacctattgg aaaacttttg ttgtttttta    780
gaatacatat agattttcgt taaatttcaa tctaagtcaa ttgaatatat ttaattaatt    840
atttatcttt atttatttcc ttctctttac gaaatcttgg aatgtgaaaa ttattatcat    900
tgtatcaaca aaaggtttct ataaacgttt ttataaataa aataaaaaaa aaactgcatt    960
ttaataatca tacattgata tgaataaagc taaacagaaa acaaacgatg ttctaatttc   1020
aagatacatt tgacagatgt cacaaccgaa ccgttacggc cattttgaat ttgtctatgg   1080
tttatttttt ttaaggagaa aatgattcga tgtctctccc gccgtgtcta tggtttaatg   1140
cagttttttt tcacccgcca agcgattgtc caatttgcgc attgtttgtt ctcag        1195
```

<210> SEQ ID NO 56
<211> LENGTH: 84
<212> TYPE: DNA
<213> ORGANISM: Spodoptera frugiperda

<400> SEQUENCE: 56

```
gaaagatgat tatcaacgaa tacgcgcgga agaacaatct gaacgtgtat cgacgggtta     60
gagctgagga actcgacacg ccag                                            84
```

<210> SEQ ID NO 57
<211> LENGTH: 15
<212> TYPE: DNA
<213> ORGANISM: Spodoptera frugiperda

<400> SEQUENCE: 57

```
tacggacatt aatag                                                      15
```

<210> SEQ ID NO 58
<211> LENGTH: 933
<212> TYPE: DNA
<213> ORGANISM: Spodoptera frugiperda

<400> SEQUENCE: 58

```
taataaatag tttttaccac caacaacact gaaactgtgc taacactttg acagtgacag     60
gtgtagtgta ggggctgtga caaacttcat tctggttcct attttaaatt taaatcattt    120
```

attttcggcc agcggcaaca gtttttcgtg ttccttttttt taatttaaat agtataatag 180
tttcttttat gccagacatt tagttctata aataagtatt tgaaagaacg ctatttaaaa 240
tgttttggac tgtaacatct attttaattt tgacaagaat gaagtttgtt acatacgaca 300
tatttcacag cacatcgtcg tgtatataaa taacacaaca ctttacagtt acacaaagta 360
tctacctaca caagacatca ctcattacac ataacgatta gatacttata cacgttcaca 420
ttaacataca gcagaaccag tggaaatgga tggtttaggt caagattgcc taatttagtc 480
aacgatcttc tcacaattta attcatttgt tgtattgggt atttgtaatt ttatatggag 540
atggtaattt tagagagagg gtagtataag agtaagtagt ttaggtaagt agttgagaaa 600
tgtcgttgta aatgtagggt tattttatga gtgaaattga gtcgtgattt ttgtctcctt 660
aagttaaatt ttgatagagg tattttattc atttgcattt gaaatataga acagcaacca 720
tgacgtaaca acgacggtgg catccgtcac cgtctcgaac ataatcaaca attcttagcc 780
atacattgtg ctacattgca acttgagttt cgtttccacg ttacacgttc cacacacaaa 840
gtgacacaac aaaatagttg cacacgataa agtggttaag tcagaatcag ctgtattaac 900
aaagtctaac cagtcgtgat ttcaacttta cag 933

<210> SEQ ID NO 59
<211> LENGTH: 134
<212> TYPE: DNA
<213> ORGANISM: Spodoptera frugiperda

<400> SEQUENCE: 59
tgaccggacg aaggtggtga aattcgaaat gcaacctcag tgacattcca tattcaaaaa 60
attcgaattt aacggccatc gtggtgctgt gctagtgtcg atattttatt tagaattatt 120
ttcttttttg tagg 134

<210> SEQ ID NO 60
<211> LENGTH: 166
<212> TYPE: DNA
<213> ORGANISM: Spodoptera frugiperda

<400> SEQUENCE: 60
aaaatggcgg aaatttatta tataagtggt gtactatcgt cgtcgatgaa gttattttgc 60
gaatgatact ttgttttaca agtgccgtgt tttgtgtgga cgcttgctgt gcgatgctgt 120
gttgcgaacg acaacggact tcactgtggc tacctccggc gtgtcg 166

<210> SEQ ID NO 61
<211> LENGTH: 901
<212> TYPE: DNA
<213> ORGANISM: Spodoptera frugiperda

<400> SEQUENCE: 61
gtgagtttat ttgatattgt tattagcaat tcaatggaca ttgcaacatg atagaatctc 60
aattatttta aaagtgtcta ttgagttgtt ttattattta agaattgcac aaacgctttt 120
caattgtata caaatgttag ttgccgatag atttgtatta cgttgcattt ctgagacgtt 180
tgtttgccgt cttgccttct ttgtgttcaa atggaaagcg ttagtgtgcg tgtcaatctg 240
tttgttccaa gtacttgttt actgctcata ttcataagta gaattttatg ttacaacgta 300
cacataaaat aaaatgctat ttatgaaata agacaatttg cgatgcgacg gaatttattt 360
atgtttttat tgcttttaca aaacggagga atgcatgcta tttcttgtct ttatctaagt 420

```
ttttacatta ttttatgatc attaaaactc acagttgtaa ggctctcttc taaggtgtac    480

agaactatgc ctctcttatt acttcaaaat atttacatat tcgaaaaaaa aaagttttta    540

gtaaaaaaaa atgtttccat actagggcgg ctgaacagtt tggagcctaa atacttattg    600

gaccttcggt aactacactc acacgggcat aacacaacgc aagcgttgtt tcacgccagc    660

tttcttgagg ccgtccaccg tggaaacact ccggtcgagc cagatcattt gaaatgatgc    720

tgaagccttg ttcccacctt taatacctta ggctcaaaag tattcagaga ccctagtata    780

gtacatatac aaaacaaaac cgttccacaa acaccttaag ctaggtctaa aacacccagc    840

tggtctacag aaaccctcaa aatccacacc agaaacctaa tcaccccctt taaaattcca    900

g                                                                    901


<210> SEQ ID NO 62
<211> LENGTH: 172
<212> TYPE: DNA
<213> ORGANISM: Spodoptera frugiperda

<400> SEQUENCE: 62

cccactggat agtccaccaa cggcggatgt acgagcggtc catacgttcc ctgctggagc     60

tgcaggcacg caagggatcc tgctccatgt gcttcacgga gtacgctccc cccttgctgc    120

cgctgcccct caccacgcag cgaccctcgc cgccgcctgc gcacttgtag cg           172


<210> SEQ ID NO 63
<211> LENGTH: 376
<212> TYPE: DNA
<213> ORGANISM: Artificial Sequence
<220> FEATURE:
<223> OTHER INFORMATION: Synthetic DNA based on sequences from turnip
      yellow mosaic virus, hCMV and 7 repeats of Tn10 tet operon

<400> SEQUENCE: 63

tttactccct atcagtgata gagaacgtat gaagagttta ctccctatca gtgatagaga     60

acgtatgcag actttactcc ctatcagtga tagagaacgt ataaggagtt tactccctat    120

cagtgataga gaacgtatga ccagtttact ccctatcagt gatagagaac gtatctacag    180

tttactccct atcagtgata gagaacgtat atccagttta ctccctatca gtgatagaga    240

acgtataagc tttaggcgtg tacggtgggc gcctataaaa gcagagctcg tttagtgaac    300

cgtcagatcg cctggagcaa ttccacaaca cttttgtctt ataccaactt tccgtaccac    360

ttcctaccct cgtaaa                                                    376


<210> SEQ ID NO 64
<211> LENGTH: 58
<212> TYPE: DNA
<213> ORGANISM: Artificial Sequence
<220> FEATURE:
<223> OTHER INFORMATION: Synthetic non-coding fragment based on turnip
      yellow mosaic virus sequence

<400> SEQUENCE: 64

aattccacaa cacttttgtc ttataccaac tttccgtacc acttcctacc ctcgtaaa       58


<210> SEQ ID NO 65
<211> LENGTH: 65
<212> TYPE: DNA
<213> ORGANISM: Human cytomegalovirus

<400> SEQUENCE: 65

taggcgtgta cggtgggcgc ctataaaagc agagctcgtt tagtgaaccg tcagatcgcc     60
```

tggag 65

<210> SEQ ID NO 66
<211> LENGTH: 246
<212> TYPE: DNA
<213> ORGANISM: Artificial Sequence
<220> FEATURE:
<223> OTHER INFORMATION: Synthetic DNA contains 7 repeats of Tn10 tet-operon

<400> SEQUENCE: 66
tttactccct atcagtgata gagaacgtat gaagagttta ctccctatca gtgatagaga 60
acgtatgcag actttactcc ctatcagtga tagagaacgt ataaggagtt tactccctat 120
cagtgataga gaacgtatga ccagtttact ccctatcagt gatagagaac gtatctacag 180
tttactccct atcagtgata gagaacgtat atccagttta ctccctatca gtgatagaga 240
acgtat 246

<210> SEQ ID NO 67
<211> LENGTH: 1014
<212> TYPE: DNA
<213> ORGANISM: Artificial Sequence
<220> FEATURE:
<223> OTHER INFORMATION: Synthetic DNA based on a fusion of sequences from E. coli (tetR - tetracycline repressor) and HSV-1 (VP16 transcriptional activator)

<400> SEQUENCE: 67
atggtcagcc gcctggataa gtccaaagtc atcaactccg cgttggagct gttgaacgaa 60
gttggcattg agggactgac gacccgcaag ttggcgcaga agctgggcgt ggagcagccc 120
accctctact ggcacgtgaa gaataagcgg gcgctgctgg atgccctggc catcgagatg 180
ctcgaccgcc accacacgca tttttgcccg ttggaaggcg agtcctggca ggacttcctc 240
cgcaataacg ccaagtcgtt ccgctgcgct ctgctgtccc accgagacgg tgccaaagtc 300
catctcggca cgcgcccgac cgaaaagcaa tacgagacac tggagaacca gctcgcgttc 360
ctgtgccagc aaggcttcag cctggaaaat gctctctacg ctctgagcgc cgtcggtcac 420
tttaccctgg gctgcgtgct ggaggaccaa gagcatcaag tcgcaaaaga ggagcgcgag 480
accccaacaa ccgattcgat gcccccactg ctgcgtcagg caatcgagct gttcgatcat 540
caaggagccg agccggcatt cctgttcggc ttggagctga ttatctgcgg attggaaaag 600
caactgaaat gcgagtcggg ctcgggcccc gcctacagcc gcgcccgcac caagaacaac 660
tacggcagca ccatcgaggg cctgctggat ctgccggatg atgatgcccc ggaggaggcg 720
ggcctggccg ccccgcgcct gagcttcctg ccggccggac acacccgccg cctgtcgacc 780
gccccgccga ccgacgtgag cctgggcgat gagctgcacc tggatggcga ggatgtggcg 840
atggcccacg ccgatgccct ggacgacttc gacctggaca tgctgggcga tggcgatagc 900
ccgggaccgg gattcacccc gcacgatagc gccccctacg gcgccctgga tatggccgat 960
ttcgagttcg agcagatgtt caccgacgcc ctgggcatcg atgagtacgg cggc 1014

<210> SEQ ID NO 68
<211> LENGTH: 1008
<212> TYPE: DNA
<213> ORGANISM: Artificial Sequence
<220> FEATURE:
<223> OTHER INFORMATION: Synthetic DNA based on a fusion of sequences from E. coli (tetR - tetracycline repressor) and HSV-1 (VP16 transcriptional activator)

<400> SEQUENCE: 68
atggagctgc gcctggacaa gagcaaggtg atcaacagcg ccctggagct gctgaacgaa 60
gtgggcatcg agggcctgac cacccgcaag ctggcccaga agctgggcgt ggaacagccg 120
accctgtact ggcacgtgaa gaacaagcgc gccctgctgg acgccctggc catcgaaatg 180
ctggatcgcc accacaccca cttctgcccg ctggagggcg agagctggca ggatttcctg 240
cgcaacaacg ccaagagctt ccgctgcgcc ctgctgtcgc accgcgatgg cgccaaggtg 300
cacctgggca cccgcccgac cgagaagcag tacgagaccc tggagaacca gctggccttc 360
ctgtgccagc agggcttcag cctggagaac gccctgtacg ccctgagcgc cgtgggccac 420
ttcaccctgg gctgtgtgct ggaggatcag gagcaccagg tggccaagga ggagcgcgag 480
accccgacca ccgatagcat gccgccgctg ctgcgccagg ccatcgagct gttcgatcac 540
cagggcgccg agccggcctt cctgttcggc ctggagctga tcatctgcgg cctggaaaag 600
cagctgaagt gcgagagcgg cagcgcctac agccgcgccc gtaccaagaa caactatggc 660
agcaccatcg agggactgct ggacctgccg gatgacgatg ccccggagga agccggcctg 720
gccgcccccc gcctgagctt cctgcccgcc ggacacacgc gccgcctgag caccgccccg 780
ccgaccgatg tgagcctggg cgacgagctg cacctggatg gagaggatgt ggcaatggcc 840
cacgccgacg ccctggacga tttcgacctg gatatgctgg gcgatggaga tagcccggga 900
ccgggcttca cgccccacga tagcgccccg tacggcgccc tggacatggc cgacttcgag 960
ttcgagcaaa tgttcaccga cgcgctgggc atcgatgagt atggcggc 1008

<210> SEQ ID NO 69
<211> LENGTH: 462
<212> TYPE: DNA
<213> ORGANISM: Spodoptera frugiperda

<400> SEQUENCE: 69
aacagtgacg tggacgaggc atcacggaaa atagacgaag gaaagatgat tatcaacgaa 60
tacgcgcgga agaacaatct gaacgtgtat cgacgggtta gagctgagga actcgacacg 120
ccagaaaatg gcggaaattt attatataag tggtgtacta tcgtcgtcga tgaagttatt 180
ttgcgaatga tactttgttt tacaagtgcc gtgttttgtg tggacgcttg ctgtgcgatg 240
ctgtgttgcg aacgacaacg gacttcactg tggctacctc cggcgtgtcg cccactggat 300
agtccaccaa cggcggatgt acgagcggtc catacgttcc ctgctggagc tgcaggcacg 360
caagggatcc tgctccatgt gcttcacgga gtacgctccc cccttgctgc cgctgcccct 420
caccacgcag cgaccctcgc cgccgcctgc gcacttgtag cg 462

<210> SEQ ID NO 70
<211> LENGTH: 154
<212> TYPE: PRT
<213> ORGANISM: Spodoptera frugiperda

<400> SEQUENCE: 70

Asn Ser Asp Val Asp Glu Ala Ser Arg Lys Ile Asp Glu Gly Lys Met
1 5 10 15

Ile Ile Asn Glu Tyr Ala Arg Lys Asn Asn Leu Asn Val Tyr Arg Arg
20 25 30

Val Arg Ala Glu Glu Leu Asp Thr Pro Glu Asn Gly Gly Asn Leu Leu
35 40 45

Tyr Lys Trp Cys Thr Ile Val Val Asp Glu Val Ile Leu Arg Met Ile

```
    50                  55                  60

Leu Cys Phe Thr Ser Ala Val Phe Cys Val Asp Ala Cys Cys Ala Met
65                  70                  75                  80

Leu Cys Cys Glu Arg Gln Arg Thr Ser Leu Trp Leu Pro Pro Ala Cys
                85                  90                  95

Arg Pro Leu Asp Ser Pro Pro Thr Ala Asp Val Arg Ala Val His Thr
            100                 105                 110

Phe Pro Ala Gly Ala Ala Gly Thr Gln Gly Ile Leu Leu His Val Leu
        115                 120                 125

His Gly Val Arg Ser Pro Leu Ala Ala Ala Ala Pro His His Ala Ala
    130                 135                 140

Thr Leu Ala Ala Ala Cys Ala Leu Val Ala
145                 150


<210> SEQ ID NO 71
<211> LENGTH: 13
<212> TYPE: PRT
<213> ORGANISM: Spodoptera frugiperda

<400> SEQUENCE: 71

Asn Ser Asp Val Asp Glu Ala Ser Arg Lys Ile Asp Glu
1               5                   10


<210> SEQ ID NO 72
<211> LENGTH: 28
<212> TYPE: PRT
<213> ORGANISM: Spodoptera frugiperda

<400> SEQUENCE: 72

Gly Lys Met Ile Ile Asn Glu Tyr Ala Arg Lys Asn Asn Leu Asn Val
1               5                   10                  15

Tyr Arg Arg Val Arg Ala Glu Glu Leu Asp Thr Pro
            20                  25


<210> SEQ ID NO 73
<211> LENGTH: 5
<212> TYPE: PRT
<213> ORGANISM: Spodoptera frugiperda

<400> SEQUENCE: 73

Val Arg Thr Leu Ile
1               5


<210> SEQ ID NO 74
<211> LENGTH: 55
<212> TYPE: PRT
<213> ORGANISM: Spodoptera frugiperda

<400> SEQUENCE: 74

Glu Asn Gly Gly Asn Leu Leu Tyr Lys Trp Cys Thr Ile Val Val Asp
1               5                   10                  15

Glu Val Ile Leu Arg Met Ile Leu Cys Phe Thr Ser Ala Val Phe Cys
            20                  25                  30

Val Asp Ala Cys Cys Ala Met Leu Cys Cys Glu Arg Gln Arg Thr Ser
        35                  40                  45

Leu Trp Leu Pro Pro Ala Cys
    50                  55


<210> SEQ ID NO 75
<211> LENGTH: 57
```

<212> TYPE: PRT
<213> ORGANISM: Spodoptera frugiperda

<400> SEQUENCE: 75

```
Pro Leu Asp Ser Pro Pro Thr Ala Asp Val Arg Ala Val His Thr Phe
1               5                   10                  15

Pro Ala Gly Ala Ala Gly Thr Gln Gly Ile Leu Leu His Val Leu His
            20                  25                  30

Gly Val Arg Ser Pro Leu Ala Ala Ala Ala Pro His His Ala Ala Thr
        35                  40                  45

Leu Ala Ala Ala Cys Ala Leu Val Ala
    50                  55
```

<210> SEQ ID NO 76
<211> LENGTH: 154
<212> TYPE: PRT
<213> ORGANISM: Spodoptera frugiperda

<400> SEQUENCE: 76

```
Asn Ser Asp Val Asp Glu Ala Ser Arg Lys Ile Asp Glu Gly Lys Met
1               5                   10                  15

Ile Ile Asn Glu Tyr Ala Arg Lys Asn Asn Leu Asn Val Tyr Arg Arg
            20                  25                  30

Val Arg Ala Glu Glu Leu Asp Thr Pro Glu Asn Gly Gly Asn Leu Leu
        35                  40                  45

Tyr Lys Trp Cys Thr Ile Val Val Asp Glu Val Ile Leu Arg Met Ile
    50                  55                  60

Leu Cys Phe Thr Ser Ala Val Phe Cys Val Asp Ala Cys Cys Ala Met
65                  70                  75                  80

Leu Cys Cys Glu Arg Gln Arg Thr Ser Leu Trp Leu Pro Pro Ala Cys
                85                  90                  95

Arg Pro Leu Asp Ser Pro Pro Thr Ala Asp Val Arg Ala Val His Thr
            100                 105                 110

Phe Pro Ala Gly Ala Ala Gly Thr Gln Gly Ile Leu Leu His Val Leu
        115                 120                 125

His Gly Val Arg Ser Pro Leu Ala Ala Ala Ala Pro His His Ala Ala
    130                 135                 140

Thr Leu Ala Ala Ala Cys Ala Leu Val Ala
145                 150
```

<210> SEQ ID NO 77
<211> LENGTH: 159
<212> TYPE: PRT
<213> ORGANISM: Spodoptera frugiperda

<400> SEQUENCE: 77

```
Asn Ser Asp Val Asp Glu Ala Ser Arg Lys Ile Asp Glu Gly Lys Met
1               5                   10                  15

Ile Ile Asn Glu Tyr Ala Arg Lys Asn Asn Leu Asn Val Tyr Arg Arg
            20                  25                  30

Val Arg Ala Glu Glu Leu Asp Thr Pro Val Arg Thr Leu Ile Glu Asn
        35                  40                  45

Gly Gly Asn Leu Leu Tyr Lys Trp Cys Thr Ile Val Val Asp Glu Val
    50                  55                  60

Ile Leu Arg Met Ile Leu Cys Phe Thr Ser Ala Val Phe Cys Val Asp
65                  70                  75                  80

Ala Cys Cys Ala Met Leu Cys Cys Glu Arg Gln Arg Thr Ser Leu Trp
```

```
                85                  90                  95

Leu Pro Pro Ala Cys Arg Pro Leu Asp Ser Pro Pro Thr Ala Asp Val
            100                 105                 110

Arg Ala Val His Thr Phe Pro Ala Gly Ala Ala Gly Thr Gln Gly Ile
        115                 120                 125

Leu Leu His Val Leu His Gly Val Arg Ser Pro Leu Ala Ala Ala Ala
    130                 135                 140

Pro His His Ala Ala Thr Leu Ala Ala Ala Cys Ala Leu Val Ala
145                 150                 155


<210> SEQ ID NO 78
<211> LENGTH: 56
<212> TYPE: PRT
<213> ORGANISM: Spodoptera frugiperda

<400> SEQUENCE: 78

Ala His Trp Ile Val His Gln Arg Arg Met Tyr Glu Arg Ser Ile Arg
1               5                   10                  15

Ser Leu Leu Glu Leu Gln Ala Arg Lys Gly Ser Cys Ser Met Cys Phe
            20                  25                  30

Thr Glu Tyr Ala Pro Pro Leu Leu Pro Leu Pro Leu Thr Thr Gln Arg
        35                  40                  45

Pro Ser Pro Pro Pro Ala His Leu
    50                  55


<210> SEQ ID NO 79
<211> LENGTH: 75
<212> TYPE: PRT
<213> ORGANISM: Drosophila melanogaster

<400> SEQUENCE: 79

Gln Ile Phe Val Lys Thr Leu Thr Gly Lys Thr Ile Thr Leu Glu Val
1               5                   10                  15

Glu Pro Ser Asp Thr Ile Glu Asn Val Lys Ala Lys Ile Gln Asp Lys
            20                  25                  30

Glu Gly Ile Pro Pro Asp Gln Gln Arg Leu Ile Phe Ala Gly Arg Gln
        35                  40                  45

Leu Glu Asp Gly Arg Thr Leu Ser Asp Tyr Asn Ile Gln Lys Glu Ser
    50                  55                  60

Thr Leu His Leu Val Leu Arg Leu Arg Gly Gly
65                  70                  75


<210> SEQ ID NO 80
<211> LENGTH: 338
<212> TYPE: PRT
<213> ORGANISM: Artificial Sequence
<220> FEATURE:
<223> OTHER INFORMATION: Synthetic DNA based on a fusion of sequences
      from E. coli (tetR - tetracycline repressor) and HSV-1 (VP16
      transcriptional activator)

<400> SEQUENCE: 80

Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
```

```
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220

Ile Glu Gly Leu Leu Asp Leu Pro Asp Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly
```

<210> SEQ ID NO 81
<211> LENGTH: 1014
<212> TYPE: DNA
<213> ORGANISM: Artificial Sequence
<220> FEATURE:
<223> OTHER INFORMATION: Synthetic DNA based on a fusion of sequences from E. coli (tetR - tetracycline repressor) and HSV-1 (VP16 transcriptional activator)

<400> SEQUENCE: 81

```
atggtcagcc gcctggataa gtccaaagtc atcaactccg cgttggagct gttgaacgaa      60

gttggcattg agggactgac gacccgcaag ttggcgcaga agctgggcgt ggagcagccc     120

accctctact ggcacgtgaa gaataagcgg gcgctgctgg atgccctggc catcgagatg     180

ctcgaccgcc accacacgca tttttgcccg ttggaaggcg agtcctggca ggacttcctc     240

cgcaataacg ccaagtcgtt ccgctgcgct ctgctgtccc accgagacgg tgccaaagtc     300

catctcggca cgcgcccgac cgaaaagcaa tacgagacac tggagaacca gctcgcgttc     360
```

```
ctgtgccagc aaggcttcag cctggaaaat gctctctacg ctctgagcgc cgtcggtcac    420

tttaccctgg gctgcgtgct ggaggaccaa gagcatcaag tcgcaaaaga ggagcgcgag    480

accccaacaa ccgattcgat gcccccactg ctgcgtcagg caatcgagct gttcgatcat    540

caaggagccg agccggcatt cctgttcggc ttggagctga ttatctgcgg attggaaaag    600

caactgaaat gcgagtcggg ctcgggcccc gcctacagcc gcgcccgcac caagaacaac    660

tacggcagca ccatcgaggg cctgctggat ctgccggatg atgatgcccc ggaggaggcg    720

ggcctggccg ccccgcgcct gagcttcctg ccggccggac acacccgccg cctgtcgacc    780

gccccgccga ccgacgtgag cctgggcgat gagctgcacc tggatggcga ggatgtggcg    840

atggcccacg ccgatgccct ggacgacttc gacctggaca tgctgggcga tggcgatagc    900

ccgggaccgg gattcacccc gcacgatagc gccccctacg gcgccctgga tatggccgat    960

ttcgagttcg agcagatgtt caccgacgcc ctgggcatcg atgagtacgg cggc         1014
```

<210> SEQ ID NO 82
<211> LENGTH: 1008
<212> TYPE: DNA
<213> ORGANISM: Artificial Sequence
<220> FEATURE:
<223> OTHER INFORMATION: Synthetic DNA based on a fusion of sequences from E. coli (tetR - tetracycline repressor) and HSV-1 (VP16 transcriptional activator)

<400> SEQUENCE: 82

```
atggtcagcc gcctggacaa gagcaaggtg atcaacagcg ccctggagct gctgaacgaa     60

gtgggcatcg agggcctgac cacccgcaag ctggcccaga agctgggcgt ggaacagccg    120

accctgtact ggcacgtgaa gaacaagcgc gccctgctgg acgccctggc catcgaaatg    180

ctggatcgcc accacaccca cttctgcccg ctggagggcg agagctggca ggatttcctg    240

cgcaacaacg ccaagagctt ccgctgcgcc ctgctgtcgc accgcgatgg cgccaaggtg    300

cacctgggca cccgcccgac cgagaagcag tacgagaccc tggagaacca gctggccttc    360

ctgtgccagc agggcttcag cctggagaac gccctgtacg ccctgagcgc cgtgggccac    420

ttcaccctgg gctgtgtgct ggaggatcag gagcaccagg tggccaagga ggagcgcgag    480

accccgacca ccgatagcat gccgccgctg ctgcgccagg ccatcgagct gttcgatcac    540

cagggcgccg agccggcctt cctgttcggc ctggagctga tcatctgcgg cctggaaaag    600

cagctgaagt gcgagagcgg cagcgcctac agccgcgccc gtaccaagaa caactatggc    660

agcaccatcg agggactgct ggacctgccg gatgacgatg ccccggagga agccggcctg    720

gccgcccccc gcctgagctt cctgcccgcc ggacacacgc gccgcctgag caccgccccg    780

ccgaccgatg tgagcctggg cgacgagctg cacctggatg gagaggatgt ggcaatggcc    840

cacgccgacg ccctggacga tttcgacctg gatatgctgg gcgatggaga tagcccggga    900

ccgggcttca cgccccacga tagcgccccg tacggcgccc tggacatggc cgacttcgag    960

ttcgagcaaa tgttcaccga cgcgctgggc atcgatgagt atggcggg                1008
```

<210> SEQ ID NO 83
<211> LENGTH: 294
<212> TYPE: DNA
<213> ORGANISM: Artificial Sequence
<220> FEATURE:
<223> OTHER INFORMATION: Synthetic DNA contains 14 repeats of Tn10 tet-operon

<400> SEQUENCE: 83

```
actccctatc agtgatagag aagtccctat cagtgataga gatgtcccta tcagtgatag     60

agagttccct atcagtgata gagacgtccc tatcagtgat agagaagtcc ctatcagtga    120

tagagagatc cctatcagtg atagagattt ccctatcagt gatagagagg tccctatcag    180

tgatagagac ttccctatca gtgatagaga aatccctatc agtgatagag acatccctat    240

cagtgataga gaactcccta tcagtgatag agacctccct atcagtgata gaga          294


<210> SEQ ID NO 84
<211> LENGTH: 671
<212> TYPE: DNA
<213> ORGANISM: Artificial Sequence
<220> FEATURE:
<223> OTHER INFORMATION: Synthetic DNA contains 21 repeats of Tn10
      tet-operon

<400> SEQUENCE: 84

tccctatcag tgatagagaa aagtgaaagt cgagtttacc actccctatc agtgatagag     60

aaaagtgaaa gtcgagttta ccactcccta tcagtgatag agaaaagtga aagtcgagtt    120

taccactccc tatcagtgat agagaaaagt gaaagtcgag tttaccactc cctatcagtg    180

atagagaaaa gtgaaagtcg agtttaccac tccctatcag tgatagagaa aagtgaaagt    240

cgagtttacc actccctatc agtgatagag aaaagtgaaa gtcgaaacct ggcgcgcccc    300

ggccatcgag aaagagagag agaagagaag agagagaaca ttcgagaaag agagagagaa    360

gagaagagag agaacatact ccctatcagt gatagagaag tccctatcag tgatagagat    420

gtccctatca gtgatagaga gttccctatc agtgatagag acgtccctat cagtgataga    480

gaagtcccta tcagtgatag agagatccct atcagtgata gagatttccc tatcagtgat    540

agagaggtcc ctatcagtga tagagacttc cctatcagtg atagagaaat ccctatcagt    600

gatagagaca tccctatcag tgatagagaa ctccctatca gtgatagaga cctccctatc    660

agtgatagag a                                                         671


<210> SEQ ID NO 85
<211> LENGTH: 225
<212> TYPE: PRT
<213> ORGANISM: Artificial Sequence
<220> FEATURE:
<223> OTHER INFORMATION: A variant of red fluorescent protein originally
      identified in Discosoma (Clontech)

<400> SEQUENCE: 85

Met Ala Ser Ser Glu Asn Val Ile Thr Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125
```

```
Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Thr His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ala Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```

<210> SEQ ID NO 86
<211> LENGTH: 8288
<212> TYPE: DNA
<213> ORGANISM: Artificial Sequence
<220> FEATURE:
<223> OTHER INFORMATION: Plasmid construct for expression in arthropods

<400> SEQUENCE: 86

```
tttactccct atcagtgata gagaacgtat gaagagttta ctccctatca gtgatagaga     60

acgtatgcag actttactcc ctatcagtga tagagaacgt ataaggagtt tactccctat    120

cagtgataga gaacgtatga ccagtttact ccctatcagt gatagagaac gtatctacag    180

tttactccct atcagtgata gagaacgtat atccagttta ctccctatca gtgatagaga    240

acgtataagc tttaggcgtg tacggtgggc gcctataaaa gcagagctcg tttagtgaac    300

cgtcagatcg cctggagcaa ttccacaaca cttttgtctt ataccaactt tccgtaccac    360

ttcctaccct cgtaaaatga acagtgacgt ggacgaggca tcacggaaaa tagacgaagg    420

taggcctttt attgtttaaa tgccaattgc aattgtcctt ctgttattta tttgcattgc    480

gattgttcgc tgtaaagtta aagagatgaa ttgagcgcta aaaagatttt tcatacagga    540

atgtgtgaaa agagttgttt aattcgtaat ttgcaactat gtattatgtt ttatgttcac    600

tgtttttgtg ttgttaacag caaattaatg ccgataaaga gaatgacaga aaaaacttac    660

aatctcaatt aatccgataa ttacaaaaag tgaatagtta accatcatga aatcgtttta    720

gaaagctttt tagcgttcgt acaaattagt tgttcgtgct acattgtagg tgagacgcct    780

aaatgtcttt cgtacttcga gtgcggatgt aacagtgtta tatgagcggc cattgttatt    840

tccatacgtg cctggaacgc tgctcagccc agcgtcgtag ggctccctgc agtctcgcac    900

gaacgaacct ttatttagcc actgccggga attgcattgg aaatagatgc ctgcttataa    960

agtaggtaat cataaacata tcacgattga atttaataat aatttaatct tagttccaat   1020

tctttggata ggttagggtt ttttgacaga ctccatctga gtgatgtcaa aaatcgatct   1080

taaaacaaag attttaggct tgtttcgacc gaatggccaa attacttcat attgacttga   1140

ctccttttttt ttcgcaatgc gaatatgtgt acctattgga aaacttttgt tgttttttag   1200

aatacatata gattttcgtt aaatttcaat ctaagtcaat tgaatatatt taattaatta   1260

tttatcttta tttatttcct tctctttacg aaatcttgga atgtgaaaat tattatcatt   1320

gtatcaacaa aaggtttcta taaacgtttt tataaataaa ataaaaaaaa aactgcattt   1380

taataatcat acattgatat gaataaagct aaacagaaaa caaacgatgt tctaatttca   1440
```

agatacattt gacagatgtc acaaccgaac cgttacggcc attttgaatt tgtctatggt 1500
ttattttttt taaggagaaa atgattcgat gtctctcccg ccgtgtctat ggtttaatgc 1560
agtttttttt cacccgccaa gcgattgtcc aatttgcgca ttgtttgttc tcaggaaaga 1620
tgattatcaa cgaatacgcg cggaagaaca atctgaacgt gtatcgacgg gttagagctg 1680
aggaactcga cacgccagta cggacattaa tagtaataaa tagtttttac caccaacaac 1740
actgaaactg tgctaacact ttgacagtga caggtgtagt gtaggggctg tgacaaactt 1800
cattctggtt cctattttaa atttaaatca tttattttcg gccagcggca acagtttttc 1860
gtgttccttt ttttaattta aatagtataa tagtttcttt tatgccagac atttagttct 1920
ataaataagt atttgaaaga acgctattta aaatgttttg gactgtaaca tctattttaa 1980
ttttgacaag aatgaagttt gttacatacg acatatttca cagcacatcg tcgtgtatat 2040
aaataacaca acactttaca gttacacaaa gtatctacct acacaagaca tcactcatta 2100
cacataacga ttagatactt atacacgttc acattaacat acagcagaac cagtggaaat 2160
ggatggttta ggtcaagatt gcctaattta gtcaacgatc ttctcacaat ttaattcatt 2220
tgttgtattg ggtatttgta attttatatg gagatggtaa ttttagagag agggtagtat 2280
aagagtaagt agtttaggta agtagttgag aaatgtcgtt gtaaatgtag ggttatttta 2340
tgagtgaaat tgagtcgtga tttttgtctc cttaagttaa attttgatag aggtatttta 2400
ttcatttgca tttgaaatat agaacagcaa ccatgacgta acaacgacgg tggcatccgt 2460
caccgtctcg aacataatca acaattctta gccatacatt gtgctacatt gcaacttgag 2520
tttcgtttcc acgttacacg ttccacacac aaagtgacac aacaaaatag ttgcacacga 2580
taaagtggtt aagtcagaat cagctgtatt aacaaagtct aaccagtcgt gatttcaact 2640
ttacagtgac cggacgaagg tggtgaaatt cgaaatgcaa cctcagtgac attccatatt 2700
caaaaaattc gaatttaacg gccatcgtgg tgctgtgcta gtgtcgatat tttatttaga 2760
attattttct tttttgtagg aaaatggcgg aaatttatta tataagtggt gtactatcgt 2820
cgtcgatgaa gttattttgc gaatgatact ttgttttaca agtgccgtgt tttgtgtgga 2880
cgcttgctgt gcgatgctgt gttgcgaacg acaacggact tcactgtggc tacctccggc 2940
gtgtcggtga gtttatttga tattgttatt agcaattcaa tggacattgc aacatgatag 3000
aatctcaatt attttaaaag tgtctattga gttgttttat tatttaagaa ttgcacaaac 3060
gcttttcaat tgtatacaaa tgttagttgc cgatagattt gtattacgtt gcatttctga 3120
gacgtttgtt tgccgtcttg ccttctttgt gttcaaatgg aaagcgttag tgtgcgtgtc 3180
aatctgtttg ttccaagtac ttgtttactg ctcatattca taagtagaat tttatgttac 3240
aacgtacaca taaaataaaa tgctatttat gaaataagac aatttgcgat gcgacggaat 3300
ttatttatgt ttttattgct tttacaaaac ggaggaatgc atgctatttc ttgtctttat 3360
ctaagttttt acattatttt atgatcatta aaactcacag ttgtaaggct ctcttctaag 3420
gtgtacagaa ctatgcctct cttattactt caaaatattt acatattcga aaaaaaaaag 3480
tttttagtaa aaaaaaatgt ttccatacta gggcggctga acagtttgga gcctaaatac 3540
ttattggacc ttcggtaact acactcacac gggcataaca caacgcaagc gttgtttcac 3600
gccagctttc ttgaggccgt ccaccgtgga aacactccgg tcgagccaga tcatttgaaa 3660
tgatgctgaa gccttgttcc cacctttaat accttaggct caaaagtatt cagagaccct 3720
agtatagtac atatacaaaa caaaaccgtt ccacaaacac cttaagctag gtctaaaaca 3780

-continued

```
cccagctggt ctacagaaac cctcaaaatc cacaccagaa acctaatcac cccctttaaa   3840
attccagccc actggatagt ccaccaacgg cggatgtacg agcggtccat acgttccctg   3900
ctggagctgc aggcacgcaa gggatcctgc tccatgtgct tcacggagta cgctcccccc   3960
ttgctgccgc tgcccctcac cacgcagcga ccctcgccgc cgcctgcgca cttgtagcgc   4020
agatcttcgt caagaccctg accggcaaga ccatcaccct ggaggtggag ccgagcgata   4080
ccatcgagaa cgtgaaggcc aagatccagg acaaggaggg catcccgccg gatcagcagc   4140
gcctgatctt cgccggacgc cagctggagg atggccgcac cctgagcgac tacaacatcc   4200
agaaggagag caccctgcac ctggtgctgc gcctgcgcgg tggtgtcagc cgcctggata   4260
agtccaaagt catcaactcc gcgttggagc tgttgaacga agttggcatt gagggactga   4320
cgacccgcaa gttggcgcag aagctgggcg tggagcagcc caccctctac tggcacgtga   4380
agaataagcg ggcgctgctg gatgccctgg ccatcgagat gctcgaccgc caccacacgc   4440
atttttgccc gttggaaggc gagtcctggc aggacttcct ccgcaataac gccaagtcgt   4500
tccgctgcgc tctgctgtcc caccgagacg gtgccaaagt ccatctcggc acgcgcccga   4560
ccgaaaagca atacgagaca ctggagaacc agctcgcgtt cctgtgccag caaggcttca   4620
gcctggaaaa tgctctctac gctctgagcg ccgtcggtca ctttaccctg ggctgcgtgc   4680
tggaggacca agagcatcaa gtcgcaaaag aggagcgcga gaccccaaca accgattcga   4740
tgccccccact gctgcgtcag gcaatcgagc tgttcgatca tcaaggagcc gagccggcat   4800
tcctgttcgg cttggagctg attatctgcg gattggaaaa gcaactgaaa tgcgagtcgg   4860
gctcgggccc cgcgtacagc cgcgcgcgta cgaaaaaacaa ttacgggtct accatcgagg   4920
gcctgctcga tctcccggac gacgacgccc ccgaagaggc ggggctggcg gctccgcgcc   4980
tgtcctttct ccccgcggga cacacgcgca gactgtcgac ggcccccccg accgatgtca   5040
gcctggggga cgagctccac ttagacggcg aggacgtggc gatggcgcat gccgacgcgc   5100
tagacgattt cgatctggac atgttggggg acggggattc cccgggtccg ggatttaccc   5160
cccacgactc cgccccctac ggcgctctgg atatggccga cttcgagttt gagcagatgt   5220
ttaccgatgc ccttggaatt gacgagtacg gtgggtagag atctgcggcc gcaatgaatc   5280
gtttttaaaa taacaaatca attgttttat aatattcgta cgattctttg attatgtaat   5340
aaaatgtgat cattaggaag attacgaaaa atataaaaaa tatgagttct gtgtgtataa   5400
caaatgctgt aaacgccaca attgtgtttg ttgcaaataa acccatgatt atttgattaa   5460
aattgttgtt ttctttgttc atagacaata gtgtgttttg cctaaacgtg tactgcataa   5520
actccatgcg agtgtatagc gagctagtgg ctaacgcttg ccccaccaaa gtagattcgt   5580
caaaatcctc aatttcatca ccctcctcca agtttaacat ttggccgtcg gaattaactt   5640
ctaaagatgc cacataatct aataaatgaa atagagattc aaacgtggcg tcatcgtccg   5700
tttcgaccat ttccgaaaag aactcgggca taaactctat gatttctctg gacgtggtgt   5760
tgtcgaaact ctcaaagtac gcagtcagga acgtgcgcga catgtcgtcg ggaaactcgc   5820
gcggaaacat gttgttgtaa ccgaacgggt cccatagcgc caaaaccaaa tctgccagcg   5880
tcaatagaat gagcacgatg ccgacaatgg agctggcttg gatagcgatt cgagttaacg   5940
gccggccgtt taaacgcccg ccaggtttcg ctttacgagt agaattctac gcgtaaaaca   6000
caatcaagta tgagtcataa gctgatgtca tgttttgcac acggctcata accgaactgg   6060
ctttacgagt agaattctac ttgtaacgca cgatcagtgg atgatgtcat ttgtttttca   6120
aatcgagatg atgtcatgtt ttgcacacgg ctcataaact cgctttacga gtagaattct   6180
```

```
acgtgtaacg cacgatcgat tgatgagtca tttgttttgc aatatgatat catacaatat   6240
gactcatttg tttttcaaaa ccgaacttga tttacgggta gaattctact tgtaaagcac   6300
aatcaaaaag atgatgtcat ttgtttttca aaactgaact cgctttacga gtagaattct   6360
acgtgtaaaa cacaatcaag aaatgatgtc atttgttata aaaataaaag ctgatgtcat   6420
gttttgcaca tggctcataa ctaaactcgc tttacgggta gaattctacg cgtaaaacat   6480
gattgataat taaataattc atttgcaagc tatacgttaa atcaaacgga cgctcgaggt   6540
tgcacaacac tattatcgat ttgcagttcg ggacataaat gtttaaatat atcgatgtct   6600
ttgtgatgcg cgcgacattt ttgtaggtta ttgataaaat gaacggatac gttgcccgac   6660
attatcatta aatccttggc gtagaatttg tcgggtccat tgtccgtgtg cgctagtagc   6720
atgcccgtaa cggacctcgt acttttggct tcaaaggttt tgcgcacaga caaaatgtgc   6780
cacacttgca gctctgcatg tgtgcgcgtt accacaaatc ccaacggcgc agtgtacttg   6840
ttgtatgcaa ataaatctcg ataaaggcgc ggcgcgcgaa tgcagctgat cacgtacgct   6900
cctcgtgttc cgttcaagga cggtgttacc gacctcagat taatgtttat cggccgactg   6960
ttttcgtatc cgctcaccaa acgcgttttt gcattaacat tgtatgtcgg cggatgttct   7020
atatctaatt tgaataaata aacgataacc gcgttggttt tagagggcat aataaaagaa   7080
atattgttat cgtgttcgcc attagggcag tataaattga cgttcatgtt ggatattgtt   7140
tcagttgcaa gttgacactg gcggcgacaa gacaattcta attggggtaa gttttcccgt   7200
tcttttctgg gttcttccct tttgctcatc cttgctgcac taccttcagg tgcaagttga   7260
gattcaggcc accatgggag atcccacccc acccaagaag aagcgcaaac cggtcgccac   7320
catggcctcc tccgagaacg tcatcaccga gttcatgcgc ttcaaggtgc gcatggaggg   7380
caccgtgaac ggccacgagt tcgagatcga gggcgagggc gagggccgcc cctacgaggg   7440
ccacaacacc gtgaagctga aggtgaccaa gggcggcccc ctgcccttcg cctgggacat   7500
cctgtccccc cagttccagt acggctccaa ggtgtacgtg aagcaccccg ccgacatccc   7560
cgactacaag aagctgtcct tccccgaggg cttcaagtgg gagcgcgtga tgaacttcga   7620
ggacggcggc gtggcgaccg tgacccagga ctcctccctg caggacggct gcttcatcta   7680
caaggtgaag ttcatcggcg tgaacttccc ctccgacggc cccgtgatgc agaagaagac   7740
catgggctgg gaggcctcca ccgagcgcct gtaccccccgc gacggcgtgc tgaagggcga  7800
gacccacaag gccctgaagc tgaaggacgg cggccactac ctggtggagt tcaagtccat   7860
ctacatggcc aagaagcccg tgcagctgcc cggctactac tacgtggacg ccaagctgga   7920
catcacctcc cacaacgagg actacaccat cgtggagcag tacgagcgca ccgagggccg   7980
ccaccacctg ttcctgagat ctcgacccaa gaaaaagcgg aaggtggagg acccgtaaga   8040
tccaccggat ctagataact gatcataatc agccatacca catttgtaga ggttttactt   8100
gctttaaaaa acctcccaca cctccccctg aacctgaaac ataaaatgaa tgcaattgtt   8160
gttgttaact tgtttattgc agcttataat ggttacaaat aaagcaatag catcacaaat   8220
ttcacaaata aagcattttt ttcactgcat tctagttgtg gtttgtccaa actcatcaat   8280
gtatctta                                                            8288
```

<210> SEQ ID NO 87
<211> LENGTH: 8471
<212> TYPE: DNA
<213> ORGANISM: Artificial Sequence
<220> FEATURE:

<223> OTHER INFORMATION: Plasmid construct for expression in arthropods

<400> SEQUENCE: 87
gactttcact tttctctatc actgataggg agtggtaaac tcgactttca cttttctcta 60
tcactgatag ggagtggtaa actcgacttt cacttttctc tatcactgat agggagtggt 120
aaactcgact ttcacttttc tctatcactg atagggagtg gtaaactcga ctttcacttt 180
tctctatcac tgatagggag tggtaaactc gactttcact tttctctatc actgataggg 240
agtggtaaac tcgactttca cttttctcta tcactgatag ggagtggtaa actcgaaaac 300
gagcgccgga gtataaatag aggcgcttcg tctacggagc gacaattcaa ttcaaacaag 360
caaagtgaac acgtcgctaa gcgaaagcta agcaaataaa caagcgcagc tgaacaagct 420
aaacaatctg ccagtgacgt ggacgaggca tcacggaaaa tagacgaagg taggcctttt 480
attgtttaaa tgccaattgc aattgtcctt ctgttattta tttgcattgc gattgttcgc 540
tgtaaagtta aagagatgaa ttgagcgcta aaaagatttt tcatacagga atgtgtgaaa 600
agagttgttt aattcgtaat ttgcaactat gtattatgtt ttatgttcac tgtttttgtg 660
ttgttaacag caaattaatg ccgataaaga gaatgacaga aaaaacttac aatctcaatt 720
aatccgataa ttacaaaaag tgaatagtta accatcatga aatcgtttta gaaagctttt 780
tagcgttcgt acaaattagt tgttcgtgct acattgtagg tgagacgcct aaatgtcttt 840
cgtacttcga gtgcggatgt aacagtgtta tatgagcggc cattgttatt tccatacgtg 900
cctggaacgc tgctcagccc agcgtcgtag ggctccctgc agtctcgcac gaacgaacct 960
ttatttagcc actgccggga attgcattgg aaatagatgc ctgcttataa agtaggtaat 1020
cataaacata tcacgattga atttaataat aatttaatct tagttccaat tctttggata 1080
ggttagggtt ttttgacaga ctccatctga gtgatgtcaa aaatcgatct taaaacaaag 1140
attttaggct tgtttcgacc gaatggccaa attacttcat attgacttga ctcctttttt 1200
ttcgcaatgc gaatatgtgt acctattgga aaacttttgt tgttttttag aatacatata 1260
gattttcgtt aaatttcaat ctaagtcaat tgaatatatt taattaatta tttatcttta 1320
tttatttcct tctctttacg aaatcttgga atgtgaaaat tattatcatt gtatcaacaa 1380
aaggtttcta taaacgtttt tataaataaa ataaaaaaaa aactgcattt taataatcat 1440
acattgatat gaataaagct aaacagaaaa caaacgatgt tctaatttca agatacattt 1500
gacagatgtc acaaccgaac cgttacggcc attttgaatt tgtctatggt ttattttttt 1560
taaggagaaa atgattcgat gtctctcccg ccgtgtctat ggtttaatgc agtttttttt 1620
cacccgccaa gcgattgtcc aatttgcgca ttgtttgttc tcaggaaaga tcattatcaa 1680
cgaatacgcg cggaagaaca atctgataac ggaccgaaac caccatgggc agccgcctgg 1740
ataagtccaa agtcatcaac tccgcgttgg agctgttgaa cgaagttggc attgagggac 1800
tgacgacccg caagttggcg cagaagctgg gcgtggagca gcccaccctc tactggcacg 1860
tgaagaataa gcgggcgctg ctggatgccc tggccatcga gatgctcgac cgccaccaca 1920
cgcatttttg cccgttggaa ggcgagtcct ggcaggactt cctccgcaat aacgccaagt 1980
cgttccgctg cgctctgctg tcccaccgag acggtgccaa agtccatctc ggcacgcgcc 2040
cgaccgaaaa gcaatacgag acactggaga accagctcgc gttcctgtgc cagcaaggct 2100
tcagcctgga aaatgctctc tacgctctga gcgccgtcgg tcactttacc ctgggctgcg 2160
tgctggagga ccaagagcat caagtcgcaa aagaggagcg cgagacccca acaaccgatt 2220
cgatgccccc actgctgcgt caggcaatcg agctgttcga tcatcaagga gccgagccgg 2280

```
cattcctgtt cggcttggag ctgattatct gcggattgga aaagcaactg aaatgcgagt   2340
cgggctcggg ccccgcctac agccgcgccc gcaccaagaa caactacggc agcaccatcg   2400
agggcctgct ggatctgccg gatgatgatg ccccggagga ggcgggcctg gccgccccgc   2460
gcctgagctt cctgccggcc ggacacaccc gccgcctgtc gaccgccccg ccgaccgacg   2520
tgagcctggg cgatgagctg cacctggatg gcgaggatgt ggcgatggcc cacgccgatg   2580
ccctggacga cttcgacctg gacatgctgg gcgatggcga tagcccggga ccgggattca   2640
ccccgcacga tagcgccccc tacggcgccc tggatatggc cgatttcgag ttcgagcaga   2700
tgttcaccga cgccctgggc atcgatgaat acggcggcta acaccggtga cgtgttcgac   2760
gggttagagc tgaggaactc gacacgccag tacggacatt aatagtaata aatagttttt   2820
accaccaaca acactgaaac tgtgctaaca ctttgacagt gacaggtgta gtgtaggggc   2880
tgtgacaaac ttcattctgg ttcctatttt aaatttaaat catttatttt cggccagcgg   2940
caacagtttt tcgtgttcct ttttttaatt taaatagtat aatagtttct tttatgccag   3000
acatttagtt ctataaataa gtatttgaaa gaacgctatt taaaatgttt tggactgtaa   3060
catctatttt aattttgaca agaatgaagt ttgttacata cgacatattt cacagcacat   3120
cgtcgtgtat ataaataaca caacacttta cagttacaca aagtatctac ctacacaaga   3180
catcactcat tacacataac gattagatac ttatacacgt tcacattaac atacagcaga   3240
accagtggaa atggatggtt taggtcaaga ttgcctaatt tagtcaacga tcttctcaca   3300
atttaattca tttgttgtat tgggtatttg taattttata tggagatggt aattttagag   3360
agagggtagt ataagagtaa gtagtttagg taagtagttg agaaatgtcg ttgtaaatgt   3420
agggttattt tatgagtgaa attgagtcgt gatttttgtc tccttaagtt aaattttgat   3480
agaggtattt tattcatttg catttgaaat atagaacagc aaccatgacg taacaacgac   3540
ggtggcatcc gtcaccgtct cgaacataat caacaattct tagccataca ttgtgctaca   3600
ttgcaacttg agtttcgttt ccacgttaca cgttccacac acaaagtgac acaacaaaat   3660
agttgcacac gataaagtgg ttaagtcaga atcagctgta ttaacaaagt ctaaccagtc   3720
gtgatttcaa ctttacagtg accggacgaa ggtggtgaaa ttcgaaatgc aacctcagtg   3780
acattccata ttcaaaaaat tcgaatttaa cggccatcgt ggtgctgtgc tagtgtcgat   3840
attttattta gaattatttt ctttttgta ggaaaatggc ggaaattaat aatataagtg   3900
gtgtactatc gtcgtcgatg aagttatttt gcgaatgata ctttgtttta caagtgccgt   3960
gttttgtgtg gacgcttgct gtgcgatgct gtgttgcgaa cgacaacgga cttgactgtg   4020
gctacctccg gcgtgtcggt gagtttattt gatattgtta ttagcaattc aatggacatt   4080
gcaacatgat agaatctcaa ttattttaaa agtgtctatt gagttgtttt attatttaag   4140
aattgcacaa acgcttttca attgtataca aatgttagtt gccgatagat ttgtattacg   4200
ttgcatttct gagacgtttg tttgccgtct tgccttcttt gtgttcaaat ggaaagcgtt   4260
agtgtgcgtg tcaatctgtt tgttccaagt acttgtttac tgctcatatt cataagtaga   4320
attttatgtt acaacgtaca cataaaataa aatgctattt atgaaataag acaatttgcg   4380
atgcgacgga atttatttat gtttttattg cttttacaaa acggaggaat gcatgctatt   4440
tcttgtcttt atctaagttt ttacattatt ttatgatcat taaaactcac agttgtaagg   4500
ctctcttcta aggtgtacag aactatgcct ctcttattac ttcaaaatat ttacatattc   4560
gaaaaaaaaa agtttttagt aaaaaaaaat gtttccatac tagggcggct gaacagtttg   4620
```

-continued

```
gagcctaaat acttattgga ccttcggtaa ctacactcac acgggcataa cacaacgcaa   4680

gcgttgtttc acgccagctt tcttgaggcc gtccaccgtg gaaacactcc ggtcgagcca   4740

gatcatttga aatgatgctg aagccttgtt cccaccttta ataccttagg ctcaaaagta   4800

ttcagagacc ctagtatagt acatatacaa aacaaaaccg ttccacaaac accttaagct   4860

aggtctaaaa cacccagctg gtctacagaa accctcaaaa tccacaccag aaacctaatc   4920

acccccttta aaattccagc ccactggata gtccaccaat ggcggatgta cgagcggtcc   4980

atatgttccc tgctggagct gcaggcacgc aagggatcct gctccatgtg cttcacggag   5040

tacgctcccc ccttgctgcc gctgcccctc accacgcagc gaccctcgcc gccgcctgcg   5100

cacttgtagc gatgcgacca tgcgccgcga ccaaaatcta gagaggccct agagtcgacc   5160

tcgaacgtta acgttaacgt aacgttaact cgaggagctt gataacatta tacctaaacc   5220

catggtcaag agtaaacatt tctgcctttg aagttgagaa cacaattaag catcccctgg   5280

ttaaacctga cattcatact tgttaatagc gccataaaca tagcaccaat ttcgaagaaa   5340

tcagttaaaa gcaattagca attagcaatt agcaataact ctgctgactt caaaacgaga   5400

agagttgcaa gtatttgtaa ggcacagttt atagaccacc gacggctcat tagggctcgt   5460

catgtaacta agcgcggtga aacccaattg aacatatagt ggaattatta ttatcaatgg   5520

ggaagattta accctcaggt agcaaagtaa tttaattgca aatagagagt cctaagacta   5580

aataatatat ttaaaaatct ggccctttga ccttgcttgt caggtgcatt tgggttcaat   5640

cgtaagttgc ttctatataa acactttccc catccccgca ataatgaaga ataccgcaga   5700

ataaagagag atttgcaaca aaaaataaag gcattgcgaa aactttttat gggggatcat   5760

tacactcggg cctacggtta caattcccag ccacttaagc gacaagtttg gccaacaatc   5820

catctaatag ctaatagcgc aatcactggt aatcgcaaga gtatataggc aatagaaccc   5880

atggatttga ccaaaggtaa ccgagacaat ggagaagcaa gaggatttca aactgaacac   5940

ccacagtact gtgtactacc actggcgcgt ttgggagctc caagcggcga ctgagatgtc   6000

ctaaatgcac agcgacggat tcgcgctatt tagaaagaga gagcaatatt tcaagaaaaa   6060

cggcgcccgg gccgatctgg ccaggccgca tggtacccat tgcttgtcat ttattaattt   6120

ggatgatgtc atttgttttt aaaattgaac tggctttacg agtagaattc tacgcgtaaa   6180

acacaatcaa gtatgagtca taagctgatg tcatgttttg cacacggctc ataaccgaac   6240

tggctttacg agtagaattc tacttgtaac gcacgatcag tggatgatgt catttgtttt   6300

tcaaatcgag atgatgtcat gttttgcaca cggctcataa actcgcttta cgagtagaat   6360

tctacgtgta acgcacgatc gattgatgag tcatttgttt tgcaatatga tatcatacaa   6420

tatgactcat ttgtttttca aaaccgaact tgatttacgg gtagaattct acttgtaaag   6480

cacaatcaaa aagatgatgt catttgtttt tcaaaactga actcgcttta cgagtagaat   6540

tctacgtgta aaacacaatc aagaaatgat gtcatttgtt ataaaaataa aagctgatgt   6600

catgttttgc acatggctca taactaaact cgctttacgg gtagaattct acgcgtaaaa   6660

catgattgat aattaaataa ttcatttgca agctatacgt taaatcaaac ggacgctcga   6720

ggttgcacaa cactattatc gatttgcagt tcgggacata aatgtttaaa tatatcgatg   6780

tctttgtgat gcgcgcgaca tttttgtagg ttattgataa aatgaacgga tacgttgccc   6840

gacattatca ttaaatcctt ggcgtagaat ttgtcgggtc cattgtccgt gtgcgctagt   6900

agcatgcccg taacggacct cgtacttttg gcttcaaagg ttttgcgcac agacaaaatg   6960

tgccacactt gcagctctgc atgtgtgcgc gttaccacaa atcccaacgg cgcagtgtac   7020
```

ttgttgtatg caaataaatc tcgataaagg cgcggcgcgc gaatgcagct gatcacgtac 7080
gctcctcgtg ttccgttcaa ggacggtgtt accgacctca gattaatgtt tatcggccga 7140
ctgttttcgt atccgctcac caaacgcgtt tttgcattaa cattgtatgt cggcggatgt 7200
tctatatcta atttgaataa ataaacgata accgcgttgg ttttagaggg cataataaaa 7260
gaaatattgt tatcgtgttc gccattaggg cagtataaat tgacgttcat gttggatatt 7320
gtttcagttg caagttgaca ctggcggcga caagacaatt ctaattgggg taagttttcc 7380
cgttcttttc tgggttcttc ccttttgctc atccttgctg cactaccttc aggtgcaagt 7440
tgagattcag gccaccatgg gagatcccac cccacccaag aagaagcgca aaccggtcgc 7500
caccatggcc tcctccgaga acgtcatcac cgagttcatg cgcttcaagg tgcgcatgga 7560
gggcaccgtg aacggccacg agttcgagat cgagggcgag ggcgagggcc gcccctacga 7620
gggccacaac accgtgaagc tgaaggtgac caagggcggc cccctgccct tcgcctggga 7680
catcctgtcc ccccagttcc agtacggctc caaggtgtac gtgaagcacc ccgccgacat 7740
ccccgactac aagaagctgt ccttccccga gggcttcaag tgggagcgcg tgatgaactt 7800
cgaggacggc ggcgtggcga ccgtgaccca ggactcctcc ctgcaggacg gctgcttcat 7860
ctacaaggtg aagttcatcg gcgtgaactt cccctccgac ggccccgtga tgcagaagaa 7920
gaccatgggc tgggaggcct ccaccgagcg cctgtacccc cgcgacggcg tgctgaaggg 7980
cgagacccac aaggccctga agctgaagga cggcggccac tacctggtgg agttcaagtc 8040
catctacatg gccaagaagc ccgtgcagct gcccggctac tactacgtgg acgccaagct 8100
ggacatcacc tcccacaacg aggactacac catcgtggag cagtacgagc gcaccgaggg 8160
ccgccaccac ctgttcctga gatctcgacc caagaaaaag cggaaggtgg aggacccgta 8220
agatccaccg gatctagata actgatcata atcagccata ccacatttgt agaggtttta 8280
cttgctttaa aaaacctccc acacctcccc ctgaacctga aacataaaat gaatgcaatt 8340
gttgttgtta acttgtttat tgcagcttat aatggttaca aataaagcaa tagcatcaca 8400
aatttcacaa ataaagcatt tttttcactg cattctagtt gtggtttgtc caaactcatc 8460
aatgtatctt a 8471

<210> SEQ ID NO 88
<211> LENGTH: 8347
<212> TYPE: DNA
<213> ORGANISM: Artificial Sequence
<220> FEATURE:
<223> OTHER INFORMATION: Plasmid construct for expression in arthropods

<400> SEQUENCE: 88
gactttcact tttctctatc actgataggg agtggtaaac tcgactttca cttttctcta 60
tcactgatag ggagtggtaa actcgacttt cacttttctc tatcactgat agggagtggt 120
aaactcgact ttcacttttc tctatcactg atagggagtg gtaaactcga ctttcacttt 180
tctctatcac tgatagggag tggtaaactc gactttcact tttctctatc actgataggg 240
agtggtaaac tcgactttca cttttctcta tcactgatag ggagtggtaa actcgaaaac 300
gagcgccgga gtataaatag aggcgcttcg tctacggagc gacaattcaa ttcaaacaag 360
caaagtgaac acgtcgctaa gcgaaagcta agcaaataaa caagcgcagc tgaacaagct 420
aaacaatctg ccaccatgaa cagtgacgtg gacgaggcat cacggaaaat agacgaaggt 480
aggcctttta ttgtttaaat gccaattgca attgtccttc tgttatttat ttgcattgcg 540
attgttcgct gtaaagttaa agagatgaat tgagcgctaa aaagattttt catacaggaa 600
tgtgtgaaaa gagttgttta attcgtaatt tgcaactatg tattatgttt tatgttcact 660
gtttttgtgt tgttaacagc aaattaatgc cgataaagag aatgacagaa aaaacttaca 720
atctcaatta atccgataat tacaaaaagt gaatagttaa ccatcatgaa atcgttttag 780
aaagcttttt agcgttcgta caaattagtt gttcgtgcta cattgtaggt gagacgccta 840
aatgtctttc gtacttcgag tgcggatgta acagtgttat atgagcggcc attgttattt 900
ccatacgtgc ctggaacgct gctcagccca gcgtcgtagg gctccctgca gtctcgcacg 960
aacgaacctt tatttagcca ctgccgggaa ttgcattgga aatagatgcc tgcttataaa 1020
gtaggtaatc ataaacatat cacgattgaa tttaataata atttaatctt agttccaatt 1080
ctttggatag gttagggttt tttgacagac tccatctgag tgatgtcaaa aatcgatctt 1140
aaaacaaaga ttttaggctt gtttcgaccg aatggccaaa ttacttcata ttgacttgac 1200
tccttttttt tcgcaatgcg aatatgtgta cctattggaa aacttttgtt gtttttttaga 1260 atacatatag attttcgtta aatttcaatc taagtcaatt gaatatattt aattaattat 1320
ttatctttat ttatttcctt ctctttacga aatcttggaa tgtgaaaatt attatcattg 1380
tatcaacaaa aggtttctat aaacgttttt ataaataaaa taaaaaaaaa actgcatttt 1440
aataatcata cattgatatg aataaagcta aacagaaaac aaacgatgtt ctaatttcaa 1500
gatacatttg acagatgtca caaccgaacc gttacggcca ttttgaattt gtctatggtt 1560
tatttttttt aaggagaaaa tgattcgatg tctctcccgc cgtgtctatg gtttaatgca 1620 gtttttttttc acccgccaag cgattgtcca atttgcgcat tgtttgttct caggaaagat 1680
gattatcaac gaatacgcgc ggaagaacaa tctgaacgtg tatcgacggg ttagagctga 1740
ggaactcgac acgccagtac ggacattaat agtaataaat agtttttacc accaacaaca 1800
ctgaaactgt gctaacactt tgacagtgac aggtgtagtg taggggctgt gacaaacttc 1860
attctggttc ctattttaaa tttaaatcat ttattttcgg ccagcggcaa cagtttttcg 1920
tgttcctttt tttaatttaa atagtataat agtttctttt atgccagaca tttagttcta 1980
taaataagta tttgaaagaa cgctatttaa aatgttttgg actgtaacat ctattttaat 2040
tttgacaaga atgaagtttg ttacatacga catatttcac agcacatcgt cgtgtatata 2100
aataacacaa cactttacag ttacacaaag tatctaccta cacaagacat cactcattac 2160
acataacgat tagatactta tacacgttca cattaacata cagcagaacc agtggaaatg 2220
gatggtttag gtcaagattg cctaatttag tcaacgatct tctcacaatt taattcattt 2280
gttgtattgg gtatttgtaa ttttatatgg agatggtaat tttagagaga gggtagtata 2340
agagtaagta gtttaggtaa gtagttgaga aatgtcgttg taaatgtagg gttattttat 2400
gagtgaaatt gagtcgtgat ttttgtctcc ttaagttaaa ttttgataga ggtattttat 2460
tcatttgcat ttgaaatata gaacagcaac catgacgtaa caacgacggt ggcatccgtc 2520
accgtctcga acataatcaa caattcttag ccatacattg tgctacattg caacttgagt 2580
ttcgtttcca cgttacacgt tccacacaca aagtgacaca acaaaatagt tgcacacgat 2640
aaagtggtta agtcagaatc agctgtatta acaaagtcta accagtcgtg atttcaactt 2700
tacagtgacc ggacgaaggt ggtgaaattc gaaatgcaac ctcagtgaca ttccatattc 2760
aaaaaattcg aatttaacgg ccatcgtggt gctgtgctag tgtcgatatt ttatttagaa 2820
ttattttctt ttttgtagga aaatggcgga aatttattat ataagtggtg tactatcgtc 2880
gtcgatgaag ttattttgcg aatgatactt tgttttacaa gtgccgtgtt ttgtgtggac 2940

```
gcttgctgtg cgatgctgtg ttgcgaacga caacggactt cactgtggct acctccggcg   3000
tgtcggtgag tttatttgat attgttatta gcaattcaat ggacattgca acatgataga   3060
atctcaatta ttttaaaagt gtctattgag ttgttttatt atttaagaat tgcacaaacg   3120
cttttcaatt gtatacaaat gttagttgcc gatagatttg tattacgttg catttctgag   3180
acgtttgttt gccgtcttgc cttctttgtg ttcaaatgga aagcgttagt gtgcgtgtca   3240
atctgtttgt tccaagtact tgtttactgc tcatattcat aagtagaatt ttatgttaca   3300
acgtacacat aaaataaaat gctatttatg aaataagaca atttgcgatg cgacggaatt   3360
tatttatgtt tttattgctt ttacaaaacg gaggaatgca tgctatttct tgtctttatc   3420
taagttttta cattatttta tgatcattaa aactcacagt tgtaaggctc tcttctaagg   3480
tgtacagaac tatgcctctc ttattacttc aaaatattta catattcgaa aaaaaaaagt   3540
ttttagtaaa aaaaaatgtt tccatactag ggcggctgaa cagtttggag cctaaatact   3600
tattggacct tcggtaacta cactcacacg ggcataacac aacgcaagcg ttgtttcacg   3660
ccagctttct tgaggccgtc caccgtggaa acactccggt cgagccagat catttgaaat   3720
gatgctgaag ccttgttccc acctttaata ccttaggctc aaaagtattc agagacccta   3780
gtatagtaca tatacaaaac aaaaccgttc cacaaacacc ttaagctagg tctaaaacac   3840
ccagctggtc tacagaaacc ctcaaaatcc acaccagaaa cctaatcacc ccctttaaaa   3900
ttccagccca ctggatagtc caccaacggc ggatgtacga gcggtccata cgttccctgc   3960
tggagctgca ggcacgcaag ggatcctgct ccatgtgctt cacggagtac gctcccccct   4020
tgctgccgct gcccctcacc acgcagcgac cctcgccgcc gcctgcgcac ttgtagcgca   4080
gatcttcgtc aagaccctga ccggcaagac catcaccctg gaggtggagc cgagcgatac   4140
catcgagaac gtgaaggcca agatccagga caaggagggc atcccgccgg atcagcagcg   4200
cctgatcttc gccggacgcc agctggagga tggccgcacc ctgagcgact acaacatcca   4260
gaaggagagc accctgcacc tggtgctgcg cctgcgcggt ggtgtcagcc gcctggataa   4320
gtccaaagtc atcaactccg cgttggagct gttgaacgaa gttggcattg agggactgac   4380
gacccgcaag ttggcgcaga agctgggcgt ggagcagccc accctctact ggcacgtgaa   4440
gaataagcgg gcgctgctgg atgccctggc catcgagatg ctcgaccgcc accacacgca   4500
tttttgcccg ttggaaggcg agtcctggca ggacttcctc cgcaataacg ccaagtcgtt   4560
ccgctgcgct ctgctgtccc accgagacgg tgccaaagtc catctcggca cgcgcccgac   4620
cgaaaagcaa tacgagacac tggagaacca gctcgcgttc ctgtgccagc aaggcttcag   4680
cctggaaaat gctctctacg ctctgagcgc cgtcggtcac tttaccctgg gctgcgtgct   4740
ggaggaccaa gagcatcaag tcgcaaaaga ggagcgcgag accccaacaa ccgattcgat   4800
gcccccactg ctgcgtcagg caatcgagct gttcgatcat caaggagccg agccggcatt   4860
cctgttcggc ttggagctga ttatctgcgg attggaaaag caactgaaat gcgagtcggg   4920
ctcgggcccc gcgtacagcc gcgcgcgtac gaaaaacaat tacgggtcta ccatcgaggg   4980
cctgctcgat ctcccggacg acgacgcccc cgaagaggcg gggctggcgg ctccgcgcct   5040
gtcctttctc cccgcgggac acacgcgcag actgtcgacg gcccccccga ccgatgtcag   5100
cctgggggac gagctccact tagacggcga ggacgtggcg atggcgcatg ccgacgcgct   5160
agacgatttc gatctggaca tgttggggga cggggattcc ccgggtccgg gatttacccc   5220
ccacgactcc gccccctacg gcgctctgga tatggccgac ttcgagtttg agcagatgtt   5280
```

taccgatgcc cttggaattg acgagtacgg tgggtagaga tctgcggccg caatgaatcg 5340
tttttaaaat aacaaatcaa ttgttttata atattcgtac gattctttga ttatgtaata 5400
aaatgtgatc attaggaaga ttacgaaaaa tataaaaaat atgagttctg tgtgtataac 5460
aaatgctgta aacgccacaa ttgtgtttgt tgcaaataaa cccatgatta tttgattaaa 5520
attgttgttt tctttgttca tagacaatag tgtgttttgc ctaaacgtgt actgcataaa 5580
ctccatgcga gtgtatagcg agctagtggc taacgcttgc cccaccaaag tagattcgtc 5640
aaaatcctca atttcatcac cctcctccaa gtttaacatt tggccgtcgg aattaacttc 5700
taaagatgcc acataatcta ataaatgaaa tagagattca aacgtggcgt catcgtccgt 5760
ttcgaccatt tccgaaaaga actcgggcat aaactctatg atttctctgg acgtggtgtt 5820
gtcgaaactc tcaaagtacg cagtcaggaa cgtgcgcgac atgtcgtcgg gaaactcgcg 5880
cggaaacatg ttgttgtaac cgaacgggtc ccatagcgcc aaaaccaaat ctgccagcgt 5940
caatagaatg agcacgatgc cgacaatgga gctggcttgg atagcgattc gagttaacgg 6000
ccggccgttt aaacgcccgc caggtttcgc tttacgagta gaattctacg cgtaaaacac 6060
aatcaagtat gagtcataag ctgatgtcat gttttgcaca cggctcataa ccgaactggc 6120
tttacgagta gaattctact tgtaacgcac gatcagtgga tgatgtcatt tgtttttcaa 6180
atcgagatga tgtcatgttt tgcacacggc tcataaactc gctttacgag tagaattcta 6240
cgtgtaacgc acgatcgatt gatgagtcat ttgttttgca atatgatatc atacaatatg 6300
actcatttgt ttttcaaaac cgaacttgat ttacgggtag aattctactt gtaaagcaca 6360
atcaaaaaga tgatgtcatt tgtttttcaa aactgaactc gctttacgag tagaattcta 6420
cgtgtaaaac acaatcaaga aatgatgtca tttgttataa aaataaaagc tgatgtcatg 6480
ttttgcacat ggctcataac taaactcgct ttacgggtag aattctacgc gtaaaacatg 6540
attgataatt aaataattca tttgcaagct atacgttaaa tcaaacggac gctcgaggtt 6600
gcacaacact attatcgatt tgcagttcgg gacataaatg tttaaatata tcgatgtctt 6660
tgtgatgcgc gcgacatttt tgtaggttat tgataaaatg aacggatacg ttgcccgaca 6720
ttatcattaa atccttggcg tagaatttgt cgggtccatt gtccgtgtgc gctagtagca 6780
tgcccgtaac ggacctcgta cttttggctt caaaggtttt gcgcacagac aaaatgtgcc 6840
acacttgcag ctctgcatgt gtgcgcgtta ccacaaatcc caacggcgca gtgtacttgt 6900
tgtatgcaaa taaatctcga taaaggcgcg gcgcgcgaat gcagctgatc acgtacgctc 6960
ctcgtgttcc gttcaaggac ggtgttaccg acctcagatt aatgtttatc ggccgactgt 7020
tttcgtatcc gctcaccaaa cgcgtttttg cattaacatt gtatgtcggc ggatgttcta 7080
tatctaattt gaataaataa acgataaccg cgttggtttt agagggcata ataaaagaaa 7140
tattgttatc gtgttcgcca ttagggcagt ataaattgac gttcatgttg gatattgttt 7200
cagttgcaag ttgacactgg cggcgacaag acaattctaa ttggggtaag ttttcccgtt 7260
cttttctggg ttcttccctt ttgctcatcc ttgctgcact accttcaggt gcaagttgag 7320
attcaggcca ccatgggaga tcccacccca cccaagaaga agcgcaaacc ggtcgccacc 7380
atggcctcct ccgagaacgt catcaccgag ttcatgcgct tcaaggtgcg catggagggc 7440
accgtgaacg gccacgagtt cgagatcgag ggcgagggcg agggccgccc ctacgagggc 7500
cacaacaccg tgaagctgaa ggtgaccaag ggcggccccc tgcccttcgc ctgggacatc 7560 ctgtccccc agttccagta cggctccaag gtgtacgtga agcaccccgc cgacatcccc 7620
gactacaaga agctgtcctt ccccgagggc ttcaagtggg agcgcgtgat gaacttcgag 7680

```
gacggcggcg tggcgaccgt gacccaggac tcctccctgc aggacggctg cttcatctac   7740

aaggtgaagt tcatcggcgt gaacttcccc tccgacggcc ccgtgatgca gaagaagacc   7800

atgggctggg aggcctccac cgagcgcctg tacccccgcg acggcgtgct gaagggcgag   7860

acccacaagg ccctgaagct gaaggacggc ggccactacc tggtggagtt caagtccatc   7920

tacatggcca agaagcccgt gcagctgccc ggctactact acgtggacgc caagctggac   7980

atcacctccc acaacgagga ctacaccatc gtggagcagt acgagcgcac cgagggccgc   8040

caccacctgt tcctgagatc tcgacccaag aaaaagcgga aggtggagga cccgtaagat   8100

ccaccggatc tagataactg atcataatca gccataccac atttgtagag gttttacttg   8160

ctttaaaaaa cctcccacac ctccccctga acctgaaaca taaaatgaat gcaattgttg   8220

ttgttaactt gtttattgca gcttataatg gttacaaata aagcaatagc atcacaaatt   8280

tcacaaataa agcatttttt tcactgcatt ctagttgtgg tttgtccaaa ctcatcaatg   8340

tatctta                                                             8347
```

<210> SEQ ID NO 89
<211> LENGTH: 76
<212> TYPE: PRT
<213> ORGANISM: Spodoptera frugiperda

<400> SEQUENCE: 89

```
Ala Met Leu Cys Cys Glu Arg Gln Arg Thr Ser Leu Trp Leu Pro Pro
1               5                   10                  15

Ala Cys Arg Pro Leu Asp Ser Pro Pro Thr Ala Asp Val Arg Ala Val
            20                  25                  30

His Thr Phe Pro Ala Gly Ala Ala Gly Thr Gln Gly Ile Leu Leu His
        35                  40                  45

Val Leu His Gly Val Arg Ser Pro Leu Ala Ala Ala Ala Pro His His
    50                  55                  60

Ala Ala Thr Leu Ala Ala Ala Cys Ala Leu Val Ala
65                  70                  75
```

<210> SEQ ID NO 90
<211> LENGTH: 300
<212> TYPE: DNA
<213> ORGANISM: Spodoptera frugiperda

<400> SEQUENCE: 90

```
tgaccggacg aaggtggtga aattcgaaat gcaacctcag tgacattcca tattcaaaaa     60

attcgaattt aacggccatc gtggtgctgt gctagtgtcg atattttatt tagaattatt    120

ttcttttttg taggaaaatg gcggaaattt attatataag tggtgtacta tcgtcgtcga    180

tgaagttatt ttgcgaatga tactttgttt tacaagtgcc gtgttttgtg tggacgcttg    240

ctgtgcgatg ctgtgttgcg aacgacaacg gacttcactg tggctacctc cggcgtgtcg    300
```

<210> SEQ ID NO 91
<211> LENGTH: 300
<212> TYPE: DNA
<213> ORGANISM: Spodoptera frugiperda

<400> SEQUENCE: 91

```
tgaccggacg aaggtggtga aattcgaaat gcaacctcag tgacattcca tattcaaaaa     60

attcgaattt aacggccatc gtggtgctgt gctagtgtcg atattttatt tagaattatt    120

ttcttttttg taggaaaatg gcggaaatta ataatataag tggtgtacta tcgtcgtcga    180
```

tgaagttatt ttgcgaatga tactttgttt tacaagtgcc gtgttttgtg tggacgcttg 240
ctgtgcgatg ctgtgttgcg aacgacaacg gacttgactg tggctacctc cggcgtgtcg 300

<210> SEQ ID NO 92
<211> LENGTH: 300
<212> TYPE: DNA
<213> ORGANISM: Spodoptera frugiperda

<400> SEQUENCE: 92
tgaccggacg aaggtggtga aattcgaaat gcaacctcag tgacattcca tattcaaaaa 60
attcgaattt aacggccatc gtggtgctgt gctagtgtcg atattttatt tagaattatt 120
ttcttttttg taggaaaatg gcggaaattt attatataag tggtgtacta tcgtcgtcga 180
tgaagttatt ttgcgaatga tactttgttt tacaagtgcc gtgttttgtg tggacgcttg 240
ctgtgcgatg ctgtgttgcg aacgacaacg gacttcactg tggctacctc cggcgtgtcg 300

<210> SEQ ID NO 93
<211> LENGTH: 35
<212> TYPE: DNA
<213> ORGANISM: Spodoptera frugiperda

<400> SEQUENCE: 93
tcgacgggtt agagctgagg aactcgacac gccag 35

<210> SEQ ID NO 94
<211> LENGTH: 42
<212> TYPE: DNA
<213> ORGANISM: Spodoptera frugiperda

<400> SEQUENCE: 94
gaaagatcat tatcaacgaa tacgcgcgga agaacaatct ga 42

<210> SEQ ID NO 95
<211> LENGTH: 18
<212> TYPE: DNA
<213> ORGANISM: Artificial Sequence
<220> FEATURE:
<223> OTHER INFORMATION: Synthetic DNA linker

<400> SEQUENCE: 95
taacggaccg aaaccacc 18

<210> SEQ ID NO 96
<211> LENGTH: 11
<212> TYPE: DNA
<213> ORGANISM: Artificial Sequence
<220> FEATURE:
<223> OTHER INFORMATION: Synthetic DNA linker

<400> SEQUENCE: 96
taacaccggt g 11

<210> SEQ ID NO 97
<211> LENGTH: 338
<212> TYPE: PRT
<213> ORGANISM: Artificial Sequence
<220> FEATURE:
<223> OTHER INFORMATION: Fusion of sequences from E. coli (tetR -
tetracycline repressor) and HSV-1 (VP16 transcriptional activator)

<400> SEQUENCE: 97

Met Val Ser Arg Leu Asp Lys Ser Lys Val Ile Asn Ser Ala Leu Glu

```
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220

Ile Glu Gly Leu Leu Asp Leu Pro Asp Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly


<210> SEQ ID NO 98
<211> LENGTH: 336
<212> TYPE: PRT
<213> ORGANISM: Artificial Sequence
<220> FEATURE:
<223> OTHER INFORMATION: Fusion of sequences from E. coli (tetR -
      tetracycline repressor) and HSV-1 (VP16 transcriptional activator)

<400> SEQUENCE: 98

Met Glu Leu Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
```

```
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Ala Tyr Ser Arg Ala Arg Thr Lys Asn Asn Tyr Gly Ser Thr Ile Glu
    210                 215                 220

Gly Leu Leu Asp Leu Pro Asp Asp Asp Ala Pro Glu Glu Ala Gly Leu
225                 230                 235                 240

Ala Ala Pro Arg Leu Ser Phe Leu Pro Ala Gly His Thr Arg Arg Leu
                245                 250                 255

Ser Thr Ala Pro Pro Thr Asp Val Ser Leu Gly Asp Glu Leu His Leu
            260                 265                 270

Asp Gly Glu Asp Val Ala Met Ala His Ala Asp Ala Leu Asp Asp Phe
        275                 280                 285

Asp Leu Asp Met Leu Gly Asp Gly Asp Ser Pro Gly Pro Gly Phe Thr
    290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335
```

<210> SEQ ID NO 99
<211> LENGTH: 1014
<212> TYPE: DNA
<213> ORGANISM: Artificial Sequence
<220> FEATURE:
<223> OTHER INFORMATION: Synthetic DNA based on a fusion of sequences from E. coli (tetR - tetracycline repressor) and HSV-1 (VP16 transcriptional activator)

<400> SEQUENCE: 99

```
atgggcagcc gcctggataa gtccaaagtc atcaactccg cgttggagct gttgaacgaa      60

gttggcattg agggactgac gacccgcaag ttggcgcaga agctgggcgt ggagcagccc     120

accctctact ggcacgtgaa gaataagcgg gcgctgctgg atgccctggc catcgagatg     180

ctcgaccgcc accacacgca tttttgcccg ttggaaggcg agtcctggca ggacttcctc     240
```

-continued

```
cgcaataacg ccaagtcgtt ccgctgcgct ctgctgtccc accgagacgg tgccaaagtc    300

catctcggca cgcgcccgac cgaaaagcaa tacgagacac tggagaacca gctcgcgttc    360

ctgtgccagc aaggcttcag cctggaaaat gctctctacg ctctgagcgc cgtcggtcac    420

tttaccctgg gctgcgtgct ggaggaccaa gagcatcaag tcgcaaaaga ggagcgcgag    480

accccaacaa ccgattcgat gcccccactg ctgcgtcagg caatcgagct gttcgatcat    540

caaggagccg agccggcatt cctgttcggc ttggagctga ttatctgcgg attggaaaag    600

caactgaaat gcgagtcggg ctcgggcccc gcctacagcc gcgcccgcac caagaacaac    660

tacggcagca ccatcgaggg cctgctggat ctgccggatg atgatgcccc ggaggaggcg    720

ggcctggccg ccccgcgcct gagcttcctg ccggccggac acacccgccg cctgtcgacc    780

gccccgccga ccgacgtgag cctgggcgat gagctgcacc tggatggcga ggatgtggcg    840

atggcccacg ccgatgccct ggacgacttc gacctggaca tgctgggcga tggcgatagc    900

ccgggaccgg gattcacccc gcacgatagc gccccctacg gcgccctgga tatggccgat    960

ttcgagttcg agcagatgtt caccgacgcc ctgggcatcg atgaatacgg cggc         1014
```

```
<210> SEQ ID NO 100
<211> LENGTH: 338
<212> TYPE: PRT
<213> ORGANISM: Artificial Sequence
<220> FEATURE:
<223> OTHER INFORMATION: Fusion of sequences from E. coli (tetR -
      tetracycline repressor) and HSV-1 (VP16 transcriptional activator)

<400> SEQUENCE: 100

Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220
```

```
Ile Glu Gly Leu Leu Asp Leu Pro Asp Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly


<210> SEQ ID NO 101
<211> LENGTH: 1011
<212> TYPE: DNA
<213> ORGANISM: Artificial Sequence
<220> FEATURE:
<223> OTHER INFORMATION: Synthetic DNA based on a fusion of sequences
      from E. coli (tetR - tetracycline repressor) and HSV-1 (VP16
      transcriptional activator)

<400> SEQUENCE: 101

gtcagccgcc tggataagtc caaagtcatc aactccgcgt tggagctgtt gaacgaagtt     60

ggcattgagg gactgacgac ccgcaagttg gcgcagaagc tgggcgtgga gcagcccacc    120

ctctactggc acgtgaagaa taagcgggcg ctgctggatg ccctggccat cgagatgctc    180

gaccgccacc acacgcattt ttgcccgttg gaaggcgagt cctggcagga cttcctccgc    240

aataacgcca agtcgttccg ctgcgctctg ctgtcccacc gagacggtgc caaagtccat    300

ctcggcacgc gcccgaccga aaagcaatac gagacactgg agaaccagct cgcgttcctg    360

tgccagcaag gcttcagcct ggaaaatgct ctctacgctc tgagcgccgt cggtcacttt    420

accctgggct gcgtgctgga ggaccaagag catcaagtcg caaaagagga gcgcgagacc    480

ccaacaaccg attcgatgcc cccactgctg cgtcaggcaa tcgagctgtt cgatcatcaa    540

ggagccgagc cggcattcct gttcggcttg gagctgatta tctgcggatt ggaaaagcaa    600

ctgaaatgcg agtcgggctc gggccccgcg tacagccgcg cgcgtacgaa aaacaattac    660

gggtctacca tcgagggcct gctcgatctc ccggacgacg acgcccccga agaggcgggg    720

ctggcggctc cgcgcctgtc ctttctcccc gcgggacaca cgcgcagact gtcgacggcc    780

cccccgaccg atgtcagcct gggggacgag ctccacttag acggcgagga cgtggcgatg    840

gcgcatgccg acgcgctaga cgatttcgat ctggacatgt tgggggacgg ggattccccg    900

ggtccgggat ttacccccca cgactccgcc ccctacggcg ctctggatat ggccgacttc    960

gagtttgagc agatgtttac cgatgccctt ggaattgacg agtacggtgg g            1011


<210> SEQ ID NO 102
<211> LENGTH: 337
<212> TYPE: PRT
<213> ORGANISM: Artificial Sequence
<220> FEATURE:
<223> OTHER INFORMATION: Fusion of sequences from E. coli (tetR -
      tetracycline repressor) and HSV-1 (VP16 transcriptional activator)

<400> SEQUENCE: 102
```

-continued

```
Val Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Gly
        195                 200                 205

Pro Ala Tyr Ser Arg Ala Arg Thr Lys Asn Asn Tyr Gly Ser Thr Ile
    210                 215                 220

Glu Gly Leu Leu Asp Leu Pro Asp Asp Asp Ala Pro Glu Glu Ala Gly
225                 230                 235                 240

Leu Ala Ala Pro Arg Leu Ser Phe Leu Pro Ala Gly His Thr Arg Arg
                245                 250                 255

Leu Ser Thr Ala Pro Pro Thr Asp Val Ser Leu Gly Asp Glu Leu His
            260                 265                 270

Leu Asp Gly Glu Asp Val Ala Met Ala His Ala Asp Ala Leu Asp Asp
        275                 280                 285

Phe Asp Leu Asp Met Leu Gly Asp Gly Asp Ser Pro Gly Pro Gly Phe
    290                 295                 300

Thr Pro His Asp Ser Ala Pro Tyr Gly Ala Leu Asp Met Ala Asp Phe
305                 310                 315                 320

Glu Phe Glu Gln Met Phe Thr Asp Ala Leu Gly Ile Asp Glu Tyr Gly
                325                 330                 335

Gly
```